(12) United States Patent
Overes et al.

(10) Patent No.: US 9,597,064 B2
(45) Date of Patent: Mar. 21, 2017

(54) METHODS FOR APPROXIMATING A TISSUE DEFECT USING AN ANCHOR ASSEMBLY

(75) Inventors: Tom Overes, Langendorf (CH); Wamis Singhatat, West Chester, PA (US); Jamie Manos, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1427 days.

(21) Appl. No.: 13/283,198

(22) Filed: Oct. 27, 2011

(65) Prior Publication Data

US 2012/0109156 A1    May 3, 2012

Related U.S. Application Data

(63) Continuation-in-part of application No. 13/172,619, filed on Jun. 29, 2011, which is a continuation-in-part of application No. 13/095,192, filed on Apr. 27, 2011.
(Continued)

(51) Int. Cl.
*A61B 17/04* (2006.01)
*A61B 17/00* (2006.01)
(Continued)

(52) U.S. Cl.
CPC ...... *A61B 17/0057* (2013.01); *A61B 17/0401* (2013.01); *A61B 17/0467* (2013.01); *A61B 17/0469* (2013.01); *A61B 17/0482* (2013.01); *A61B 17/0483* (2013.01); *A61B 17/0487* (2013.01); *A61B 17/842* (2013.01); *A61B 2017/00477* (2013.01); *A61B 2017/00623* (2013.01); *A61B 2017/00663* (2013.01); *A61B 2017/0406* (2013.01);
(Continued)

(58) Field of Classification Search
CPC ............ A61B 17/0401; A61B 17/0057; A61B 2017/0409; A61B 2017/0417; A61B 2017/0419
See application file for complete search history.

(56) References Cited

U.S. PATENT DOCUMENTS

| 233,475 A | 10/1880 | Cook et al. |
|---|---|---|
| 261,501 A | 7/1882 | Vanermark |

(Continued)

FOREIGN PATENT DOCUMENTS

| CN | 101056587 | 10/2007 |
|---|---|---|
| DE | 4207854 | 9/1993 |

(Continued)

OTHER PUBLICATIONS

U.S. Appl. No. 61/328,251, filed Apr. 27, 2010, Overes.
(Continued)

*Primary Examiner* — Gregory Anderson
*Assistant Examiner* — Christina Lauer
(74) *Attorney, Agent, or Firm* — Baker & Hostetler LLP

(57) ABSTRACT

An insertion instrument is configured to eject one or more of anchor bodies across an anatomical gap so as to approximate the gap. The insertion instrument can include a single cannula that retains the pair of anchor bodies in a stacked relationship, or a pair of adjacent cannulas that each retains respective anchor bodies. The insertion instrument can be actuated so as to eject the anchor bodies into respective target anatomical locations.

73 Claims, 103 Drawing Sheets

Related U.S. Application Data

(60) Provisional application No. 61/398,699, filed on Jun. 29, 2010, provisional application No. 61/432,755, filed on Jan. 14, 2011, provisional application No. 61/461,490, filed on Jan. 18, 2011, provisional application No. 61/443,142, filed on Feb. 15, 2011, provisional application No. 61/328,251, filed on Apr. 27, 2010.

(51) Int. Cl.
  *A61B 17/84* (2006.01)
  *A61B 17/06* (2006.01)
  *A61B 17/29* (2006.01)

(52) U.S. Cl.
  CPC ............... *A61B 2017/0409* (2013.01); *A61B 2017/0414* (2013.01); *A61B 2017/0417* (2013.01); *A61B 2017/0419* (2013.01); *A61B 2017/0464* (2013.01); *A61B 2017/0475* (2013.01); *A61B 2017/0477* (2013.01); *A61B 2017/0496* (2013.01); *A61B 2017/06042* (2013.01); *A61B 2017/06052* (2013.01); *A61B 2017/06176* (2013.01); *A61B 2017/292* (2013.01); *A61B 2017/2917* (2013.01)

(56) References Cited

U.S. PATENT DOCUMENTS

| | | | |
|---|---|---|---|
| 330,087 | A | 11/1885 | Binns |
| 400,743 | A | 4/1889 | Brown |
| 2,490,364 | A | 12/1949 | Livingston |
| 3,580,256 | A | 5/1971 | Wilkinson |
| 3,867,728 | A | 2/1975 | Stubstad et al. |
| 3,908,677 | A | 9/1975 | Beach |
| 3,987,806 | A | 10/1976 | Gilbert |
| 4,006,747 | A | 2/1977 | Kronenthal et al. |
| 4,235,238 | A | 11/1980 | Ogiv et al. |
| 4,669,473 | A | 6/1987 | Richards et al. |
| 4,741,330 | A | 5/1988 | Hayhurst |
| 4,778,990 | A | 10/1988 | Laughlin |
| 4,994,028 | A | 2/1991 | Leonard et al. |
| 5,021,059 | A | 6/1991 | Kensey et al. |
| 5,041,129 | A | 8/1991 | Hayhurst et al. |
| 5,053,046 | A | 10/1991 | Janese |
| 5,062,344 | A | 11/1991 | Gerker |
| 5,120,596 | A | 6/1992 | Yamada |
| 5,156,616 | A * | 10/1992 | Meadows .......... A61B 17/0401 411/395 |
| 5,269,809 | A | 12/1993 | Hayhurst et al. |
| 5,281,238 | A | 1/1994 | Chin et al. |
| 5,403,348 | A | 4/1995 | Bonutti |
| 5,417,691 | A | 5/1995 | Hayhurst |
| 5,464,426 | A | 11/1995 | Bonutti |
| 5,478,353 | A | 12/1995 | Yoon |
| 5,507,754 | A | 4/1996 | Green et al. |
| 5,522,846 | A | 6/1996 | Bonutti |
| 5,527,343 | A | 6/1996 | Bonutti |
| 5,540,703 | A | 7/1996 | Barker et al. |
| 5,549,630 | A | 8/1996 | Bonutti |
| 5,562,684 | A | 10/1996 | Kammerer |
| 5,562,736 | A | 10/1996 | Ray et al. |
| 5,571,189 | A | 11/1996 | Kuslich |
| 5,584,862 | A | 12/1996 | Bonutti |
| 5,601,557 | A | 2/1997 | Hayhurst |
| 5,626,614 | A | 5/1997 | Hart |
| 5,628,756 | A | 5/1997 | Barker, Jr. et al. |
| 5,643,319 | A | 7/1997 | Green et al. |
| 5,649,945 | A | 7/1997 | Ray et al. |
| 5,699,657 | A | 12/1997 | Paulson |
| 5,702,462 | A | 12/1997 | Oberlander |
| 5,728,109 | A | 3/1998 | Schulze et al. |
| 5,733,306 | A | 3/1998 | Bonutti |
| 5,824,093 | A | 10/1998 | Ray et al. |
| 5,906,626 | A | 5/1999 | Carrillo |
| 5,941,900 | A | 8/1999 | Bonutti |
| 5,944,739 | A | 8/1999 | Zlock et al. |
| 5,948,002 | A | 9/1999 | Bonutti |
| 5,951,590 | A | 9/1999 | Goldfarb |
| 5,957,953 | A | 9/1999 | DiPoto et al. |
| 5,970,697 | A | 10/1999 | Jacobs et al. |
| 5,989,252 | A | 11/1999 | Fumex |
| 6,056,773 | A | 5/2000 | Bonutti |
| 6,068,648 | A | 5/2000 | Cole |
| 6,077,292 | A | 6/2000 | Bonutti |
| 6,110,183 | A | 8/2000 | Cope |
| 6,113,611 | A | 9/2000 | Allen et al. |
| 6,146,422 | A | 11/2000 | Lawson |
| 6,179,860 | B1 | 1/2001 | Fulton et al. |
| 6,187,048 | B1 | 2/2001 | Milner et al. |
| 6,209,550 | B1 | 4/2001 | Powell |
| 6,224,630 | B1 | 5/2001 | Bao et al. |
| 6,245,107 | B1 | 6/2001 | Ferree |
| 6,287,325 | B1 | 9/2001 | Bonutti |
| 6,296,659 | B1 | 10/2001 | Foerster |
| 6,306,159 | B1 | 10/2001 | Schwartz et al. |
| 6,325,816 | B1 | 12/2001 | Fulton et al. |
| 6,409,742 | B1 | 6/2002 | Fulton et al. |
| 6,432,123 | B2 | 8/2002 | Schwartz et al. |
| 6,482,235 | B1 | 11/2002 | Lambrecht et al. |
| 6,508,839 | B1 | 1/2003 | Lambrecht et al. |
| 6,511,498 | B1 | 1/2003 | Fumex |
| 6,530,933 | B1 | 3/2003 | Yeung et al. |
| 6,579,291 | B1 | 6/2003 | Keith et al. |
| 6,592,625 | B2 | 7/2003 | Cauthen |
| 6,656,182 | B1 | 12/2003 | Hayhurst |
| 6,689,125 | B1 | 2/2004 | Keith et al. |
| 6,719,797 | B1 | 4/2004 | Ferree |
| 6,758,855 | B2 | 7/2004 | Fulton et al. |
| 6,964,674 | B1 | 11/2005 | Matsuura et al. |
| 6,972,027 | B2 | 12/2005 | Fallin et al. |
| 6,984,247 | B2 | 1/2006 | Cauthen |
| 6,986,775 | B2 | 1/2006 | Morales et al. |
| 6,991,643 | B2 | 1/2006 | Saadat |
| 6,997,956 | B2 | 2/2006 | Cauthen |
| 7,004,970 | B2 | 2/2006 | Cauthen, III et al. |
| 7,033,393 | B2 | 4/2006 | Gainor et al. |
| 7,033,395 | B2 | 4/2006 | Cauthen |
| 7,041,052 | B2 | 5/2006 | Saadat et al. |
| 7,048,754 | B2 | 5/2006 | Martin et al. |
| 7,052,516 | B2 | 5/2006 | Cauthen et al. |
| 7,128,708 | B2 | 10/2006 | Saadat et al. |
| 7,153,312 | B1 | 12/2006 | Torrie et al. |
| 7,189,235 | B2 | 3/2007 | Cauthen |
| 7,285,124 | B2 | 10/2007 | Foerster |
| 7,303,575 | B2 | 12/2007 | Ogle |
| 7,326,221 | B2 | 2/2008 | Sakamoto et al. |
| 7,329,279 | B2 | 2/2008 | Haug et al. |
| 7,335,221 | B2 | 2/2008 | Collier et al. |
| 7,347,863 | B2 | 3/2008 | Rothe et al. |
| 7,390,332 | B2 | 6/2008 | Selvitelli et al. |
| 7,468,074 | B2 | 12/2008 | Caborn et al. |
| 7,491,212 | B2 | 2/2009 | Sikora et al. |
| 7,494,496 | B2 | 2/2009 | Swain et al. |
| 7,601,165 | B2 | 10/2009 | Stone |
| 7,615,076 | B2 | 11/2009 | Cauthen, III et al. |
| 7,621,925 | B2 | 11/2009 | Saadat et al. |
| 7,651,509 | B2 | 1/2010 | Bojarski et al. |
| 7,658,750 | B2 | 2/2010 | Li |
| 7,666,193 | B2 | 2/2010 | Starksen et al. |
| 7,670,379 | B2 | 3/2010 | Cauthen |
| 7,670,380 | B2 | 3/2010 | Cauthen, III |
| 7,678,135 | B2 | 3/2010 | Maahs et al. |
| 7,731,732 | B2 | 6/2010 | Ken |
| 7,736,379 | B2 | 6/2010 | Ewers et al. |
| 7,749,250 | B2 | 7/2010 | Stone et al. |
| 7,749,273 | B2 | 7/2010 | Cauthen, III et al. |
| 7,753,941 | B2 | 7/2010 | Keith et al. |
| 7,776,096 | B2 | 8/2010 | Cauthen |
| 7,828,850 | B2 | 11/2010 | Cauthen, III et al. |
| 7,846,208 | B2 | 12/2010 | Cauthen, III et al. |
| 7,857,830 | B2 | 12/2010 | Stone et al. |
| 7,905,904 | B2 | 3/2011 | Stone et al. |

(56) References Cited

U.S. PATENT DOCUMENTS

| | | |
|---|---|---|
| 7,905,923 B2 | 3/2011 | Keith et al. |
| 7,909,851 B2 | 3/2011 | Stone et al. |
| 7,909,879 B2 | 3/2011 | Cauthen |
| 7,922,768 B2 | 4/2011 | Cauthen, III et al. |
| 7,935,147 B2 | 5/2011 | Wales |
| 7,951,201 B2 | 5/2011 | Cauthen et al. |
| 7,959,650 B2 | 6/2011 | Kaiser et al. |
| 7,963,992 B2 | 6/2011 | Cauthen et al. |
| 7,985,257 B2 | 7/2011 | Cauthen et al. |
| 7,993,405 B2 | 8/2011 | Cauthen et al. |
| 7,998,108 B2 | 8/2011 | Nazzaro et al. |
| 8,034,112 B2 | 10/2011 | Cauthen et al. |
| 8,048,160 B2 | 11/2011 | Cauthen |
| 8,083,768 B2 | 12/2011 | Ginn et al. |
| 8,088,130 B2 | 1/2012 | Kaiser et al. |
| 8,088,165 B2 | 1/2012 | Cauthen et al. |
| 8,100,914 B2 | 1/2012 | Cauthen et al. |
| 8,118,836 B2 | 2/2012 | Denham et al. |
| 8,128,640 B2 | 3/2012 | Harris et al. |
| 8,128,658 B2 | 3/2012 | Kaiser et al. |
| 8,128,698 B2 | 3/2012 | Bentley et al. |
| 8,137,382 B2 | 3/2012 | Denham et al. |
| 8,216,253 B2 | 7/2012 | Saadat et al. |
| 8,216,260 B2 | 7/2012 | Lam et al. |
| 8,298,291 B2 | 10/2012 | Ewers et al. |
| 8,814,903 B2 | 8/2014 | Sengun et al. |
| 8,828,053 B2 | 9/2014 | DeMatteo et al. |
| 8,920,436 B2 | 12/2014 | Lam et al. |
| 8,926,634 B2 | 1/2015 | Rothe et al. |
| 9,149,266 B2 | 10/2015 | Lamson |
| 2002/0029782 A1 | 3/2002 | Linderoth |
| 2002/0065536 A1 | 5/2002 | Hart et al. |
| 2002/0115999 A1 | 8/2002 | McDevitt et al. |
| 2002/0143359 A1 | 10/2002 | Fulton et al. |
| 2002/0188301 A1 | 12/2002 | Dallara et al. |
| 2003/0167071 A1 | 9/2003 | Martin et al. |
| 2004/0097980 A1 | 5/2004 | Ferree |
| 2004/0153074 A1 | 8/2004 | Bojarski |
| 2004/0162618 A1 | 8/2004 | Mujwid et al. |
| 2004/0225183 A1 | 11/2004 | Michlitsch et al. |
| 2004/0225359 A1 | 11/2004 | Bojarski |
| 2004/0243171 A1 | 12/2004 | Fulton et al. |
| 2005/0080422 A1 | 4/2005 | Otte et al. |
| 2005/0228448 A1 | 10/2005 | Li |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0277966 A1 | 12/2005 | Ewers et al. |
| 2005/0277981 A1 | 12/2005 | Maahs et al. |
| 2005/0283192 A1 | 12/2005 | Torrie et al. |
| 2005/0283246 A1 | 12/2005 | Cauthen, III et al. |
| 2006/0064126 A1 | 3/2006 | Fallin et al. |
| 2006/0178680 A1 | 8/2006 | Nelson et al. |
| 2006/0190042 A1 | 8/2006 | Stone et al. |
| 2006/0259076 A1 | 11/2006 | Burkhart et al. |
| 2006/0265008 A1 | 11/2006 | Maruyama et al. |
| 2007/0010857 A1 | 1/2007 | Sugimoto et al. |
| 2007/0027476 A1 | 2/2007 | Harris et al. |
| 2007/0073320 A1 | 3/2007 | Mikkaichi et al. |
| 2007/0083236 A1 | 4/2007 | Sikora et al. |
| 2007/0100348 A1 | 5/2007 | Cauthen, III et al. |
| 2007/0129804 A1 | 6/2007 | Bentley et al. |
| 2007/0142846 A1 | 6/2007 | Catanese |
| 2007/0156245 A1 | 7/2007 | Cauthen, III et al. |
| 2007/0162054 A1 | 7/2007 | Horaguchi |
| 2007/0162120 A1 | 7/2007 | Bouffier |
| 2007/0185532 A1* | 8/2007 | Stone ............... A61B 17/0401 606/232 |
| 2007/0255285 A1 | 11/2007 | Trieu |
| 2007/0276433 A1 | 11/2007 | Huss |
| 2008/0009888 A1 | 1/2008 | Ewers et al. |
| 2008/0015635 A1 | 1/2008 | Olsen et al. |
| 2008/0015636 A1 | 1/2008 | Olsen et al. |
| 2008/0033487 A1 | 2/2008 | Schwartz et al. |
| 2008/0086155 A1 | 4/2008 | Rothe et al. |
| 2008/0097484 A1 | 4/2008 | Lim et al. |
| 2008/0097522 A1 | 4/2008 | Chopra |
| 2008/0140092 A1 | 6/2008 | Stone et al. |
| 2008/0140093 A1 | 6/2008 | Stone et al. |
| 2008/0147086 A1 | 6/2008 | Pfister et al. |
| 2008/0147102 A1 | 6/2008 | Rotella et al. |
| 2008/0167658 A1 | 7/2008 | Kerr et al. |
| 2008/0177302 A1 | 7/2008 | Shumas |
| 2008/0177304 A1 | 7/2008 | Westra et al. |
| 2008/0188893 A1 | 8/2008 | Selvitelli et al. |
| 2008/0195145 A1 | 8/2008 | Bonutti et al. |
| 2008/0200930 A1 | 8/2008 | Saadat et al. |
| 2008/0208225 A1 | 8/2008 | Seibold et al. |
| 2008/0208226 A1 | 8/2008 | Seibold et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0243151 A1 | 10/2008 | Binmoeller |
| 2008/0269781 A1 | 10/2008 | Funamura et al. |
| 2008/0281355 A1 | 11/2008 | Mayer et al. |
| 2008/0294193 A1 | 11/2008 | Schwartz |
| 2008/0312689 A1 | 12/2008 | Denham et al. |
| 2008/0319524 A1 | 12/2008 | Yachia et al. |
| 2009/0018561 A1 | 1/2009 | Schwartz et al. |
| 2009/0030522 A1 | 1/2009 | Cauthen, III et al. |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0062846 A1 | 3/2009 | Ken |
| 2009/0062847 A1 | 3/2009 | Ken |
| 2009/0062848 A1 | 3/2009 | Ken |
| 2009/0062850 A1 | 3/2009 | Ken |
| 2009/0062854 A1 | 3/2009 | Kaiser et al. |
| 2009/0069823 A1 | 3/2009 | Foerster et al. |
| 2009/0076547 A1 | 3/2009 | Sugimoto et al. |
| 2009/0082805 A1 | 3/2009 | Kaiser et al. |
| 2009/0157184 A1 | 6/2009 | Cauthen, III et al. |
| 2009/0228042 A1 | 9/2009 | Koogle et al. |
| 2009/0259260 A1 | 10/2009 | Bentley et al. |
| 2009/0306711 A1 | 12/2009 | Stone et al. |
| 2010/0049212 A1 | 2/2010 | Caborn et al. |
| 2010/0069923 A1 | 3/2010 | Nguyen et al. |
| 2010/0094337 A1 | 4/2010 | Maiorino |
| 2010/0094425 A1 | 4/2010 | Bentley et al. |
| 2010/0121376 A1 | 5/2010 | Li |
| 2010/0292731 A1 | 11/2010 | Gittings et al. |
| 2011/0022083 A1 | 1/2011 | DiMatteo et al. |
| 2011/0022084 A1 | 1/2011 | Sengun et al. |
| 2011/0077667 A1 | 3/2011 | Singhatal et al. |
| 2011/0082472 A1 | 4/2011 | Harris et al. |
| 2011/0172701 A1 | 7/2011 | Wales et al. |
| 2011/0270278 A1 | 11/2011 | Overes et al. |
| 2012/0004669 A1 | 1/2012 | Overes et al. |
| 2012/0035654 A1 | 2/2012 | Belson |
| 2012/0046693 A1 | 2/2012 | Denham et al. |
| 2012/0053630 A1 | 3/2012 | Denham et al. |
| 2012/0109156 A1 | 5/2012 | Overes et al. |
| 2012/0130422 A1 | 5/2012 | Hootstein |
| 2012/0143215 A1 | 6/2012 | Corrao et al. |
| 2012/0150223 A1 | 6/2012 | Manos et al. |
| 2013/0110165 A1 | 5/2013 | Burkhart et al. |
| 2014/0336703 A1 | 11/2014 | Sengun et al. |
| 2015/0038992 A1 | 2/2015 | DiMatteo et al. |

FOREIGN PATENT DOCUMENTS

| | | |
|---|---|---|
| EP | 0834281 | 4/1998 |
| EP | 0838197 | 4/1998 |
| EP | 1938760 A1 | 7/2008 |
| EP | 1964520 | 9/2008 |
| EP | 2238944 | 10/2010 |

(56) References Cited

FOREIGN PATENT DOCUMENTS

| | | |
|---|---|---|
| EP | 2663240 | 11/2013 |
| EP | 2663242 | 11/2013 |
| WO | WO 92/11810 | 7/1992 |
| WO | WO 99/22648 | 5/1999 |
| WO | WO 03/096910 | 11/2003 |
| WO | WO 2004/071307 | 8/2004 |
| WO | WO 2005/011463 | 2/2005 |
| WO | WO 2005/065553 A1 | 7/2005 |
| WO | WO 2006/039296 A2 | 4/2006 |
| WO | WO 2006/117398 | 11/2006 |
| WO | WO 2007/005394 | 1/2007 |
| WO | WO 2008/010738 | 1/2008 |
| WO | WO 2008/048667 | 4/2008 |
| WO | WO 2009/126781 | 10/2009 |
| WO | WO 2009/146402 | 12/2009 |
| WO | WO 2010/088561 | 8/2010 |
| WO | WO 2011/137159 | 11/2011 |
| WO | WO 2012/006161 | 1/2012 |
| WO | WO 2012/096706 | 7/2012 |
| WO | WO 2012/096707 | 7/2012 |

OTHER PUBLICATIONS

U.S. Appl. No. 61/398,699, filed Jun. 29, 2010, Overes et al.
U.S. Appl. No. 61/432,755, filed Jan. 14, 2010, Henrichsen et al.
U.S. Appl. No. 61/443,142, filed Feb. 15, 2011, Henrichsen et al.
U.S. Appl. No. 61/461,490, filed Jan. 18, 2011, Henrichsen et al.
U.S. Appl. No. 60/160,710, filed Oct. 20, 1999, Cauthen.
U.S. Appl. No. 09/484,706, filed Jan. 18, 2000, Cauthen.
U.S. Appl. No. 12/509,112: Non-Final Office Action, dated Jul. 12, 2012, 8 pages.
U.S. Appl. No. 12/509,112: Restriction Requirement, dated Nov. 17, 2011, 8 pages.
U.S. Appl. No. 12/509,112: Restriction Requirement, dated Apr. 10, 2012, 6 pages.
U.S. Appl. No. 13/095,192: Restriction Requirement, dated Sep. 6, 2012, 10 pages.
European Search Report for Application No. 10251328.0 dated Oct. 29, 2010.
European Search Report for Application No. 05802651.9 dated Aug. 31, 2009, 7 pages.
Brinckmann et al., "A laboratory model of lumbar disc protrusion", Fissure and Fragment Institut fur Experimentelle Biomechanik, Universitat, Munster, German, Spine (Phila., PA 1976) Jan. 15, 1994, 19(2): 228-235.
Maroon et al., "Microdiscectomy versus Chemonucleolysis", Neurosurgery, vol. 16(5), 644-649, May 1985.
Mitek Brochure, Rapid Loc, "Surgical Technique Guide for Repair of Meniscal Tears", 2001, 6 pages.
Biomet Maxfire Technique Guide, Meniscal Repair, 1994, 16 pages.
Cayenne Medical, Crossfix Meniscal Repair System, Surgical Technique Guide, Jul. 2009, 4 pages.
Hoffmann et al., "Arthroscopic shoulder stablilization using Mitek anchors", Knee Surg., Sports Traumatol., Arthroscopy, Mar. 1995, vol. 3, Issue 1, 50-54.
Klinger, "Proceedings of the 1976 Meeting of the Deutsche Gesellschaft fur Neurochirurgica in Berlin", Acta Neurochirurgica, Sep. 1977, vol. 36, Issue 3-4, 265-294.
Mayer et al., "Percutaneous Endoscopic Lumbar Discectomy (PELD)", Neurosurg., Rev., Jun. 1993, 115-120.
Mayer et al., "Endoscopic Discectomy in Pediatric and Juvenile Lumbar Disc Herniation's", Journal of the Pediatric Orthopaedics, Part B, Jan. 1996, 39-43.
Abstracts of the 7$^{th}$ Annual Meeting of the Japanese Society of Micosurgery, Oct. 1980, Niigata, Japan, 8 pages.
Vuono-Hawkins et al., "Mechanical Evaluation of a Canine Intervertebral Disc Spacer: In Situ and In Vivo Studies", Journal of Orthopaedic Research, Jan. 1994, 119-127.

International Patent Application No. PCT/US2005/034495: International Search Report and Written Opinion dated Apr. 4, 2007, 2 pages.
U.S. Appl. No. 60/113,548, filed Dec. 23, 1998, Schwartz.
U.S. Appl. No. 60/148,913, filed Aug. 13, 1999, Ferree.
U.S. Appl. No. 60/149,490, filed Aug. 18, 1999, Lambrecht.
U.S. Appl. No. 60/154,969, filed Sep. 20, 1999, Matsuura.
U.S. Appl. No. 60/161,085, filed Oct. 25, 1999, Lambrecht.
U.S. Appl. No. 09/453,120, filed Dec. 2, 1999, Torrie.
U.S. Appl. No. 60/263,343, filed Jan. 22, 2001, Keith.
Ahlgren et al., "Anular incision technique on the strength and multidirectional flexibility of the healing intervertebral disc," Spine, Apr. 15, 1994, 19(8), 948-954.
Ahlgren et al., "Effect of anular repair on the healing strength of the intervertebral disc: a sheep model," Spine, Sep. 1, 2000, 25(17), 2165-2170.
Arthrex, Inc., "Arthroscopic Meniscal Repair using the Meniscal Cinch: Surgical Technique," www.arthrex.com, © 2008, 6 pages.
Barrett et al., "T-Fix endoscopic meniscal repair: technique and approach to different types of tears," Arthroscopy: The Journal of Arthroscopic and Related Surgery, Apr. 1995, 11(2), 245-251.
Burg et al., "Modulation of Surface and Bulk Properties of Biomedical Polymers," Annals of the New York Academy of Sciences, Dec. 1997, 831, 217-222.
Caborn, D., "Meniscal Repair with the Fast T-Fix Suture System," Smith & Nephew Technique Plus Illustrated Guide, Mar. 2002, 10 pages.
Cauthen, J., "Annulotomy Study Table", Feb. 8, 1999, 1 page.
Cauthen, J., "Microsurgical Annular Reconstruction (Annuloplasty) Following Lumbar Microdiscectomy: A New Technique," Draft Abstract, Sep. 4, 1998, 4 pages.
Cauthen, J., "Microsurgical Annular Reconstruction (Annuloplasty) Following Lumbar Microdiscectomy: A New Technique," Abstract, AANS CNS Section on Disorders of the Spine and Peripheral Nerves Annual Meeting, 1999, 2 pages.
Cauthen, "Microsurgical Annular Reconstruction (Annuloplasty) Following Lumbar Microdiscectomy: Preliminary Report of a New Technique", CNS Boston Massachusetts, Spine & Peripheral Nerves Section (abstract only), http://abstracts.neurosurgeon.org/view.php?id=2790, accessed Oct. 6, 2010, 1999, 1 page.
Cobey, M., "Arthroplasties using compressed ivalon sponge ("intramedic sponge") long-term follow-up studies in 109 cases," Clinical Orthopaedics and Related Research, Sep.-Oct. 1967, 54, 139-144.
Coen et al., "An anatomic evaluation of T-Fix suture device placement for arthroscopic all-inside meniscal repair," Arthroscopy: The Journal of Arthroscopic and Related Surgery, Apr. 1999, 15(3), 275-280.
Dodge, Jr. et al., "Use of Polyvinyl Sponge in Neurosurgery," Journal of Neurosurgery, May 1954, 11(3), 258-261.
Edgerton et al., "Augmentation Mammaplasty: Psychiatric Implications and Surgical Indications," Plastic & Reconstructive Surgery, Apr. 1958, 21(4), 279-305.
Hampton et al., "Healing Potential of the Anulus Fibrosus," Spine, Apr. 1989, 14(4), 398-401.
International Patent Application No. PCT/US2011/034084: International Search Report and Written Opinion dated Jul. 1, 2011, 5 pages.
International Patent Application No. PCT/US2011/042384: International Search Report and Written Opinion dated Feb. 6, 2012, 26 pages.
International Patent Application No. PCT/US2011/058065: International Search Report and Written Opinion dated Apr. 5, 2012, 23 pages.
International Patent Application No. PCT/US2011/058071: International Search Report and Written Opinion dated Feb. 6, 2012, 14 pages.
Kambin et al., "Development of degenerative spondylosis of the lumbar spine after partial discectomy. Comparison of laminotomy, discectomy, and posterolateral discectomy," Spine, Mar. 1, 1995, 20(5), 599-607.
Kotilainen et al., "Microsurgical treatment of lumbar disc herniation: Follow-up of 237 patients," Acta Neurochirurgica, 1993, 120(3-4) 143-149.

(56) References Cited

OTHER PUBLICATIONS

Kroschwitz, J. I., "Concise Encyclopedia of Polymer Science and Engineering: Vinyl Alcohol Polymers," Wiley & Sons, 1990, 1233-1236.
Kusaka et al., "The Effect of Annulus Fibrosus Perforation on the Intradiscal Matrix Strain of the Axially Loaded Intervertebral Disc," Transactions of the 44th Annual Meeting, Orthopaedic Research Society, Mar. 16-19, 1998, New Orleans, Louisiana, 23(1), p. 190-32 (Abstract).
Lehmann et al., "Refinements in technique for open lumbar discectomy," International Society for the Study of the Lumbar Spine, 1997, 2 pages.
Liu et al., "Morphologic Characterization of Polyvinyl Sponge (Ivalon) Breast Prosthesis," Archives of Pathol. & Lab. Medicine, Sep. 1996, 120(9), 876-878.
Malemud, C. J., "The Role of Growth Factors in Cartilage Metabolism," Rheum. Dis. Clin. North Am., Aug. 1993, 19(3), 569-580.
Ordway et al., "Failure Properties of a Hydrogel Nucleus in the Intervertebral Disc," North American Spine Society, Oct. 22-25, 1997, 168-169.
Osti et al., "1990 Volvo Award in Experimental Studies: Anulus Tears and Intervertebral Disc Degeneration: An Experimental Study Using an Animal Model," Spine, Aug. 1990, 15(8), 762-767.
Osti et al., "Annular Tears and Disc Degeneration in the Lumbar Spine. A post-mortem study of 135 discs," The Journal of Bone and Joint Surgery, Sep. 1992, 74(5), 678-682.
Panjabi et al., "Intrinsic Disc Pressure as a Measure of Integrity of the Lumbar Spine," Spine, Aug. 1988, 13(8), 913-917.
Peters et al., "Ivalon Breast Prostheses: Evaluation 19 Years after Implantation," Plastic and Reconstructive Surgery, Apr. 1981, 67(4), 514-518.
PR Newswire, "Smith & Nephew Launches Fast-Fix™ AB Meniscal Repair System," http://www.prnewswire.com/news-releases/smith--nephew-launches-fast-fixtm-ab-menis . . . , Accessed Aug. 23, 2010, 1 page.
Ray, C. D., "Prosthetic Disc Nucleus Implants: Update," North American Spine Society 13th Annual Meeting, 1999, 252-253.
Sgaglione et al., "All-Inside Meniscal Repair with the ULTRA FAST-FIX™ Meniscal Repair System," Smith & Nephew Knee Series Technique Guide, Feb. 2008, 12 pages.
Silver et al., "Cartilage Wound Healing: An Overview," Otolaryngol. Clin. North Am., Oct. 1995, 28(5), 847-863.
Smith & Nephew Endoscopy, "Endoscopic Meniscal Repair Using the T-Fix™," Smith & Nephew, May 1996, 16 pages.
Smith & Nephew Endoscopy, "Fast-Fix Meniscal Repair System: Technique Information," http://endo.smith-nephew.com/no/node.asp?NodeId=3045, Accessed Apr. 26, 2011, 3 pages.
Southwick et al., "Prosthetic Replacement of Chest-Wall Defects: An Experimental and Clinical Study", A. M. A. Archives of Surgery, 1956, 72, 901-907.
Unipoint Industries, Inc., "Polyvinyl Alcohol Foam for Surgical and Industrial Use: Data Sheets," Jul. 15, 1989, 6 pages.
Urbaniak et al., "Replacement of intervertebral discs in chimpanzees by silicone-dacron implants: a preliminary report," J. Biomed. Mater. Res. Symposium, May 1973, 7(4), 165-186.
Wageck et al., "Arthroscopic meniscal suture with the "double-loop technique"," Arthroscopy: The Journal of Arthroscopic and Related Surgery, Feb. 1997, 13(1), 120-123.
Yasargil, M. G., "Microsurgical Operation of Herniated Lumbar Disc," Advances in Neurosurgery, Lumbar Disc Adult Hydrocephalus, Springer-Verlag, 1977, 4(81), p. 81.
Snyder, S.J., "Shoulder Arthroscopy: Arthroscopic Treatment of the Acromioclavicular Joint", Chapter 13, 2nd Edition, 2003, 167-183.
The Free Dictionary, definition of "knot", http://medical-dictionary.thefreedisctionary.com/knot as accessed on Jun. 21, 2016, 5 pages.

\* cited by examiner

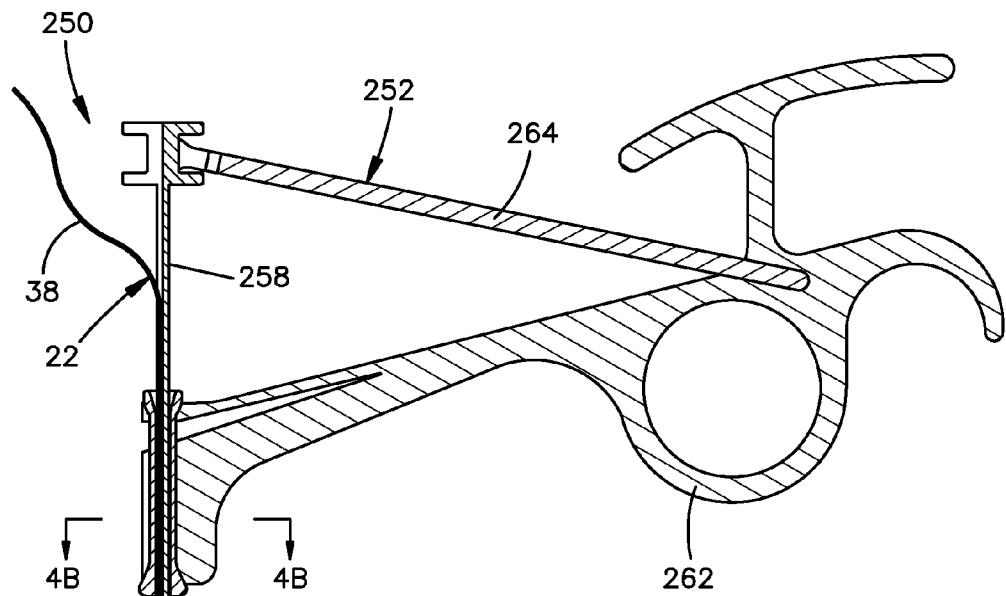
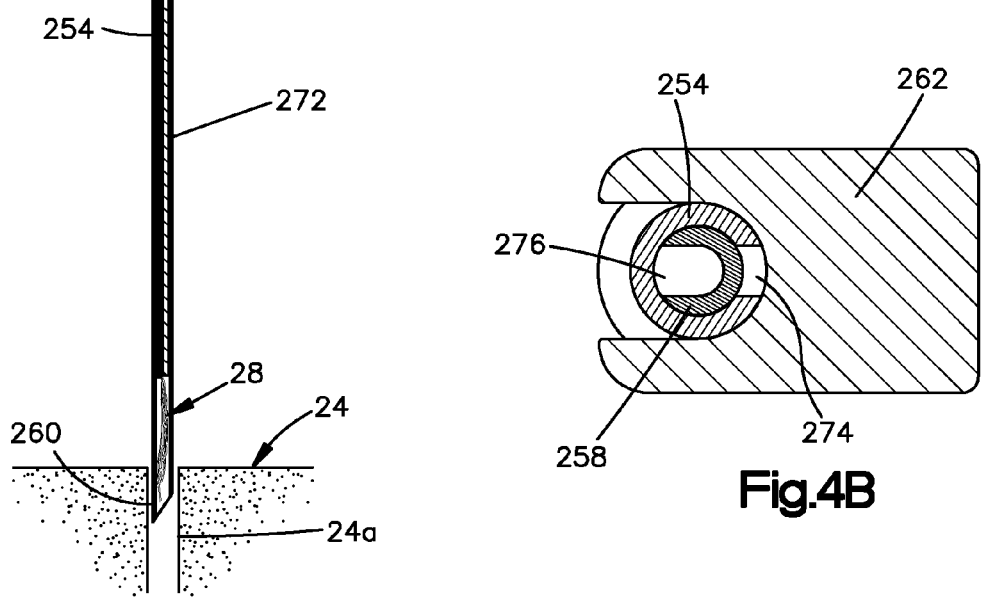
Fig.4A
Fig.4B

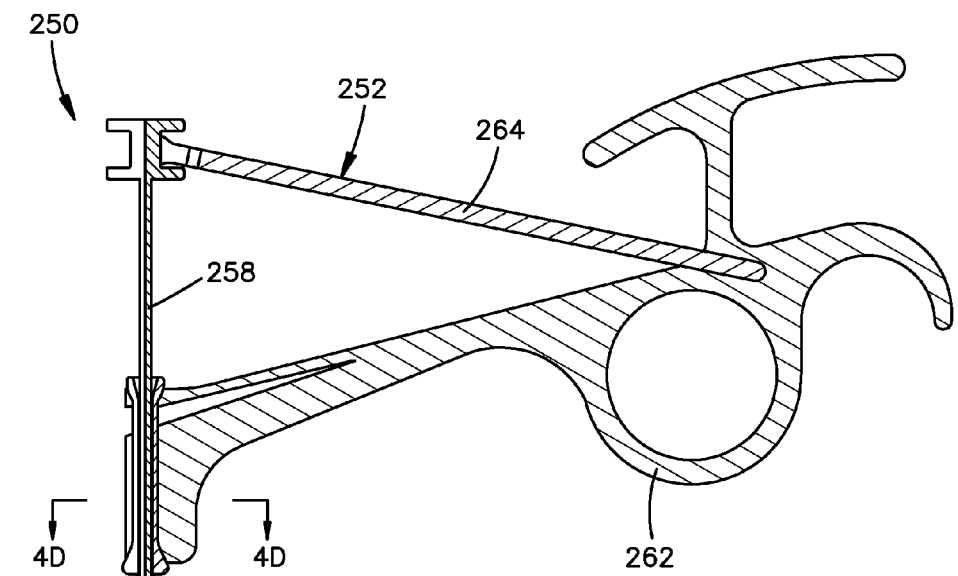
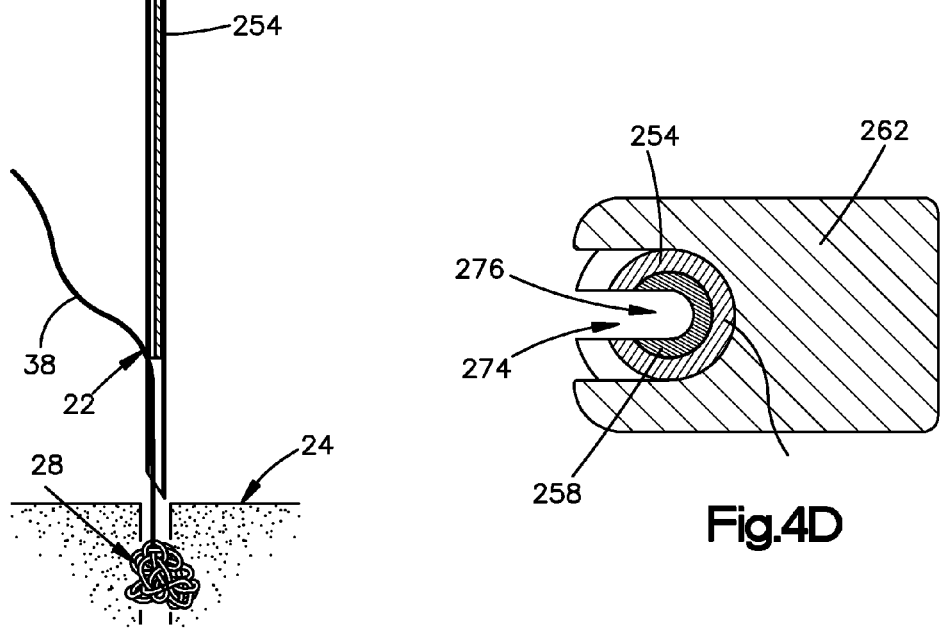
Fig.4C
Fig.4D

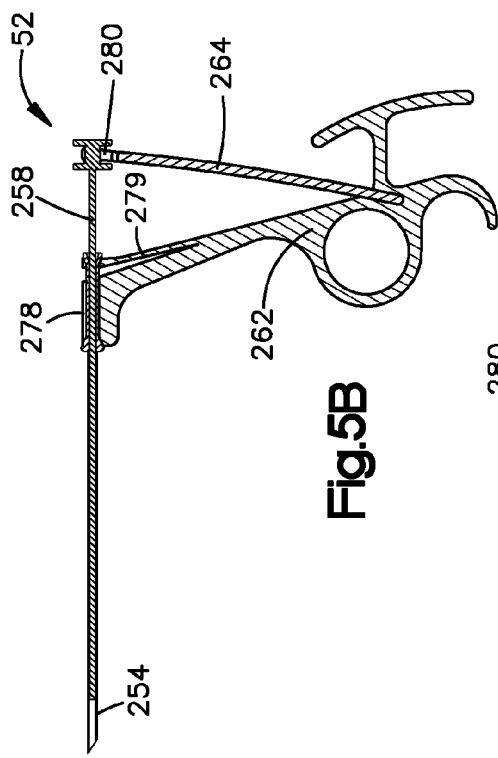
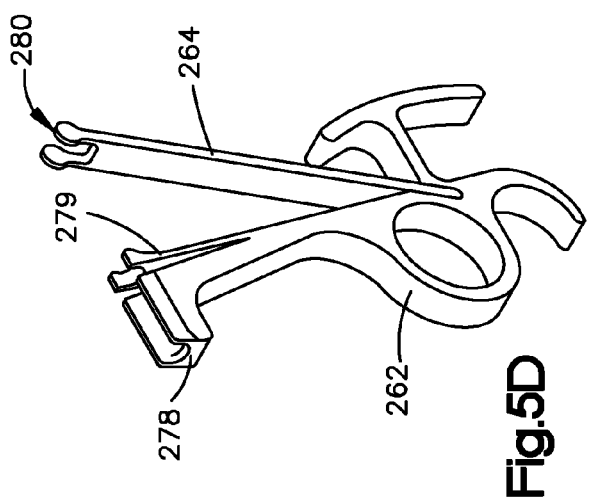
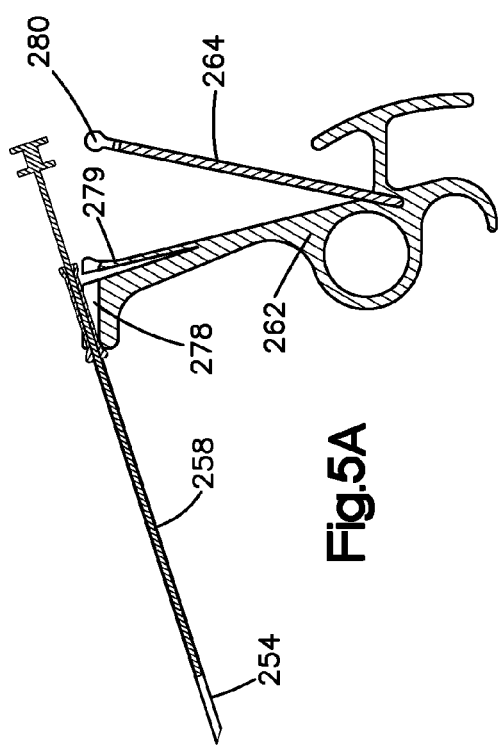
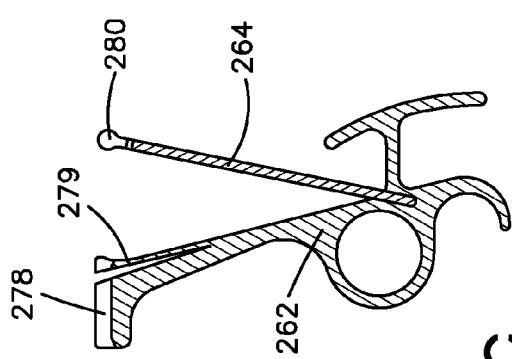
Fig.5A
Fig.5B
Fig.5C
Fig.5D

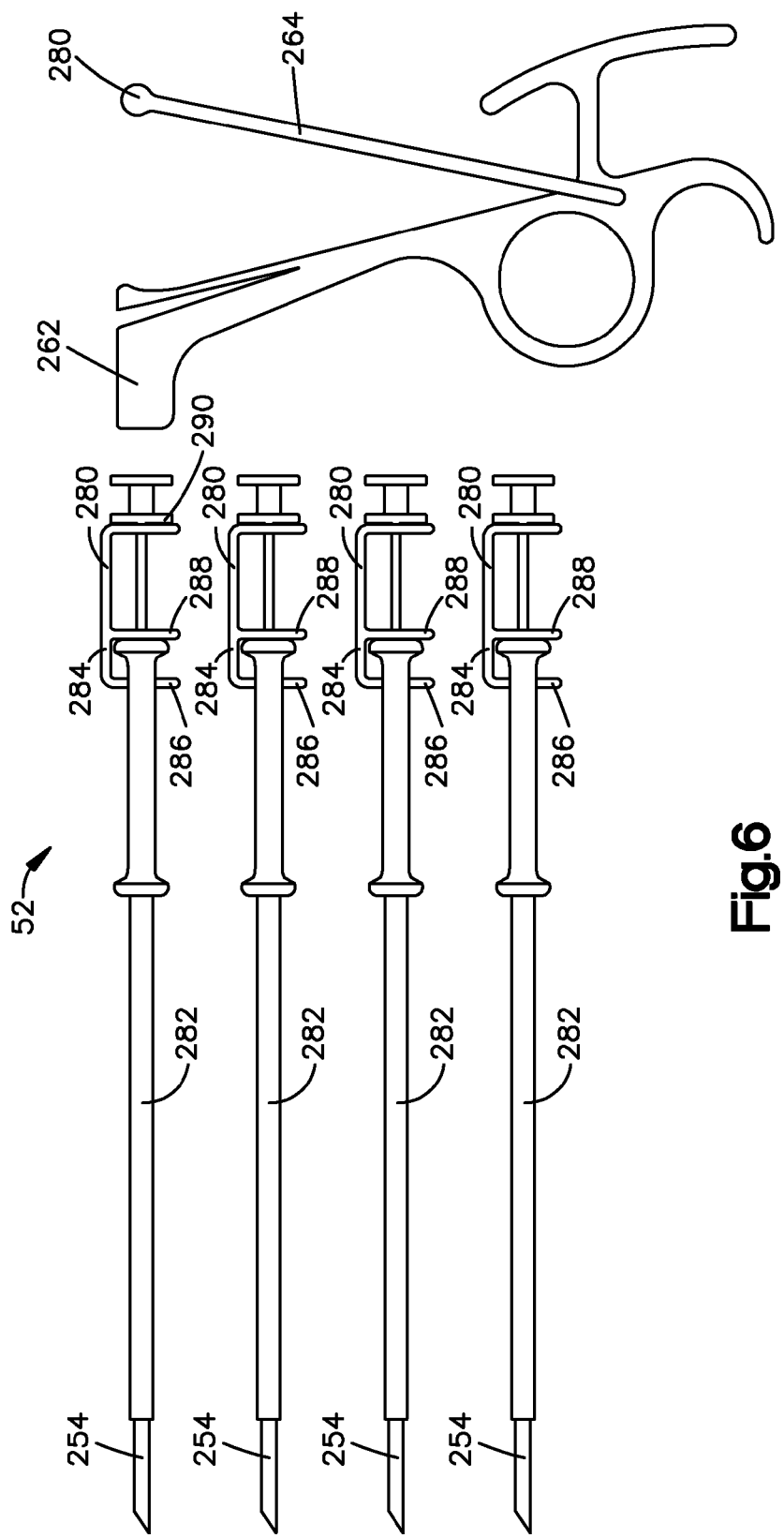

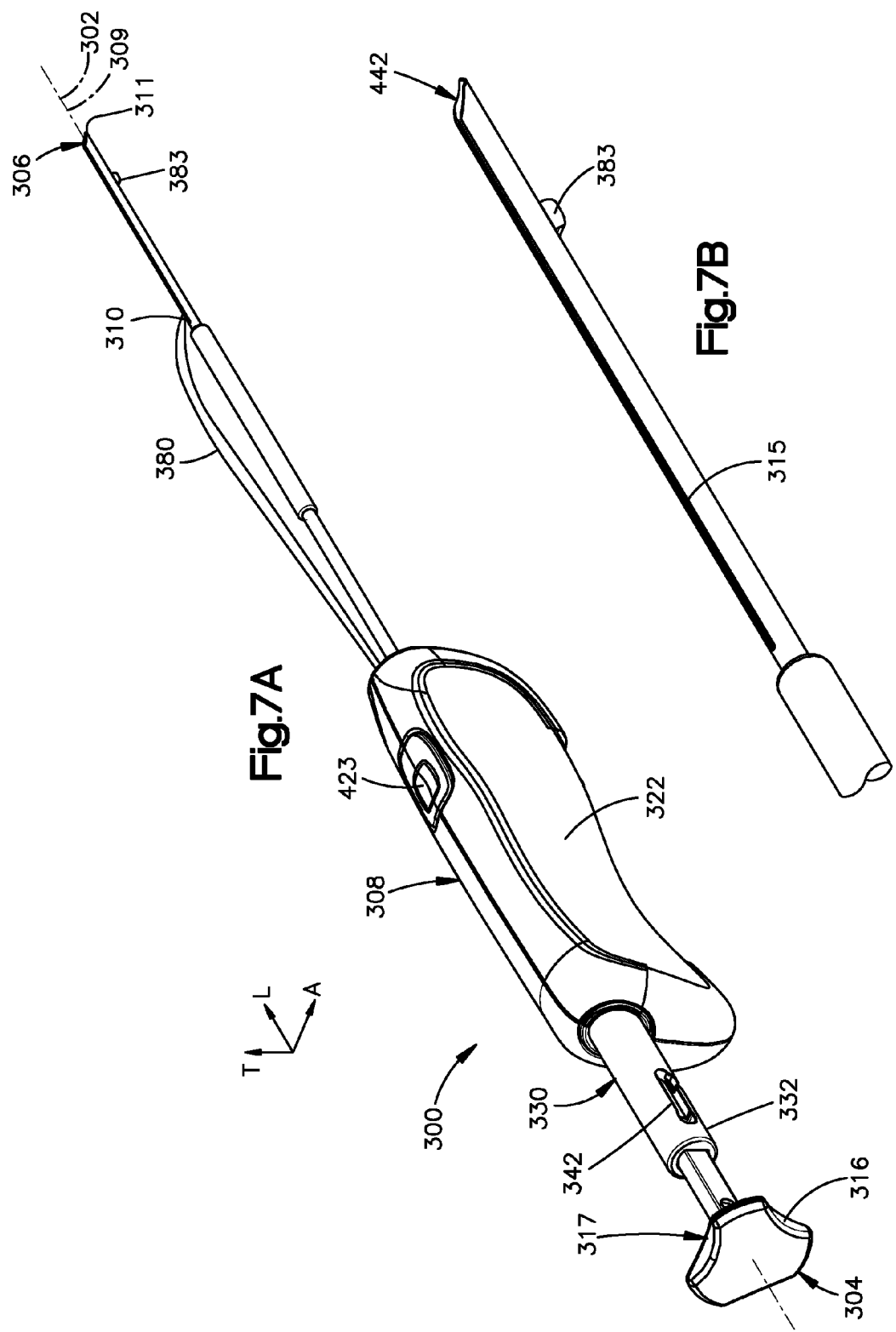

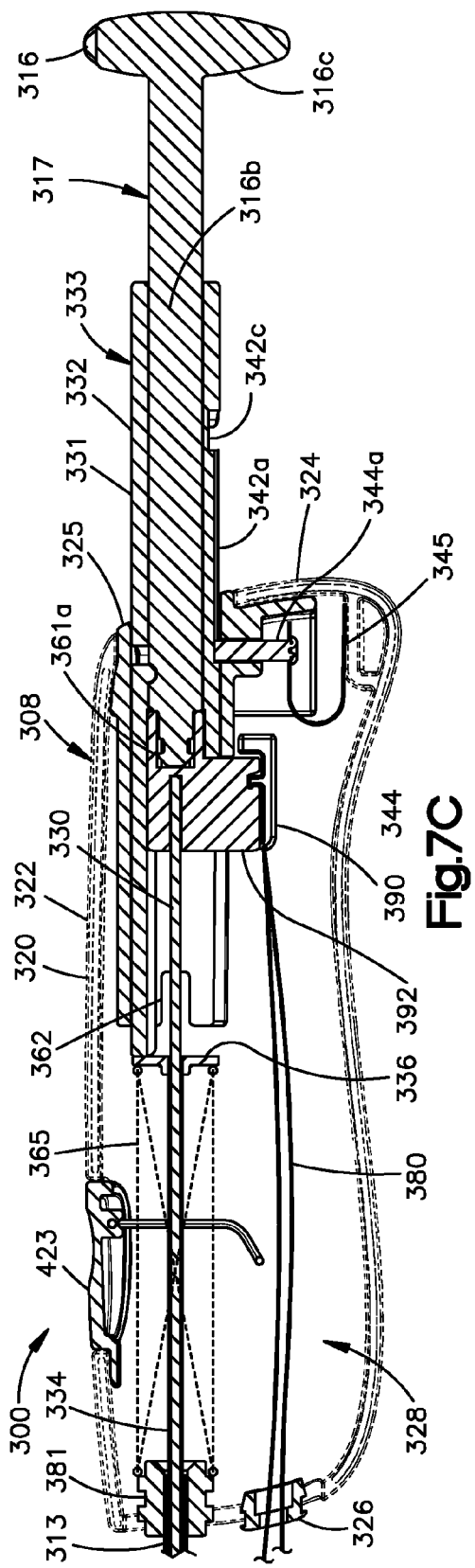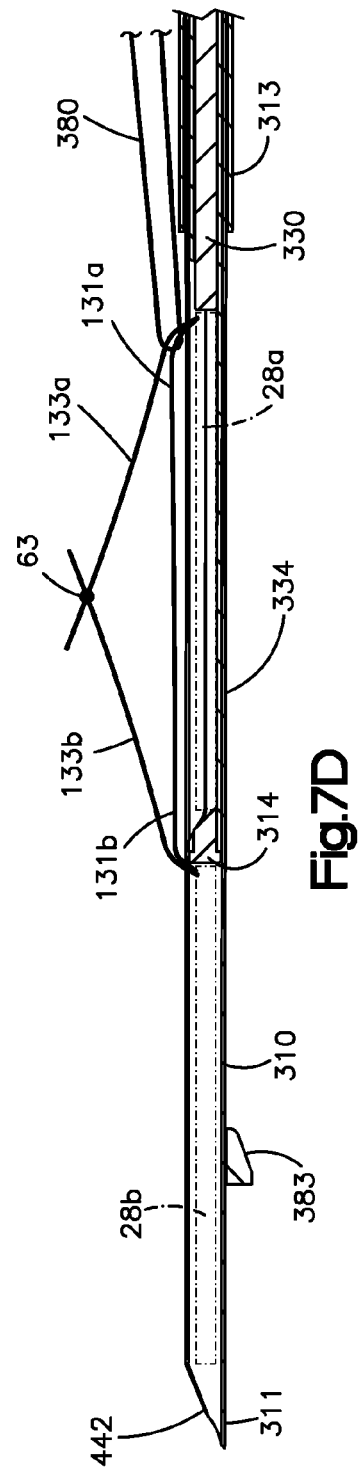
Fig.7C
Fig.7D

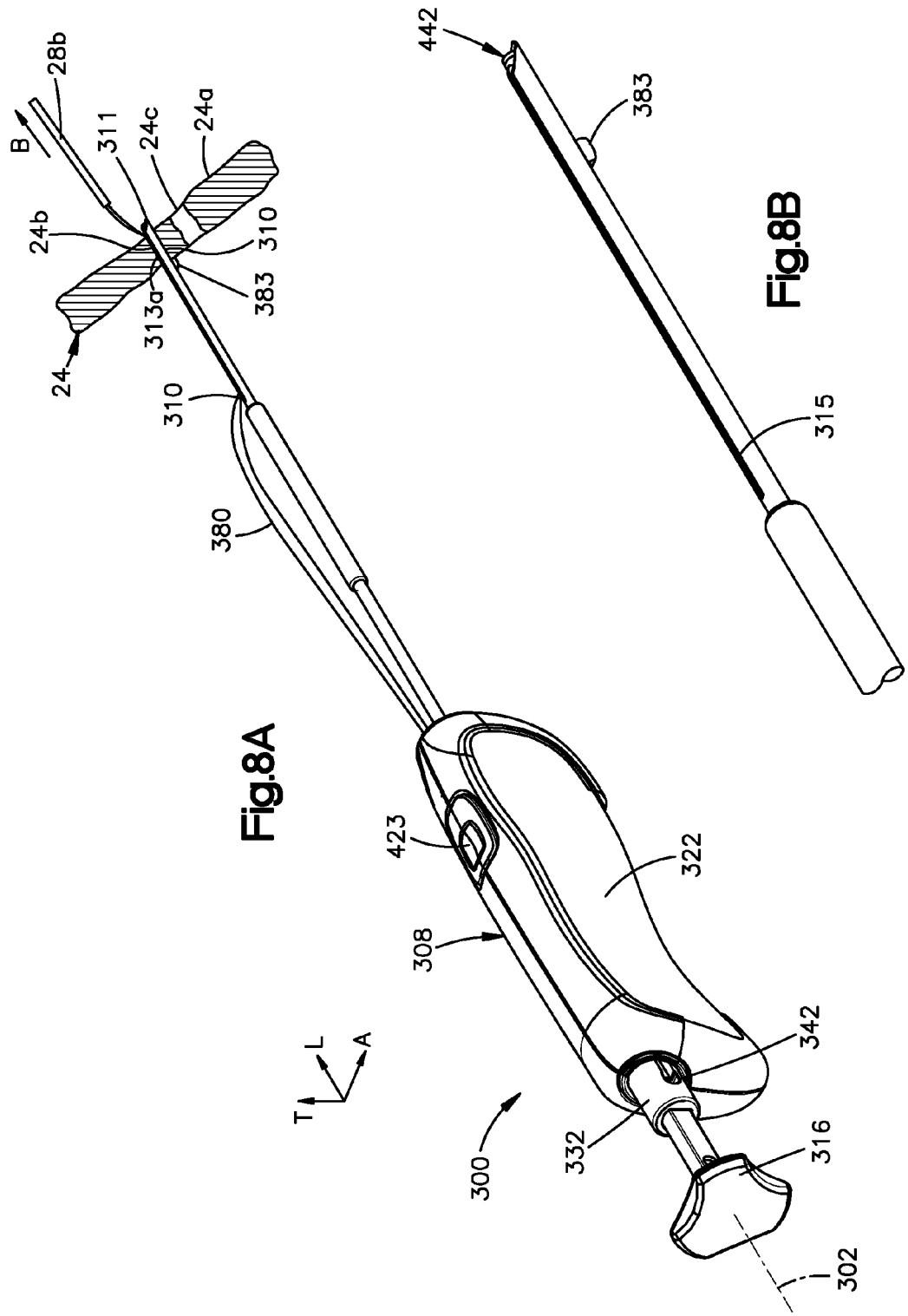

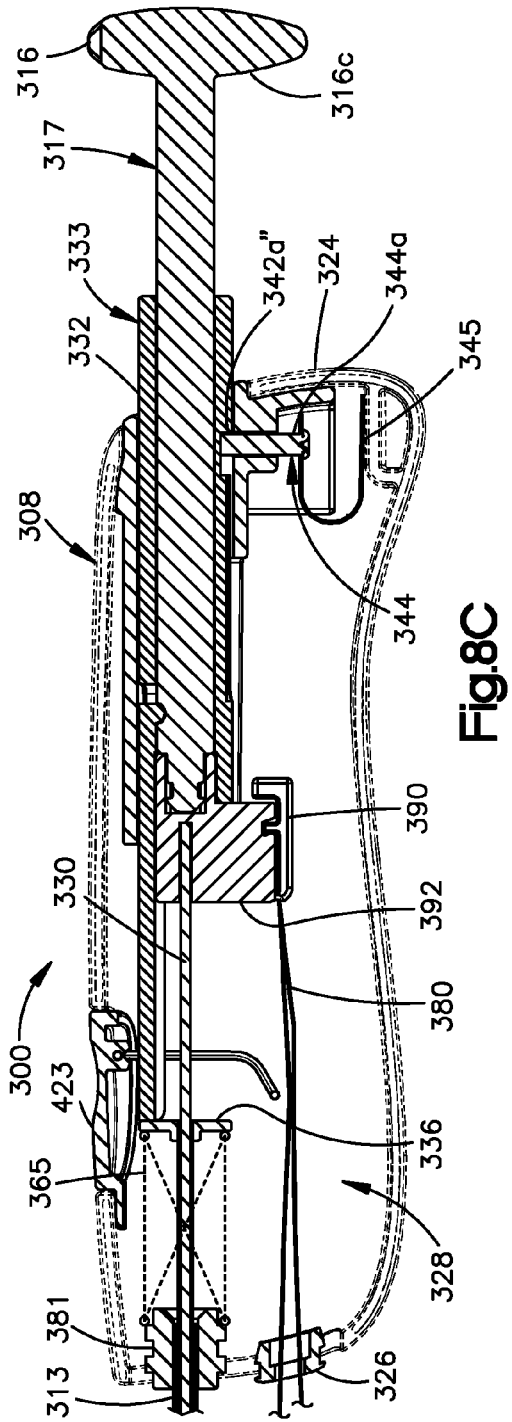
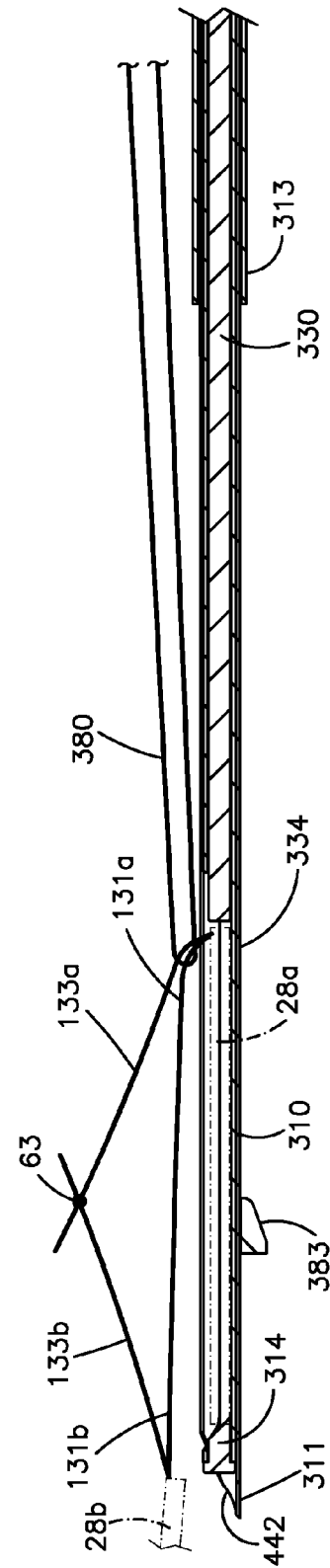
Fig.8C
Fig.8D

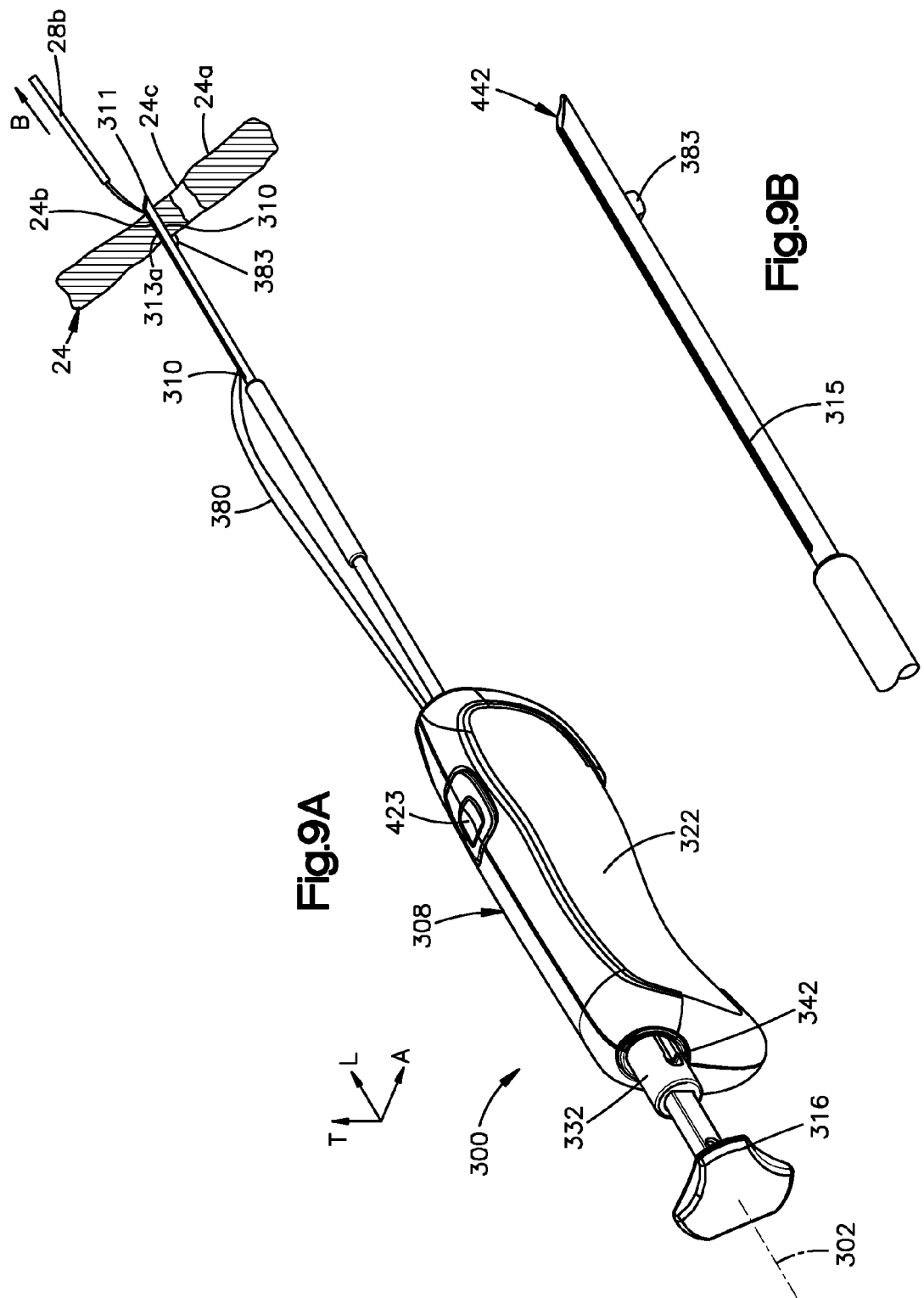

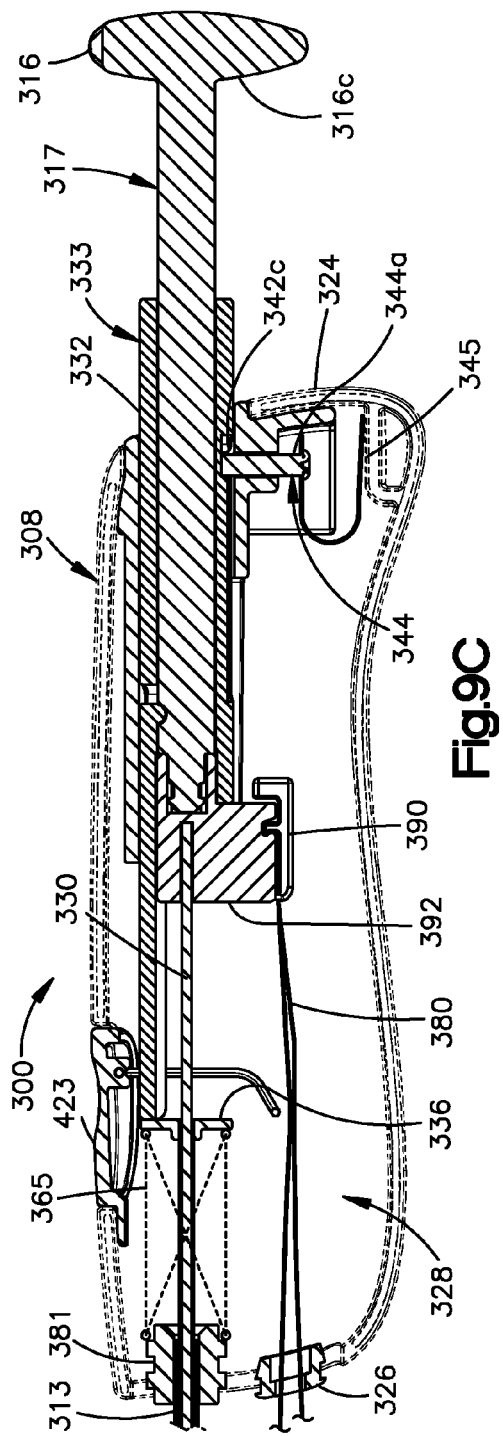
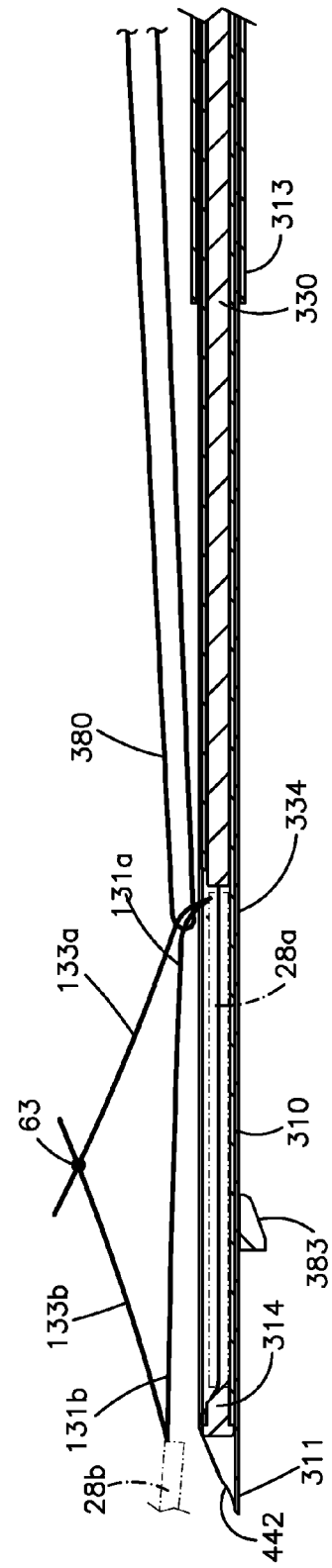
Fig.9C
Fig.9D

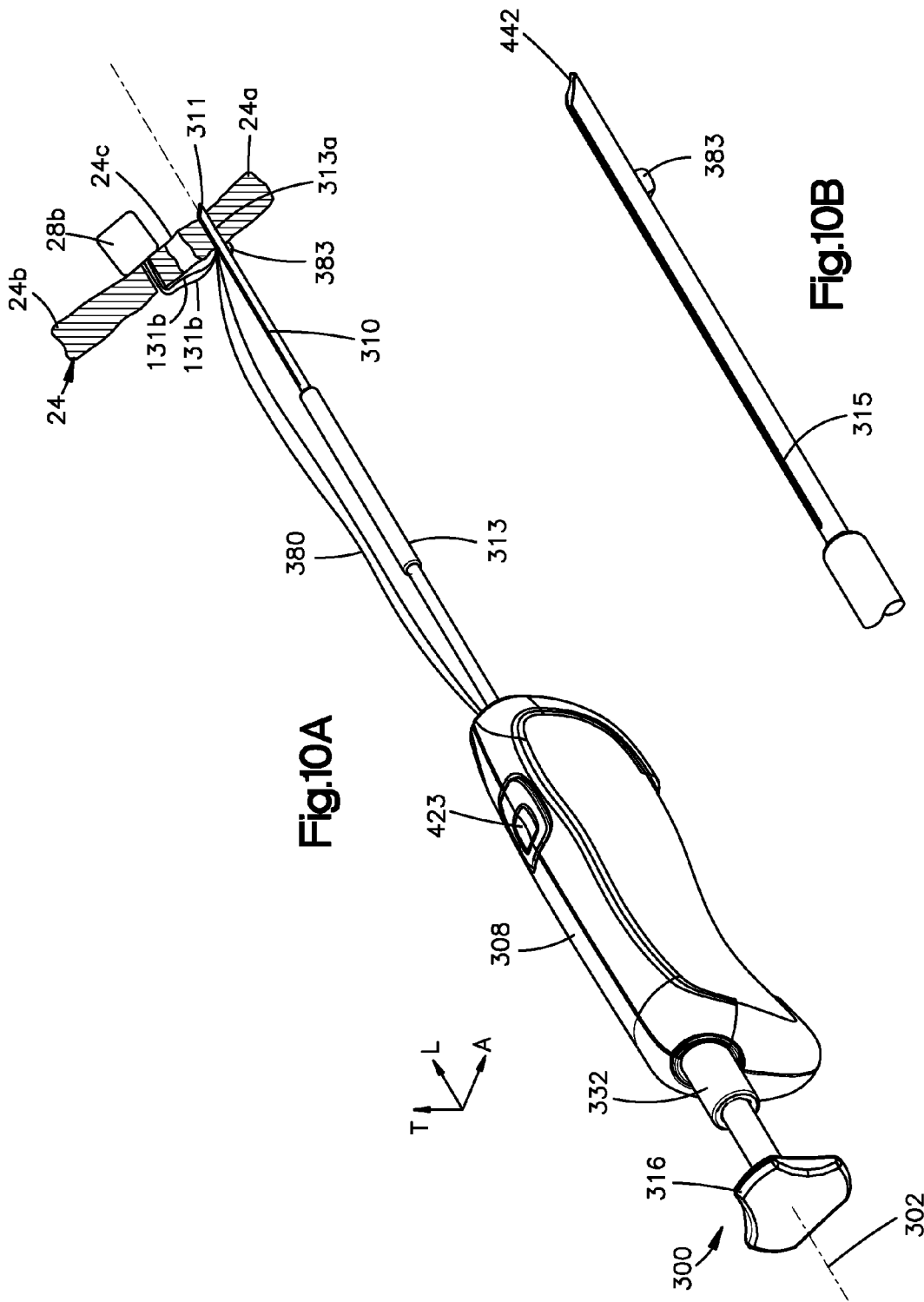

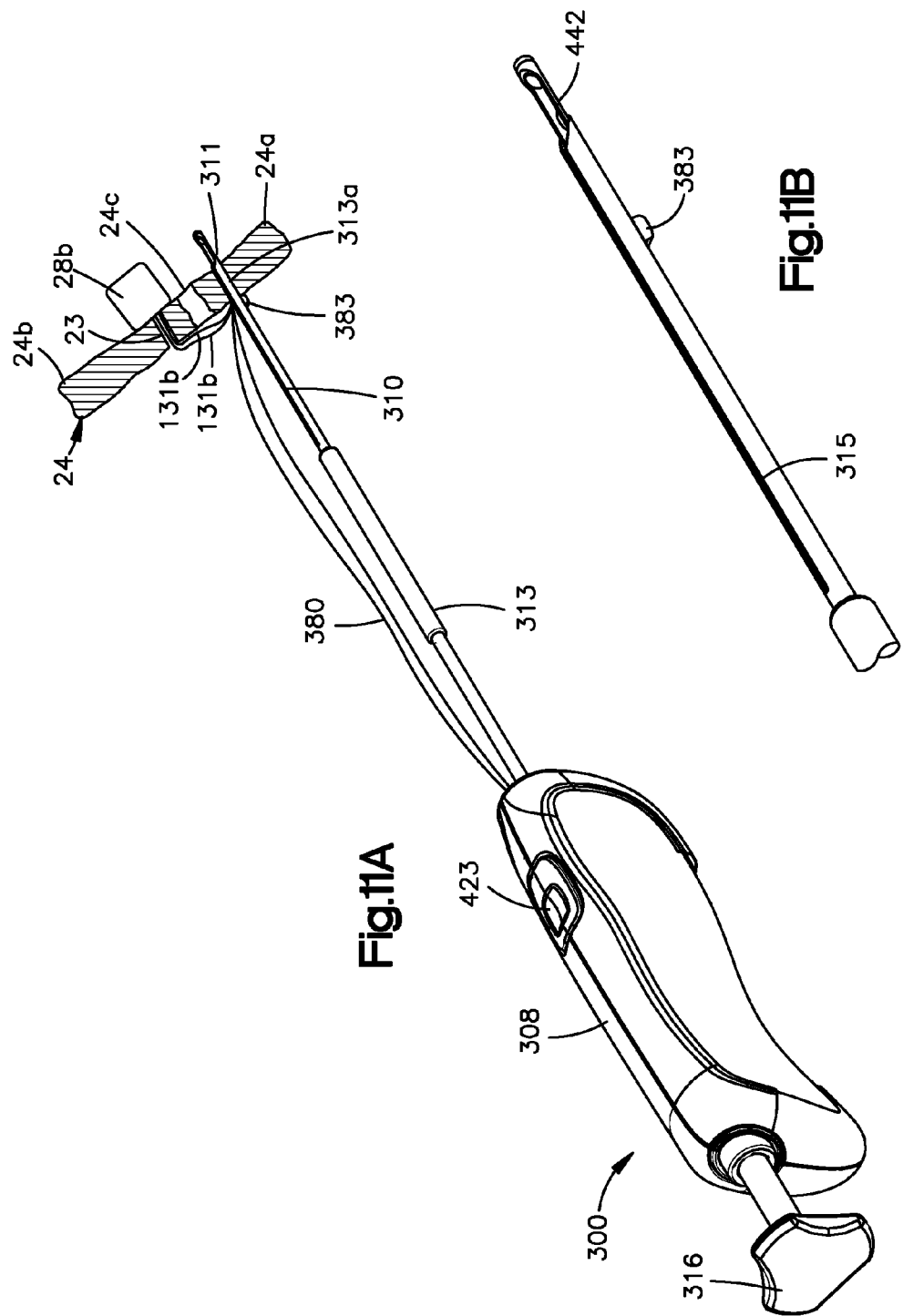

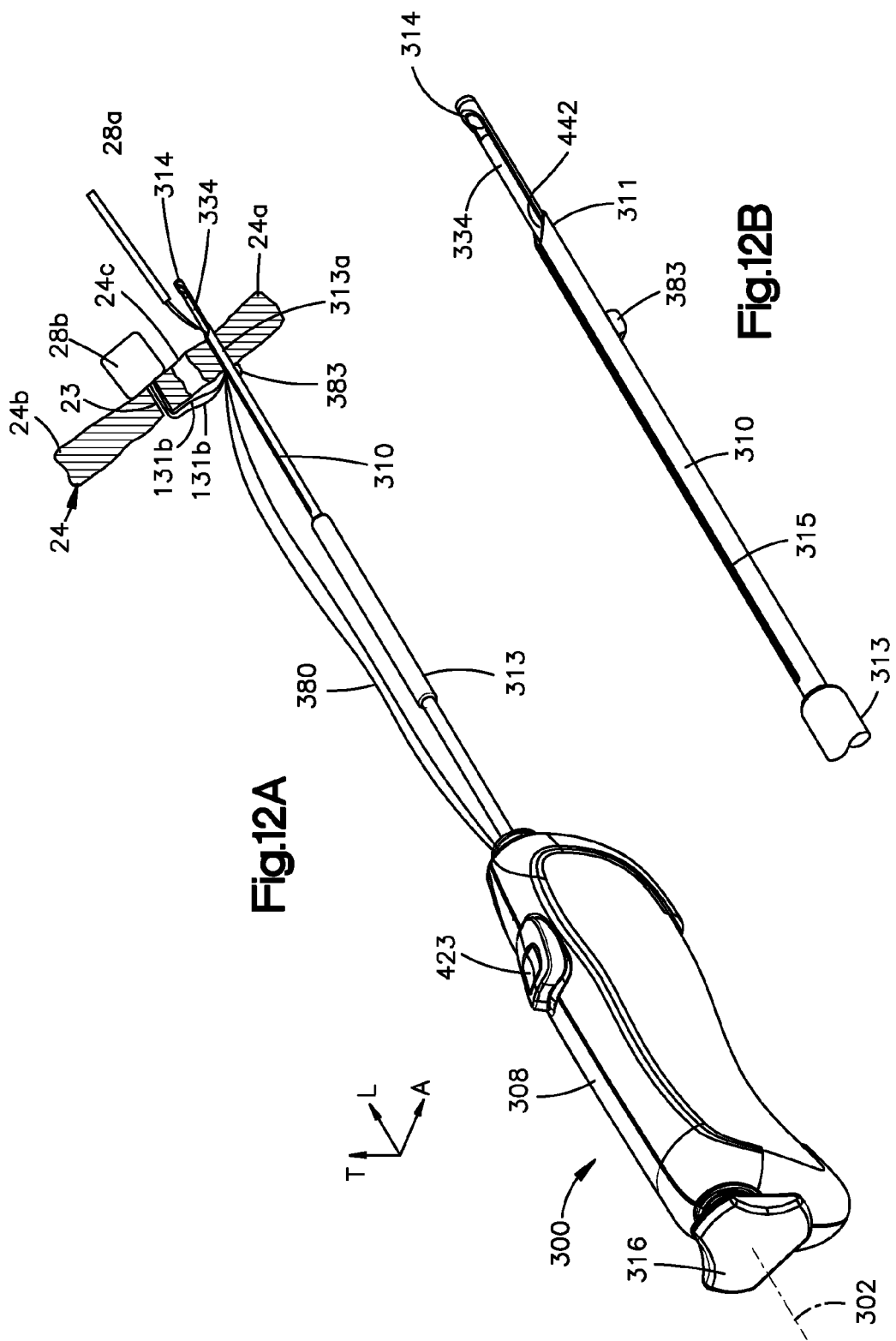

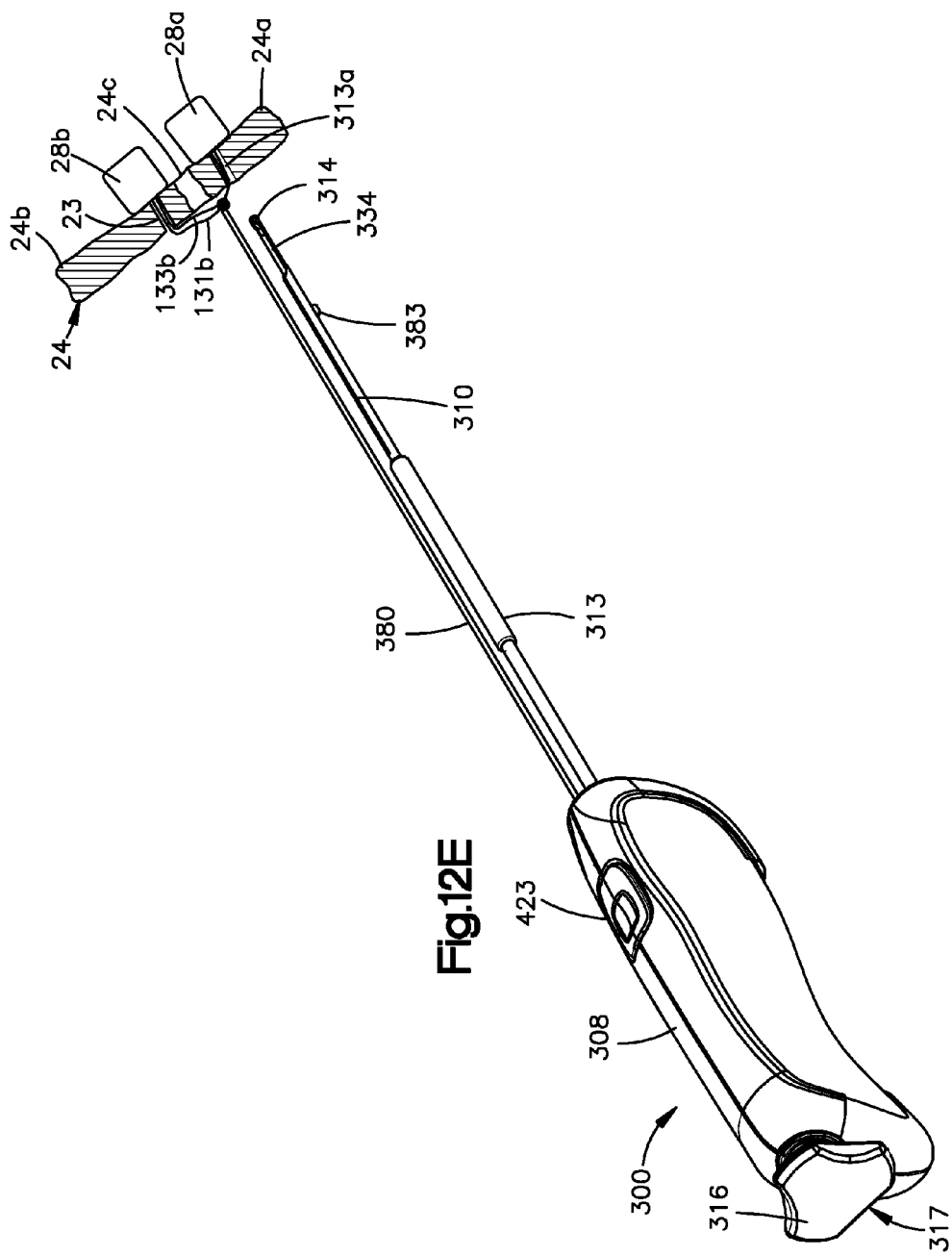

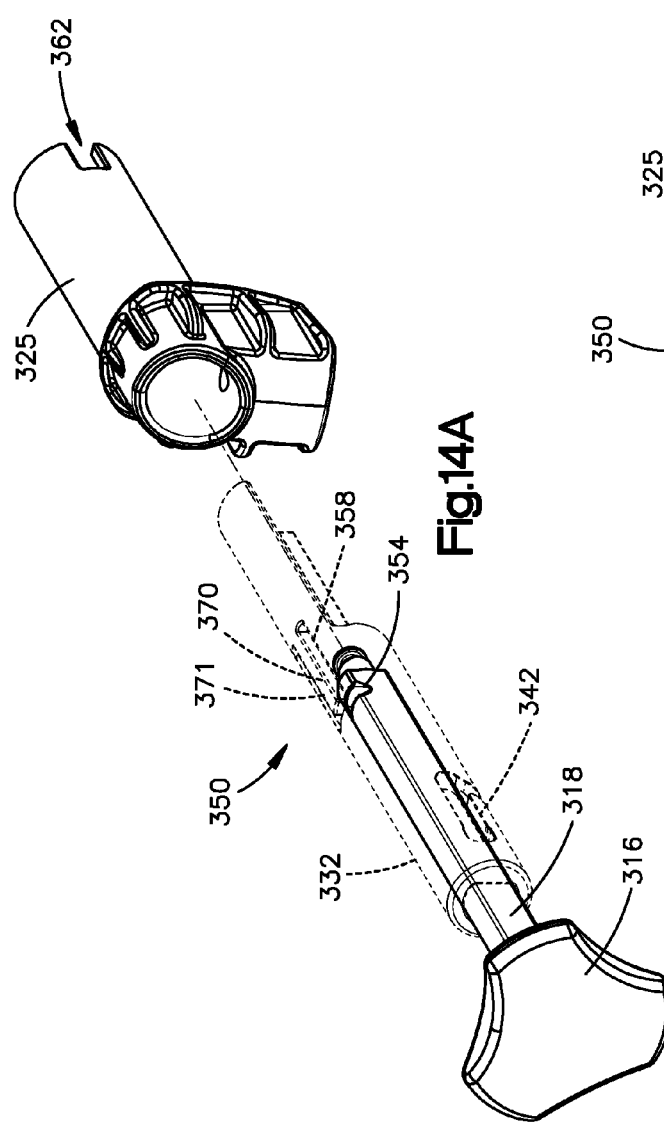
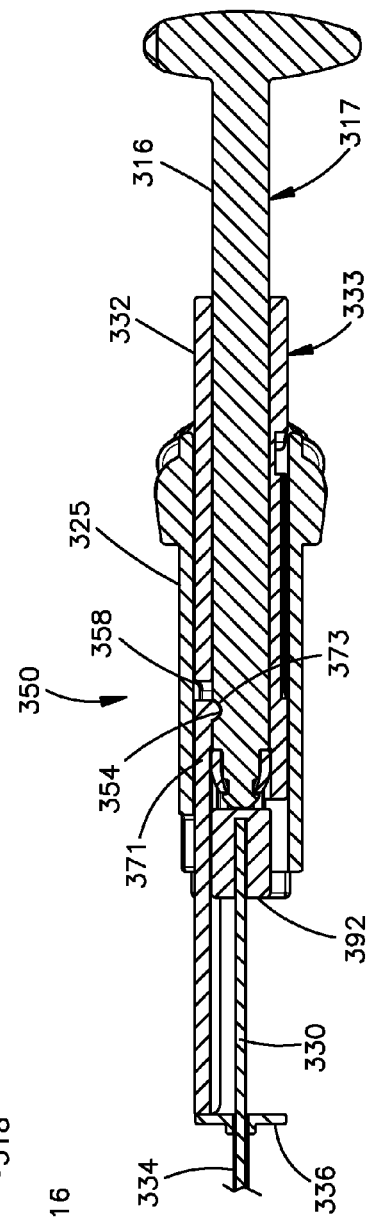

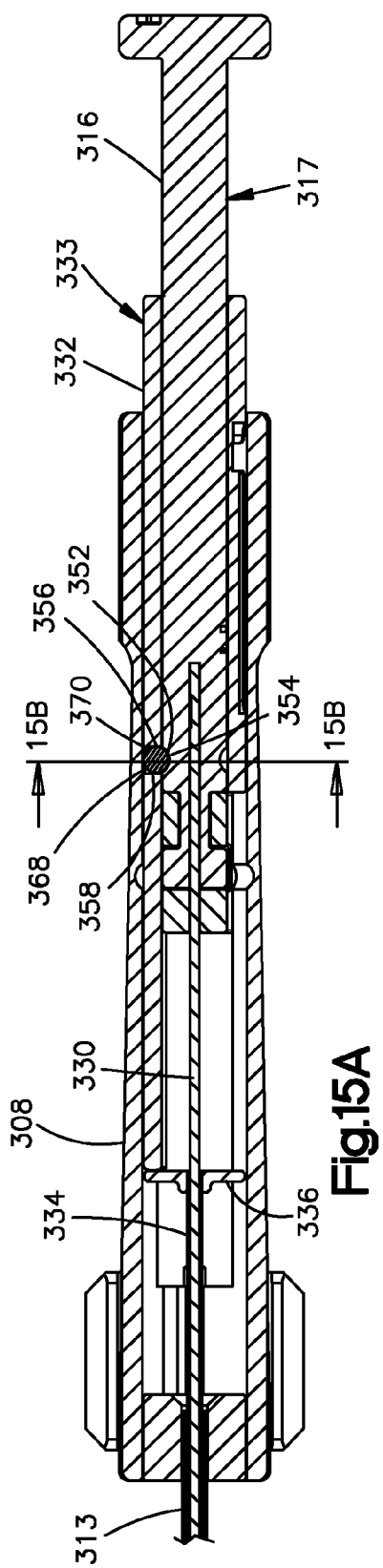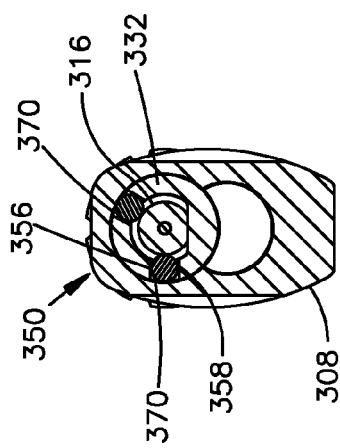
Fig.15A
Fig.15B

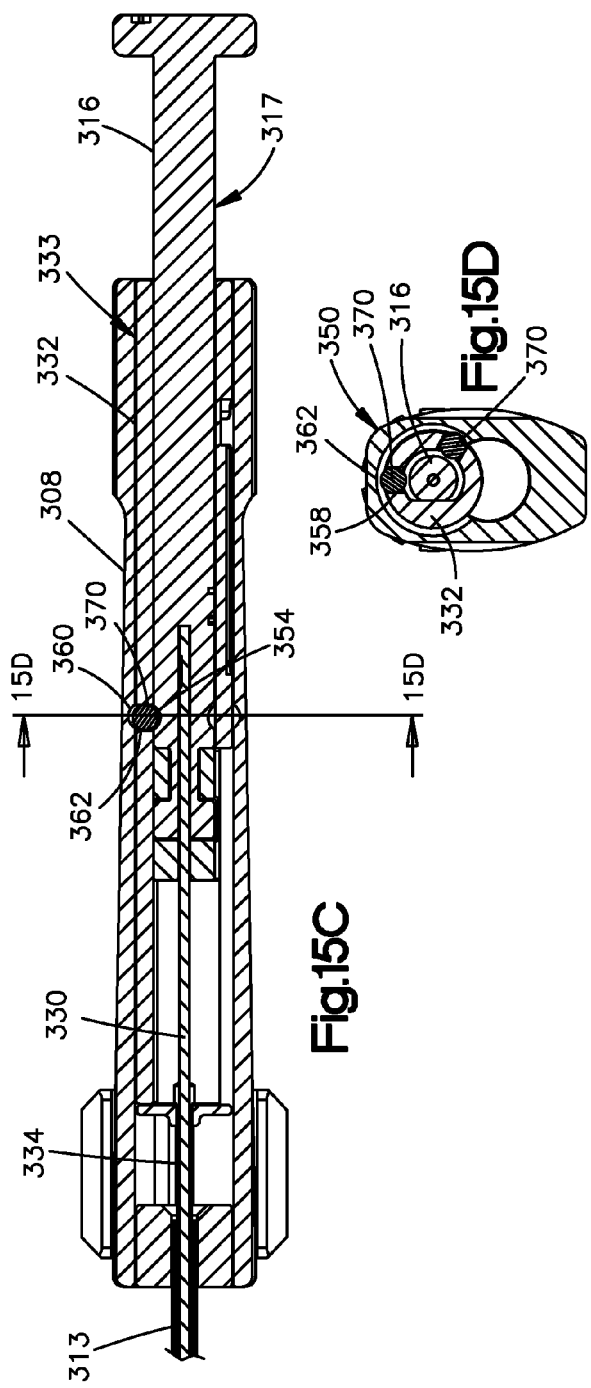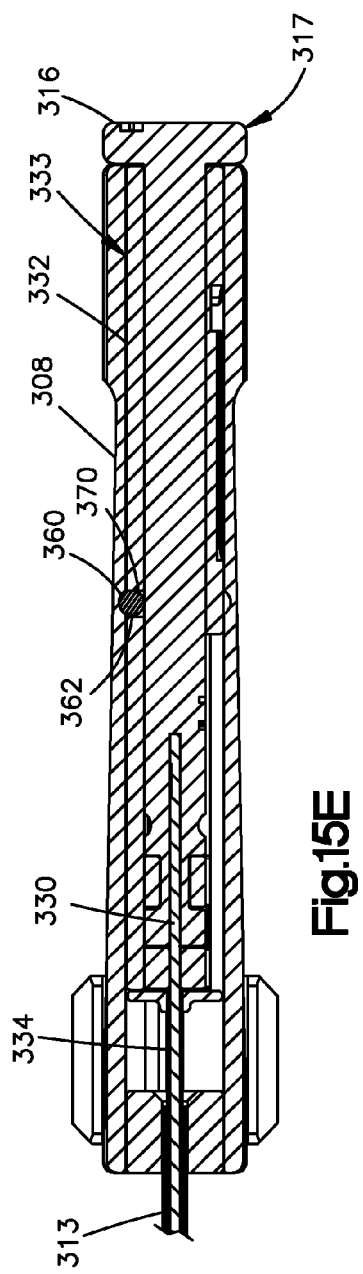
Fig.15C
Fig.15D
Fig.15E

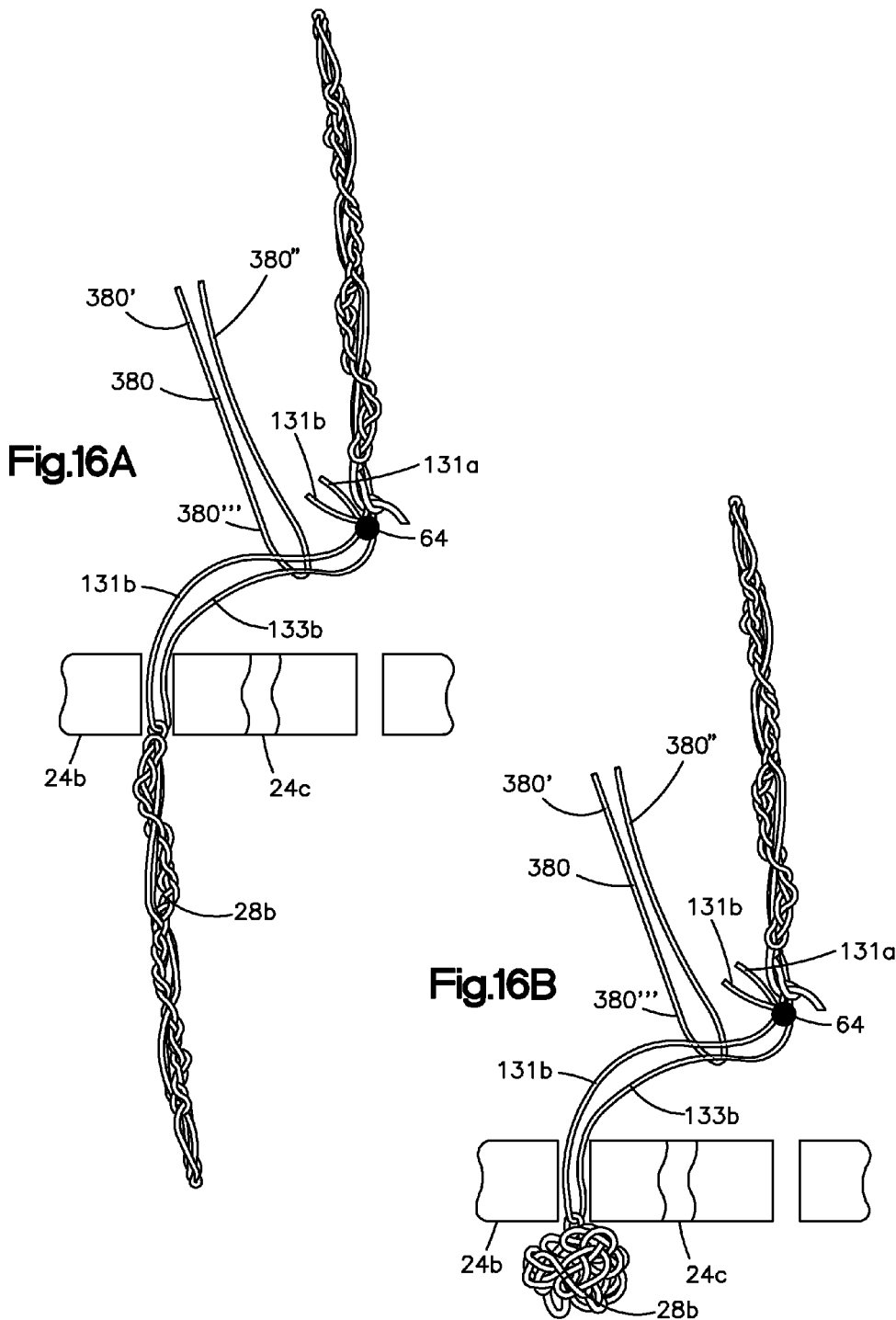

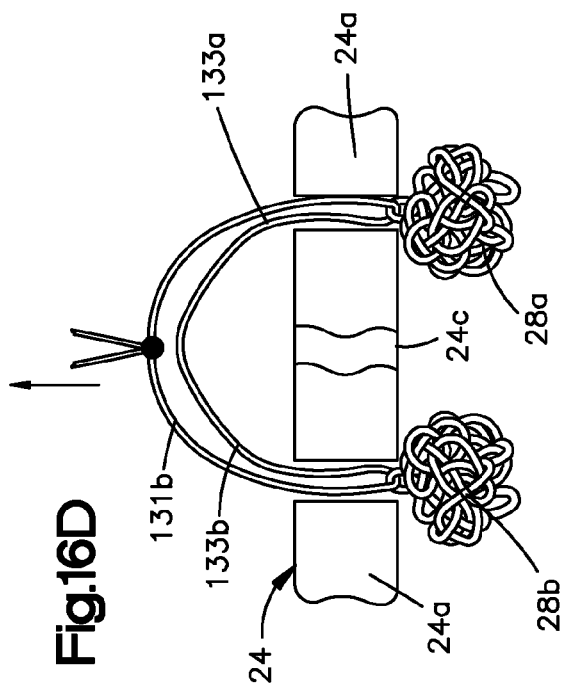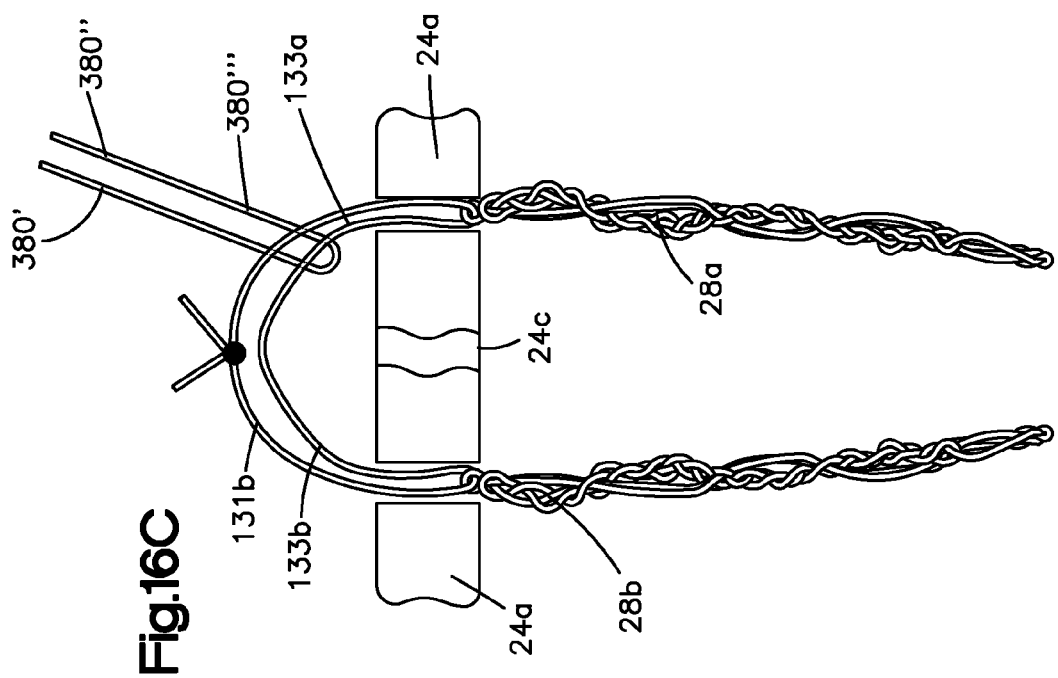

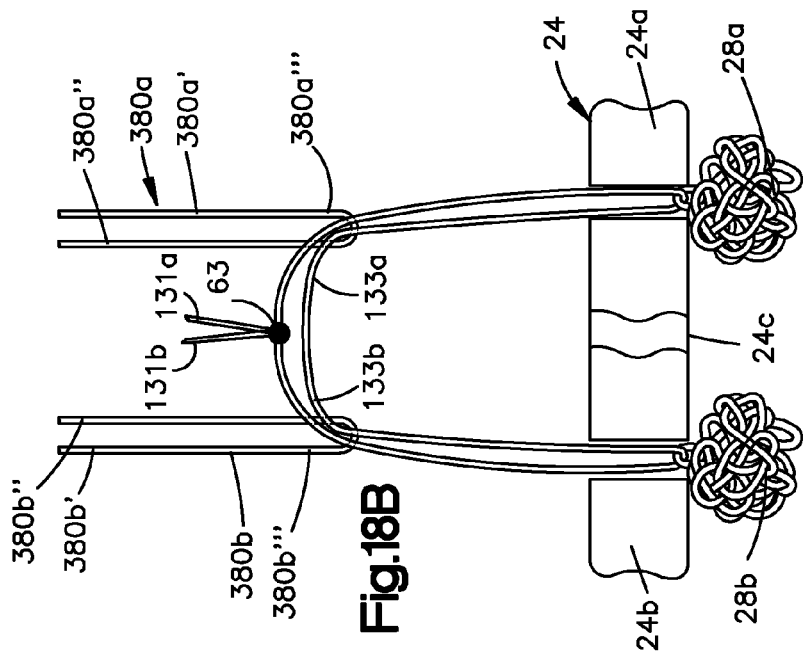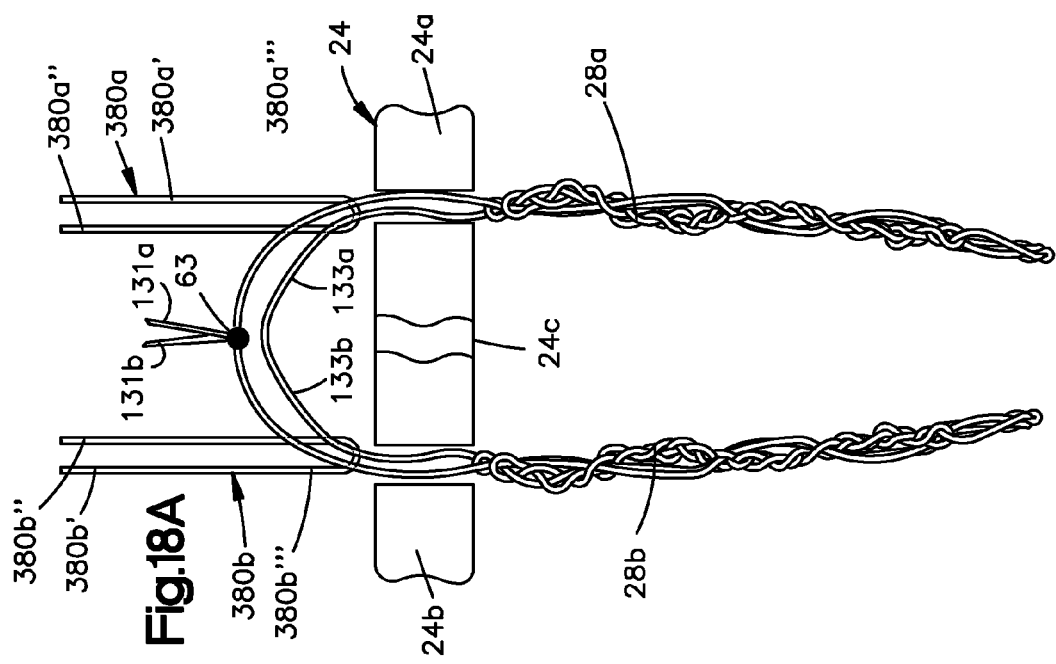

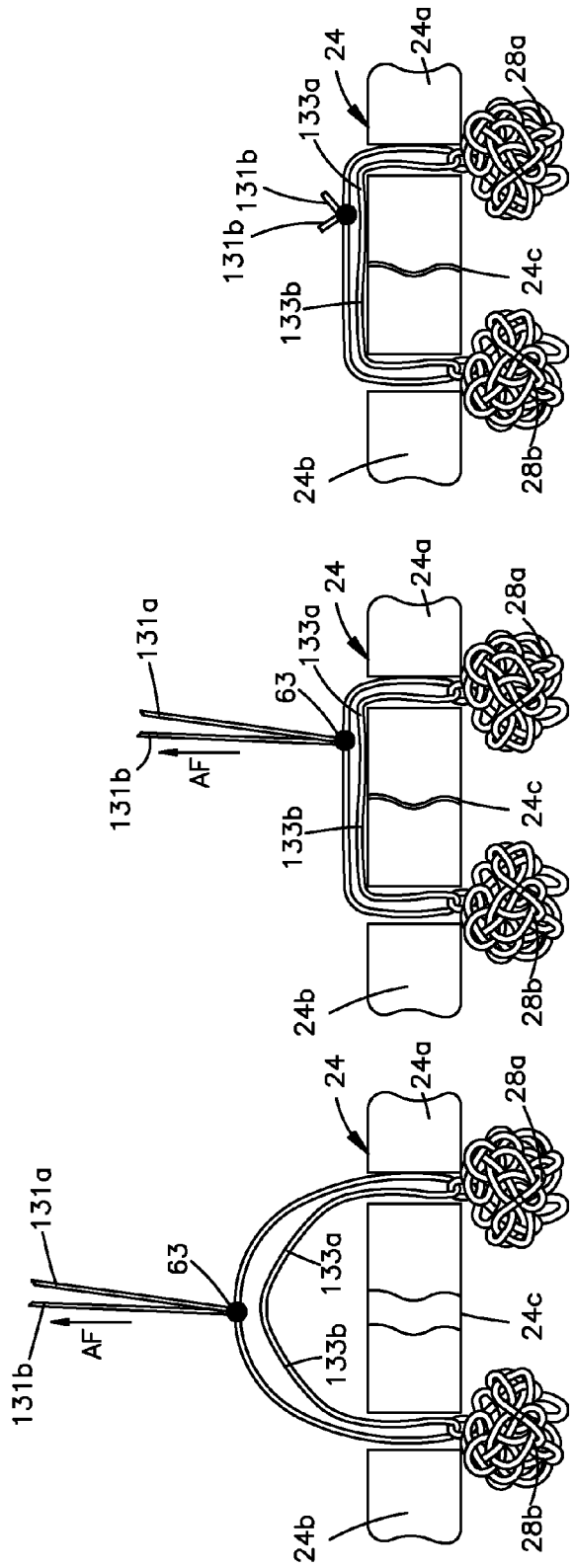

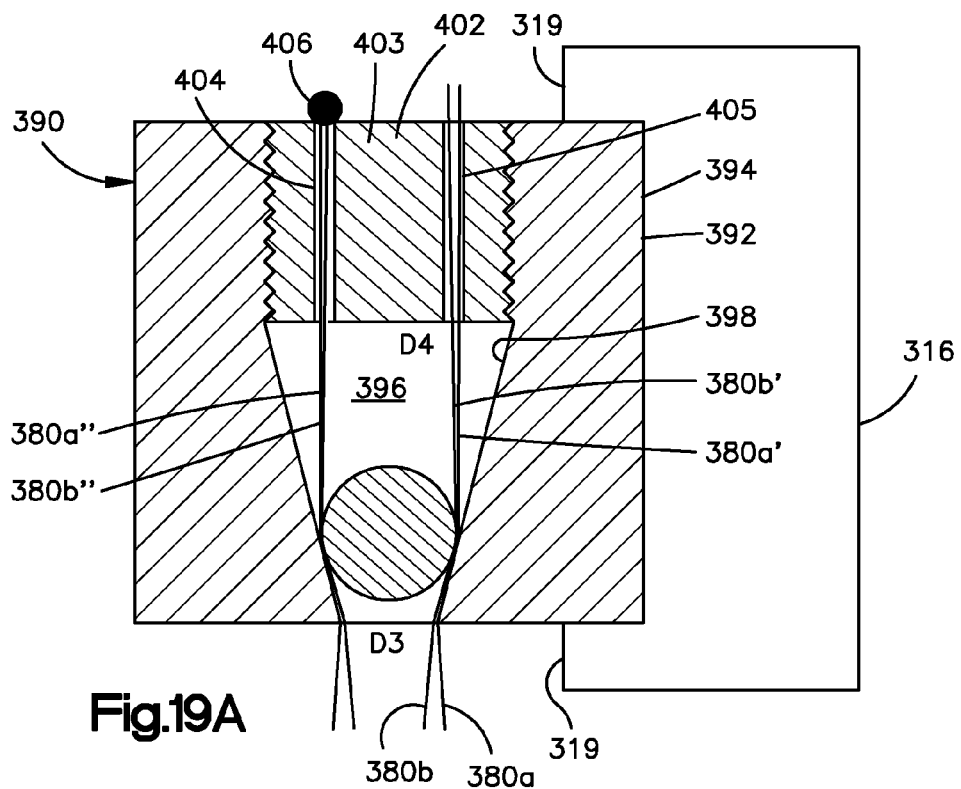
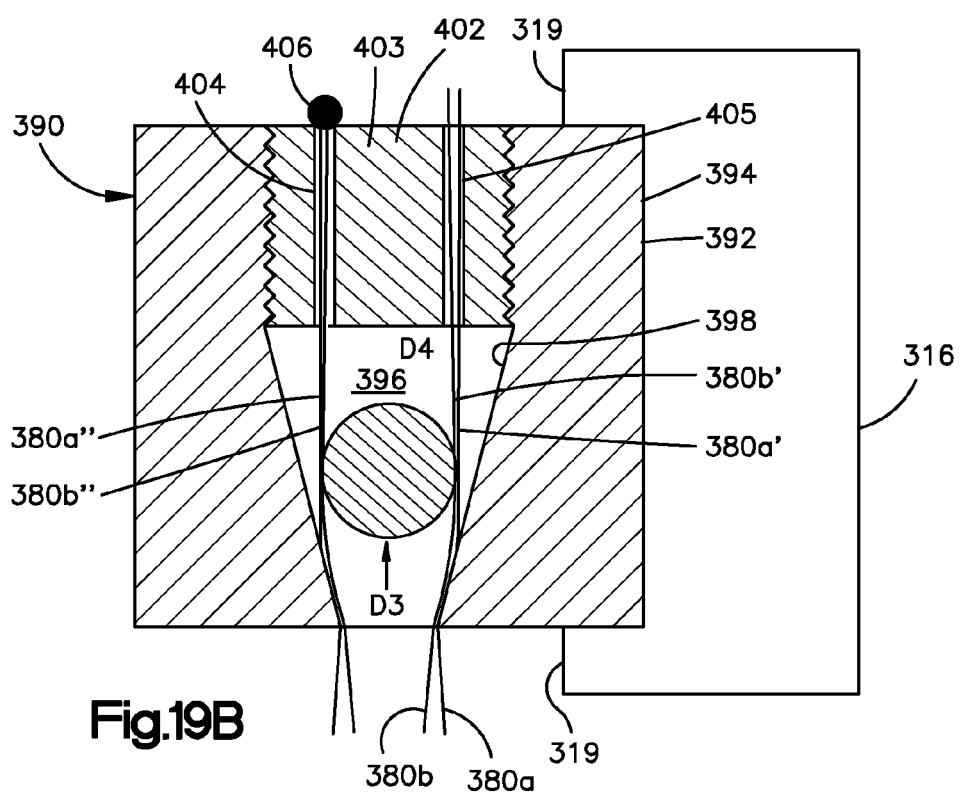

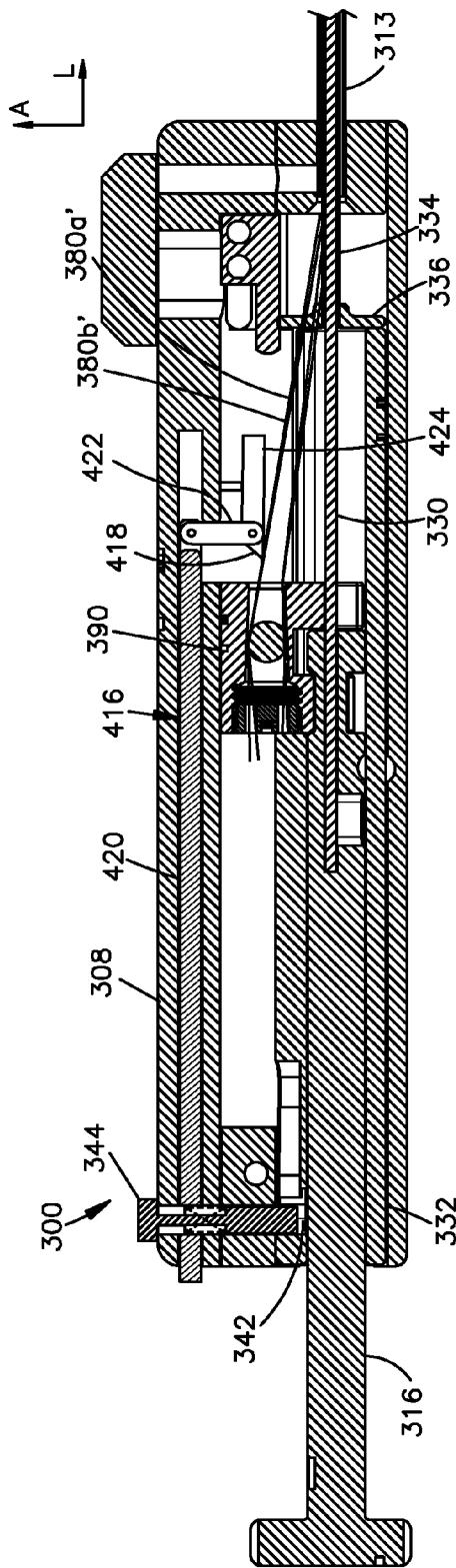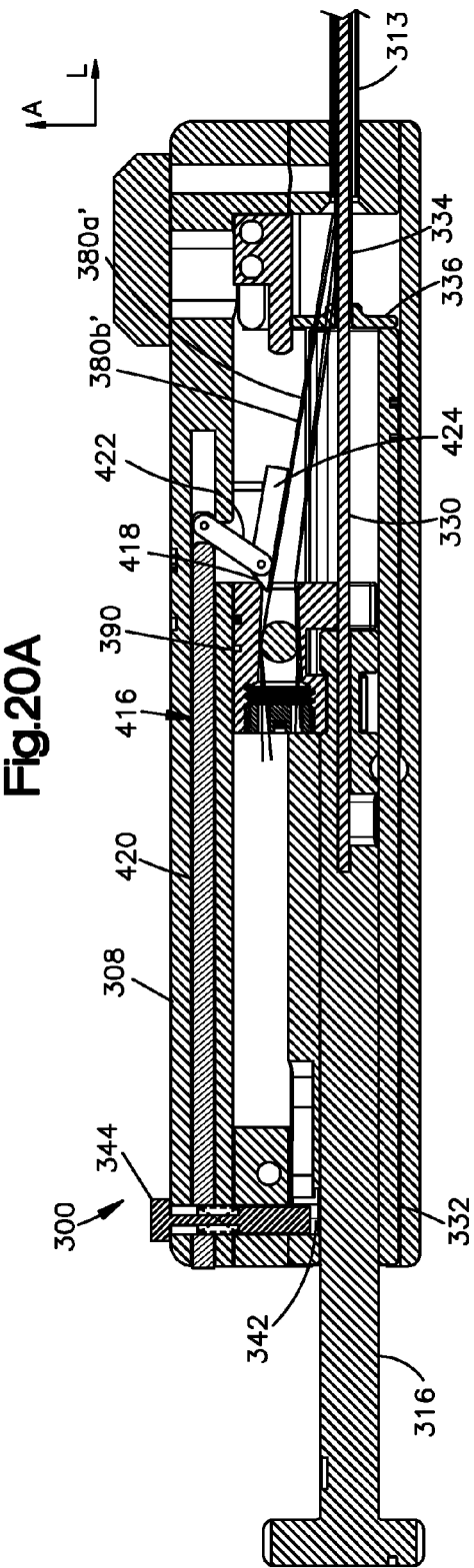
Fig.20A
Fig.20B

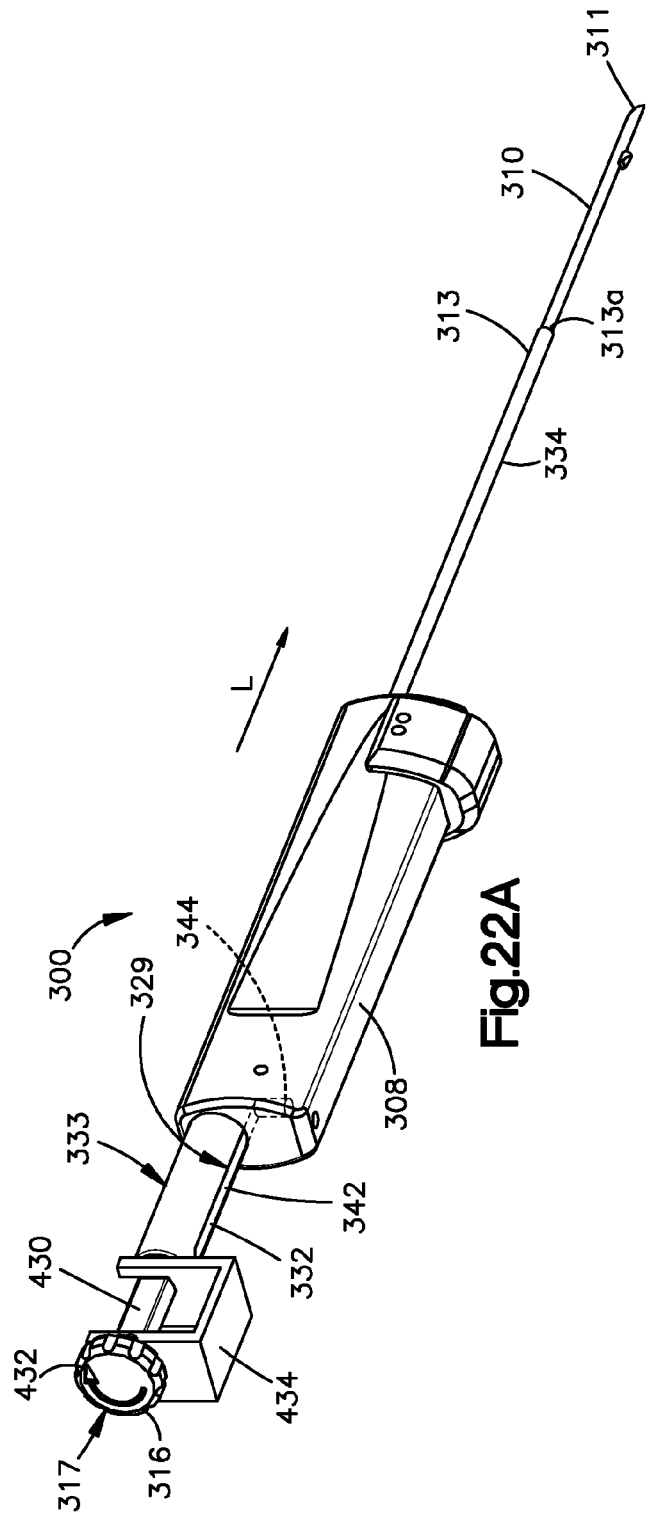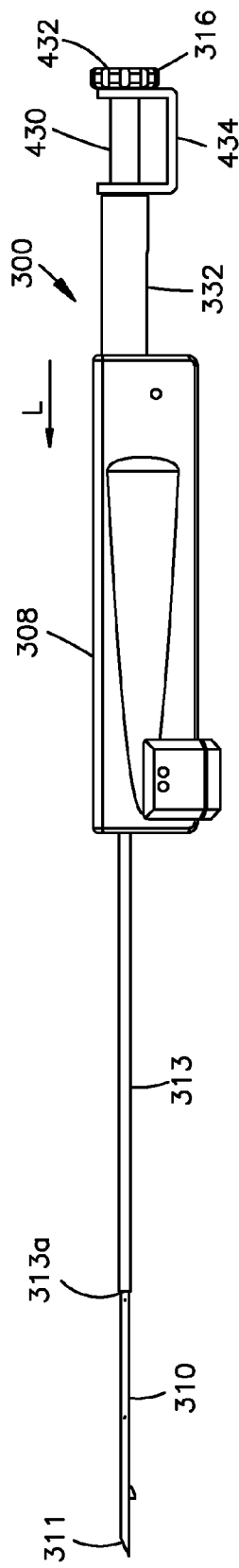

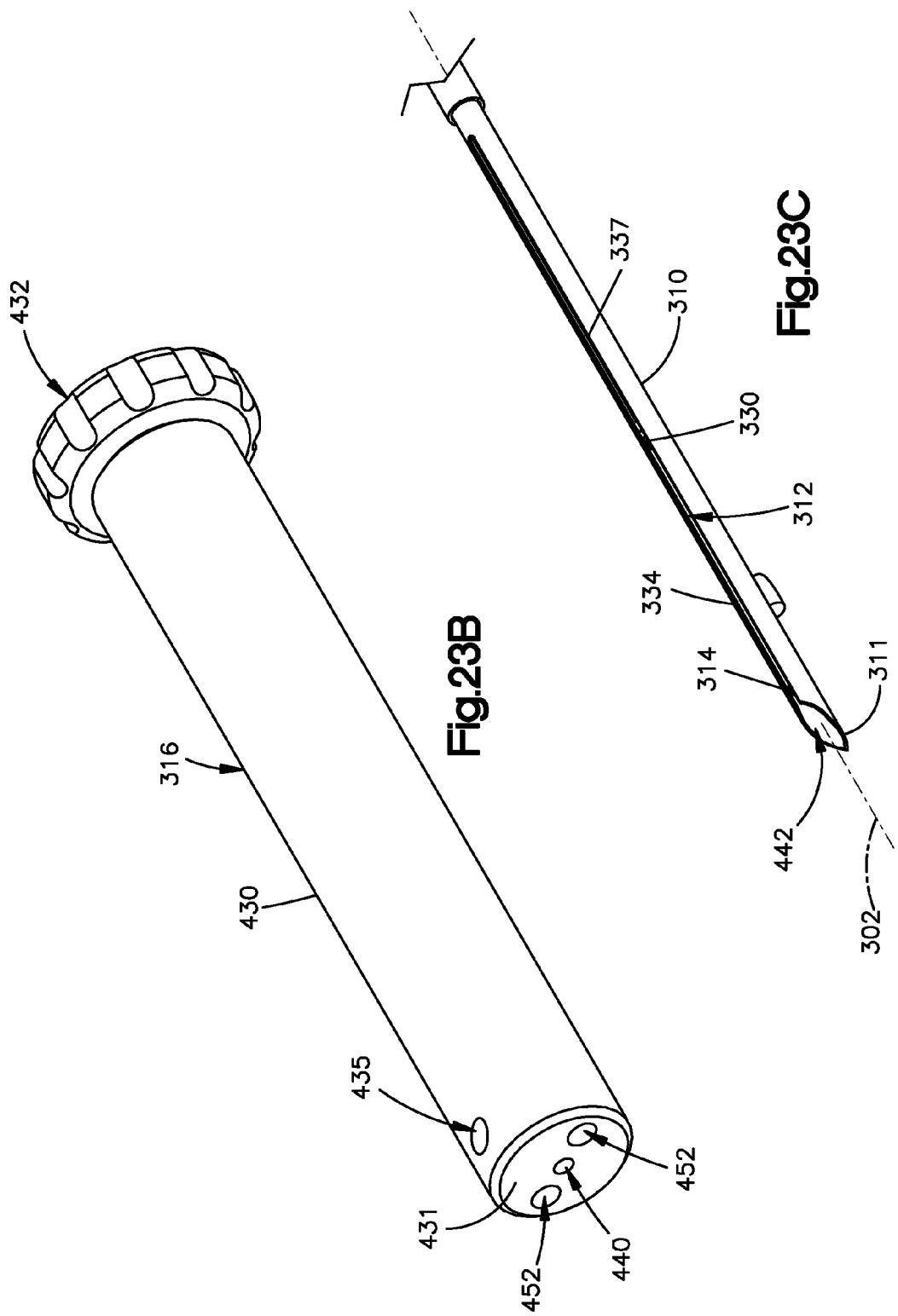

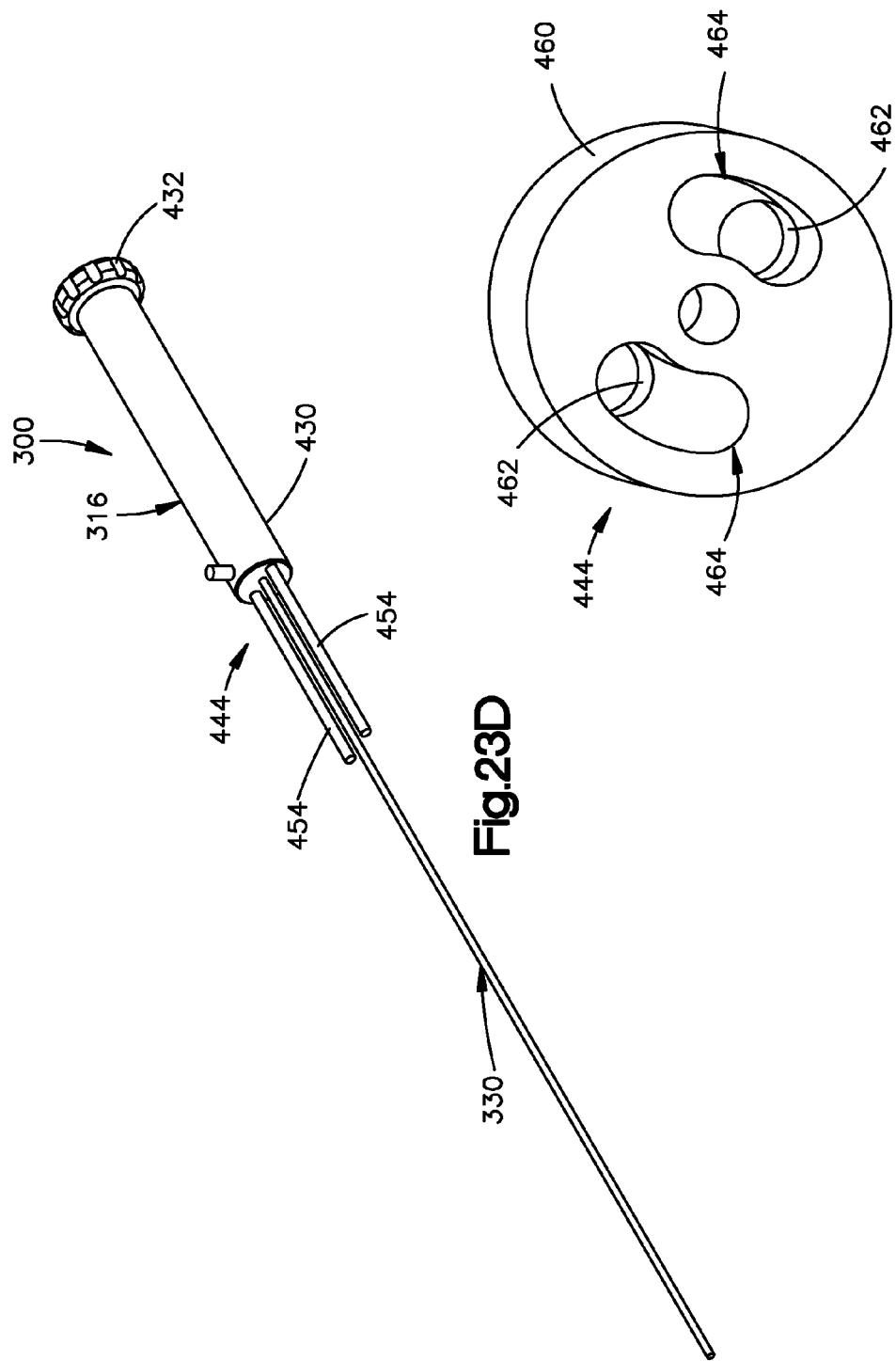

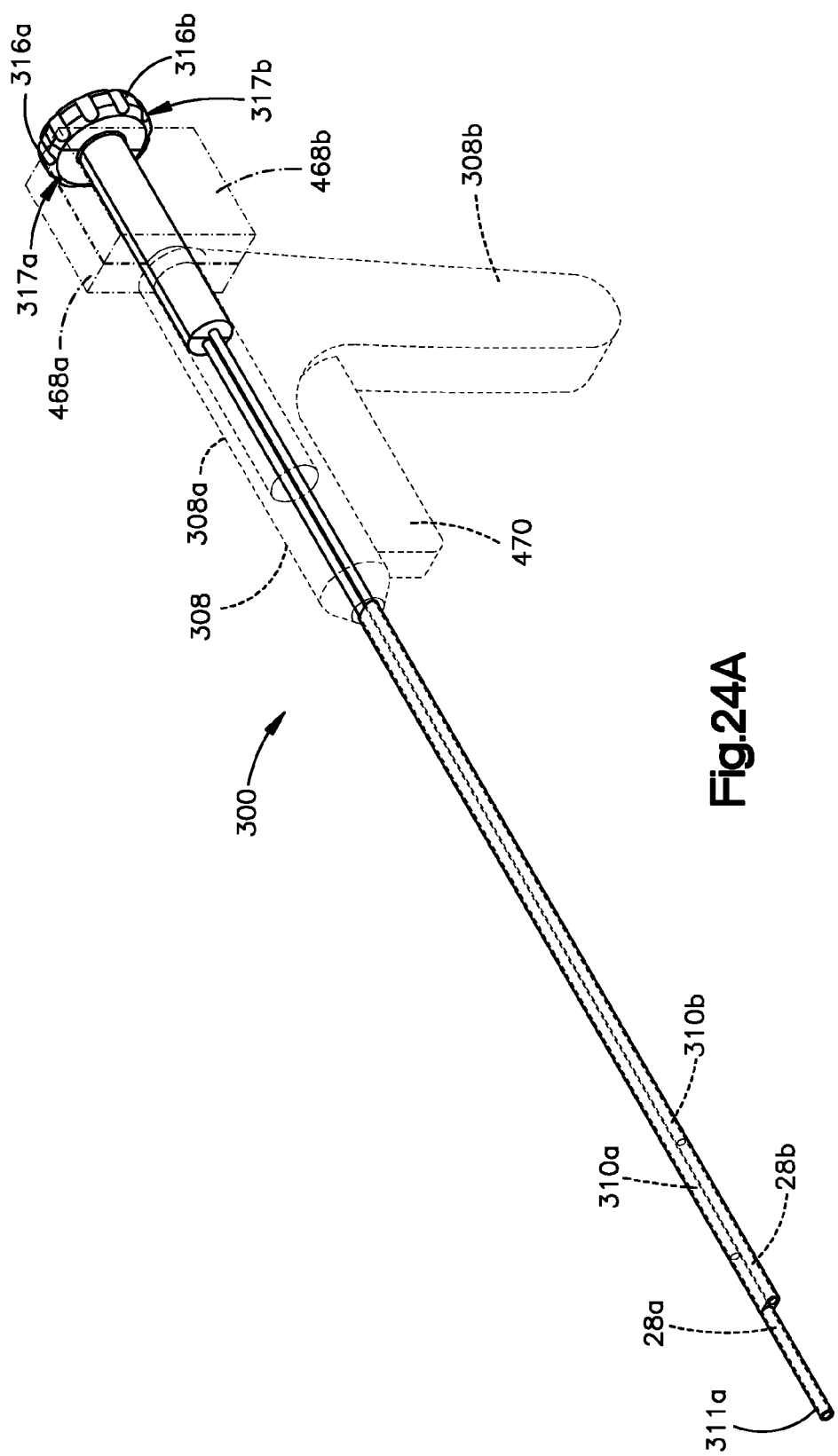

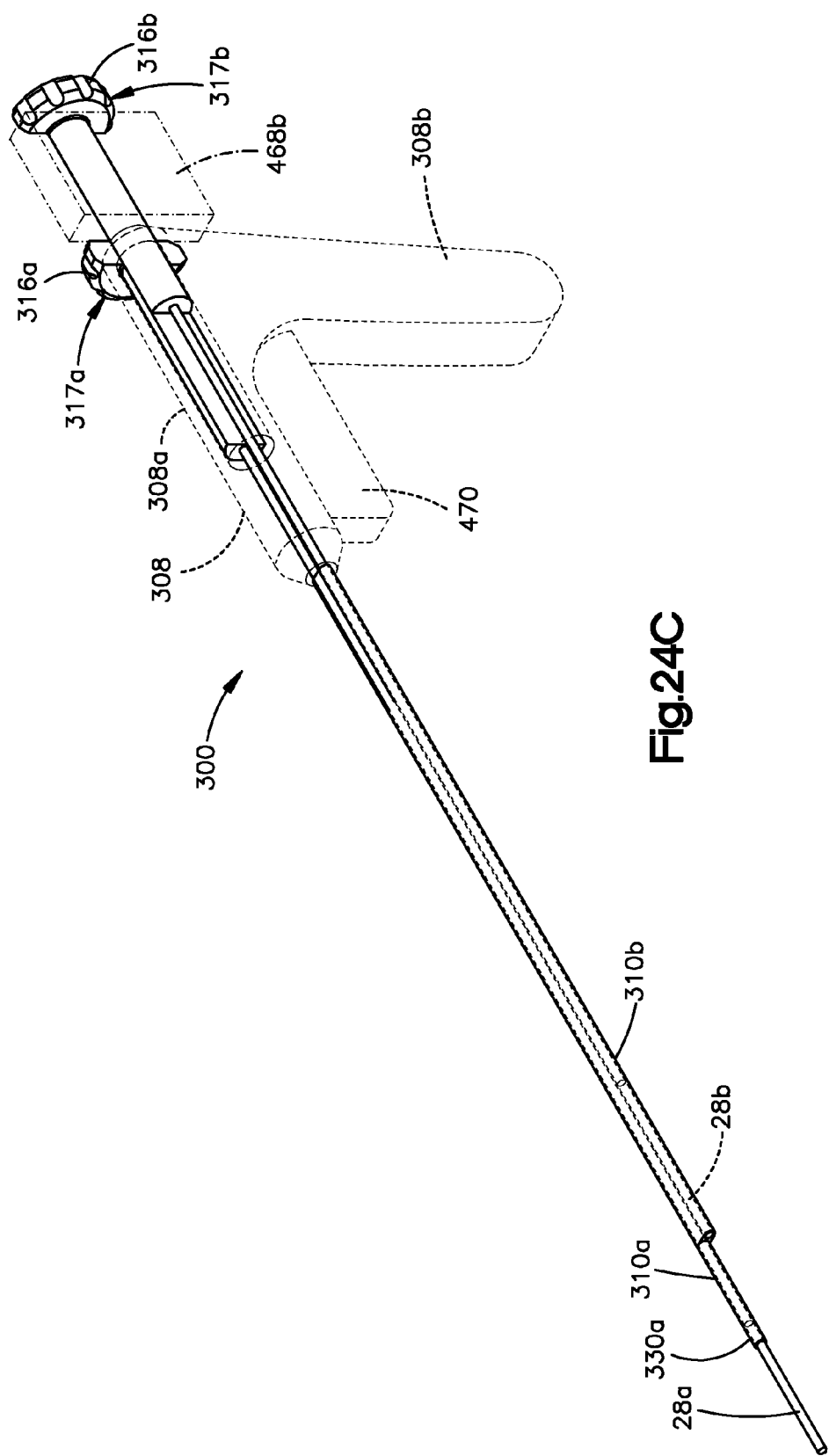

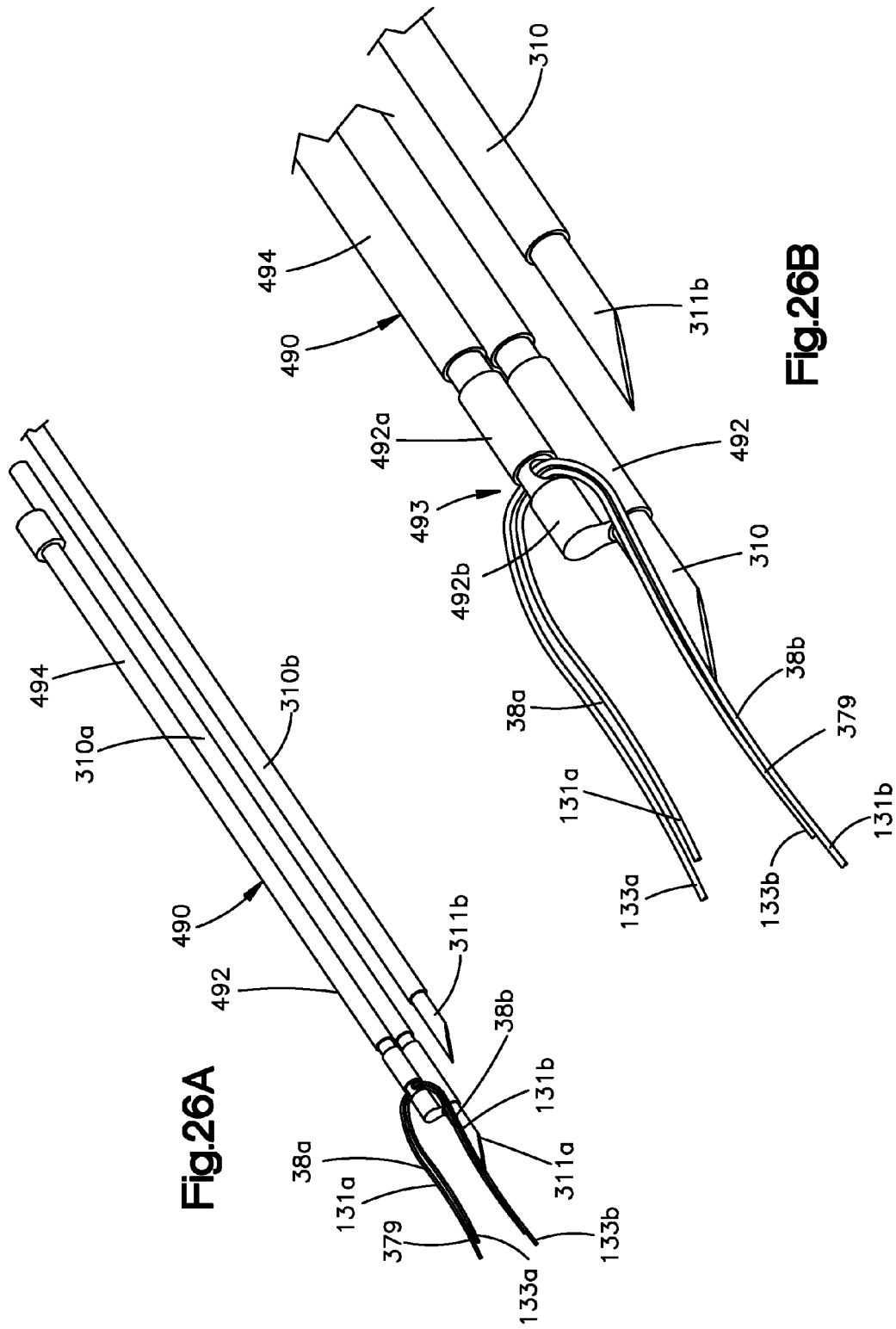

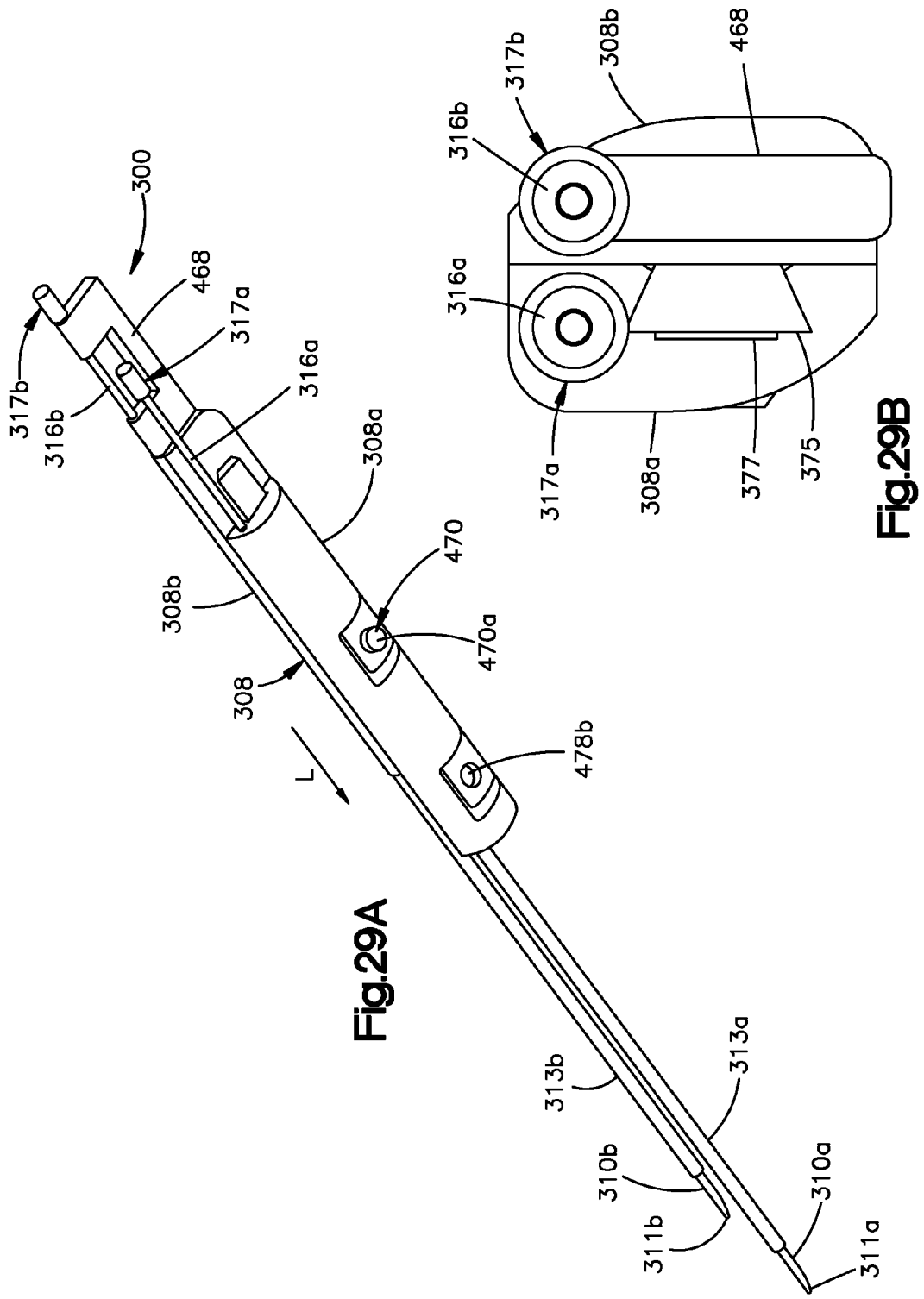

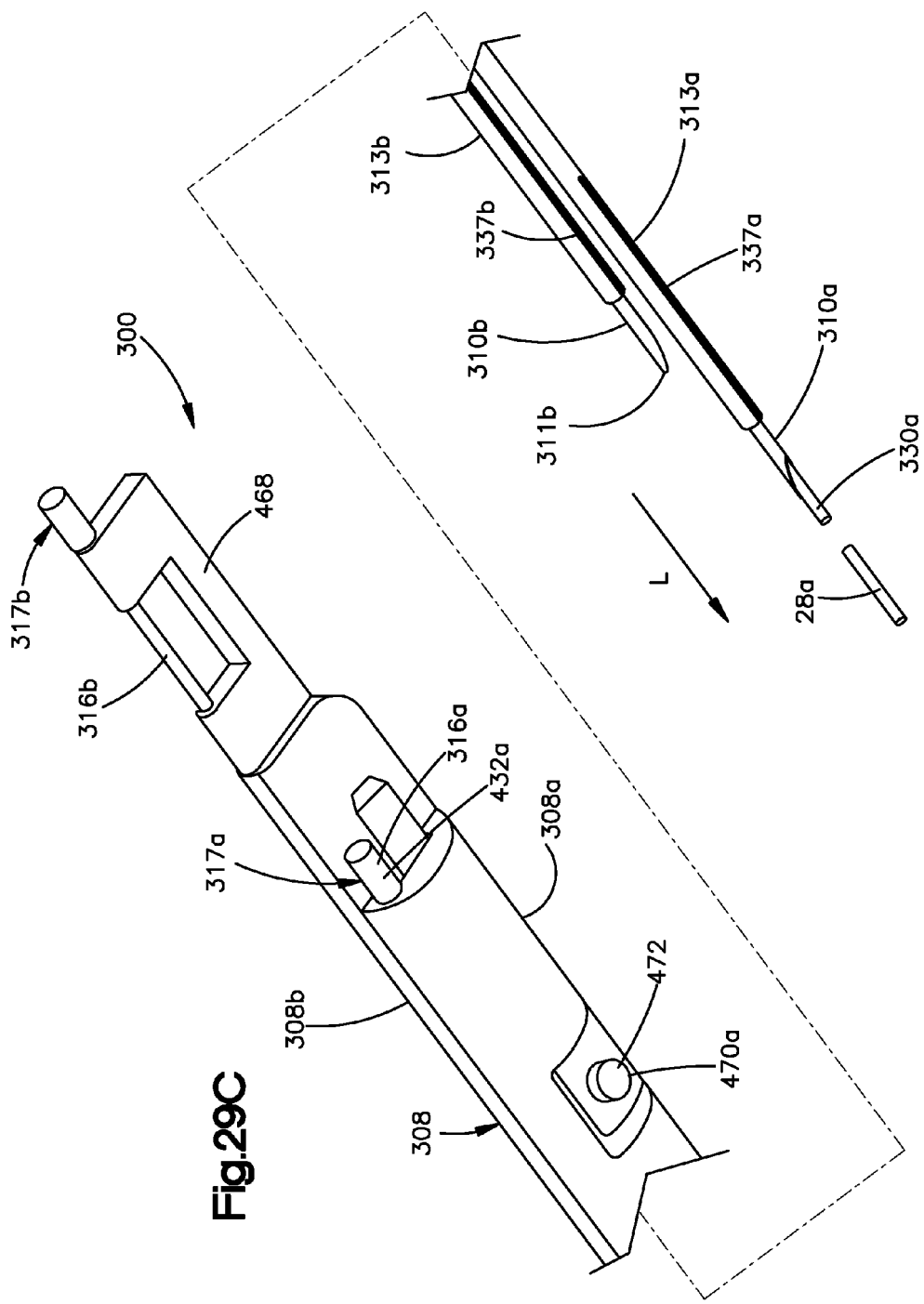

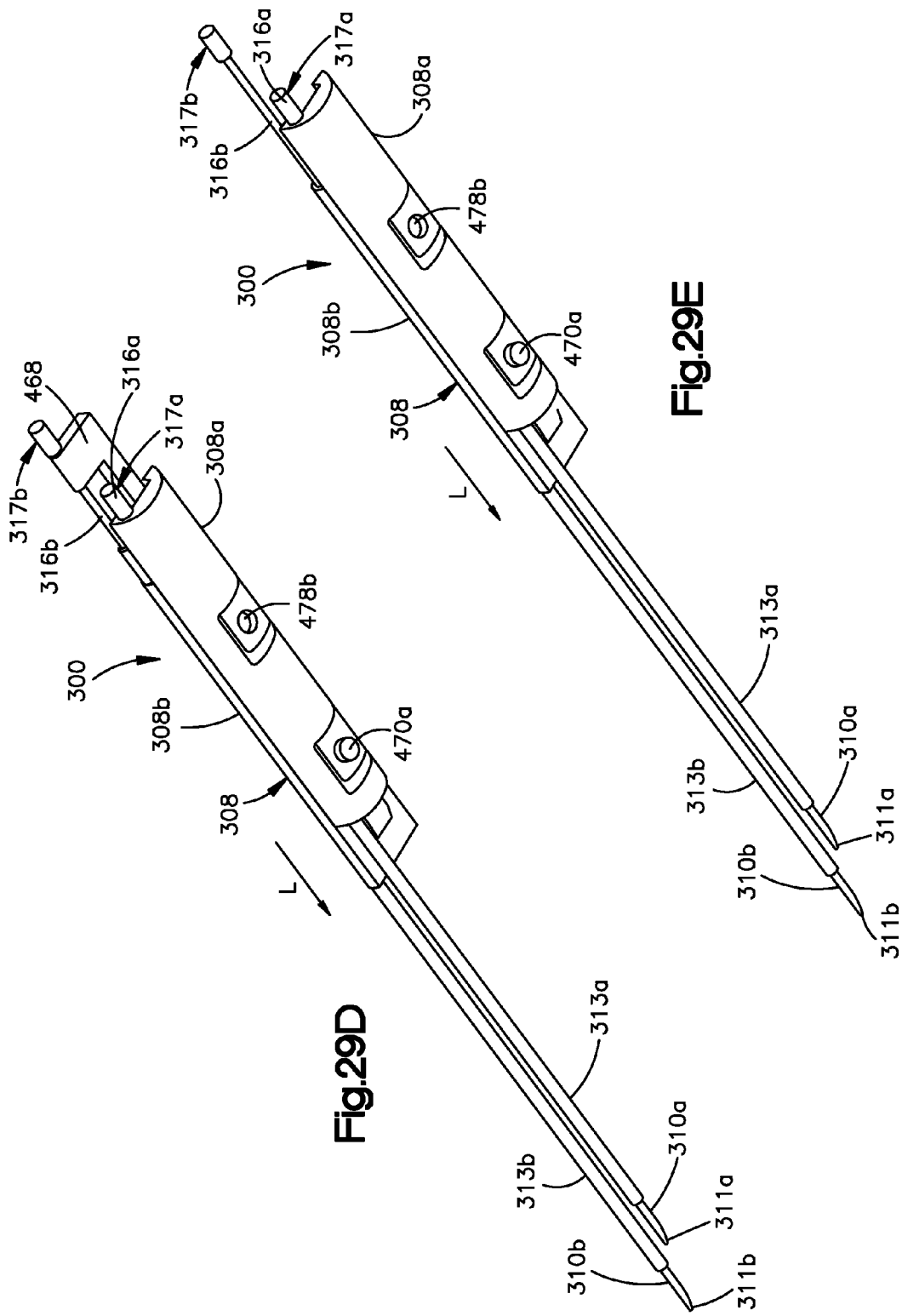

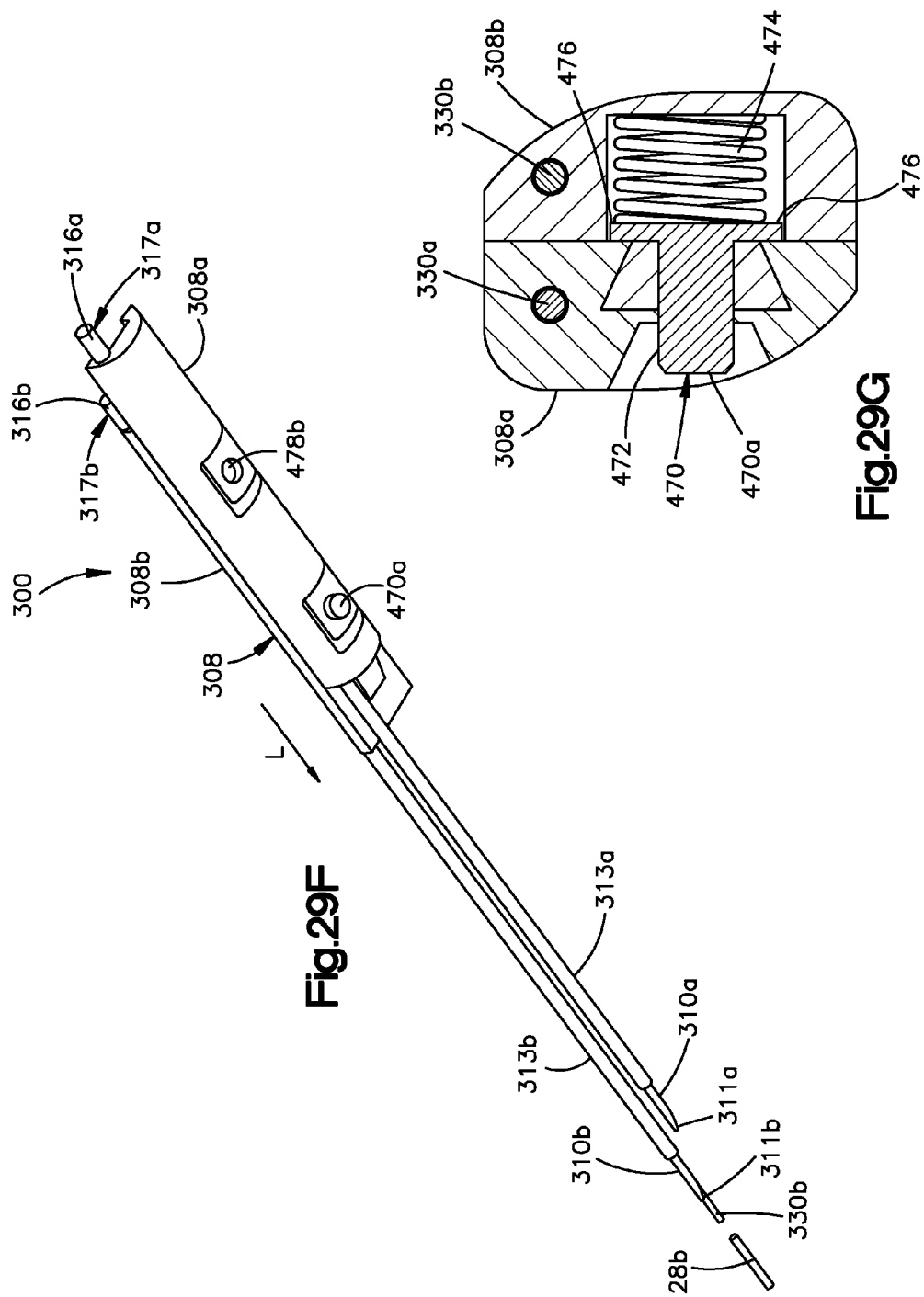

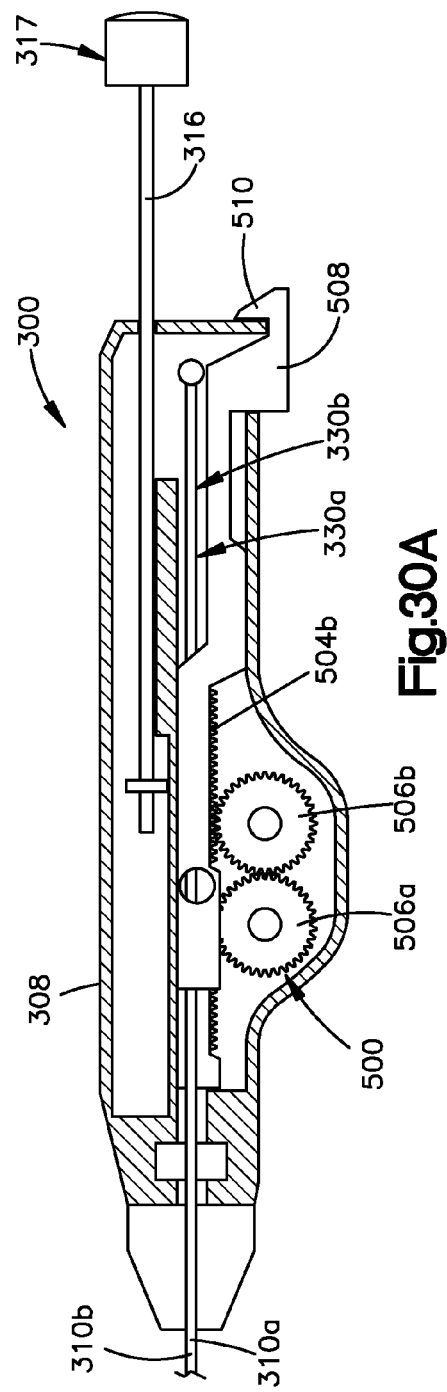
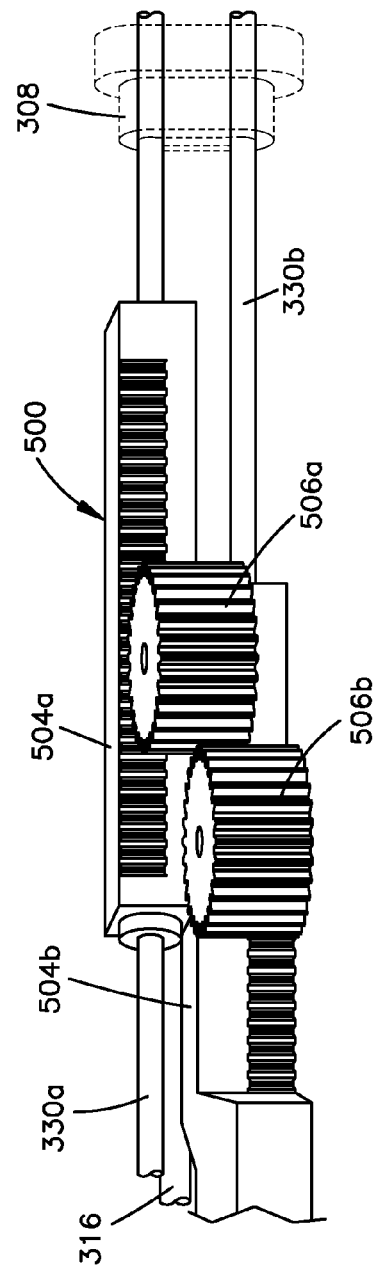
Fig.30A
Fig.30B

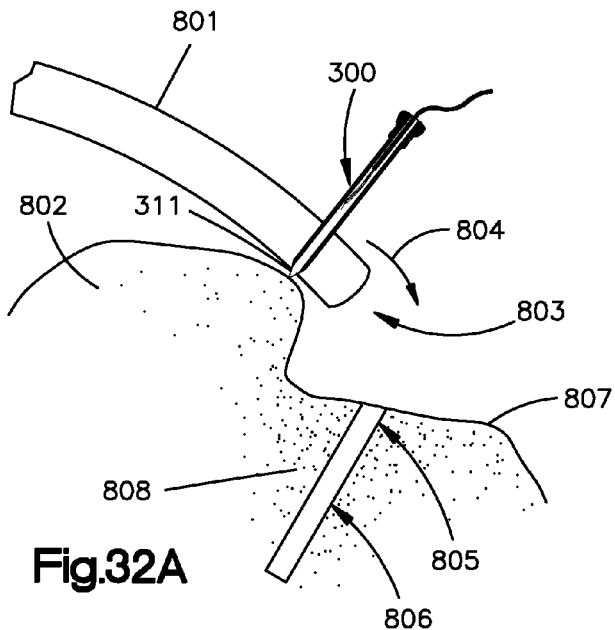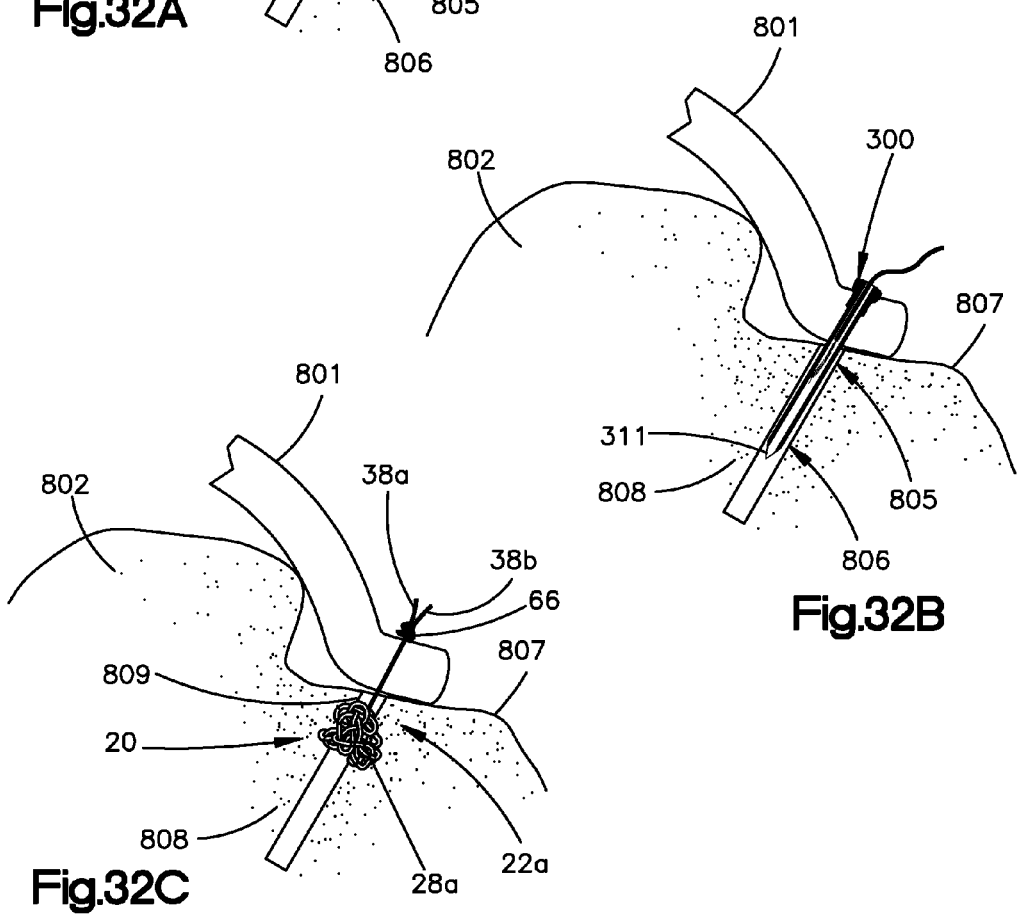

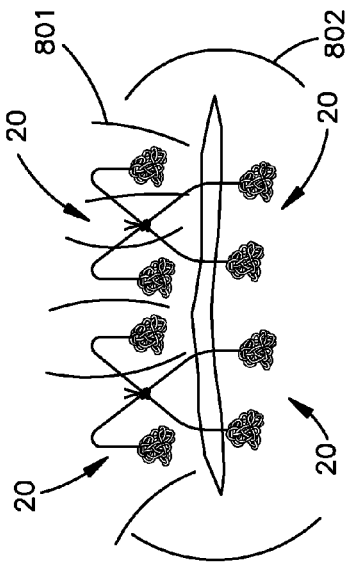
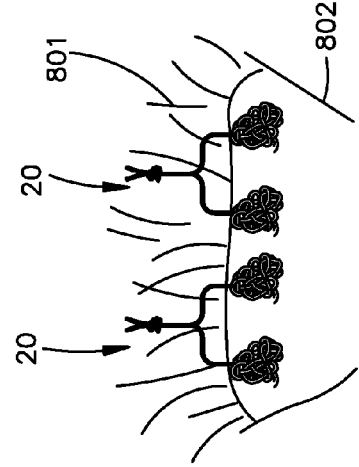
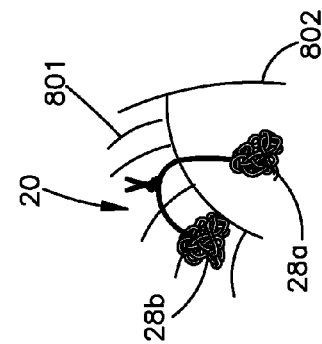
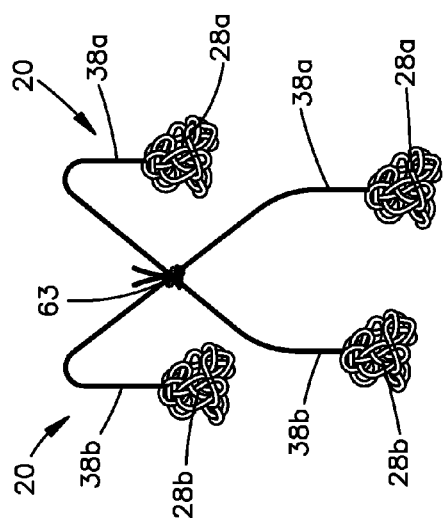

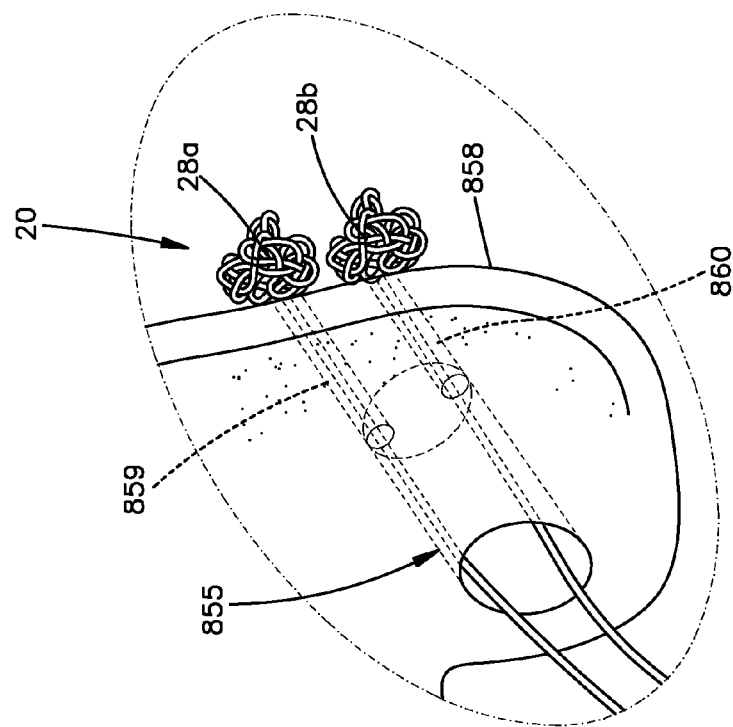
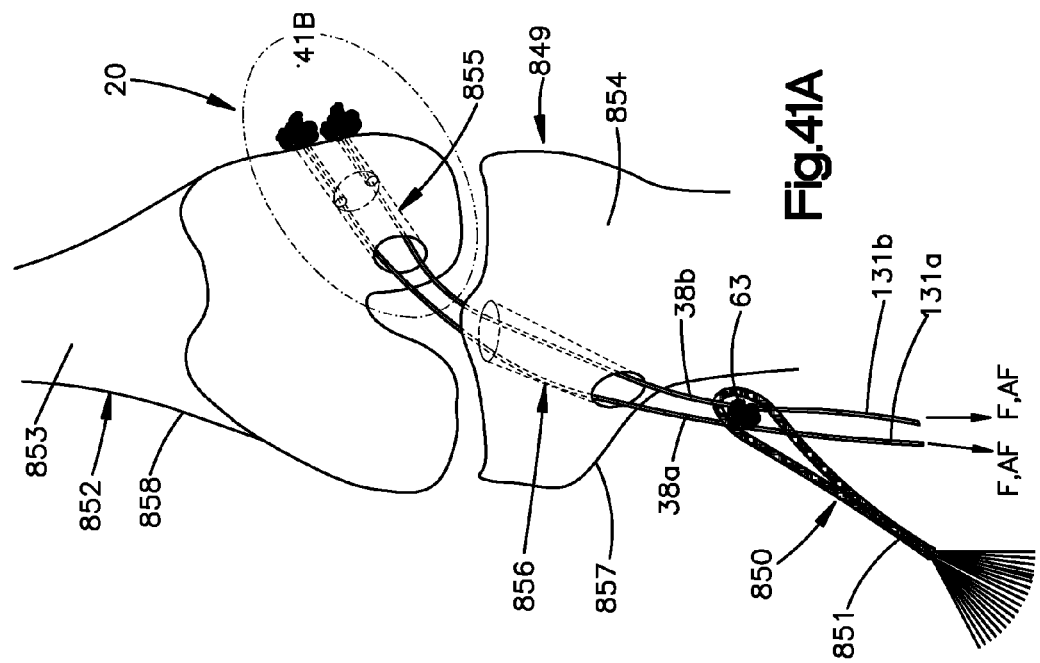

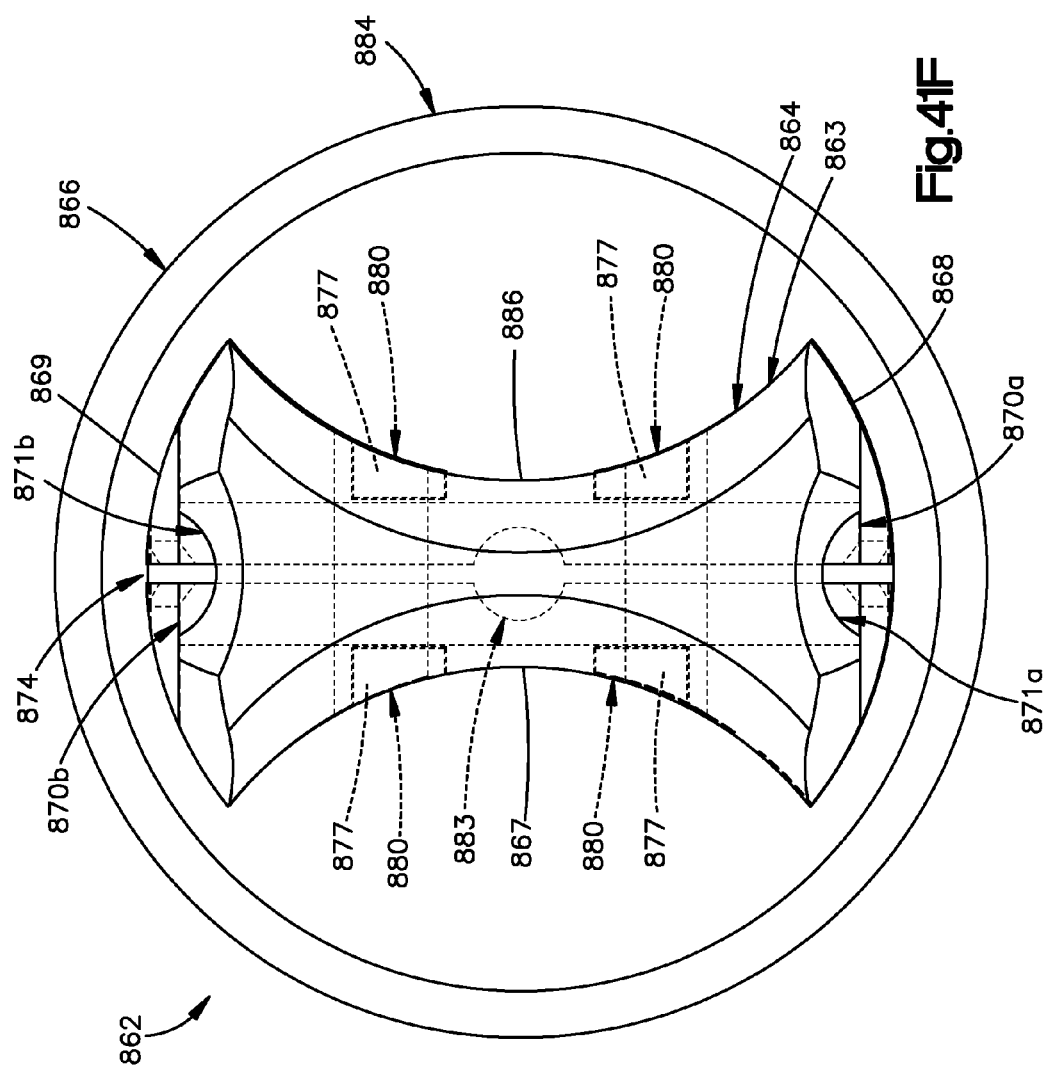

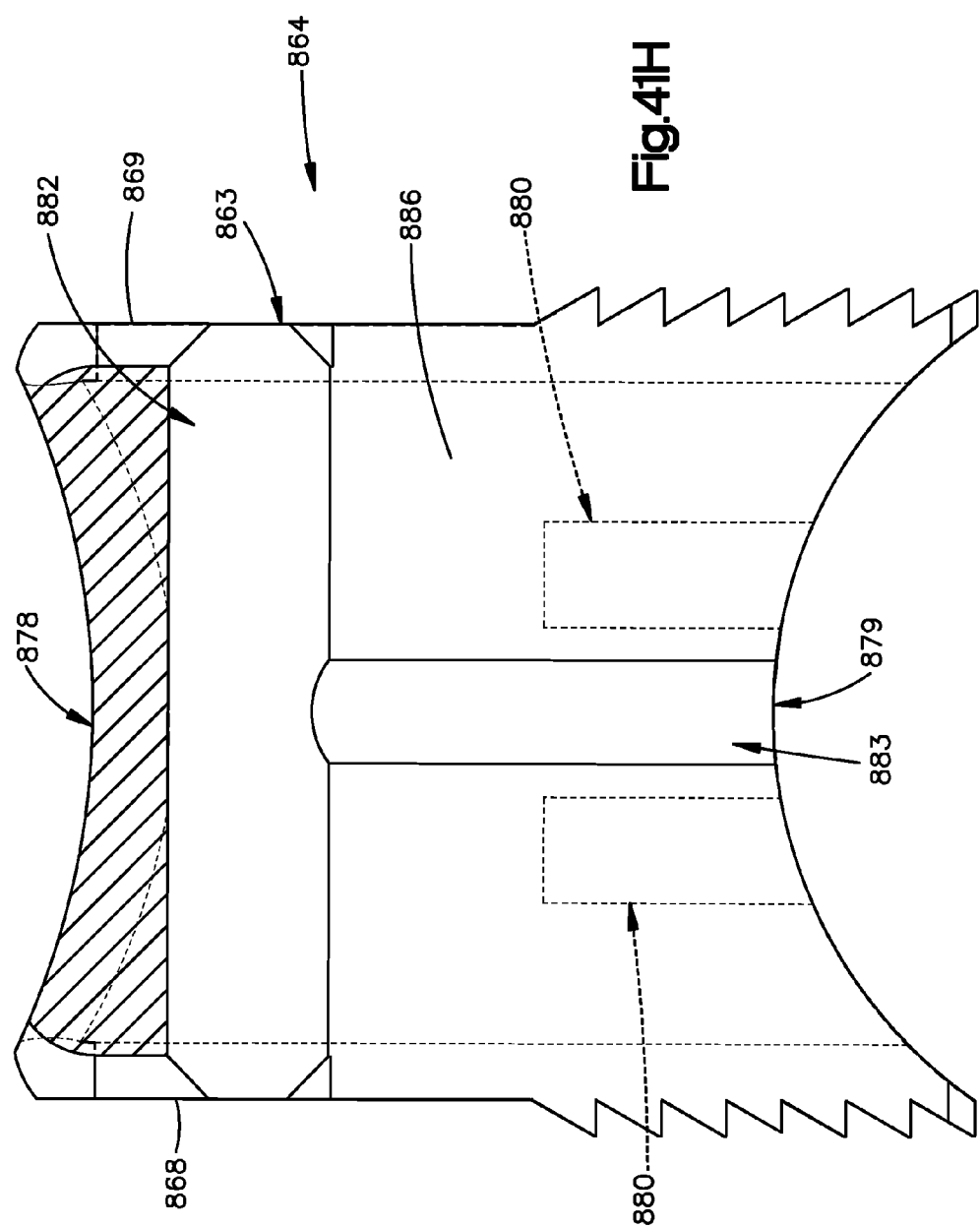

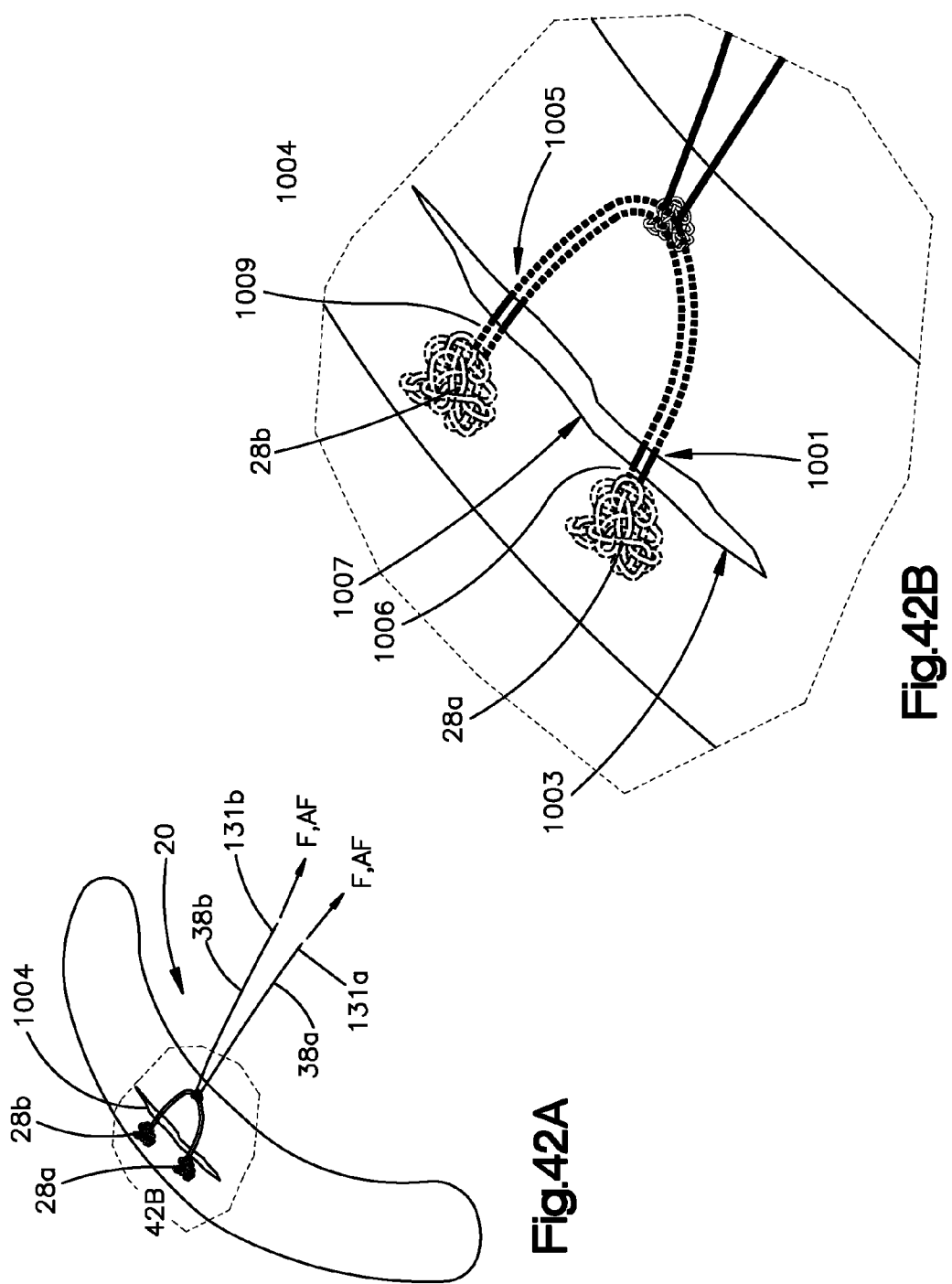

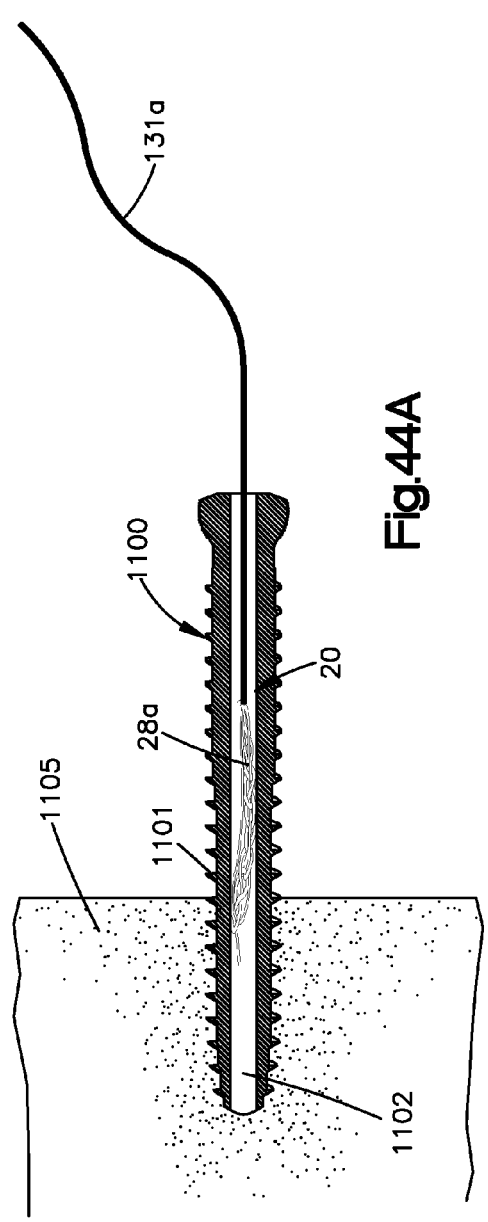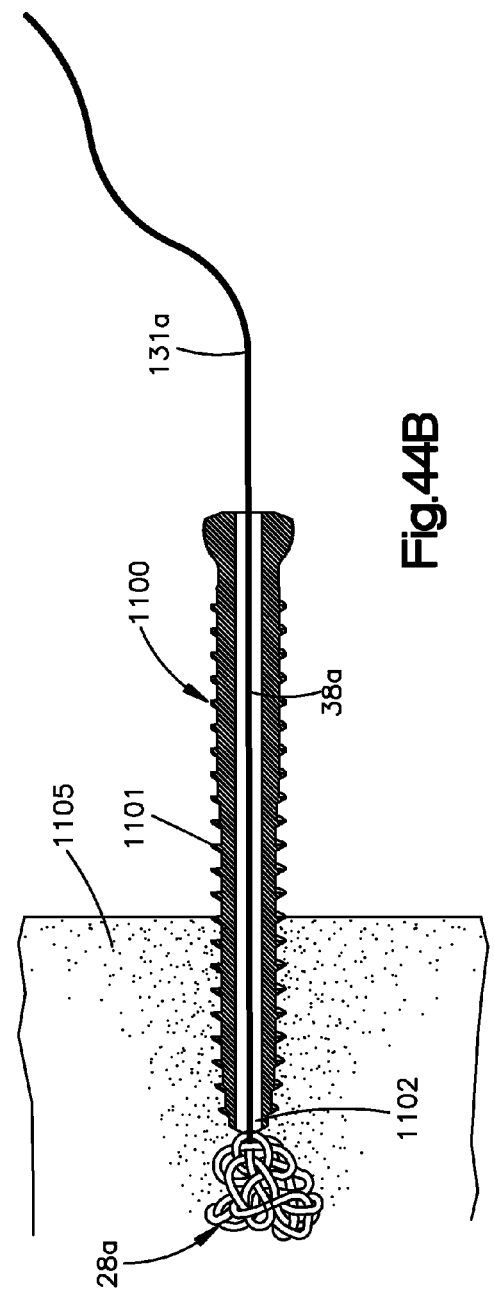

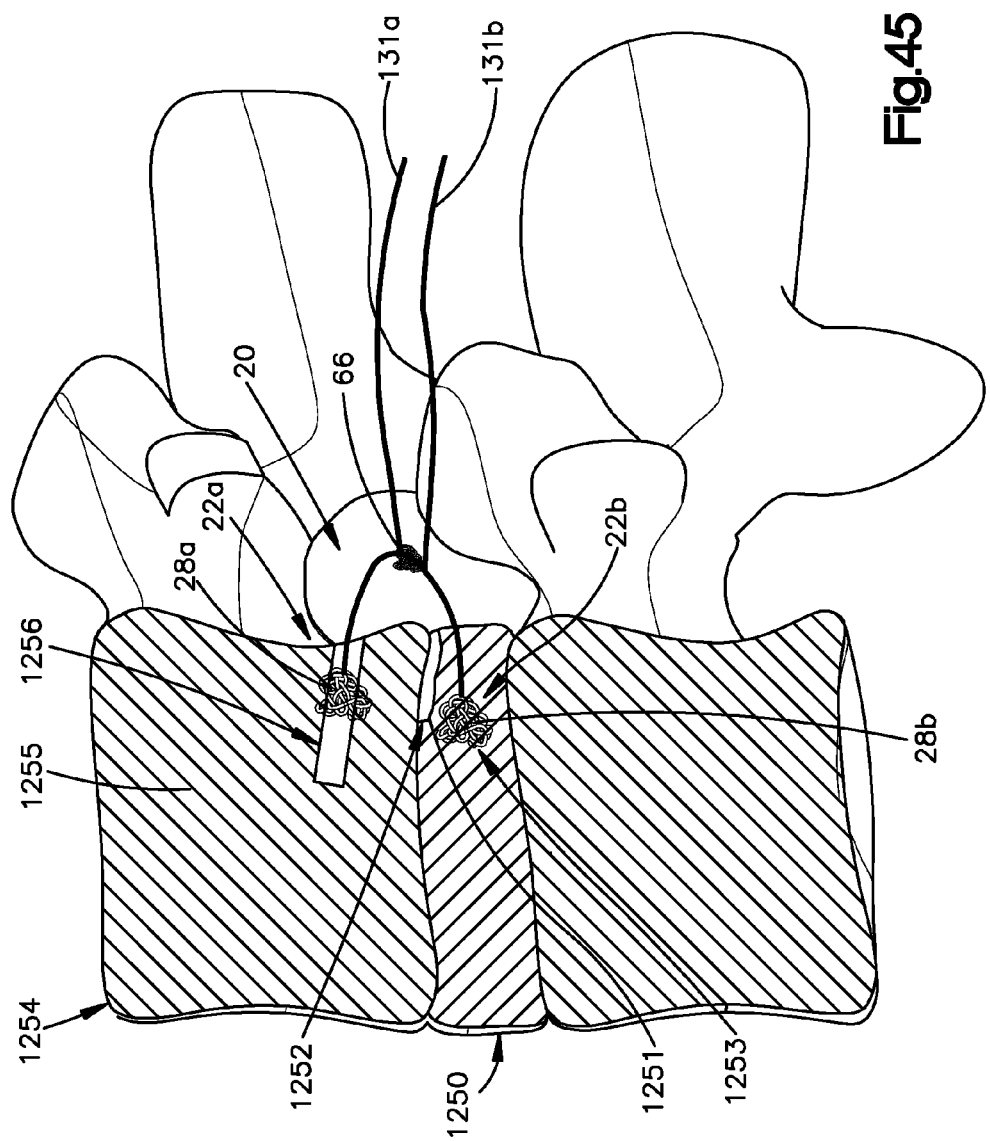

METHODS FOR APPROXIMATING A TISSUE DEFECT USING AN ANCHOR ASSEMBLY

CROSS-REFERENCE TO RELATED APPLICATIONS

This application is a continuation-in-part of U.S. patent application Ser. No. 13/172,619, filed Jun. 29, 2011, which is a continuation-in-part of U.S. patent application Ser. No. 13/095,192, filed Apr. 27, 2011. U.S. patent application Ser. No. 13/172,619 further claims the benefit of U.S. Patent Application Ser. No, 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes). U.S. patent application Ser. No. 13/095,192 claims the benefit of U.S. Patent Application Ser. No. 61/328,251 filed on Apr. 27, 2010 (Overes), U.S. Patent Application Ser. No, 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes). The disclosure of each of the above-identified patent applications is incorporated by reference as if set forth in its entirety herein. The disclosure of co-pending U.S. patent application Ser. No. 13/283,063 filed on Oct. 27, 2011 and entitled "Insertion Instrument for Anchor Assembly" is hereby incorporated by reference as if set forth in its entirety herein. The disclosure of co-pending U.S. patent application Ser. No. 13/283,002 filed on Oct. 27, 2011 and entitled "Stitch Lock for Attaching Two or More Structures" is hereby incorporated by reference as if set forth in its entirety herein.

BACKGROUND

Orthopaedic surgical procedures often involve the use of a fixation device. Usually an access hole is produced in a bone or soft tissue wherein a suitable fixation device can be fastened. Apart from screws, expandable fixations devices can be used which are inserted into the hole in a collapsed state and transformed into an expanded state once being correctly positioned.

In one example orthopaedic surgical procedure, such as a lumbar microdiscectomy, radiculopathy is treated by surgically removing the herniated nucleus pulposus to achieve neural decompression. The lumbar microdiscectomy is one of the most common spinal surgeries performed today. Many patients find relief with this procedure, but for others, the disc could re-herniate through the opening in the annulus resulting in continuing pain and potentially requiring additional surgery. Currently, the standard microdiscectomy technique does not involve closing the annular defect and presents the surgeon with a dilemma. The surgeon may elect to remove the herniated portion of the nucleus impinging on the nerves, which treats radiculopathy, but may increase the risk of post-operative reherniation of the remaining nucleus through the existing defect of the annulus. Alternately, the surgeon may elect to perform extensive debulking, in which most of the remaining nucleus material is removed in addition to the herniated portion to minimize the risk of post-operative reherniation. However, the risk of post-operative disc height collapse and subsequent progression to lower back pain increases.

Conventional expandable implants include a sleeve with an expandable portion having plurality of fingers or expandable parts formed by intermediate slots or holes in the peripheral wall of the sleeve and a compression element extending through the central bore of the sleeve. The compression element can be coupled to the front end of the sleeve so that upon pulling said compression element towards the rear end of the sleeve said fingers or expandable parts are bent radially outwards so as to transform said expandable portion from its collapsed state to its expanded state.

SUMMARY

In accordance with one embodiment, an insertion instrument is configured to eject at least one anchor at a target location. The anchor includes an anchor body that has a substrate that extends substantially along a direction of elongation. The substrate defines a plurality of openings spaced along the direction of elongation. The anchor further includes an actuation member that is woven through at least two of the openings. The insertion instrument includes a cannula that defines an elongate opening sized to receive the anchor body. The insertion instrument further includes a pusher member insertable into the cannula and configured to be depressed in the elongate opening so as to eject the anchor body from the cannula and into the target location. When a tensile force is applied to the actuation member along a direction substantially along the direction of elongation, the anchor body collapses along the direction of elongation and expands along a second perpendicular with respect to the direction of elongation.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIG. 4A is a sectional elevation view of a fixation kit constructed in accordance with an alternative embodiment, shown in a first rotative state;

FIG. 4B is a sectional side elevation view of the kit illustrated in FIG. 4A, taken along line 4B-4B;

FIG. 4C is a sectional side elevation view of the fixation kit as illustrated in FIG. 4A, but shown in a second rotative state whereby a pair of apertures is aligned;

FIG. 4D-sectional side elevation view of the fixation kit illustrated in FIG. 4C, taken along line 4D-4D;

FIG. 5A is a sectional side elevation view of an insertion instrument during assembly;

FIG. 5B is a sectional side elevation view of the insertion instrument illustrated in FIG. 5A, but shown assembled;

FIG. 5C is a sectional side elevation view of a handle of the insertion instrument illustrated in FIG. 5B;

FIG. 5D is a perspective view of the handle illustrated in FIG. 5C;

FIG. 6 is a side elevation view of the fixation kit constructed in accordance with another embodiment;

FIG. 7A is a perspective view of a fixation kit including an insertion instrument constructed in accordance with an alternative embodiment including a casing and a cannula extending from the casing, the instrument shown in a first configuration with first and second anchor bodies loaded in the insertion instrument;

FIG. 7B is an enlarged perspective view of the cannula of the insertion instrument illustrated in FIG. 7A;

FIG. 7C is a sectional side elevation view of the casing of the insertion instrument illustrated in FIG. 7A;

FIG. 7D is an enlarged sectional side elevation view of the cannula of the insertion instrument illustrated in FIG. 7A;

FIG. 8A is a perspective view of the fixation kit illustrated in FIG. 7A, showing the insertion instrument in the second position so as to eject the second anchor body from the insertion instrument, the second anchor body shown in a first configuration FIG. 8B is an enlarged perspective view of the cannula of the insertion instrument illustrated in FIG. 8A;

FIG. 8C is a sectional side elevation view of the casing illustrated in FIG. 8A;

FIG. 8D is a sectional side elevation view of the cannula illustrated in FIG. 8A;

FIG. 9A is a perspective view of the fixation kit illustrated in FIG. 8A, showing the insertion instrument in an offset position;

FIG. 9B is an enlarged perspective view of the cannula of the insertion instrument illustrated in FIG. 9A FIG. 9C is a sectional side elevation view of the casing of the insertion instrument illustrated in FIG. 9A;

FIG. 9D is a sectional side elevation view of the cannula of the insertion instrument illustrated in FIG. 9A;

FIG. 10A is a perspective view of the fixation kit illustrated in FIG. 9A, showing the insertion instrument in an intermediate position upon completion of an intermediate stroke;

FIG. 10B is an enlarged perspective view of the cannula of the insertion instrument illustrated in FIG. 10A

FIG. 11A is a perspective view of the fixation kit illustrated in FIG. 10A, showing the insertion instrument upon completion of a first portion of a second stroke after the intermediate stroke;

FIG. 11B is an enlarged perspective view of the cannula of the insertion instrument illustrated in FIG. 11A

FIG. 12A perspective view of the fixation kit illustrated in FIG. 11A, showing the insertion instrument in a third position upon completion of a second portion of the second stroke, ejecting a first anchor body from the insertion instrument, the first anchor body shown in a first configuration;

FIG. 12B is an enlarged perspective view of the cannula of the insertion instrument illustrated in FIG. 12A;

FIG. 12E is a perspective view of the fixation kit similar to FIG. 12A, but showing the first anchor body in an expanded configuration;

FIG. 14A is a perspective view of a coupling assembly constructed in accordance with one embodiment, FIG. 14B is a sectional side elevation view of the coupling assembly illustrated in FIG. 14A, shown in a first mode of operation;

FIG. 15A is a sectional side elevation view of the insertion instrument constructed in accordance with another embodiment, showing a coupling assembly disposed in a first mode of operation;

FIG. 15B is a sectional end elevation view of the coupling assembly illustrated in FIG. 15A, taken along line 15B-15B;

FIG. 15C is a sectional side elevation view of the insertion instrument illustrated in FIG. 15A, but showing the coupling assembly transitioning from the first mode of operation to a second mode of operation;

FIG. 15D is a sectional end elevation view of the coupling assembly illustrated in FIG. 15C, taken along line 15D-15D;

FIG. 15E is a sectional side elevation view of the insertion instrument illustrated in FIG. 15C, but showing the coupling assembly in the second mode of operation;

FIG. 16A is a schematic side elevation view of the anchor assembly as illustrated in FIG. 1G, including a tensioning strand in accordance with an alternative embodiment, showing on of the anchor bodies implanted in the first configuration;

FIG. 16B is a schematic side elevation view of the anchor assembly as illustrated in FIG. 16A, but showing the implanted anchor body in the expanded configuration;

FIG. 16C is a schematic side elevation view of the anchor assembly as illustrated in FIG. 16B, showing the other anchor body implanted in the first configuration;

FIG. 16D is a schematic side elevation view of the anchor assembly as illustrated in FIG. 16C, showing the other anchor body in the expanded configuration;

FIG. 18A is a schematic side elevation view of the anchor assembly as illustrated in FIG. 1G, including a pair of tensioning strands in accordance with an alternative embodiment, showing the anchor bodies in the first configuration;

FIG. 18B is a schematic side elevation view of the anchor assembly as illustrated in FIG. 18A, but showing the anchor bodies in the expanded configuration;

FIG. 18C is a schematic side elevation view of the anchor assembly as illustrated in FIG. 18B, showing actuation of a locking member and approximation of an anatomical gap;

FIG. 18D is a schematic side elevation view of the anchor assembly as illustrated in FIG. 18C, showing locking of the locking member;

FIG. 18E is a schematic side elevation view of the anchor assembly as illustrated in FIG. 18D, show in a final assembled configuration;

FIG. 19A is a schematic sectional side elevation view of a retention assembly of the insertion instrument constructed in accordance with another embodiment, shown in a locked configuration;

FIG. 19B is a schematic sectional side elevation view of a retention assembly of the insertion instrument illustrated in FIG. 19A, shown in an unlocked configuration;

FIG. 20A is a sectional side elevation view of the insertion instrument including a cutting assembly in accordance with another embodiment, showing the cutting assembly in a disengaged position;

FIG. 20B is a sectional side elevation view of the insertion instrument as illustrated in FIG. 20A, but showing the cutting assembly in an engaged position;

FIG. 22A is a perspective view of the insertion instrument illustrated in FIG. 7A, but constructed in accordance with an alternative embodiment, shown in the first position;

FIG. 22B is a side elevation view of the insertion instrument as illustrated in FIG. 22A;

FIG. 23B is a perspective view of a plunger of the insertion instrument illustrated in FIG. 23A;

FIG. 23C is a perspective view of a distal end of the insertion instrument illustrated in FIG. 23A;

FIG. 23D is a perspective view of various components of the insertion instrument illustrated in FIG. 23A, including the plunger illustrated in FIG. 23B, a push rod, and a pair of first coupling members;

FIG. 23E is a perspective view of a second coupling member configured to engage the first coupling members illustrated in FIG. 23D;

FIG. 24A is a perspective view of an insertion instrument including first and second pusher assemblies disposed in a side-by-side relationship, showing each of the pusher assemblies in a first position;

FIG. 24C is a perspective view of the insertion instrument illustrated in FIG. 24B, after actuation of the first pusher assembly to a second position;

FIG. 26A is a perspective view of a retention assembly constructed in accordance with one embodiment;

FIG. 26B is an enlarged perspective view of a portion of the retention assembly illustrated in FIG. 26A;

FIG. 29A is a perspective view of an insertion instrument constructed in accordance with another embodiment, the insertion instrument including first and second pusher assemblies disposed in a side-by-side relationship, showing each of the pusher assemblies in a first position;

FIG. 29B is an end elevation view of the insertion instrument illustrated in FIG. 29A;

FIG. 29C is a perspective view of the insertion instrument illustrated in FIG. 29A, showing the first pusher assembly in a second position;

FIG. 29D is a perspective view of the insertion instrument illustrated in FIG. 29C, after actuation of a swap actuator from a first position to a second position;

FIG. 29E is a perspective view of the insertion instrument illustrated in FIG. 29D, after removal of a lockout tab from the second pusher assembly;

FIG. 29F is a perspective view of the insertion instrument illustrated in FIG. 29E, showing the second pusher assembly in a second position;

FIG. 29G is a schematic sectional end elevation view of the insertion instrument illustrated in FIG. 29D, showing a portion of the swap actuator;

FIG. 30A is a perspective view of an insertion instrument constructed in accordance with another embodiment, the insertion instrument including first and second reciprocally movable cannulas, the drawing showing a portion of the casing cut away so as to expose internal components of the insertion instrument;

FIG. 30B is a perspective view of a reciprocal motion assembly of the insertion instrument illustrated in FIG. 30A, the reciprocal motion assembly configured to reciprocally drive the first and second cannulas;

FIG. 30C is a perspective view of a drive member of the reciprocal motion assembly illustrated in FIG. 30B;

FIG. 30D is a perspective view of a selective plunger engagement assembly configured to selectively move the plunger between operably communication with the first and second cannulas; and FIG. 31 is a perspective view of an insertion instrument, wherein the cannula defines a side ejection port in accordance with another embodiment;

FIG. 32A-32C illustrate a method of fixing soft tissue to a bone in accordance with an embodiment of the present disclosure;

FIG. 32D is a perspective view of one anchor assembly fixing soft tissue to bone;

FIG. 32E is a perspective view of two anchor assemblies fixing soft tissue to bone;

FIG. 32F is a perspective view of a plurality of anchor assemblies fixing soft tissue to bone;

FIG. 32H is a perspective view of two anchor assemblies arranged in a cross or X-shaped pattern;

FIG. 33 is a cross-sectional view of a rotator cuff, illustrating a method of repairing an anatomical defect of the rotator cuff using an anchor assembly in accordance with an embodiment of the present disclosure;

FIG. 34 is a cross-sectional view of a shoulder illustrating a method of repairing a Bankart lesion;

FIG. 35 is a cross-sectional view of a shoulder, illustrating a method of repairing a superior labral tear from anterior to posterior (SLAP) lesion;

Figure 36:
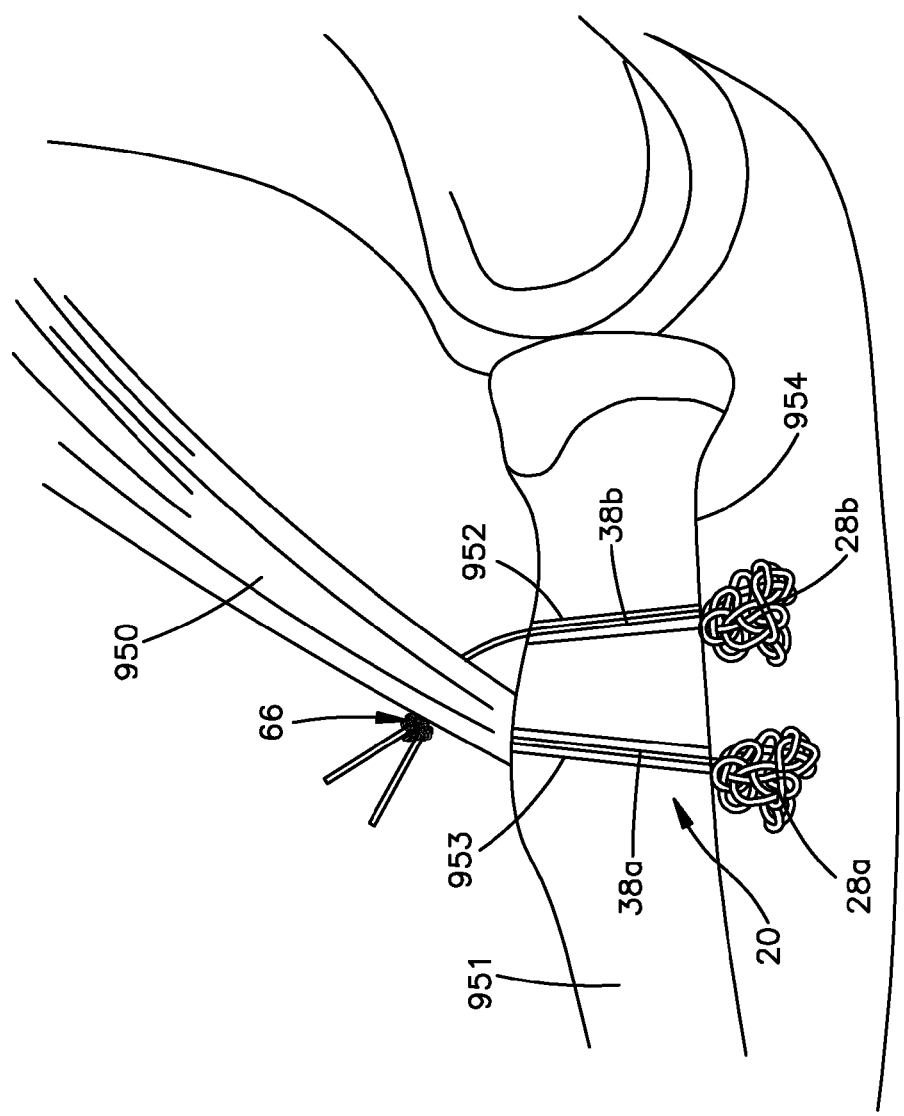

FIG. 36 is a side view of an elbow joint, illustrating a method of repairing biceps tendon injury.

Figure 37:
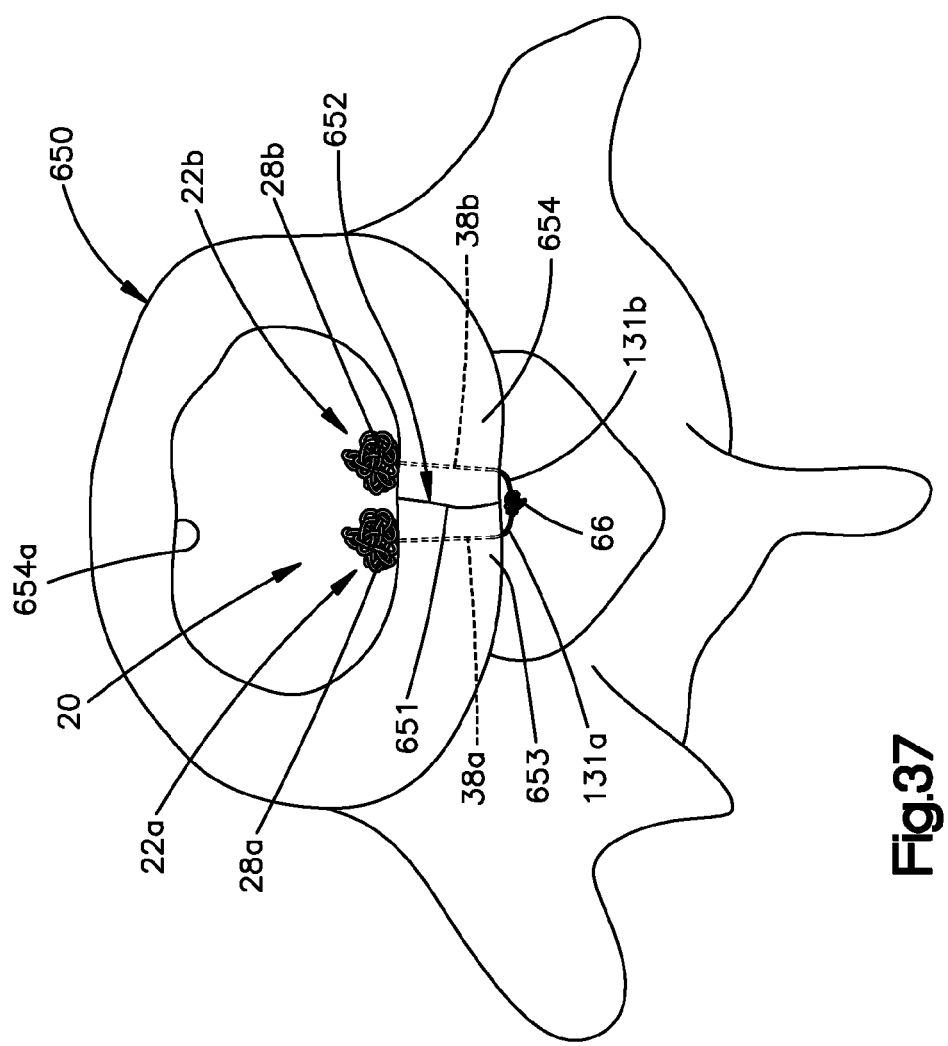
Figure 38:
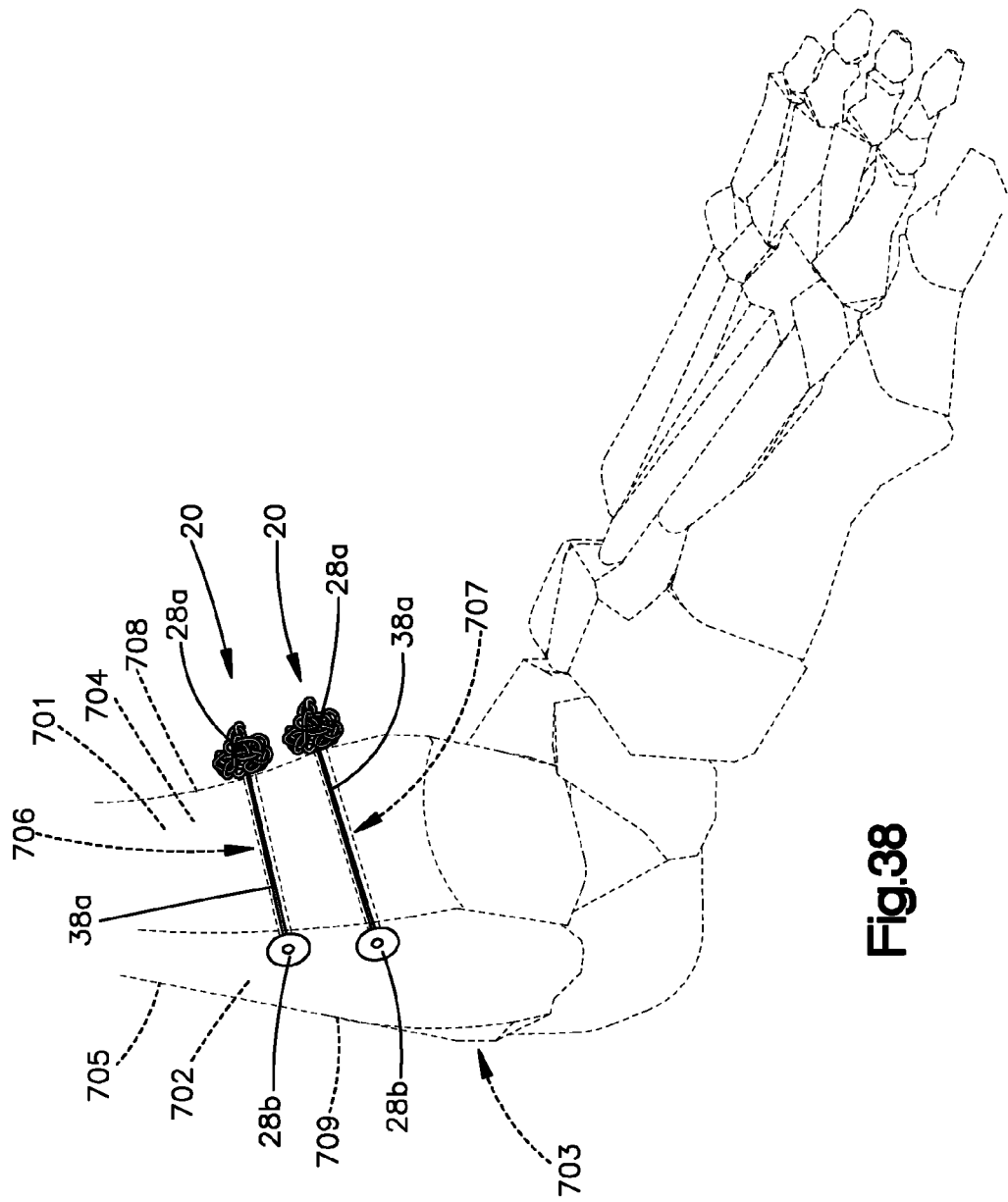
Figure 39:
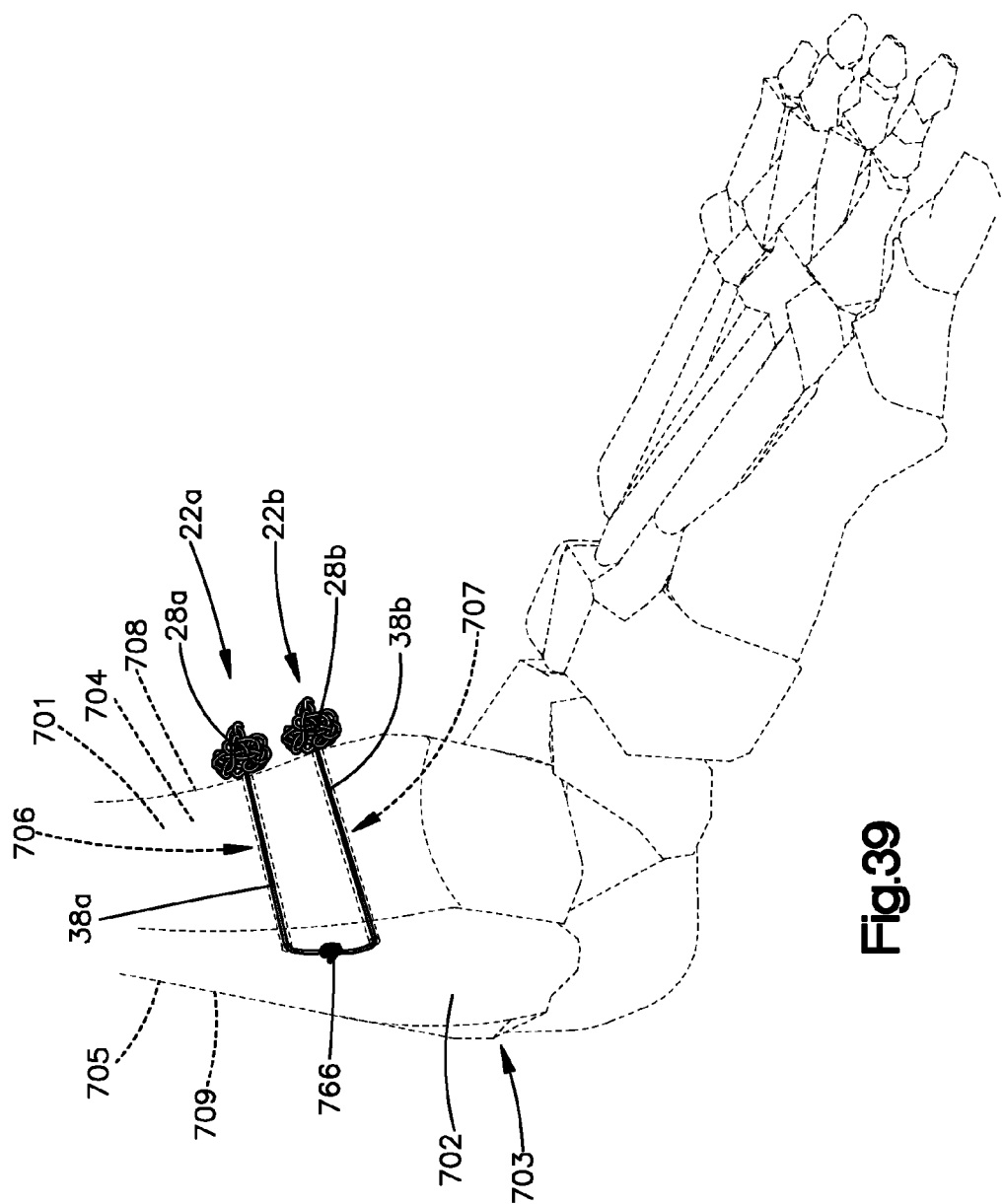
Figure 40B:
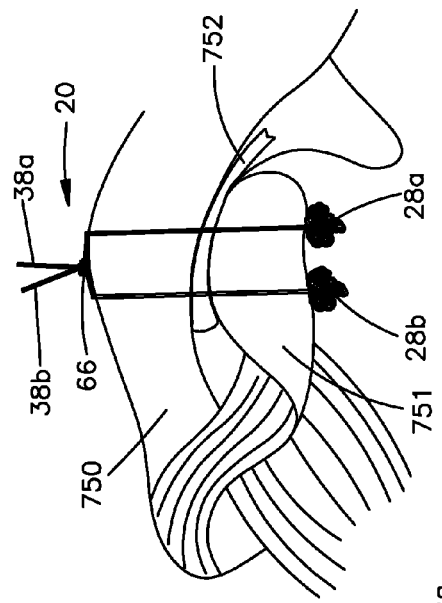
Figure 40A:
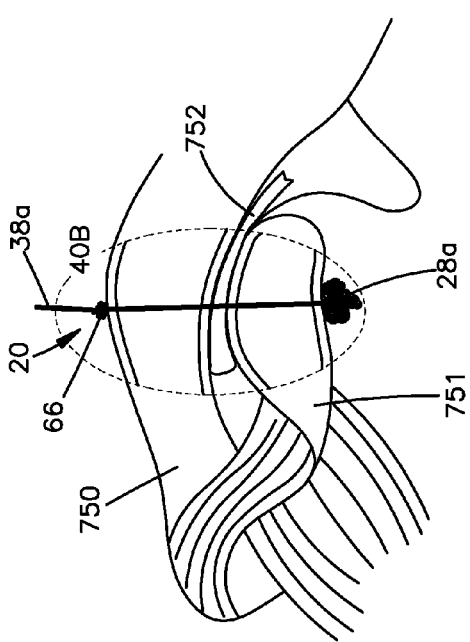
Figure 40C:
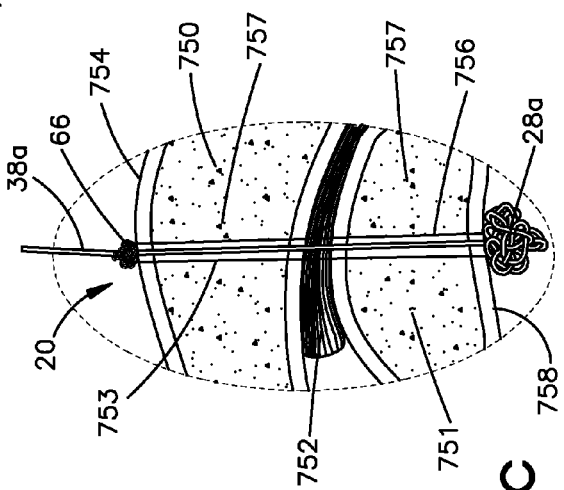
Figure 41C:
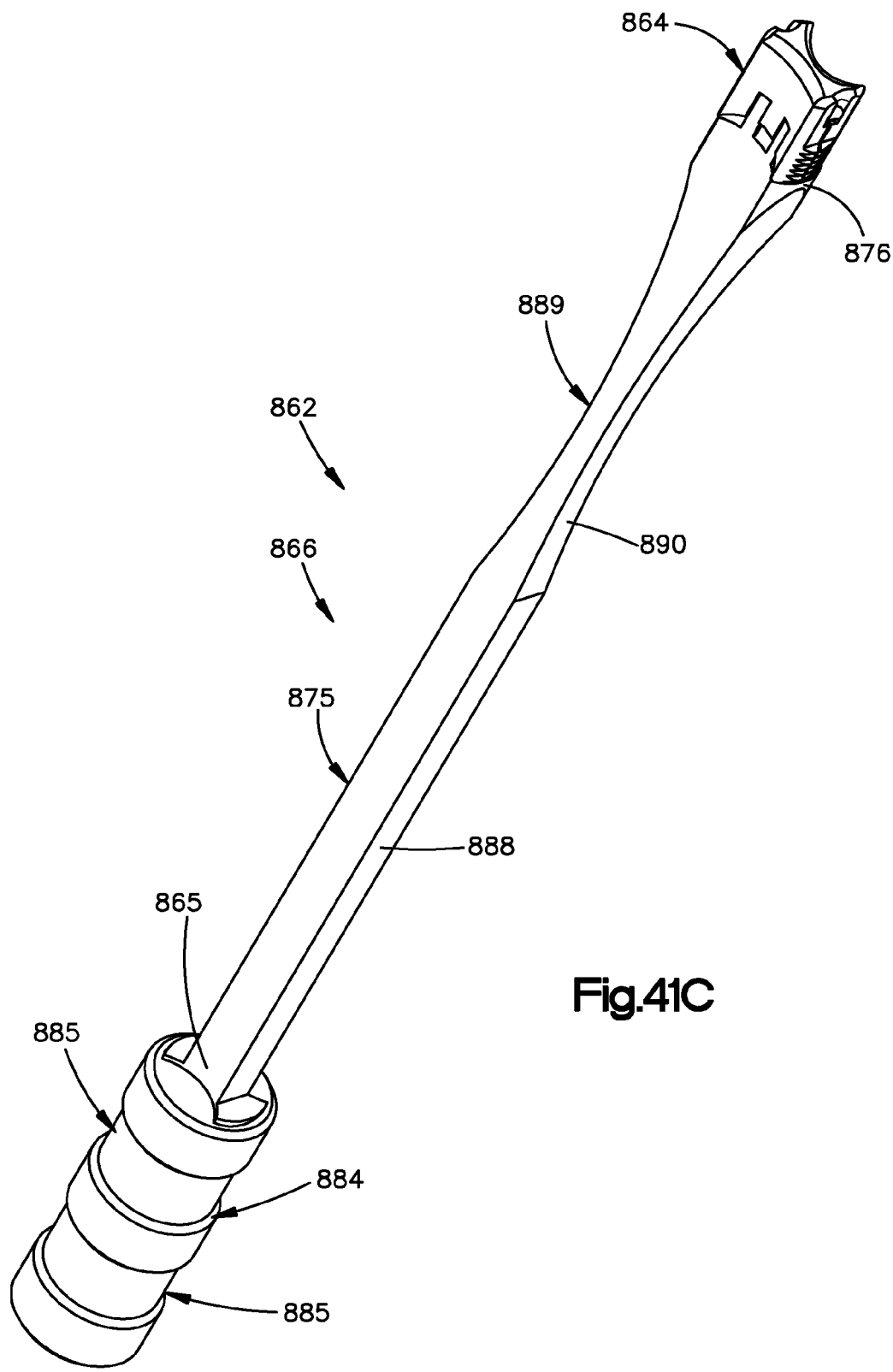
Figure 41D:
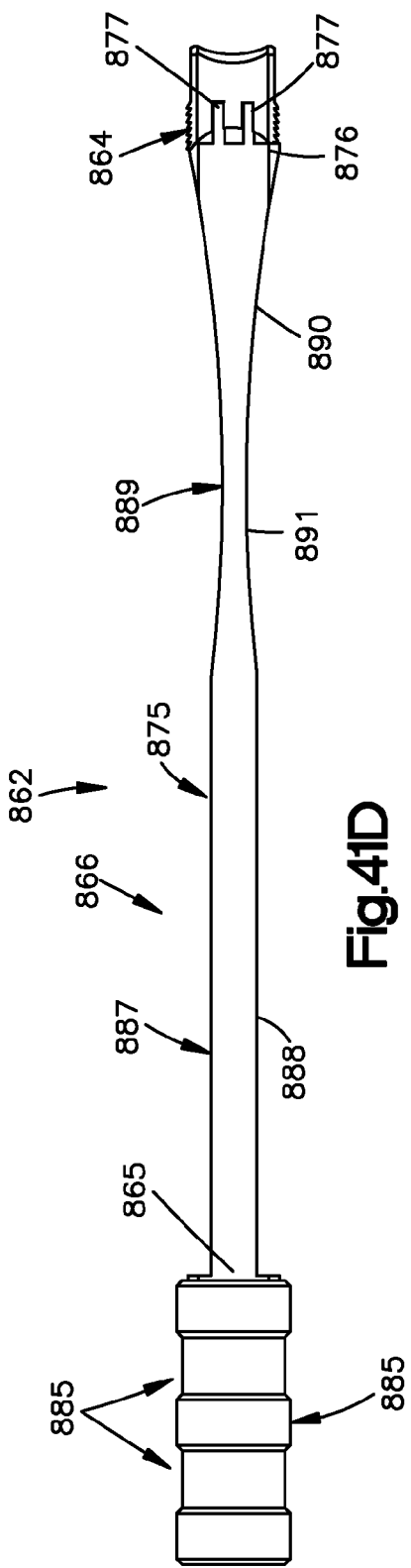
Figure 41E:
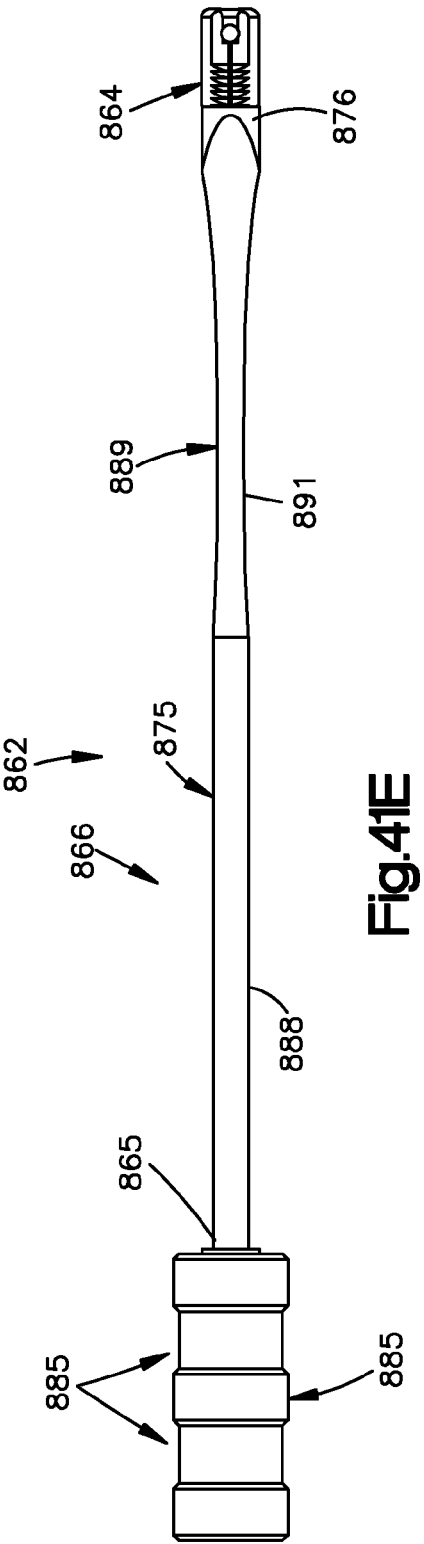
Figure 41G:
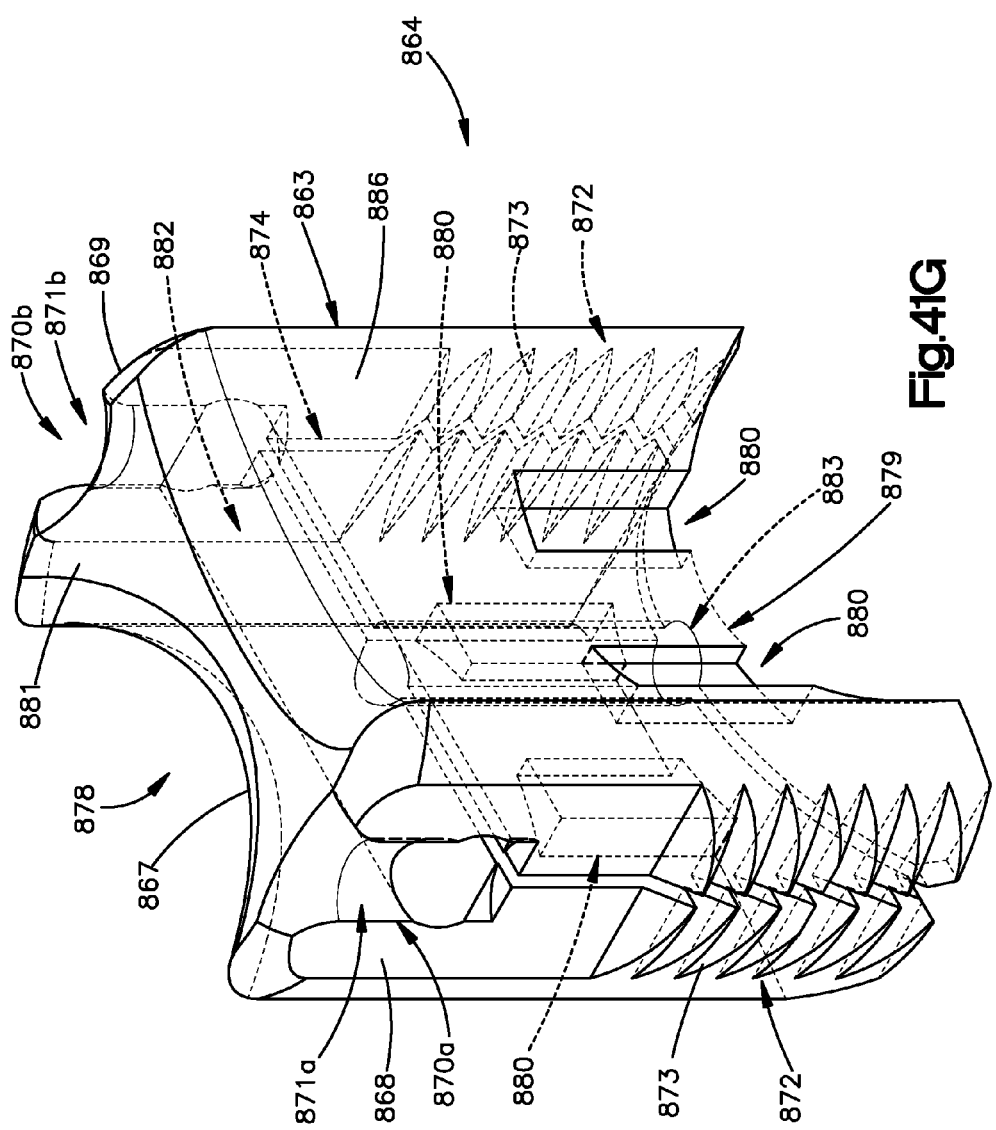
Figure 43A:
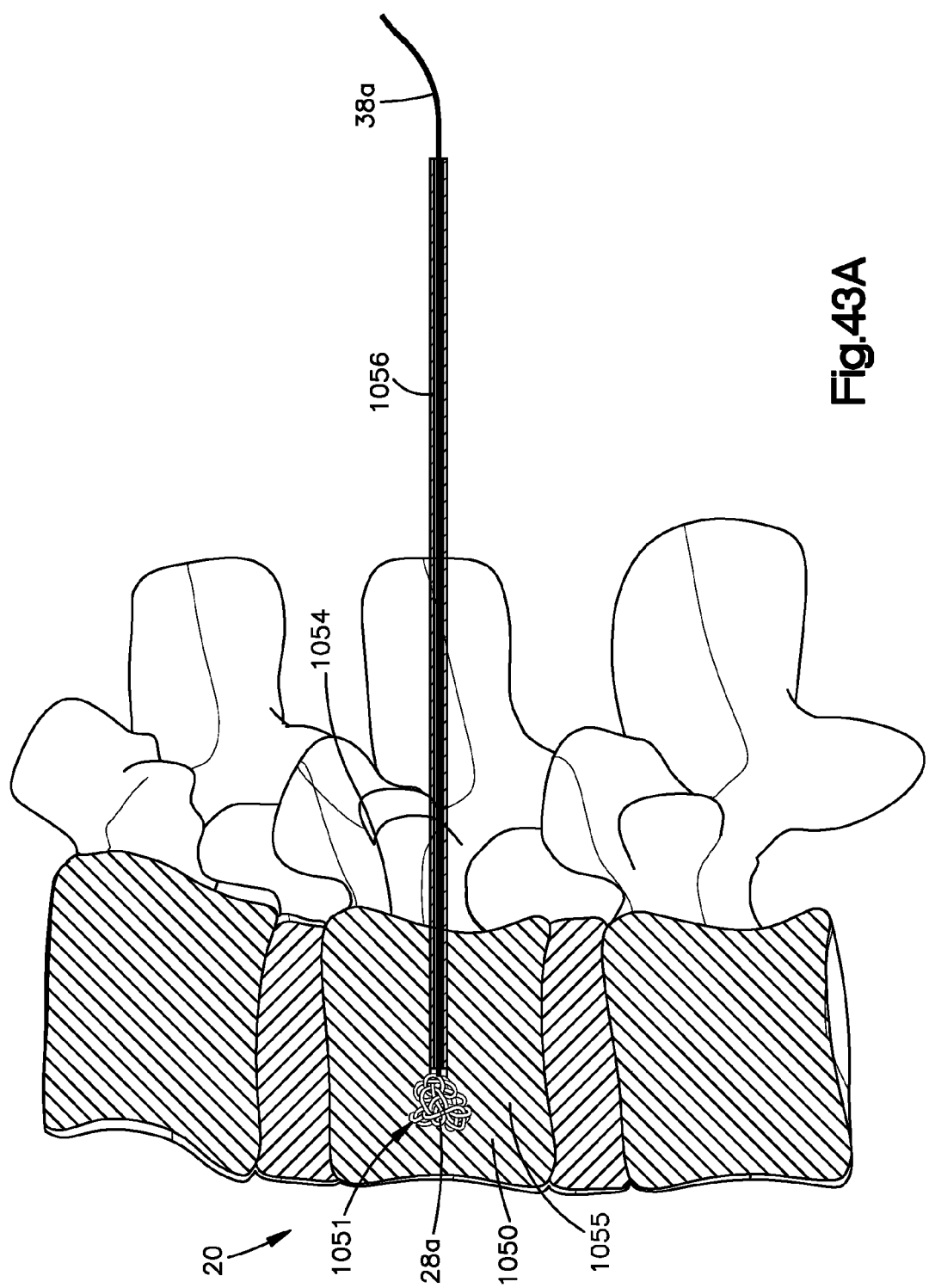
Figure 43B:
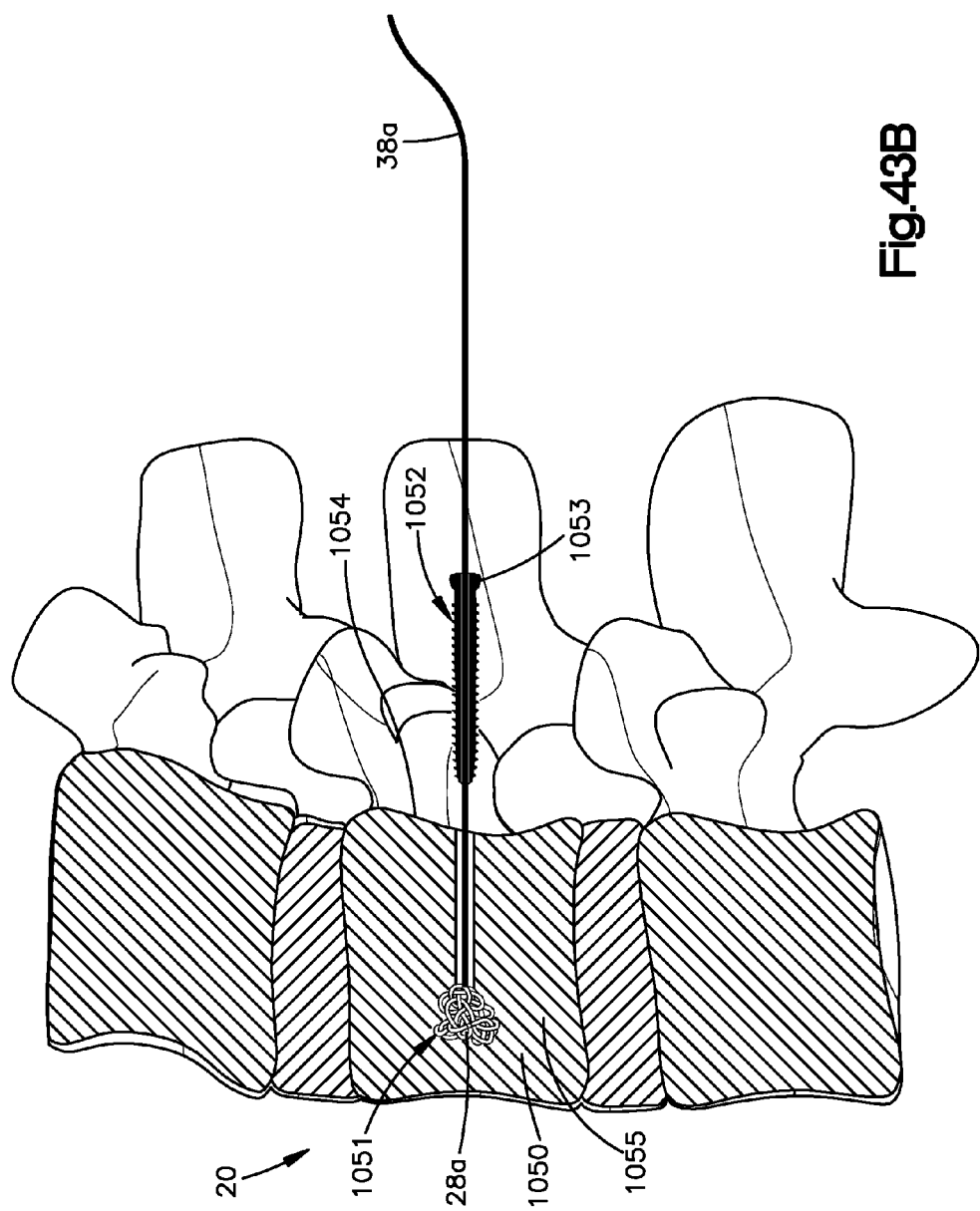

FIG. 37 is a cross-sectional top view of a spine, illustrating a method of repairing a defective or damaged annulus fibrosus;

FIG. 38 is a perspective view of an ankle, a portion of a fibula, and a portion of a tibia, illustrating a method of fixing a first bone to a second bone in accordance with one embodiment;

FIG. 39 is a perspective view of an ankle, a portion of a fibula, and a portion of the tibia, illustrating a method of fixing a first bone to a second bone in accordance with another embodiment;

FIGS. 40A-40C illustrate a method of reconstructing an acromioclavicular (AC) joint;

FIGS. 41A and 41B illustrate a method of anterior cruciate ligament (ACL) reconstruction;

FIG. 41C is a perspective view of an instrument for inserting and attaching a graft into an opening of a bone;

FIG. 41D is front view of the instrument shown in FIG. 41C;

FIG. 41E is a side view of the instrument shown in FIG. 41C;

FIG. 41F is a top view of the instrument shown in FIG. 41C;

FIG. 41G is a perspective view of an attachment member of the instrument shown in FIG. 41C;

FIG. 41H is a front view of the attachment member shown in FIG. 41G;

FIGS. 42A and 42B illustrate a method of meniscal repair;

FIGS. 43A and 43B illustrate a method for using an anchor assembly to guide a pedicle screw;

FIGS. 44A and 44B illustrate a method of augmentation of bone tissue;

FIG. 45 illustrates a method of repairing an rim tear of the annulus fibrosus.

DETAILED DESCRIPTION

Figure 1A:
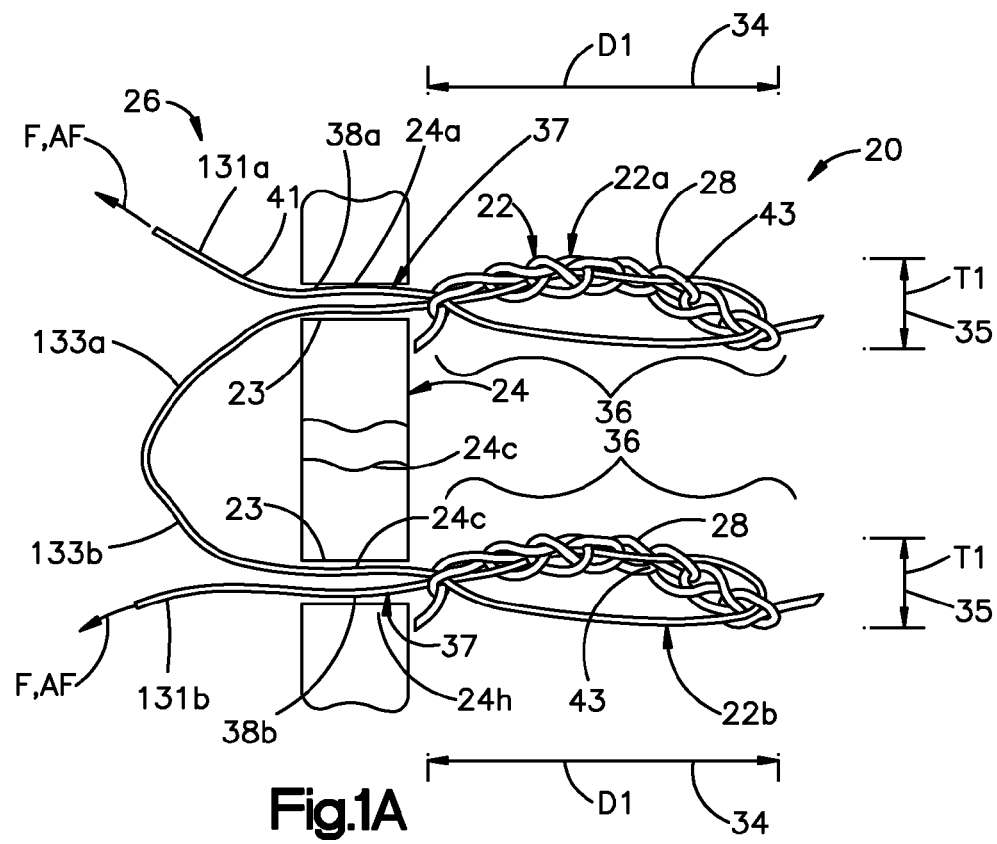
FIG. 1A is a schematic side elevation view of an anchor assembly including a pair of anchor bodies implanted across an anatomical defect and shown in a first configuration.
Figure 1B:
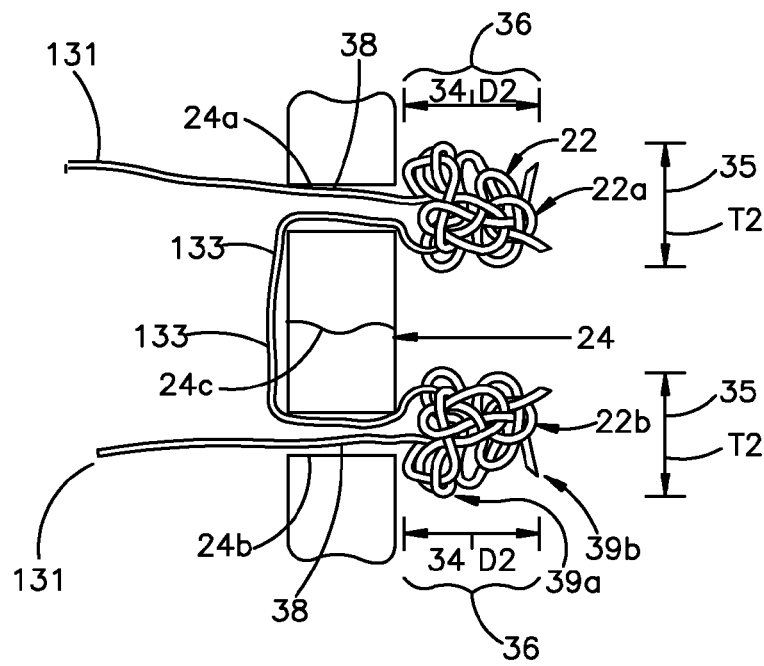
FIG. 1B is a schematic side elevation view of the anchor assembly illustrated in FIG. 1A, showing the anchor bodies in an expanded configuration and in an approximated position.

Referring initially to FIGS. 1A-B, an anchor assembly 20 can include at least one expandable anchor 22 such as a first expandable anchor 22a and a second expandable anchor 22b that, in turn, include respective anchor bodies 28a and 28b that are configured to be secured to an anatomical location, which can be defined by at least one anatomical structure 24. The anatomical structure 24 can be defined by, for instance, anatomy of a human or other animal, or an implant that is secured or configured to be secured to anatomy of a human or other animal. The anatomy can be defined by tissue that can include at least one of bone and soft tissue such as a tendon, a ligament, cartilage, the annulus of an intervertebral disc, or the like.

In accordance with one embodiment, the at least one anatomical structure 24 can define first and second target anatomical locations 24a and 24b on opposite sides of a gap, such as a gap 24c. Thus, the gap 24c can be disposed in an anatomical structure, and can for instance define an anatomical defect, or can be disposed between different anatomical structures. First and second anchors 22a and 22b can be injected or otherwise driven or inserted into the respective first and second target anatomical locations 24a and 24b on opposite sides of the gap 24c, and subsequently drawn toward each other so as to approximate the gap 24c. Alternatively or additionally still, the anchor assembly 20 can be configured to secure an auxiliary structure to the anatomical structure. In this regard, it should be further appreciated that the anchor assembly 20 can include any number of anchors 22 as desired.

Each anchor body 28a and 28b can include a respective expandable portion 36a and 36b, and an actuation member 37a and 37b, such as an actuation strand 38a and 38b, that is configured to actuate the respective expandable portion 36a and 36b, and thus the respective anchor body 28a and 28b, from a first configuration illustrated in FIG. 1A, whereby the anchor body 28a and 28b is initially placed at the target anatomical location, to an expanded configuration illustrated in FIG. 1B, whereby the respective anchor body 28a and 28b can be secured to the anatomical structure 24. Thus, the anchor bodies 28a and 28b of the anchors 22a and 22b can be inserted through an opening 23 at the respective target anatomical locations 24a and 24b that can be created, for example, when delivering the anchor bodies 28a and 28b to the respective target anatomical locations 24a and 24b, for instance by injecting the anchor bodies 28a and 28b to the respective target anatomical locations 24a and 24b.

The expandable portion 36 of the anchor body 28 extends along the direction of elongation 34 so as to define an initial distance D1 as measured from the proximal end 39a to the distal end 39b along the direction of elongation 34 when in the first configuration. The initial distance D1 can be any length as desired, such within a range having a lower end that can be defined by approximately 5 mm, alternatively approximately 10 mm, alternatively still approximately 20 mm, and alternatively still approximately 24.5 mm, and having an upper end that can be defined by approximately 50 mm, alternatively approximately 40 mm, alternatively still approximately 30 mm, and alternatively still approximately 25.5 mm.

Furthermore, when in the first configuration, the expandable portion 36 defines an initial maximum thickness T1 that extends in a second direction 35 that is substantially perpendicular, with respect to the direction of elongation 34. The initial maximum thickness T1 can be sized as desired. As illustrated in FIG. 1B, when the expandable portion 36 in the expanded configuration, the expandable portion 36 is collapsed, for instance compressed or tangled, along the direction of elongation 34 to a second distance D2 as measured from the proximal end 39a to the distal end 39b along the direction of elongation 34. The second distance D2 can be less than the initial distance D1. As the expandable portion 36 collapses along the direction of elongation, for instance as it is actuated from the first configuration to the expanded configuration, the expandable portion 36 expands along the second direction 35 to a second maximum thickness T2 that is greater than the initial maximum thickness T1. The second maximum thickness T2 extends along the second direction 35 which is substantially perpendicular to the direction of elongation 34.

The maximum thicknesses T1 and T2 in the second direction 35 can be defined such the anchor body 28 does not define a thickness in the second direction 35 that is greater than the maximum thicknesses T1 and T2, respectively. It should be appreciated that the proximal and distal ends 39a and 39b can change locations on the expandable portion 36 as the expandable portion 36 actuates to the expanded configuration, for instance due to configuration of the expandable portion 36 when in the expanded configuration. However, when the expandable portion 36 is in the expanded configuration, the proximal and distal ends 39a and 39b continue to define the proximal-most and distal-most ends of the expandable portion 36, such that the distance D2 along the direction of elongation 34 is defined linearly between the proximal and distal ends 39a and 39b of the expandable portion 36 when the expandable portion 36 is in the expanded configuration.

Each of the actuation strands 38 of the first and second anchors 22a and 22b can be attached to each other. For instance, the actuation strand 38 of the first anchor 22a can be integral with the actuation strand 38 of the second anchor 22b. Alternatively, as will be described in more detail below with reference to FIGS. 2A-C, the actuation strand 38 of the first anchor 22a can be separate from the actuation strand 38 of the second anchor 22a, such that the actuation strands 38 of the first and second anchors 22a and 22b are subsequently attached, directly or indirectly, using any suitable connector member 63. The connector member 63 can be integral with either or both of the actuation strands 38a and 38b or can be separately attached to each of the actuation strands 38a and 38b. In accordance with one embodiment, the actuation strands 38a and 38b of each of the first and second anchors 22a and 22b defines at least one respective actuation portion 131a and 131b and can further include at least one respective attachment portion 133a and 133b. The actuation portions 131a and 131b are each configured to receive an actuation force that causes the respective anchor 22a and 22b to actuate from the first configuration to the expanded configuration.

In accordance with the illustrated embodiment, the attachment portions 133a and 133b of the actuation strands 38a and 38b of the first and second anchors are configured to be attached to each other so as to span across the gap 24c and attach the first anchor body 28a to the second anchor body 28b. The attachment portions 133a and 133b can be integral with each other, or attached to each other using any suitable connector member. Furthermore, in accordance with the illustrated embodiment, the actuation portions 131a and 131b can also define attachment portions that are configured to be attached to each other in any suitable manner, either before or after the actuation force F is applied to the actuation portions 131a and 131b. Thus, the attachment portion 133a and 133b of a respective anchor 22a and 22b is configured to attach the respective anchor to another anchor, such as an attachment portion of the other anchor. Furthermore, the actuation portion 131a of the first anchor 22a is configured to attach the respective anchor 22a to the second anchor 22b. In accordance with the illustrated embodiment, the attachment portion 133a of the actuation strand 38a of the first anchor 22a is integral with the attachment portion 133b of the actuation strand 38b of the second anchor 22b, though it should be appreciated that the attachment portions 133a-b of the first and second anchors 22a-b can be separate from each other and attached to each other, as described in more detail below.

With continuing reference to FIGS. 1A-B, once the expandable portions 36a-b of the anchors 22a-b have actuated to the expanded configuration, the actuation strands 38a-b can be placed in tension. For instance, in accordance with one embodiment, an approximation Force AF can be applied to either or both of the actuation portion 131a-b of the actuation strands 38a-b of the first and second anchors 22a-b, thereby inducing a tension in the actuation strands 38a-b of the first and second anchors 22a-b so as to apply a biasing force that draws the first and second anchors 22a and 22b toward each other. Accordingly, if a gap 24c is disposed between the first and second anchors 22a and 22b, movement of the anchors 22a and 22b toward each other in response to the biasing force approximates the gap 24c which, in certain embodiments, can be an anatomical defect, such as a tissue defect as described above.

Furthermore, when the actuation strands 38a-b are maintained in tension after the defect 24 has been approximated, the anchor bodies 28a-b are prevented from backing out from the anatomy through the respective target locations 24a-b, which could allow the gap 24c to open. Thus, once the gap 24c has been approximated, the actuation strand 38a of the first anchor 22a can be attached to the actuation strand 38b of the second anchor 22b so as to maintain tension between the first and second anchors 22a and 22b and prevent the first and second anchors 22a and 22b from separating.

The anchor bodies 28a and 28b can be constructed by weaving any suitable substrate, such as a strand, for instance a strand of suture, in any manner desired so as to produce a plurality of openings 43 that extend through the respective anchor bodies 28a and 28b. The first and second actuation strands 38a and 38b can be woven through at least two of the openings 43 along the direction of elongation 34 of the anchor bodies 28a and 28b.

In accordance with the embodiment illustrated in FIGS. 1A-1F, the first and second actuation strands 38a and 38b are integral with the respective first and second anchor bodies 28a and 28b. In accordance with other embodiments, the first and second actuation strands 38a and 38b are illustrated as separate from and attached to the respective first and second anchor bodies 28a and 28b (see FIG. 2C). In accordance with still other embodiments, one of the first and second actuation strands 38a and 38b is integral with the respective anchor body and the other of the first and second actuation strands 38a and 38b is separate from and attached to the respective anchor body. In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated. Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated.

Referring to FIGS. 1C-1F, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b, can be integral with one or both of the first and second anchor bodies, or can be separate from and attached (directly or indirectly) to one or both of the first and second anchors 22a and 22b. For instance, the connector member 63 can be separate from and attached between the first and second anchors 22a and 22b, as will be described in more detail below. While connector members 63 are described herein in accordance with various embodiments, it should be appreciated that the anchor assembly 20 can alternatively include any suitable connector member configured to attach the first anchor 22a to the second anchor 22b.

Figure 2A:
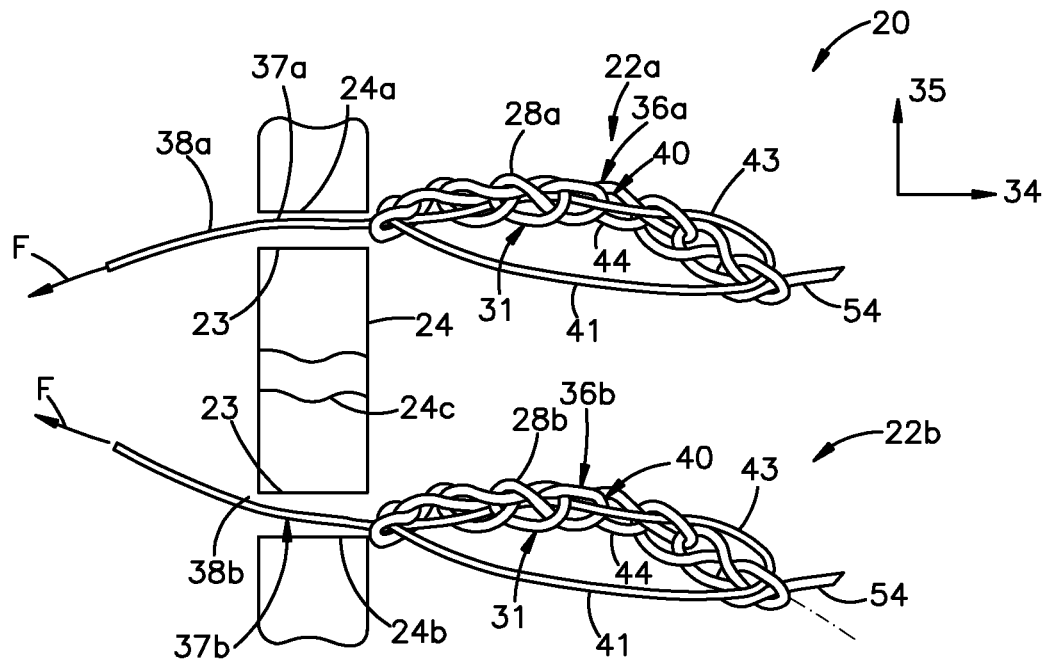
FIG. 2A is a side elevation view of an anchor assembly including first and second anchors implanted in an anatomical structure on opposed sides of an anatomical defect and shown in a first configuration.

The anchor assembly 20 can include a connector member 63 that is integral with the corresponding actuation strands 38a and 38b. As described above, each of the first and second anchor bodies 28a and 28b can be implanted at respective first and target anatomical locations 24a and 24b that are disposed on opposite sides of a gap 24c as illustrated in FIG. 2A. Each of the first and second actuation strands 38a and 38b can receive an actuation force F substantially along the direction of elongation 34 that causes the respective first and second anchor bodies 28a and 28b, and in particular the respective expandable portions 36a and 36b, to actuate from the first configuration to the expanded configuration so as to fix the first and second anchor bodies 28a and 28b at the respective first and second target anatomical locations 24a and 24b. The actuation force F applied to each of the actuation strands 38a and 38b can be in the form of different actuation forces, or can be the same actuation force.

Figure 1C:
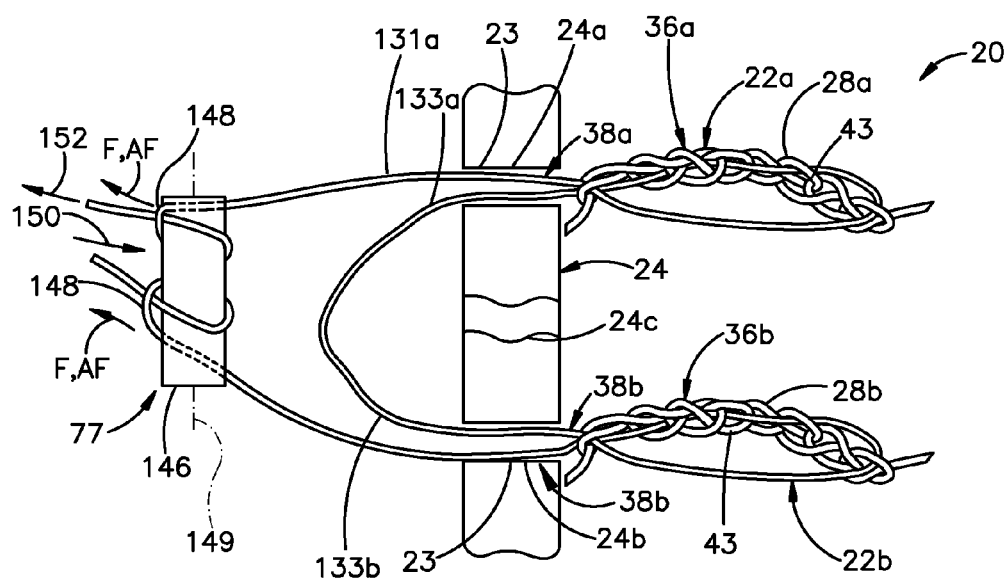
FIG. 1C is a side elevation view of an anchor assembly including the anchor bodies illustrated in FIG. 1A and a connector member configured to attach actuation portions of the anchor bodies, showing the anchor bodies in the first configuration.
Figure 1D:
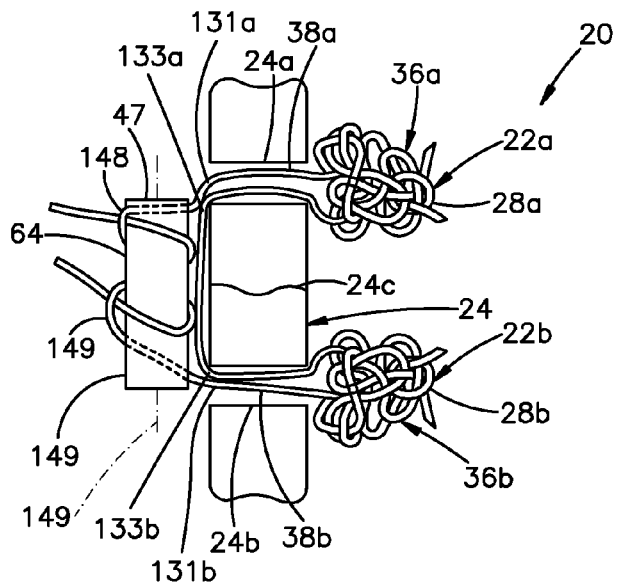
FIG. 1D is a side elevation view of the anchor assembly illustrated in FIG. 1C, showing the connector member tightened with the anchor bodies in the expanded configuration.

For instance, referring to FIGS. 1C-1D, the connector member 63 can be configured as an auxiliary connector member 77, that is a connector member that is separate from one or both of the first and second actuation strands 38a and 38b and configured to attach to the first and second actuation strands 38a and 38b to each other. For instance, the auxiliary connector member 77 can be made from any suitable metal, plastic, or any alternative biocompatible material, and can be configured as a body 146, which can be flexible or rigid, that is configured to attach to either or both of the first actuation strands 38a and 38b, and in particular to the actuation portions 131a-b, at a location between the anchors 22a and 22b. For instance, each of the first and second actuation portions 131a-b can be stitched through the body 146 and tied about the body 146 so as to define a knot 148 that can be actuated from an unlocked configuration to a locked configuration. The first and second actuation portions 131a-b are slidable with respect to the body 146 when the knots 148 are in the unlocked configuration, and fixed with respect to sliding movement relative to the body 146 when the knots 148 are in the locked configuration. The body 146 can define any shape as desired, such as substantially cylindrical, and can be flexible or substantially rigid as desired.

During operation, the actuation portions 131a-b can be stitched through the body 146 along a direction away from the anatomical structure 24 and tied about the body 146 such that the respective knots 148 are in the unlocked configuration. The body 146 can be oriented such that its long axis 149 is oriented substantially parallel to the anatomical structure 24. The body 146 can be translated along the first and second actuation strands 38a and 38b along the direction of Arrow 150 toward the anatomical structure 24 while the actuation strands 38a and 38b are under tension, which causes the actuation strands 38a and 38b to translate relative to the body 146 along an opposite direction indicated by Arrow 152. As the body 146 translates along the actuation strands 38a and 38b toward the gap 24c, the body 146 applies the actuation force F to the actuation strands 38a and 38b, thereby causing the anchors 22a and 22b to actuate from the first configuration to the expanded configuration.

As the body 146 further translates toward the gap 24c after the anchors 22a and 22b have been actuated to their expanded configuration, the body 146 applies the approximation force AF to at least one or both of the actuation strands 38a and 38b that draws at least one or both of the anchors 22a and 22b inward toward the other, thereby approximating the gap 24c. In this regard, it should be appreciated that the approximation force AF can be a continuation of the actuation force F. Alternatively, the actuation force F can be applied to the actuation strands 38a and 38b at a location upstream of the body 146, or prior to attaching the actuation strands 38a and 38b to the body 146. The knot 148 can then be tightened so as to secure the first and second actuation strands 38a and 38b to the body 146, and therefore also to each other so as to prevent separation of the first and second anchors 22a and 22b. Once the gap 24c has been approximated, the body 146, and thus the knots 148, can be disposed along the outer surface of the anatomical structure 24. Alternatively, the body 146 can be sized such that a portion of the body 146, and thus the knots 148, is disposed in the opening 23 that receives the anchor bodies 28a and 28b once the gap 24c has been approximated. Accordingly, the knots 148 can be disposed behind the anatomical structure 24, or can be embedded in the anatomical structure 24.

The body 146 can thus define a sliding member 47 that allows one of the first and second actuation strands 38a and 38b to slide with respect to the other of the first and second actuation strands 38a and 38b so as to approximate the gap 24c, and can further define a locking member 64 that secures the first and second actuation strands 38a and 38b to each other, for example with respect with respect to relative movement that would allow the first and second anchor bodies 28a and 28b to separate.

Figure 1E:
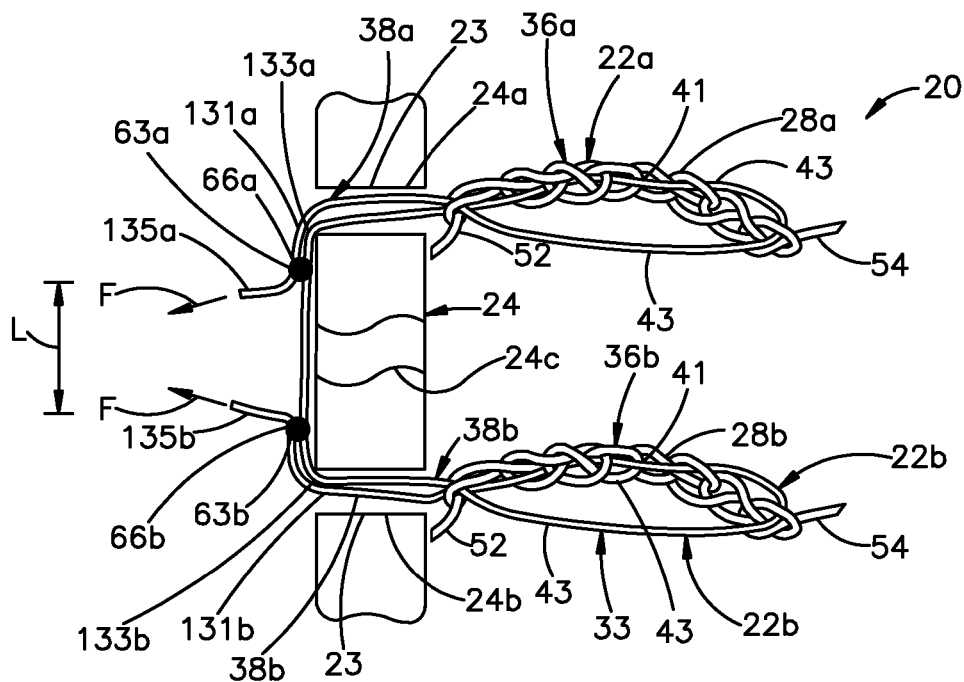
FIG. 1E is a side elevation view of an anchor assembly similar to FIG. 1C, but including an integral connector member.
Figure 1F:
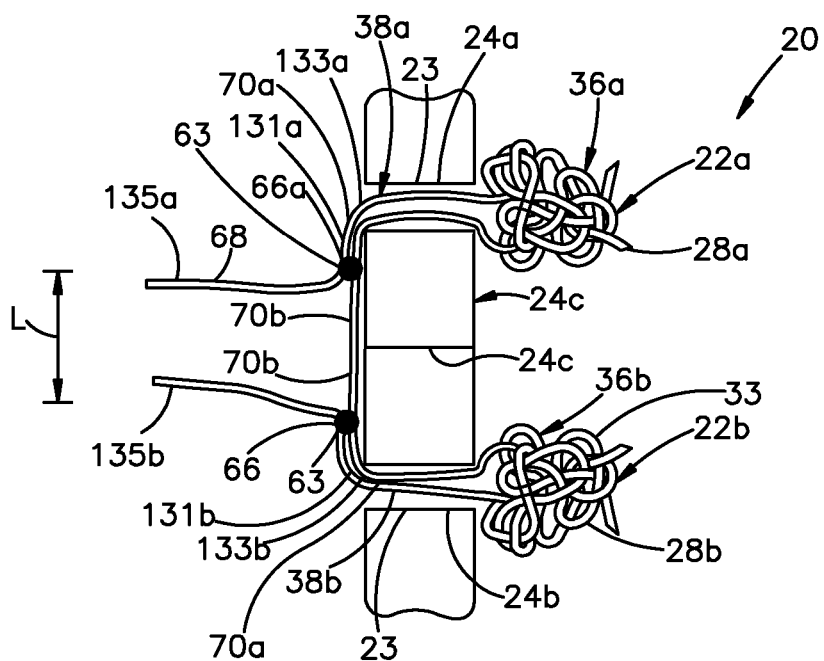
FIG. 1F is a side elevation view of the anchor assembly illustrated in FIG. 1E, showing the connector member tightened with the anchor bodies in the expanded configuration.

Referring now to FIGS. 1E-1F, the anchor assembly 20 can include a pair of connector members 63a and 63b configured to attach at least one or both of the actuation portions 131a and 131b to the respective attachment portions 133a and 133b. In accordance with the illustrated embodiment, the actuation strands 38a and 38b are defined by a common actuation member, such as a common strand, which can be an auxiliary strand 33 that is separate from, and woven through, at least one such as a pair or a plurality of openings of both the first and second anchor bodies 28a-b, such that the respective attachment portions 133a and 133b are integral with each other. Thus, in accordance with the illustrated embodiment, the first and second actuation strands 38a and 38b are integral with each other. The anchor assembly 20 can include first and second connector members 63a and 63b that are defined by the actuation strands 38a and 38b, and are configured to attach the actuation portions 131a and 131b to other locations of the common strand, and thus to each other. In accordance with the illustrated embodiment, the first and connector member 63a can attach the corresponding first actuation portion 131a to another location of the auxiliary strand 33 that is spaced from the first actuation portion 131a. Likewise, the second and connector member 63b can attach the corresponding second first actuation portion 131b to another location of the auxiliary strand 33 that is spaced from the second first actuation portion 131b. For instance, in accordance with the illustrated embodiment, the first connector member 63a attaches the first actuation portion 131a to the first attachment portion 133a, and the second connector member 63b attaches the second actuation portion 131b to the second attachment portion 133b.

Thus, it can be said that at least one connector member, such as the first and second connector members 63a and 63b, can attach the first and second actuation portions 131a and 131b to respective other locations of the auxiliary strand 33 so as to attach the first and second actuation portions 131a and 131b to each other, for instance indirectly through at least one or both of the attachment portions 133a and 133b. It can further be said that the first connector member 63a operably attaches one portion of the first actuation strand 38a to another location of the actuation strand 38a, and the second connector member 63b operably attaches one portion of the second actuation strand 38b to another location of the second actuation strand 38b. Alternatively, it should be appreciated that the first and second connector members 63a and 63b can attach the respective first and second actuation portions 131a and 131b to the anchor body 28, such as at respective first and second end portions 52 and 54. While the actuation strands 38a and 38b are illustrated as separate from each other, the actuation strands 38a and 38b can alternatively be attached to each other, for instance via any suitable connector member 63 of the type described herein, so as to define an outer connector strand.

In accordance with the illustrated embodiment, each of the first and second connector members 63a and 63b can be configured as respective knots 66a and 66b that are defined by the auxiliary strand 33. In accordance with the illustrated embodiment, the first knot 66a includes a post end 68, which can be defined by the actuation portion 131a of the first actuation strand 38a, and a free end, which can include a static portion 70a that is defined by a first end 137a of the first attachment portion 133a and a free portion 70b that is defined by a second end 139a of the first attachment portion 133a. The first end 137a can be disposed between the knot 66a and the first anchor body 28a, and the second end 139a can be disposed between the knot 66a and the second connector member 63b. Alternatively, the free portion 70b can be defined by the attachment portion 133b of the second actuation strand 38b.

In accordance with one embodiment, the second knot 66a includes a post end 68, which can be defined by the actuation portion 131b of the second actuation strand 38b, and a free end, which can include a static portion 70a that is defined by a first end 137b of the second attachment portion 133b and a free portion 70b that is defined by a second end 139b of the second attachment portion 133b. The first end 137b can be disposed between the knot 66b and the second anchor body 28b, and the second end 139b can be disposed between the knot 66b and the first connector member 63a. Alternatively, the free portion 70b can be defined by the attachment portion 133a of the first actuation strand 38a. The attachment portions 133a and 133b are illustrated as being integral with each other, though it should be appreciated that the attachment portions 133a and 133b can be separate and attached to each other as desired.

Each of the first and second knots 66a and 66b can define respective sliding members 47 that allow the respective post ends 68 to translate therethrough relative to the free ends. Thus, the sliding members 47 allow the first and second actuation portions 131a and 131b to translate relative to the first and second attachment portions 133a and 133b, for instance in response to the applied actuation force F when the knots 66a and 66b are in unlocked configurations, thereby actuating the respective anchor body 28a and 28b from the first configuration to the expanded configuration. Each knot 66 further defines a locking member 64 that can be actuated to a locked configuration so as to secure the at least one or both of the anchors 22a and 22b in their respective biased positions. For instance, a tensile locking force can be applied to the free portions 70b of the free ends of the knots 66a and 66b so as to prevent the actuation portions 131a and 131b from translating through the knots 66a and 66b relative to the attachment portions 133a and 133b.

The first and second knots 66a and 66b can be spaced apart a fixed distance L along the auxiliary strand 33, such that the gap 24c is maintained approximated when the anchor bodies 22a and 22b are inserted into the respective target anatomical locations 24a and 24b. For instance, the gap 24c can be approximated prior to injecting the knots 66a and 66b into the respective target anatomical locations 24a and 24b. During operation, once the first and second anchors 22a and 22b are implanted at the respective first and second target anatomical locations 24a and 24b, the knots 66a-b can be in an unlocked configuration such that application of the actuation force F to the respective actuation strands 38a-b, for instance the actuation portions 131a-b, causes the respective anchor bodies 28a-b to actuate from the first configuration to the expanded configuration. Next, a tensile locking force can be applied to the respective attachment portions 133a-b against the corresponding knots 66a-b, so as to actuate the knots 66a-b to their locked configurations and maintain the anchor 22a-b in their expanded configurations.

The distance L between the first and second knots 66a and 66b can be substantially equal to or less than the distance between the target anatomical locations 24a and 24b, such that the gap 24c is approximated when the first and second anchors 22a and 22b are expanded behind the anatomy and joined by the auxiliary strand 33, such that tension induced in the actuation strands 38a and 38b maintains the approximation of the gap 24c. While the first and second connector members 63a-b can be configured as respective knots 66, it should be appreciated that either or both of the first and second connector members 63a and 63b can be alternatively configured as any suitable locking member 63 of any type described herein or any suitable alternatively constructed locking member. For instance, at least one or both of the connector members 63a-b can define a splice, whereby the respective actuation strands 38a-b can be spliced through the other of the actuation strands 38a-b or itself, and the connector strand is placed in tension after actuation of the anchors 22a and 22b so as to apply a compressive force that prevents translation of the anchor strands 38a-b.

It should be appreciated that the anchor bodies 28a and 28b can be constructed in accordance with any suitable embodiment as desired. For instance, referring now to FIGS. 1G-1H, each of the anchor bodies 28a and 28b can include an eyelet 90 that extends from a distal end of the respective expandable portions 36a and 36b. The actuation strand 38 can be configured as an auxiliary strand 33 that is separate from the anchor bodies 28. The actuation strand can be woven through the anchor bodies 28a and 28b, and can extend through the respective eyelets 90a and 90b so as to define a path for the eyelets 90a and 90b to travel through the respective anchor bodies 28a and 28b when the anchor bodies 28a and 28b are actuated from the first configuration to the expanded configuration. The auxiliary strand 33 can thus attach the first anchor body 28a to the second anchor body 28b, and can further be configured to receive the actuation force F that cases the anchor bodies 28a and 28b to actuate from the first configuration to the expanded configuration once implanted in the respective target anatomical locations 24a and 24b.

As described above, the anchor assembly 20 can include any suitable connector member 63 that can be configured to attach to the first and second actuation portions 131a and 131b, thereby attaching the first and second actuation strands 38a and 38b to each other, and also attaching the anchors 22a and 22b to each other. The first and second actuation strands 38a and 38b are illustrated as integral with each other, and thus define a common actuation strand. Alternatively, the first and second actuation strands 38a and 38b can be separate from each other and attached to each other in any manner desired.

Figure 1G:
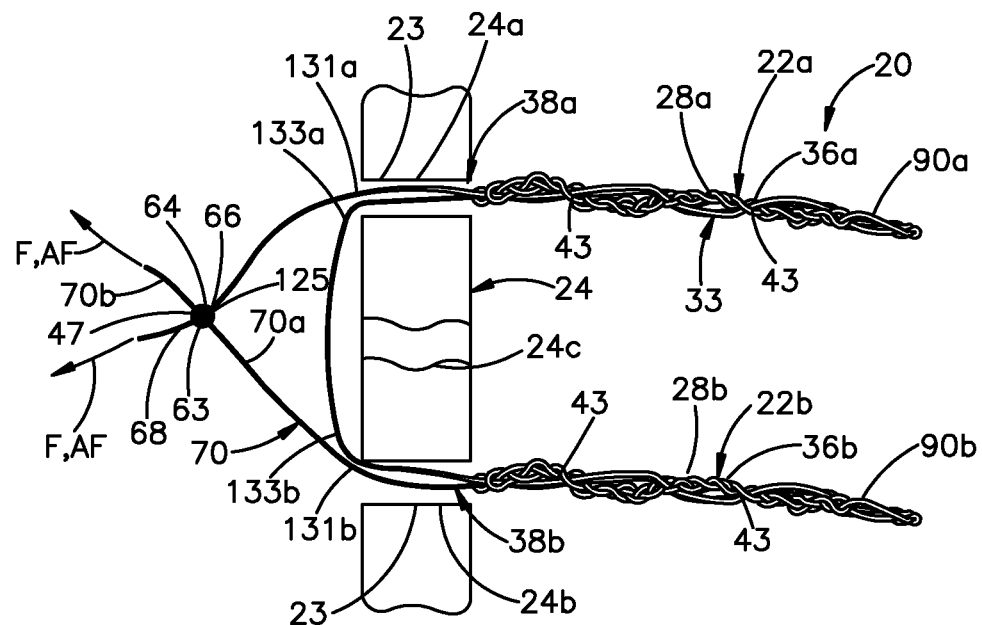
FIG. 1G is a schematic side elevation view of an anchor assembly including a pair of anchor bodies constructed in accordance with an alternative embodiment, shown implanted across an anatomical defect and shown in a first configuration.
Figure 1H:
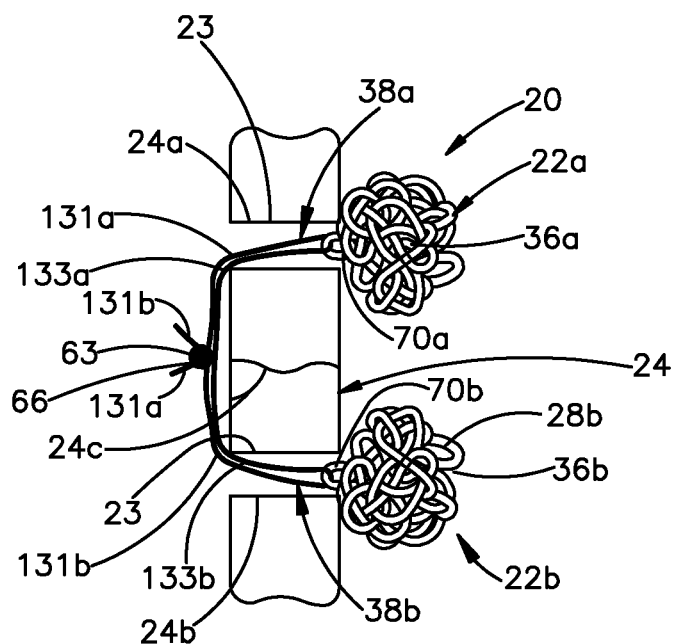
FIG. 1H is a schematic side elevation view of the anchor assembly illustrated in FIG. 1G, showing the anchor bodies in an expanded configuration and in an approximated position.

In accordance with the embodiment illustrated in FIGS. 1G-H, the connector member 63 is defined by and integral with the first and second actuation strands 38a and 38b. Thus, the actuation portions 131a and 131b of the actuation strands 38a and 38b are attached directly to each other. The connector member 63 can define a sliding member 47 and a locking member 64 at a junction 125. For instance, the connector member 63 can define a knot 66 that can be constructed as desired, and can be defined by one or both of the actuation strands 38a and 38b. Thus, at least a portion of the connector member 63 can be integral with at least one or both of the actuation strands 38a and 38b.

One of the first and second actuation strands 38a and 38b can define the post end 68 of the knot 66, and the other of the first and second actuation strands 38a and 38b can define the free end 70 of the knot 66. In accordance with the illustrated embodiment, the first actuation strand, such as the first actuation portion 131a, defines the post end 68 and the second actuation strand 38b, such as the second actuation portion 131b, defines the free end 70.

The first and second actuation strands 38a and 38b can be tied into the knot 66 prior to applying tension to the actuation strands 38a and 38b that biases the first and second anchors 22a and 22b toward each other and approximates the gap 24c. Once the knot 66 is formed, and when the knot 66 is in an unlocked configuration, the actuation force F can be applied to the actuation strands 38a and 38b, and in particular to the actuation portions 131a-b, so as to actuate the respective expandable portions 36 from the first configuration to the expanded configuration. Next, the approximation force AF can be applied to the terminal portion 135a of the first actuation strand 38a, which defines the post strand 68, thereby causing the post end 68 to slide through the knot 66 and draw the respective anchor, such as the first anchor 22a, toward the other anchor, such as the second anchor 22b. Once the gap 24c has been approximated, the free strand 70b of the free end 70, for instance defined by the terminal portion 135b of the second actuation strand 38b, can be placed in tension so as to lock knot 66 and prevent the first actuation strand 38a from translating through the knot 66, thereby fixing the actuation strands 38a and 38b in tension. While the connector member 63 can be configured as the knot 66, it should be appreciated that the connector member 63 can alternatively be configured in accordance with any embodiment described herein or any suitable alternative connector as desired.

Figure 2B:
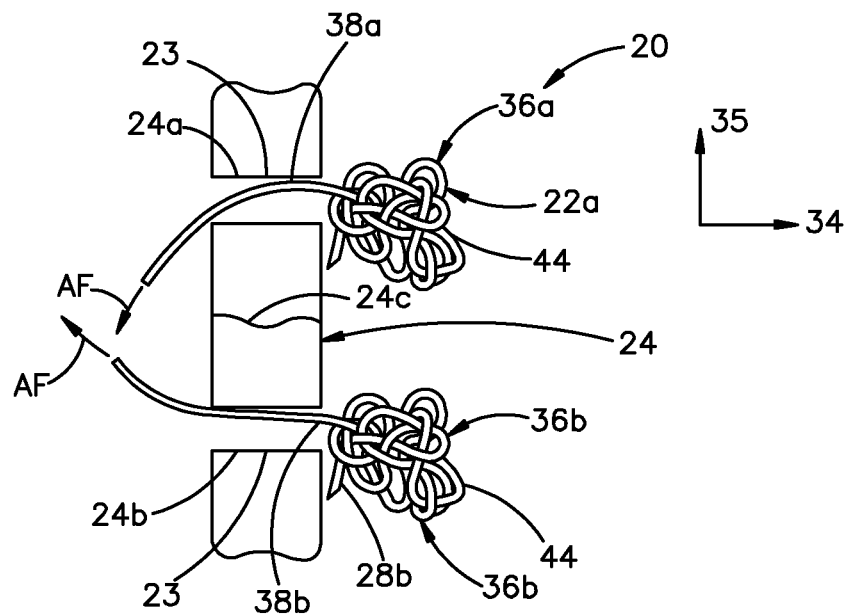
FIG. 2B is a side elevation view of the anchor assembly illustrated in FIG. 2A, showing the first and second anchors in respective expanded configurations.
Figure 2C:
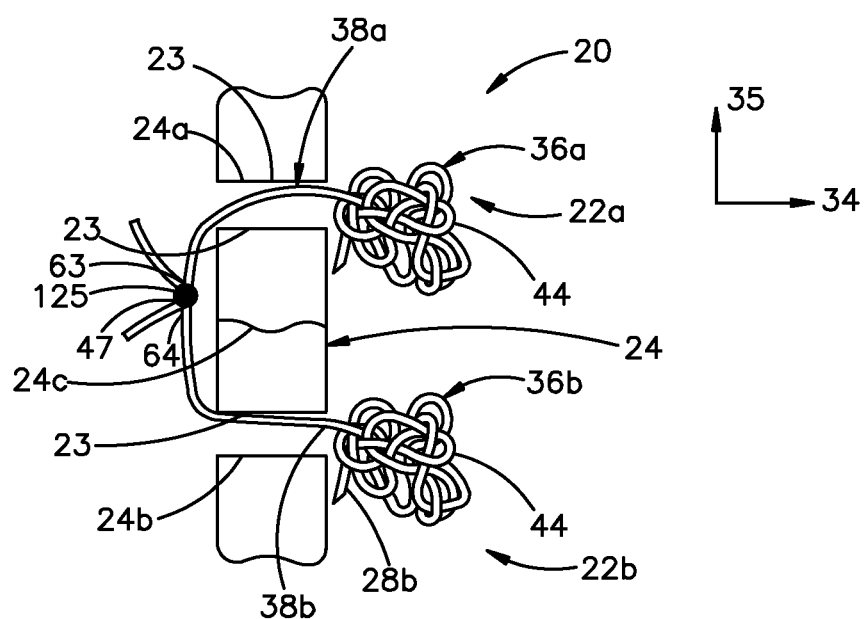
FIG. 2C is a side elevation view of the anchor assembly illustrated in FIG. 2A, including a connector member that attaches the first anchor to the second anchor.

Referring now to FIGS. 2A-C, and as generally described above with respect to FIGS. 1A-B, the anchor assembly 20 can include first and second anchors 22a and 22b. The first anchor 22a includes a first anchor body 28a that extends substantially along the direction of elongation 34 and defines a first plurality of openings 40a that extend through the first anchor body 28a. The first anchor 22a further includes a first actuation strand 38a that extends through at least one of the openings 40a, such as a plurality of the openings, and is configured to receive an actuation force F that causes the first anchor body 28a to actuate from the first configuration to the expanded configuration in the manner described above. The first actuation strand 38a can be separate from and attached to, for instance woven through openings of, the first anchor body 28a, or can be integral with the first anchor body 28a and extend through openings of the first anchor body 28a.

The second anchor 22b includes a second anchor body 28b that extends substantially along the direction of elongation 34 and defines a second plurality of openings 40b that extend through the second anchor body 28b. The second anchor 22b further includes a second actuation strand 38b that extends through at least one of the openings 40b, such as a plurality of the openings, and is configured to receive an actuation force F that causes the second anchor body 28b to actuate from the first configuration to the expanded configuration in the manner described above. The second actuation strand 38b can be separate from and attached to, for instance woven through openings of, the second anchor body 28b, or can be integral with the second anchor body 28b and extend through openings of the second anchor body 28b.

In accordance with the embodiment illustrated in FIGS. 2A-B, the first and second actuation strands 38a and 38b are integral with the respective first and second anchor bodies 28a and 28b. In accordance with other embodiments, the first and second actuation strands 38a and 38b are illustrated as separate from and attached to the respective first and second anchor bodies 28a and 28b. In accordance with still other embodiments, one of the first and second actuation strands 38a and 38b is integral with the respective anchor body and the other of the first and second actuation strands 38a and 38b is separate from and attached to the respective anchor body. In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated. Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated.

With continuing reference to FIG. 2C, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b, can be integral with one or both of the first and second anchor bodies, or can be separate from and attached (directly or indirectly) to one or both of the first and second anchors 22a and 22b. For instance, the connector member 63 can be separate from and attached between the first and second anchors 22a and 22b, as will be described in more detail below. While connector members 63 are described herein in accordance with various embodiments, it should be appreciated that the anchor assembly 20 can alternatively include any suitable connector member configured to attach the first anchor 22a to the second anchor 22b. At least one or both of the actuation strands 38a-b can be configured to receive an approximation force AF that biases at least one of the first and second anchors 22a and 22b toward the other so as to approximate the gap 24c.

The anchor assembly 20 can include a connector member 63 that is integral with the corresponding actuation strands 38a and 38b. As described above, each of the first and second anchor bodies 28a and 28b can be implanted at respective first and target anatomical locations 24a and 24b that are disposed on opposite sides of a gap 24c as illustrated in FIG. 2A. Each of the first and second actuation strands 38a and 38b can receive an actuation force F substantially along the direction of elongation 34 that causes the respective first and second anchor bodies 28a and 28b, and in particular the respective expandable portions 36a and 36b, to actuate from the first configuration to the expanded configuration so as to fix the first and second anchor bodies 28a and 28b at the respective first and second target anatomical locations 24a and 24b. The actuation force F applied to each of the actuation strands 38a and 38b can be in the form of different actuation forces, or, as is described in more detail below, can be the same actuation force.

Referring now to FIG. 2B, once the first and second anchor bodies 28a and 28b are secured to the respective first and second target anatomical locations 24a and 24b, an approximation force AF can be applied to at least one or both of the first and second actuation segments 38a and 38b substantially along a direction toward the other of the respective first and second anchor bodies 28a and 28b, which can also be toward the respective gap 24c. Thus the approximation force AF can have a directional component that is toward the other of the respective first and second anchor bodies 28a and 28b, for instance can be directed purely toward the other of the first and second anchor bodies 28a and 28b. Likewise, the approximation force AF can have a directional component that is directed toward the gap 24c, for instance directed purely toward the gap 24c. Accordingly, the approximation force AF biases at least one or both of the anchor bodies 28a and 28b toward the other of the anchor bodies 28a and 28b to respective biased positions that to approximate the gap 24c.

Referring again to FIG. 2C, the connector member 63 that can define at least one or both of a sliding member 47 and a locking member 64 that attaches the first and second connector actuation strands 38a and 38b together, for instance at a junction 125. Thus, it should be appreciated that the at least one of the sliding member 47 and locking member 64 can likewise attach the first actuation strand 38a to the second actuation strand 38b. In accordance with one embodiment, the connector member 63 can attach the first and second actuation strands 38a and 38b after the first and second actuation strands 38a and 38b have been put under tension so as to maintain the gap 24c in an approximated state. The member 63 can be actuated to the locked configuration so as to prevent or resist separation of the first and second anchors 22a and 22b that would cause the gap 24c to open from the approximated state. Alternatively or additionally, the connector member 63 can attach the first and second actuation strands 38a and 38b to each other prior to applying the approximation force AF to the actuation strands 38a and 38b, and placing the actuation strands 38a and 38b under tension, and therefore prior to approximating the gap 24c.

In accordance with certain embodiments, the connector member 63 is defined by, and integral with, the first and second actuation strands 38a and 38b, and can be configured as a sliding and locking knot that can iterate from an unlocked or unapproximated configuration, whereby one of the actuation strands 38a and 38b to slide relative to the other so as to approximate the gap 24c, and a locked or approximated configuration, whereby the actuation strands 38a and 38b are prevented from sliding relative to each other through the knot. The connector member 63 defines the at least one of the sliding member 47 and the locking member 64 at the junction 125. Thus, it can be said that the connector member 63 can directly or indirectly attach the first and second actuation strands 38a and 38b together.

Figure 3A:
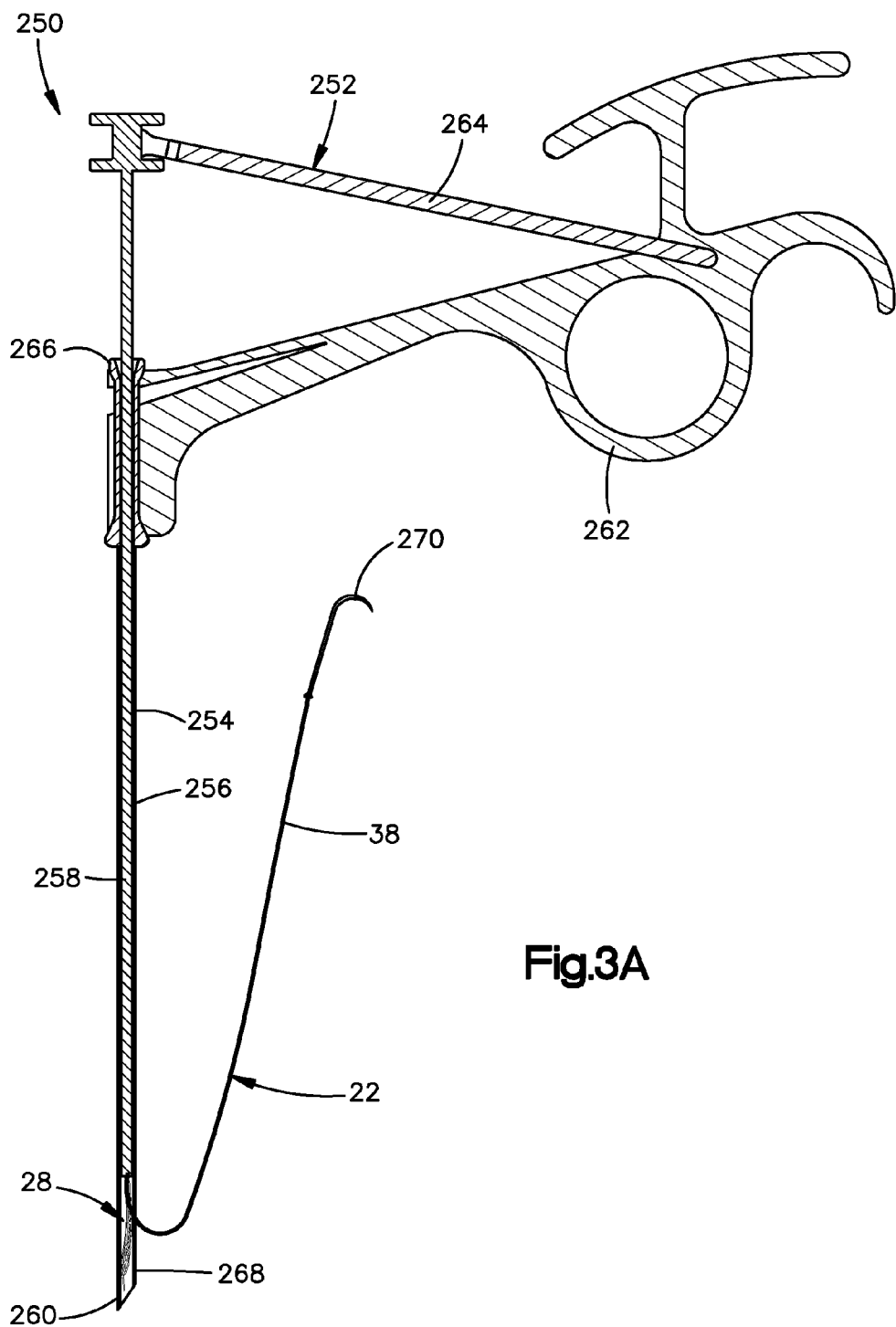
FIG. 3A is a side elevation view of a fixation kit including at least one anchor and an insertion instrument.

Referring now to FIG. 3A, a fixation assembly 250 can include the anchor assembly 20, such as at least one anchor 22, and an insertion instrument 252 configured to inject the anchor 22 in the anatomical structure 24 as illustrated in FIGS. 1A-B. It should be appreciated that the fixation kit 250 can include at least one or more up to all of the anchors 22 described herein alone, attached to each other, or configured to be attached to each other in accordance with any of the embodiments describer herein. The insertion instrument 252 can include a cannula 254 with a central opening 256 and a first pusher member such as a plunger or push rod 258 which is coaxially insertable into the central opening 256. the cannula 254 has an acuminated tip 260 and a slot 268 extending axially from the tip 260. The cannula 254 can extends substantially straight as illustrated, or can be curved or define any suitable shape as desired so as to eject an anchor body 28.

Further, the insertion instrument 252 comprises a handle 262 with an operating lever 264. One end of the handle 262 is detachably attached to the cannula 254 and the operating lever 264 is detachably attached to the plunger 258. The outer diameter of the plunger 258 corresponds to the inner diameter of the central opening 256 of the cannula 254. At the rear end the central opening of the cannula 254 is conically configured in such a manner that it enlarges towards the rear end of the cannula 254 at an inlet 266. Thus, the anchor body 28 of the anchor 22 can be inserted in its first configuration through the conical inlet 266 and into the central opening 256 of the cannula 254, such that the anchor body 28 can be compressed.

When the anchor body 28 is pressed out of the cannula 254 by pressing the plunger 258 forward the anchor body 28 can radially expand, for instance in the second direction 35 (see FIGS. 1A-B) in such a manner that it can be retained by the front face of the cannula 254 when a tensile force is exerted onto the actuation strand 38 in order to tighten the anchor body 28. the actuation strand 38 is led through the slot 268 so that it can be led alongside the cannula 254 when the cannula 254 is inserted into the anatomical structure 24. At the free end of the actuation strand 38 a needle 270 is attached that can be used for finishing a surgical procedure when the anchor body 28 of the anchor 22 has been actuated to the expanded configuration and secured to the anatomical structure 24.

Figure 3B:
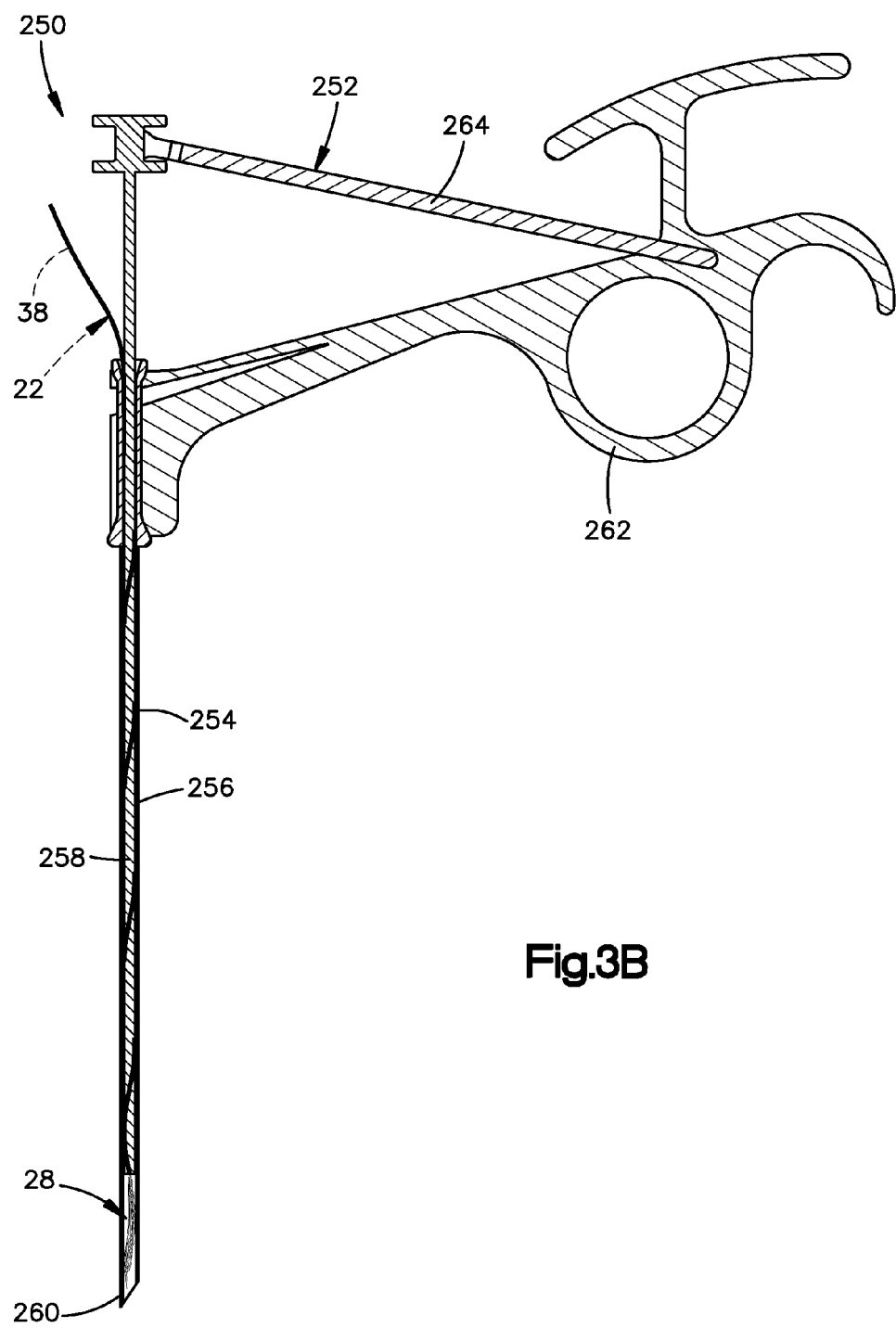
FIG. 3B is a sectional side elevation view of the fixation kit illustrated in FIG. 3A.

Referring to FIG. 3B, the plunger 258 can have an outer diameter or alternative cross-sectional dimension that is less than the inner diameter or cross-sectional dimension of the central opening 256 of the cannula 254. The actuation strand 38 of the anchor 22 can thus be led through the central opening 256 of the cannula 254 when the plunger 258 is inserted in the central opening 256 of the cannula 254. By actuating the operating lever 264 at the handle 262, the plunger 258 can push the anchor 22 forward in the cannula 254 as far as the anchor body 28 exits from the central opening 256 at the tip 260 of the cannula 254. Once the anchor body 28 is positioned in the central opening 256 the actuation strand 38 can be pulled backward at the rear end of the cannula 254 so that the anchor body 28 can be actuated in the cavity 256 to its expanded configuration.

Referring to FIGS. 4A-D, the plunger 258 can define a central bore 272 where the actuation strand 38 of the anchor 22 can be led through. Further, the cannula 254 has a first longitudinal aperture 274 extending between the tip 260 and the rear end of the cannula 254 so that the cannula 254 is slotted over its entire length. A second longitudinal aperture 276 extends on the plunger 258 between the front end and the rear end of the plunger 258 so that the plunger 258 is slotted over its entire length as well. As shown in FIG. 4B when the cannula 254 is in a first rotative position relative to the plunger 258 the first longitudinal aperture 274 of the cannula 254 is diametrically opposite to the second longitudinal aperture 276 of the plunger 258. In the first rotative position of the cannula 254 the actuation strand 38 of the anchor 22 is retained by the central bore 272. Once the anchor body 28 of the anchor 22 has been fixed in a cavity of a patient's body by pulling the actuation strand 38 of the anchor 22 backward the cannula 254 can be rotated into a second rotative position relative to the plunger 258 (FIG. 4D). In this second rotative position of the cannula 254 the first longitudinal aperture 274 of the cannula 254 is aligned with the second longitudinal aperture 276 of the plunger 258 and the insertion instrument 252 can be released from the actuation strand 38 of the anchor 22.

FIGS. 5A-D illustrate the handle 262 and the attachment of the cannula 254 to the handle 262 of an embodiment of the insertion instrument 252 of FIGS. 3A to 4D. The upper end portion of the handle 262 comprises a groove 278 into which the cannula 254 can be inserted and a spring member such as a leaf spring 279 so as to provide a releasable snap lock configured to releasably attach the cannula 254 to the handle 262. The rear end of the plunger 258 can be snapped into a resilient fork 280 arranged at the upper end of the operating lever 264.

Referring to FIG. 6, the insertion instrument 52 can include a depth control tube 282 slid over the cannula 254 and a clamping element 284. The insertion instrument 52 is pre-operatively prepared by inserting the anchor 22 into the cannula 254 and inserting the plunger 258. Once the anchor 22 and the plunger 258 have been inserted any one of a plurality of clamping elements 284 is attached to the rear end of the insertion instrument 252 by snapping a first tab 286 onto the rear portion of the cannula 254. To prevent an unintended displacement of the plunger 258 relative to the cannula 254 the clamping element 284 comprises a second tab 288 which abuts the rear end of the cannula 254 and a third tab 290 which abuts an enlarged portion at the rear end of the plunger 258. Before using the insertion instrument 252, the clamping element 284 is removed from the cannula 254 and the handle 262 is attached to the cannula 254, and the insertion instrument 252 can be operated in the manner described herein.

Referring now to FIGS. 1A and 7A-D, an insertion instrument 300 constructed in accordance with an alternative embodiment is configured to deliver at least one anchor knot, such as the first and second anchor knots 22a and 22b, to a respective target location, such as target locations 24a and 24b (FIG. 1A). The insertion instrument 300 is illustrated as elongate along a longitudinal axis 302 that extends substantially along a longitudinal direction L, and defines a proximal end 304 and an opposed distal end 306 that is spaced from the proximal end 304 along the longitudinal axis 302. Thus, it should be appreciated that the terms "distal" and "proximal" and derivatives thereof refer to a spatial orientation closer to the distal end 306 and the proximal end 304, respectively. Furthermore, the directional term "downstream" and "upstream" and derivatives thereof refer to a direction that extends from the proximal end 304 toward the distal end 306, and a direction that extends from the distal end 306 toward the proximal end 304, respectively. The insertion instrument 300 further extends along a lateral direction A that is substantially perpendicular to the longitudinal direction L, and a transverse direction T that is substantially perpendicular to the longitudinal direction L and the lateral direction A. It can also be said that the lateral and transverse directions A and T extend radially with respect to the longitudinal axis 302. Thus, the terms "radially outward" and "radially inward" and derivatives thereof refer to a direction away from and toward the longitudinal axis 302, respectively, and can be used synonymously with laterally and transversely as desired.

The insertion instrument 300 includes a casing 308 that can provide a handle, and a cannula 310 that is supported by the casing 308 and extends distally out from the casing 308 along a central axis 309. The cannula 310 can be fixed to the casing 308 with respect to translation. The central axis 309 can extend longitudinally and can thus be inline with the longitudinal axis 302 of the insertion instrument 300, or can be offset with respect to the longitudinal axis 302 of the insertion instrument 300. The cannula 310 extends substantially straight as illustrated, but can alternatively be curved or define any suitable alternative shape as desired. The cannula 310 defines an elongate opening 312, which can be elongate longitudinally or along any other direction or combination of directions as desired, that is sized to receive the at least one anchor knot, such as the first and second anchor knots 22a and 22b. The insertion instrument 300 can further include a biasing member such as a plug 314 that is disposed in the elongate opening 312, such that the first knot anchor body 28a is disposed in the cannula 310 at a location upstream of the plug 314, and the second knot anchor 28b is disposed in the cannula 310 at a location downstream of the plug 314. Thus, the plug 314 can further provide a divider that separates the first anchor body 28a from the second anchor body 28b along the longitudinal direction. The first and second anchor bodies 28a and 28b are stacked in the instrument 300 along the longitudinal axis 302. The cannula 310 defines a distal tip 311 that is configured to pierce tissue at a target location so as to deliver at least one anchor to the target location.

The insertion instrument 300 further includes a plunger 316 that is supported by the casing 308, and extends proximally out from the casing 308. The plunger 316 is configured to translate distally from an initial or first position illustrated in FIGS. 7A-D along a first stroke to a second position illustrated in FIGS. 8A-D, thereby causing the plug 314 to bias the second anchor 22b distally so as to eject the second anchor 22b out the cannula 310, for instance out a distal ejection port 442 that extends substantially longitudinally through the tip 311.

Figure 11C:
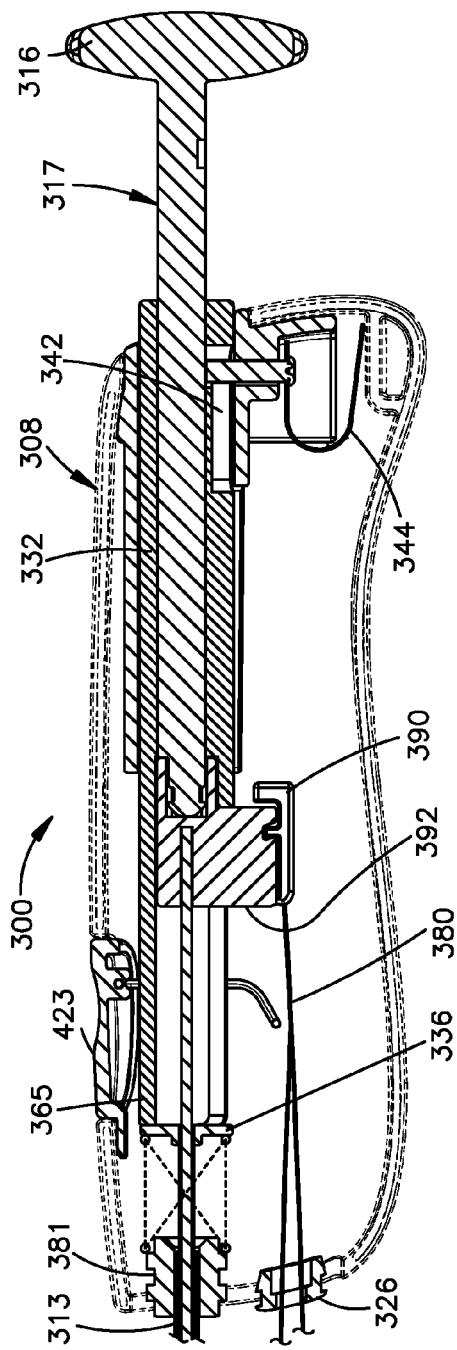
FIG. 11C is a sectional side elevation view of the casing of the insertion instrument illustrated in FIG. 11A.
Figure 11D:
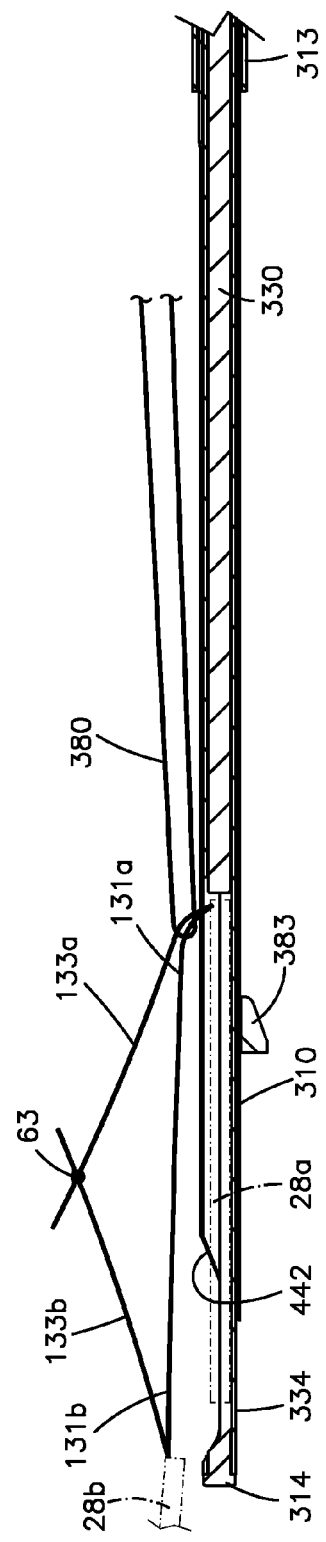
FIG. 11D is a sectional side elevation view of the cannula of the insertion instrument illustrated in FIG. 11A.
Figure 12C:
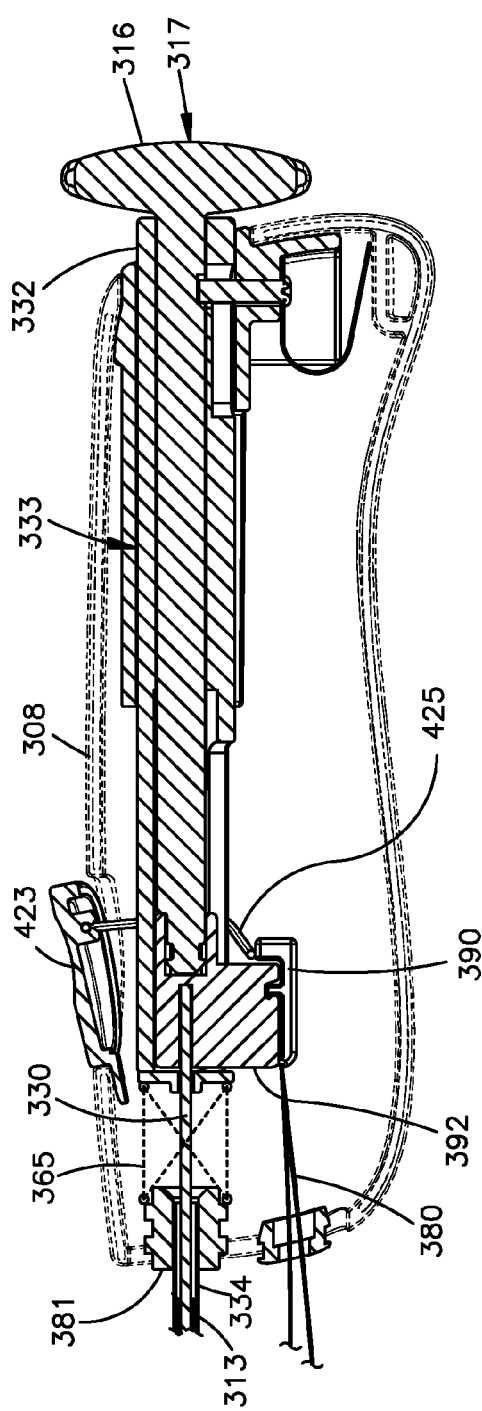
FIG. 12C is a sectional side elevation view of the casing of the insertion instrument illustrated in FIG. 12A.
Figure 12D:
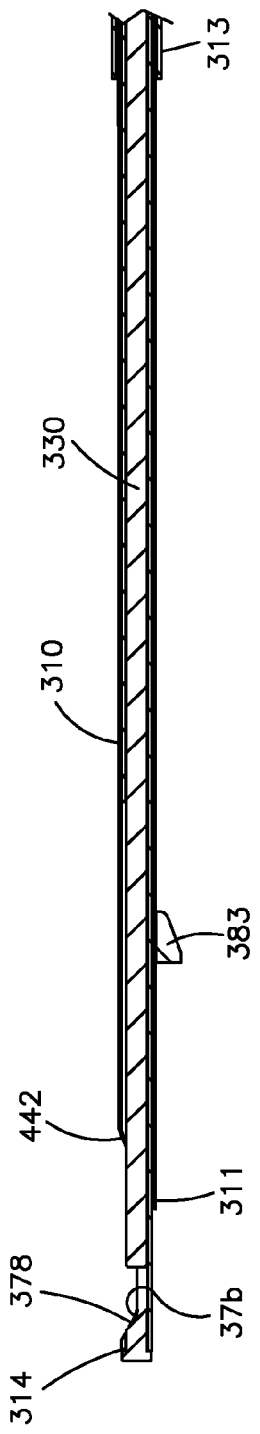
FIG. 12D is a sectional side elevation view of the cannula of the insertion instrument illustrated in FIG. 12A.
Figure 12F:
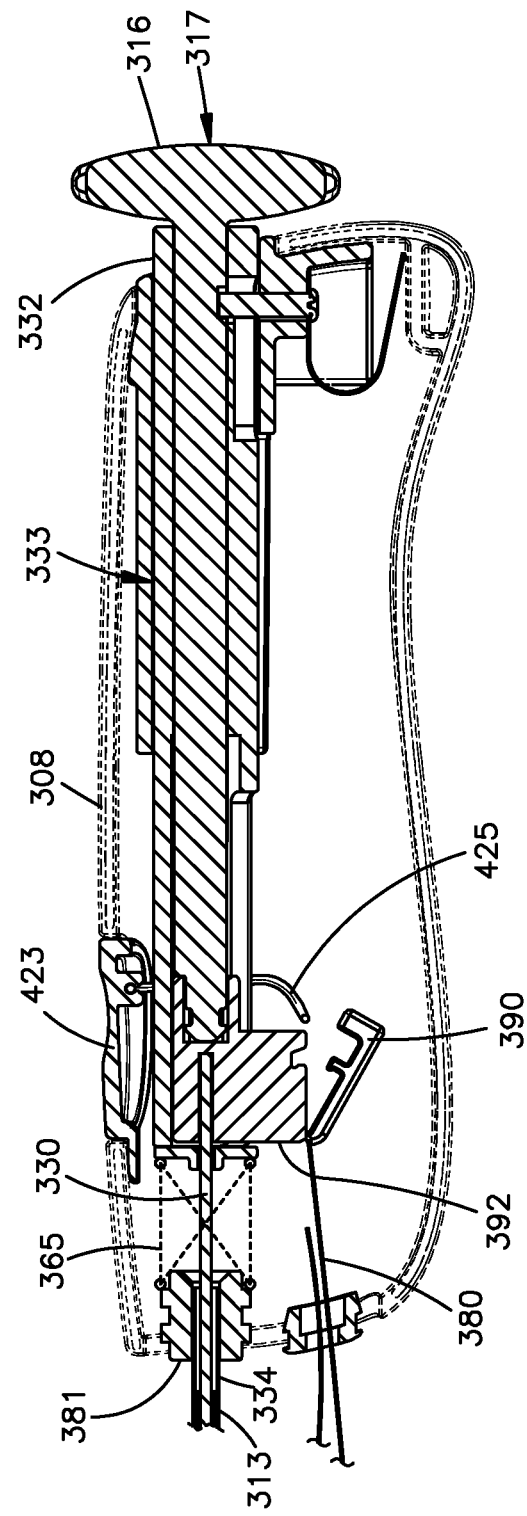
FIG. 12F is a sectional side elevation view of the casing of the insertion instrument illustrated in FIG. 12A, after release of a strand retention mechanism.

Once the second anchor 22b has been ejected out the ejection port 442, the plunger 316 is configured to translate further distally along a first portion of a second stroke illustrated in FIGS. 11A-C, and along a second portion of the second stroke illustrated in FIGS. 12A-C, such that a push rod 330 (see FIG. 7C) biases the first anchor body 28a distally so as to eject the first anchor 22a out the cannula 310, for instance out the ejection port 442, into the first target anatomical location 22a. Alternatively, as described in more detail below, the cannula 310 can define a side ejection port 318 (described below with reference to FIG. 31) that is configured to eject the first and second anchor bodies 28a and 28b out the cannula 310 along a direction angularly offset with respect to the central axis 309.

The insertion instrument 300 can be configured such that the plunger 316 moves distally from the second position to an offset position as illustrated in FIGS. 9A-D before moving along an intermediate stroke from the offset position to an intermediate position as illustrated in FIGS. 10A-D. Accordingly, the plunger 316 can move from the second position, to the offset position, to the intermediate position, and finally to the third position illustrated in FIGS. 12A-D. In accordance with the illustrated embodiment, the plunger 316 is rotated from the second position to the intermediate position prior to translating along the second stroke to the third position. For instance, the plunger 316 can move along a first portion of the second stroke as illustrated in FIGS. 11A-D prior to moving along a second portion of the second stroke as illustrated in FIGS. 12A-D. An actuation force can be applied to the actuation portion 131*a* and 131*b* of the first and second anchors 22*a* and 22*b*, respectively, after each anchor has been ejected, or can alternatively be applied after both anchors 22*a* and 22*b* have been ejected. The anchors 22*a* and 22*b* can be attached to each other in any manner as desired, for instance across the gap 24*c*.

Referring now to FIGS. 7A-C in particular, the casing 308 defines a body 320 that defines at least one radially outer side wall 322, such as a plurality of joined walls that can be of any size and shape, and further defines a proximal wall 324 and an opposed distal wall 326. The at least one outer wall 322, the proximal wall 324, and the distal wall 326 at least partially define an interior 328 that can be in fluid communication with the elongate opening 312 of the cannula 310. The cannula 310 is attached to the distal wall 326 of the casing 308 and is thus fixed to the casing 308. The cannula 310 extends distally from the casing 308 to the tip 311. The tip 311 can be tapered distally, such that the cannula 310 defines a tapered distal end. For instance, the tip 311 can be conical, that is the tip 311 can define a portion that is conical, and can define the shape of a cone or any suitable alternative shape as desired. The insertion instrument 300 can further include a support sleeve 313 that at least partially surrounds the cannula 310 at the interface with the casing 308, and extends distally along a portion of the length of the cannula 310. The support sleeve 313 provides structural support and rigidity to the cannula 310.

The plunger 316 defines a distal end 316*a* that is disposed in the interior 328, a body portion 316*b* that extends proximally from the distal end 316*a* and out the proximal wall 324 of the casing 308, and a proximal end 316*c* that can define a grip that is disposed outside the casing 308. The insertion instrument 300 further includes a first pusher assembly 317 that can include the plunger 316 and a first pusher member, such as a push rod 330 that is attached, directly or indirectly, to the distal end 316*a* of the plunger 316. The push rod 330 can be attached to the plunger 316 (for instance integral with the plunger 316 or separately attached to the plunger 316 via any suitable fastener or intermediate apparatus as desired). For instance, in accordance with the illustrated embodiment, the distal end 316*a* of the plunger is attached to a retention housing 392 as is described in more detail below with reference to FIG. 17. The push rod 330 is attached to the retention housing 392, and is thus attached to the plunger 316. The push rod 330 can extend distally from the plunger 316 into the opening 312 of the cannula 310 and out the distal wall 326 of the casing 308. It should be appreciated that reference to at least one or both of the plunger 316 and the push rod 330 can be applicable to the first pusher assembly 317. For instance, description with respect to the structure that is fixed or coupled to at least one or both of the plunger 316 and the push rod 330 can be said to be fixed or coupled, respectively, to the first pusher assembly 317.

Because the push rod 330 is translatably fixed to the plunger 316, movement of the plunger 316 proximally and distally causes the push rod 330 to likewise move proximally and distally. The push rod 330 defines a distal end 330*a* disposed in the opening 312 of the cannula 310. Accordingly, the distal end 330*a* of the push rod 330 is configured to brace against the first anchor 22*a* when the insertion instrument 300 is in the first position as illustrated in FIGS. 7A-D. The distal end 330*a* of the push rod 330 is configured to brace against the first anchor 22*a* when the insertion instrument 300 is in the first position, and also as the plunger 316, and thus the push rod 330, translates distally from the first position to the second position, such that the push rod 330 ejects the first anchor 22*a* out the insertion instrument 300 and into the respective target location 24*a*. When a tensile force is applied to the respective actuation member 37*a* substantially along the direction of elongation of the anchor body 28*a* after the first anchor body 28*a* has been ejected and is braced against the anatomical structure 24, the anchor body 28*a* expands along the second direction 35 that is perpendicular with respect to the direction of elongation 34 of the anchor body 28*a* (see, for instance, FIGS. 1A-B).

The insertion instrument 300 can further includes a second pusher assembly 333 that includes an attachment member 331, such as a collar 332 that extends about the plunger 316 and can at least partially surround the plunger 316, and a second pusher member, such as a push tube 334 that extends distally from the collar 332 and at least partially surrounds the push rod 330. The push tube 334 can be attached to the collar 332 (for instance integral with the collar 332 or separately attached to the collar 332 via any suitable fastener as desired). Accordingly, description of at least one or both of the push tube and the collar 332 can be applicable to the second pusher assembly 333. For instance, description with respect to the structure that is fixed or coupled to at least one or both of the push tube 334 and the collar 332 can be said to be fixed or coupled, respectively, to the second pusher assembly 333.

The push tube 334 can include the plug 314 that can define the distal end of the push tube 334. The push tube 334 can be cannulated in accordance with the illustrated embodiment so as to define a longitudinally elongate opening 335, and the push rod 330 has an outer diameter that is less than that of the opening 335, such that the push rod 330 is disposed inside the elongate opening 335 of the push tube 334. It should be appreciated that structures described herein as defining a diameter can alternatively define any suitably configured cross section, which can be circular or alternatively shaped, and thus can define any cross-sectional dimension which can be a diameter or not. The cannula 310 can contain both the first and second anchor bodies 28*a* and 28*b*. For instance, the push tube 334 can contain the first anchor body 28*a* at a location upstream of the plug 314, and the cannula 310 can contain the second anchor body 28*b* at a location distal to the plug 314, and thus distal to the first anchor body 28*a*.

The insertion instrument 300 can include a force transfer member 336 that can extend radially inward from the distal end of the collar 332, such that the push rod 330 extends distally through or from force transfer member 336. The force transfer member 336 can abut the collar 332, or can be fixed to the distal end of the collar 332. The force transfer member 336 can further abut or be fixed to the proximal end of the push tube 334. If the force transfer member 336 abuts one or both of the collar 332 and the push tube 334, then 1) distal movement of the collar 332 biases the force transfer member 336 distally, which in turn biases the push tube 334, including the plug 314, distally, and 2) proximal movement of the collar 332 does not bias the push tube 334 proximally. If the force transfer member 336 is attached to the collar 332 and the push tube 334, then 1) distal movement of the collar 332 biases the force transfer member 336 distally, which in turn biases the push tube 334, including the plug 314, distally, and 2) proximal movement of the collar 332 biases the force transfer member 336 distally, which in turn biases the push tube 334, including the plug 314, distally. Whether the force transfer member 336 abuts or is fixed to the collar 332 and the push tube 334, it can be said that the collar 332 is translatably coupled to the push tube 334, such that distal translation of the collar 332 causes the push tube 334 to translate distally.

The collar 332, and thus the push tube 334, including the plug 314, is configured to be selectively coupled to and decoupled from the first pusher assembly 317 with respect to translation, and configured to be selectively coupled to and decoupled from the casing 308 with respect to translation. For instance, in a first configuration, the collar 332 is translatably fixed to the plunger 316, and thus also to the push rod 330. Furthermore, in the first configuration, the collar 332 is translatably decoupled from the casing 308 and thus also translatably decoupled from the cannula 310. Accordingly, in the first configuration, proximal and distal movement of the plunger 316 and push rod 330 relative to the casing 308 and cannula 310 causes the collar 332 to correspondingly move proximally and distally relative to the casing 308 and cannula 310. It should be appreciated that in the first configuration, the push rod 330 is translatably coupled to the push tube 334, such that the push rod 330 and the push tube 334 translate in tandem, for instance during the first stroke, thereby causing the push tube 334 to eject the second anchor body 28b out the cannula 310, as will be described in more detail below. As described above, when a tensile force is applied to the respective actuation member 37b substantially along the direction of elongation of the second anchor body 28b after the second anchor body 28b has been ejected, the second anchor body 28b expands along the second direction 35 that is perpendicular with respect to the direction of elongation 34 of the anchor body 28b (see, for instance, FIGS. 1A-B).

In a second configuration, the collar 332 is translatably decoupled from the plunger 316, and thus the push rod 330, and is translatably coupled to the casing 308, and thus the cannula 310. Accordingly, in the second configuration, the plunger 316 and push rod 330 move proximally and distally relative to the collar 332 and the casing 308 and the cannula 310. It should be appreciated that in the second configuration, after the first stroke, the push rod 330 is translatably decoupled from the push tube 334, such that the push rod 330 translates distally relative to the push tube 334 and thus the plug 314, for instance during at least a portion of the second stroke, thereby causing the push rod 330 to eject the first anchor body 28a out the cannula 310, as will be described in more detail below.

Referring now to FIGS. 13A-G, the insertion instrument 300 includes a guide system 329 that operably couples the casing 308 and the push tube 334 so as to guide relative movement between the casing 308 and the push rod 330. In accordance with the illustrated embodiment, the guide system 329 includes complementary first and second guide members 338 and 340, respectively, that are coupled between the casing 308 and the collar 332. In accordance with the illustrated embodiment, during the first stroke and a first portion of the second stroke, the first and second guide members 338 and 340 cooperate to guide the movement of the plunger 316 (and push rod 330) and collar 332 (and push tube 334) in tandem relative to the casing 308. In that regard, it should be appreciated that the first and second guide members 338 and 340 are operably coupled between the plunger 316 and the collar 332 during the first stroke and a first portion of the second stroke. In accordance with the illustrated embodiment, during a second portion of the second stroke, the first and second guide members 338 and 340 cooperate to guide the movement of the plunger 316 and push rod 330 relative to both the collar 332 (and push tube 334) and the casing 308. In that regard, it should be appreciated that the first and second guide members 338 and 340 are operably coupled between the casing 308 and the collar 332 during the second portion of the second stroke.

In accordance with the illustrated embodiment, one of the first and second guide members 338 and 340 is provided as a guide track 342 that extends into one of the collar 332 and the casing 308, and the other of the guide members 338 and 340 is provided as a guide pin 344 that extends into the guide track 342, such that the guide pin 344 rides in the guide track 342, thereby operably coupling the collar 332 to the casing 308. In accordance with the illustrated embodiment, the first guide member 338 is provided as the guide track 342 that is carried, and defined, by the collar 332, and the second guide member 340 is provided as the guide pin 344 that is translatably fixed to the casing 308 and extends into the guide track 342. For instance, the guide pin 344 extends radially into or through the side wall 322 of the casing 308 and into the guide track 342. It should be appreciated in accordance with an alternative embodiment that the guide track 342 can be carried, and defined, by the casing 308 and the guide pin 344 can be translatably fixed to the collar 332.

Figure 13A:
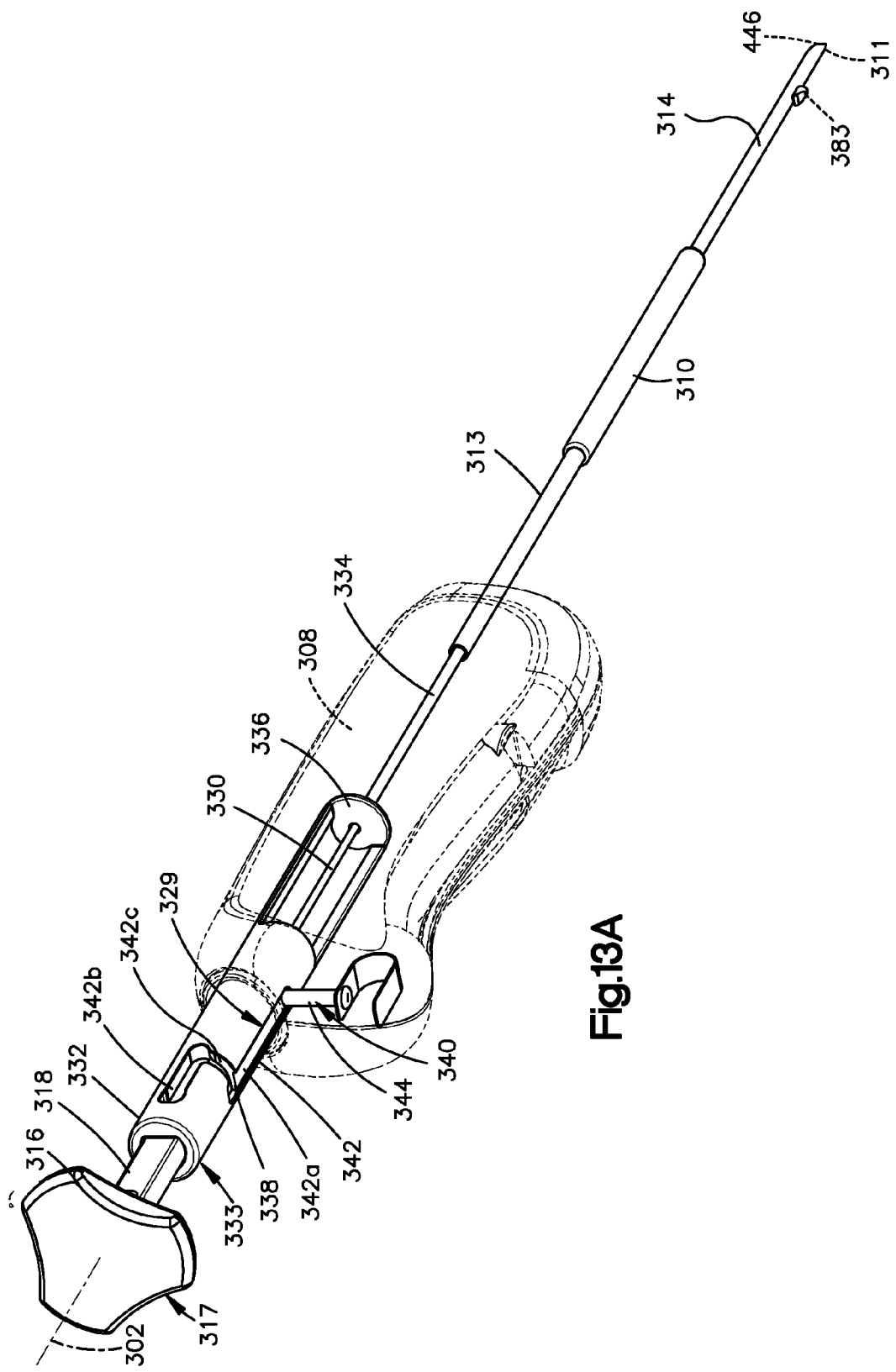
FIG. 13A is a perspective view of the insertion instrument illustrated in FIG. 7A, with portions removed so as to illustrate a guide system when the instrument is in the first position.
Figure 13B:
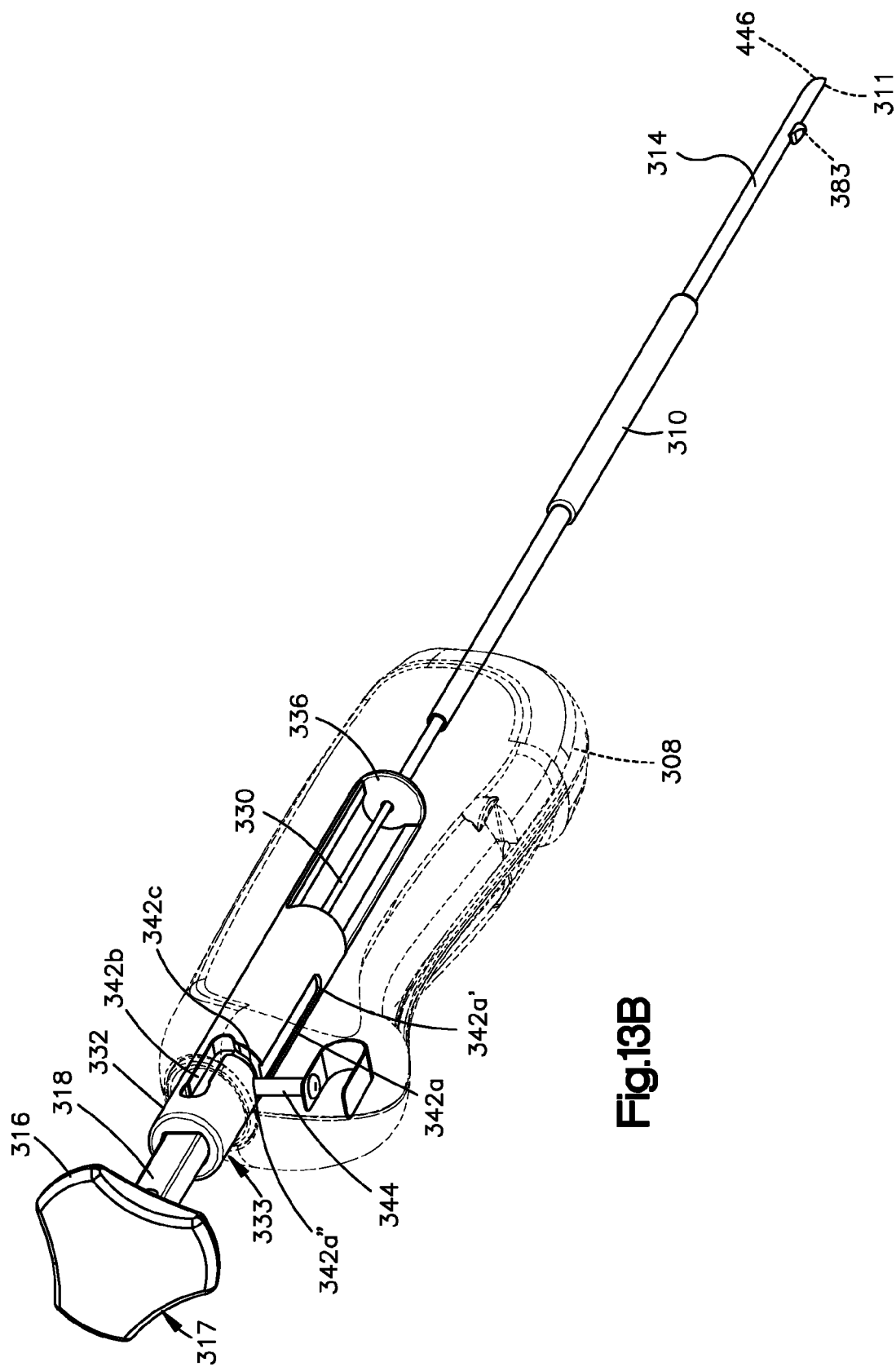
FIG. 13B is a perspective view of the insertion instrument illustrated in FIG. 8A, showing the guide system when the instrument is in the second position.
Figure 13C:
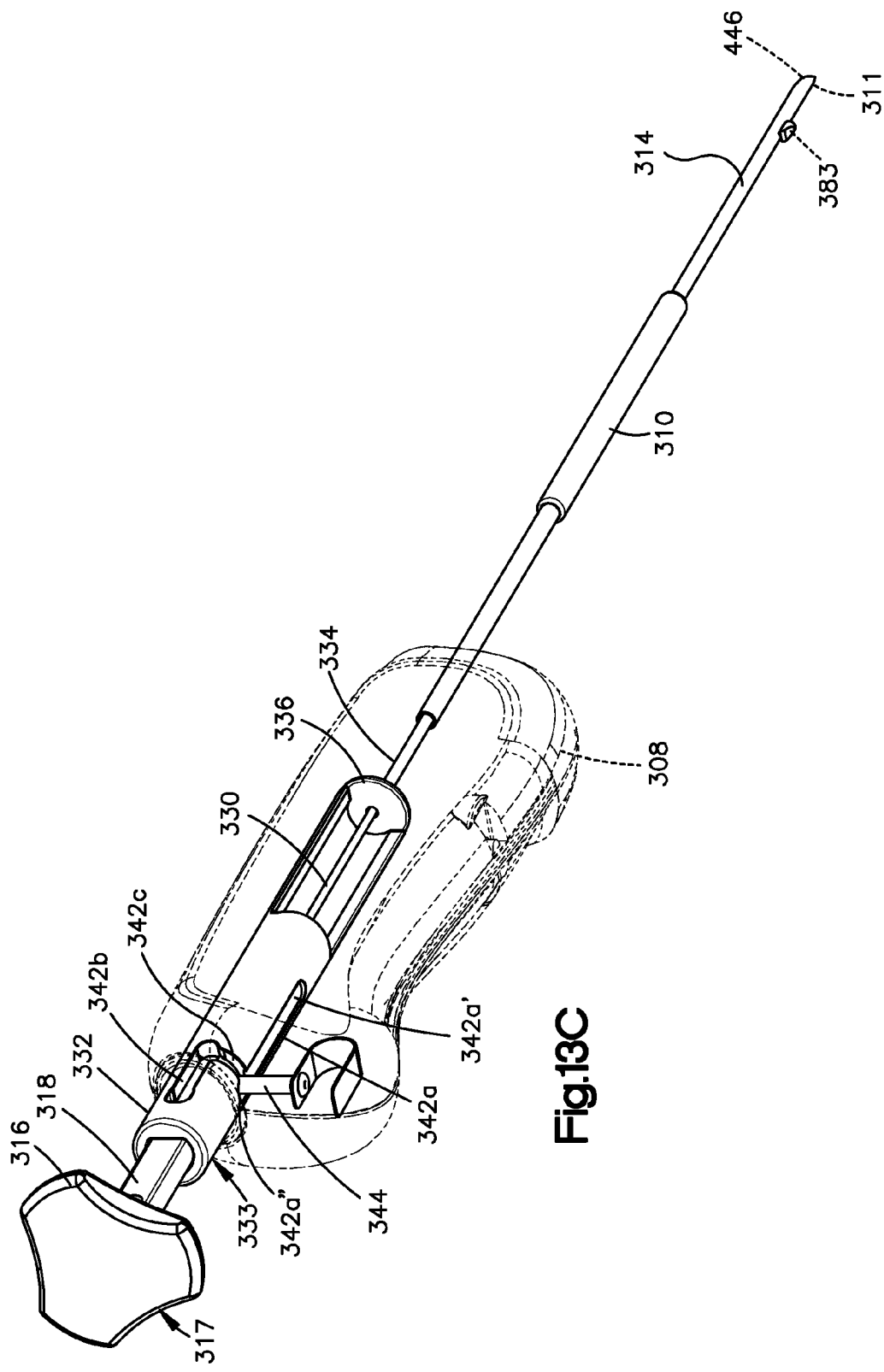
FIG. 13C is a perspective view of the insertion instrument illustrated in FIG. 9A, with portions removed so as to illustrate the guide system when the insertion instrument is in the offset position.
Figure 13D:
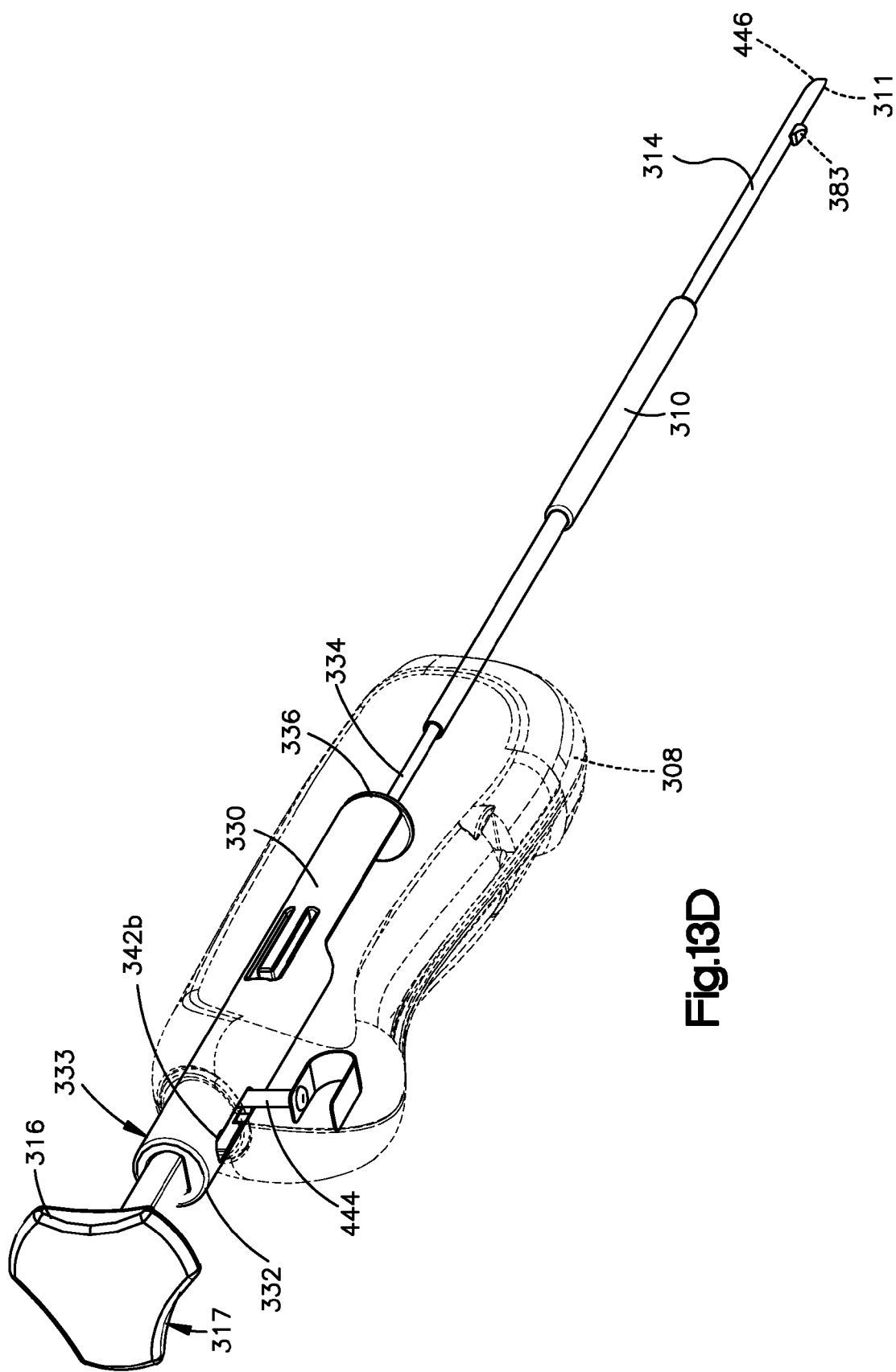
FIG. 13D is a perspective view of the insertion instrument illustrated in FIG. 10A, with portions removed so as to illustrate the guide system when the insertion instrument is in the intermediate position.
Figure 13E:
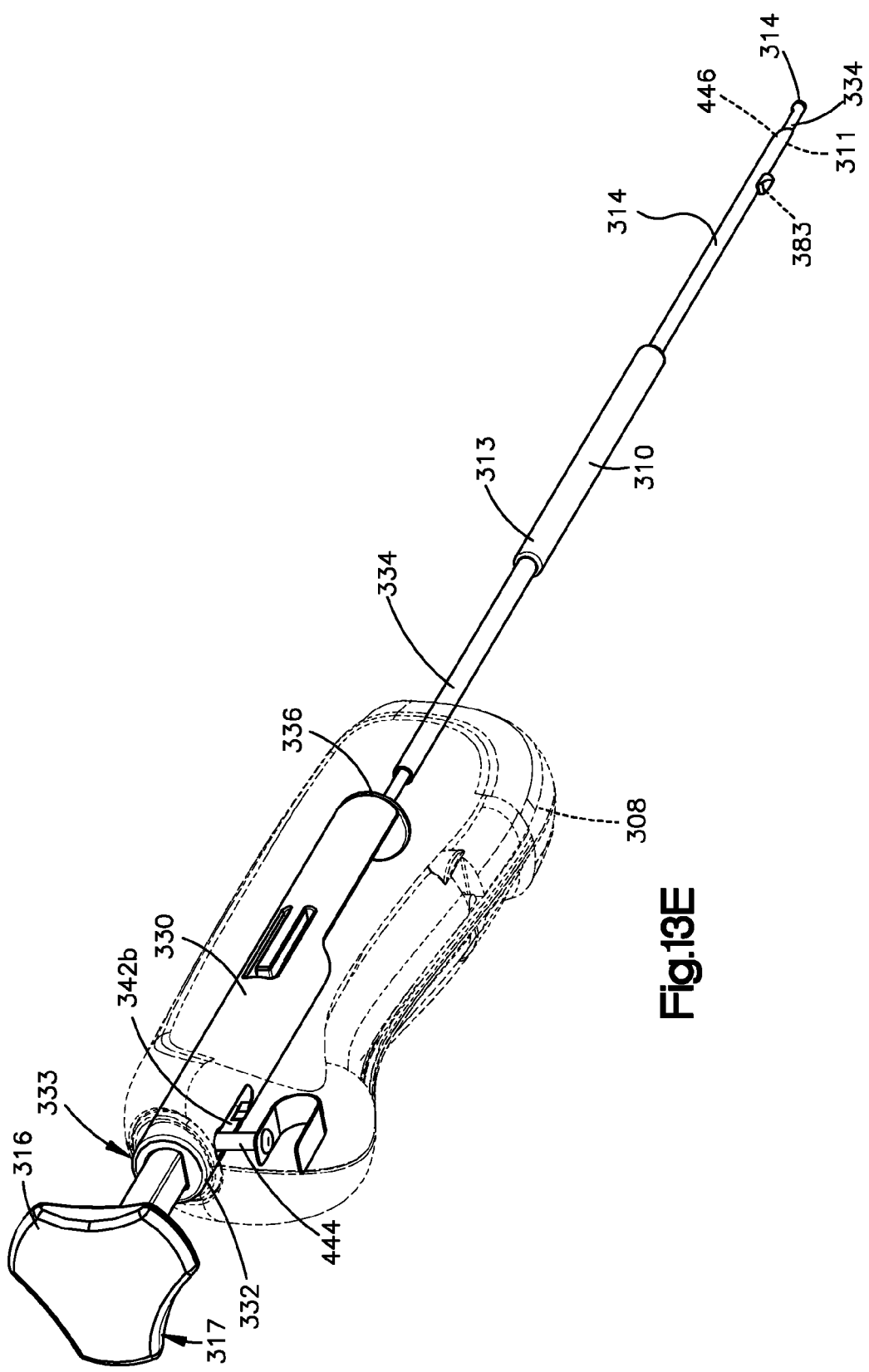
FIG. 13E is a perspective view of the insertion instrument illustrated in FIG. 11A, with portions removed so as to illustrate the guide system when the insertion instrument has completed the first portion of the second stroke.
Figure 13F:
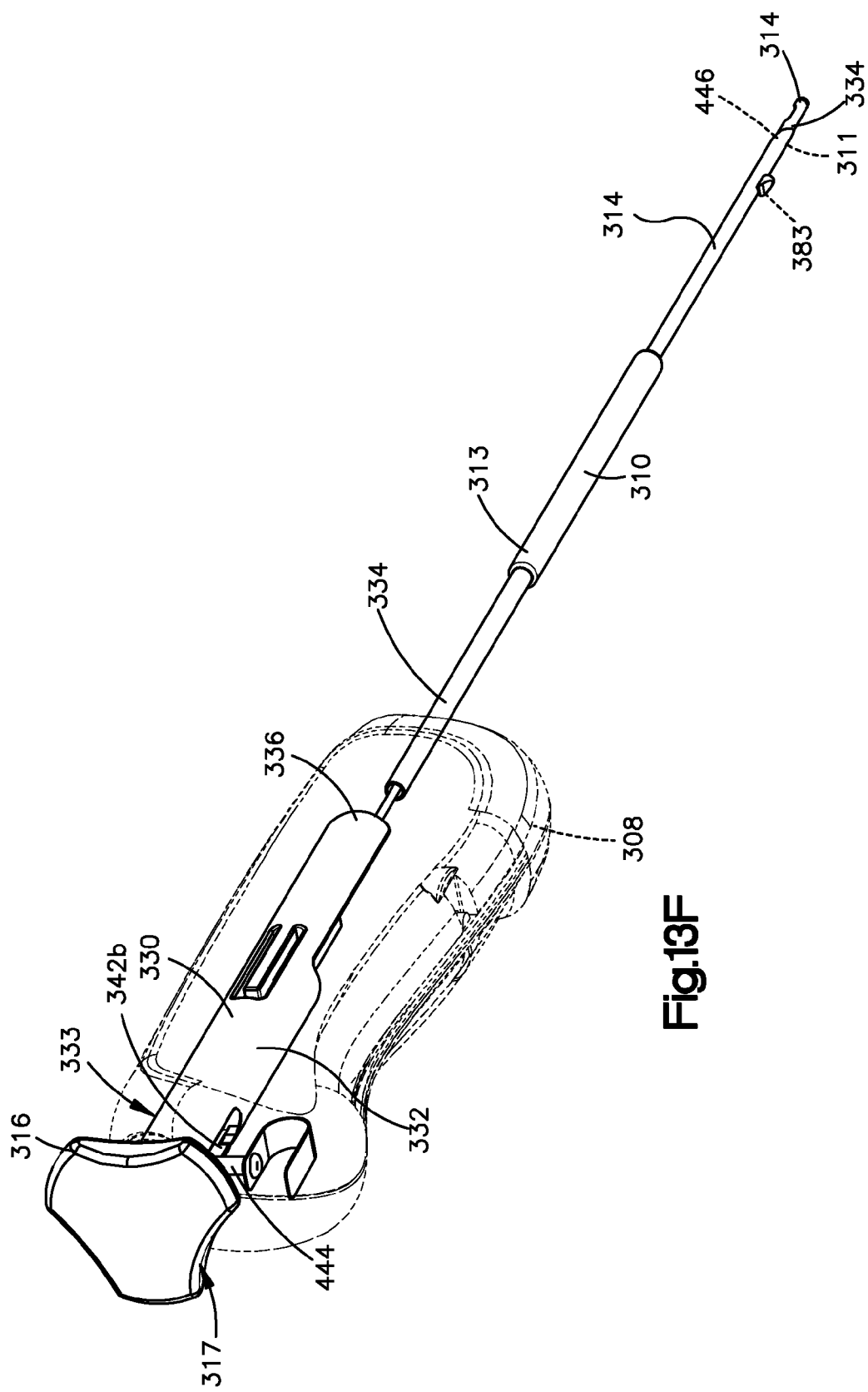
FIG. 13F is a perspective view of the insertion instrument illustrated in FIG. 12A, with portions removed so as to illustrate the guide system when the insertion instrument has completed the second portion of the second stroke.
Figure 13G:
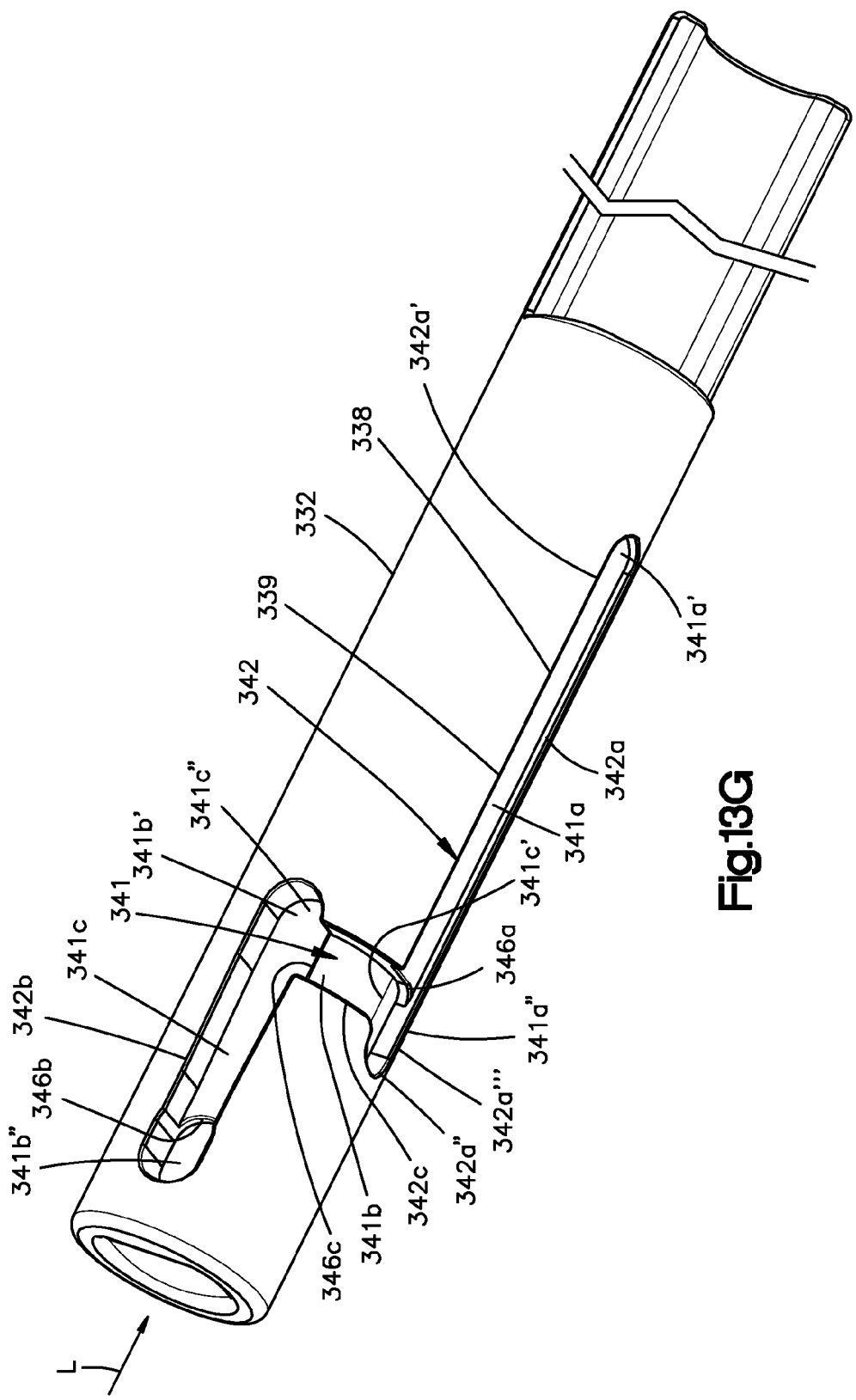
FIG. 13G is a perspective view of a guide track of the guide system illustrated in FIG. 13A.

In accordance with the embodiment illustrated in FIG. 13G, the track 342 defines a slot 339 that extends radially into the collar 332 but not through the collar 332, and a base 341 of the collar 332 that is located at the radially inner end of the slot 339. The guide track 342 defines a first guide portion such as a first track portion 342a, a second guide portion such as a second track portion 342b that is offset, for instance radially, with respect to the first track portion 342a, and an angled intermediate guide portion such as an angled intermediate track portion 342c that connects the first track portion 342a to the second track portion 342a. Accordingly, the guide pin 344 is configured to travel along the first track portion 342a during the first stroke as the plunger 316 is translated from the first position to the second position. In particular, the second track portion 342a defines a first or distal end 342a' an opposed second or proximal end 342a", and an offset position 342a''' between the distal end 342a and the proximal end 342a". The offset position 342a''' is aligned with an intermediate track portion 342c that extends between the first track portion 342a and the second track portion 342b. Once the guide pin 344 has translated from the proximal end 342a" to the offset position 342a''', the guide pin 344 can travel along the intermediate track portion 342c toward the second track portion 342b as the plunger 316 is rotated to the intermediate position. The guide pin 344 can subsequently travel distally along the second track portion 342b as the plunger 316 is further translated toward the third position.

The first and second guide track portions 342a and 342b extend substantially longitudinally, such that distal translation of the collar 332 relative to the casing 308 during the first stroke causes the guide pin 344 and the guide track 342 to translate relative to each other. In accordance with the illustrated embodiment as shown in FIGS. 13A-B, the guide track 342 translates distally with respect to the guide pin 344, thereby causing the guide pin 344 to translate proximally along the first guide track portion 342a during the first stroke of the plunger 316 and the collar 332. Once the first stroke is completed, and the second anchor body 28b has been ejected from the cannula 310, the guide pin 344 is disposed at the proximal end 342a" of the first track portion 342a. The collar 332 defines a stop member at the proximal end of the first track portion 342a. Thus, the guide pin 344 interferes with the collar 332, thereby preventing the plunger 316 and collar 332 from further translating distally relative to the casing 308. Accordingly, the user is prevented from inadvertently ejecting the first anchor body 308a by continued distal translation of the plunger 316 after the second anchor body 28b has been ejected.

It should be appreciated during the first stroke that the guide pin 344 translates from the distal position 342a' (illustrated in FIG. 13A), past the offset position 342a''' (illustrated in FIG. 13C), to the proximal end 342a" (illustrated in FIG. 13B). When the guide pin 344 is at the offset position 342a''', the push tube 344 is slightly recessed proximally with respect to the distal ejection port 442 (see FIG. 9D). As the guide pin 344 moves to the proximal end 342a", the push tube 344 translates distally with respect to the ejection port 442 (see FIG. 8D). As further illustrated in FIGS. 8A and 9A, the insertion instrument 300 includes a spring member 365, which can be a coil spring, that extends between a spring seat 381 that is secured to the casing 308, for instance at the distal wall 326 of the casing 308, and the force transfer member 336. Thus, the spring member 365 is operably coupled between the casing 308 and the second pusher assembly 333. When the second pusher assembly 333 is coupled to the first pusher assembly 317 with respect to translation, the spring member 365 is operably coupled between the casing 308 and the first pusher assembly 317.

The spring member 365 provides a force that biases the collar 332, and thus the plunger 316, proximally as the plunger 316 translates distally along the first stroke. Accordingly, referring to FIGS. 13B-C, once the guide pin 344 is in the second position at the proximal end 342a" of the first track portion 342a, the spring force biases the collar 332 to move such that the guide pin 344 translates distally from the proximal end 342a" of the first track portion 342a toward the distal end 342a' of the first track portion 342a. However, as is described in more detail below, the track 342 includes a base 341 that interferes with movement of the guide pin 344 along a distal direction from the offset position 342a'. When the guide pin 344 is in the offset position 342a''', the plug 314 of the push tube 334 is recessed proximally with respect to, or substantially aligned with, the distal ejection port 442 (see FIG. 9D) such that the plug 314 does not extend distally beyond the distal ejection port 442.

Referring now to FIGS. 13C-D, the plunger 316 can be rotated along the direction of Arrow A as it travels along the intermediate stroke. The insertion instrument 300 defines a key 318 that rotatably couples the plunger 316 and the collar 332. In accordance with the illustrated embodiment, the key 318 is provided as complementary flat surfaces of the plunger 316 and the collar 332 that prevents defines the plunger 316 from rotating with respect to the collar 332. As a result, rotation of the plunger 316 along the direction of Arrow A causes the collar 332 to likewise rotate along the direction of Arrow A. Accordingly, upon completion of the first stroke, rotation of the plunger 316 causes the guide pin 344 to travel along the intermediate stroke from the first track portion 342a, along intermediate track portion 342c, and to the distal end of the second track portion 342b. Referring now to FIGS. 13D-E, once the guide pin 344 is disposed in the second track portion 342b, further translation of the plunger 316 and the collar 332 along a first portion of the second stroke causes the guide pin 344 to translate distally relative to the casing 308 until the guide pin 344 has traveled to the proximal end of the second track portion 342b. The collar 332 defines a stop member at the proximal end of the second track portion 342b that prevents the collar 332 from continuing to move distally with respect to the casing 308. It can be said that the collar 332 defines a stop member at the terminal ends of the first and second track portions 342a and 342b.

Referring now to FIGS. 13E-F, and as is described in more detail below, once the guide pin 344 has traveled to the proximal end of the second track portion 342b, further distal translation of the plunger 316 along a second portion of the second stroke is decoupled from the collar 332, such that the plunger 316 and push rod 330 translate relative to the collar 332, the push tube 334, and the casing 308. The plunger 316 is configured to translate distally relative to the collar 332 and casing 308 during the second portion of the second stroke until the distal end 316c of the plunger abuts the casing 308, for instance at the proximal wall 324, thereby completing the second stroke and ejecting the second anchor body 28b out the cannula, as illustrated in FIGS. 12A-C.

Referring now to FIG. 13G in particular, the base 341 of the track 342 defines a first base portion 341a at the first track portion 342a, a second base portion 341b at the second track portion 342b, and an intermediate base portion 341c at the intermediate track portion 342c. The base 341 has portions that are deeper than others such that as the guide pin 344 rides along the track, at least one or both of audible and tactile feedback can be detected by the user to indicate that the collar 332, and in some instances the plunger 316, have completed a stroke or a portion of a stroke. The base 341 can further provide a stop that prevents the guide pin 344 from moving proximally along portions of the track 342. For instance, the first base portion 341a defines a first or distal first base portion 341a' and a second or proximal first base portion 341a" that is deeper than the distal first base portion 341a'. The first base portion 341a defines an edge 346a that is disposed between the proximal first base portion 341a' and the distal first base portion 341a". The edge 346a can extend radially, or along a direction having a radial component that extends toward the longitudinal axis 302.

The guide pin 344 can define a post 344a and a spring member 345 that is connected between the casing 308 and the post 344a, and biases the post 344a into the track 342 and against the base 341. Thus, as the guide pin 344 moves proximally relative to the first track portion 342a when the collar 332 and the plunger 316 move along the first stroke, the distal portion 344b of the guide pin 344 moves along the distal first base portion 341a' and over the edge 346a as the guide pin 344 travels to the distal first base portion 341a". As the guide pin 344 travels over the edge 346a and is biased against the track 341 by a spring force of the spring member 345, at least one of a tactile and an audible feedback can be communicated to the user that the plunger 316 and the collar 332 have completed the first stroke. The edge 346a can be disposed at the offset position 342a''' of the first track portion, such that once the guide pin 344 has traveled along the first base portion 341a to the proximal end 342a" of the first track portion 342a, the edge 346a prevents the force of the spring member 365 from causing the guide pin 344 to translate proximal with respect to the offset position 342a''' of the first track portion 342a. Rather, because the guide pin 344 abuts the edge 346a, the biasing force of the spring member 365 brings the guide pin 344 into alignment with the intermediate track portion 342c, and in position to be moved or rotated along the intermediate stroke.

With continuing reference to FIG. 13G, the intermediate base portion 341c defines a first or proximal intermediate base portion 341c' and a second or distal intermediate base portion 341c" that is deeper than the proximal intermediate base portion 341c'. The distal intermediate base portion 341c" can be aligned with the second base portion 341b. The intermediate base portion 341c defines an edge 346c that is disposed between the proximal intermediate base portion 341a' and the distal intermediate base portion 341a". Alternatively, the intermediate base portion 341c can be devoid of the distal portion, such that the edge 346c is disposed between the intermediate base portion 341c and the second base portion 341b. The edge 346c can extend radially, or along a direction having a radial component that extends toward the longitudinal axis 302. As the distal portion 344b of the guide pin 344 travels over the edge 346c during a transition between the intermediate stroke and the second stroke, and is aligned with the second track portion 342b, at least one of a tactile and an audible feedback can be communicated to the user that the plunger 316 and the collar 332 have completed the intermediate stroke, and are in position to be moved along the first portion of the second stroke. Furthermore, the edge 346c prevents the plunger 316 from being rotated along a direction opposite the direction of Arrow A (FIG. 13C) once the guide pin 344 is positioned in the second track portion 342b.

The second base portion 341b defines a first or proximal second base portion 341b' and a second or distal second base portion 341b" that is deeper than the proximal second base portion 341b'. The distal second base portion 341b" can be disposed at the terminal distal end of the second track portion 342b. The second base portion 341b defines an edge 346b that is disposed between the proximal second base portion 341b' and the distal second base portion 341b". The edge 346b can extend radially, or along a direction having a radial component that extends toward the longitudinal axis 302. As the distal portion 344b of the guide pin 344 travels over the edge 346b, at least one of a tactile and an audible feedback can be communicated to the user that the plunger 316 and the collar 332 have completed the first portion of the second stroke. The feedback can indicate that the plunger 316 is decoupled from the collar 332, and can translate along the second portion of the second stroke independent of the collar 332, as will now be described. Furthermore, the edge 346b prevents the guide pin 344 from moving proximally along the second track portion 342b once the plunger 316 and the collar 332 have been decoupled.

Referring now to FIG. 7C and FIGS. 14A-D, the insertion instrument 300 includes a coupling assembly 350 that is configured to iterate between a first mode of operation and a second mode of operation. In the first mode of operation, the coupling assembly 350 translatably fixes the first pusher member, illustrated as the push rod 330, and the second pusher member, illustrated as the push tube 334 with respect to translation during the first stroke. In the first mode of operation, the coupling assembly 350 releasably translatably fixes the push rod 330 to the push tube 334, such that in a second mode of operation, the coupling assembly 350 decouples the push rod 330 from the push tube 334 such that the push rod 330 can translate distally relative to the push tube 334 after the first stroke, for instance during the second stroke. Furthermore, in the second mode of operation, the coupling assembly 350 can translatably fix the push tube 334 to the casing 308, such that a distal translation force applied to the plunger 316 causes the plunger 316, and thus the push rod 330, to translate distally relative to the push tube 334, and thus the collar 332. In accordance with the illustrated embodiment, the coupling assembly 350 is in the first mode of operation during the first stroke of the first pusher assembly 317, the intermediate stroke of the first pusher assembly 317, and the first portion of the second stroke of the first pusher assembly 317. In accordance with the illustrated embodiment, the coupling assembly 350 transitions to the second mode of operation, as the first pusher assembly 317 transitions between the first portion of the second stroke and the second portion of the second stroke.

In accordance with the illustrated embodiment, the coupling assembly 350 is in the second mode of operation when the first pusher assembly 317 translates along the second portion of the second stroke and the second portion of the second stroke.

The coupling assembly 350 can include at least one first coupling member 352 illustrated as a first recess 354 that extends radially into the first pusher assembly 317, such as the plunger 316, in accordance with the illustrated embodiment. The coupling assembly 350 can further include at least one second coupling member 356 illustrated as a channel 358, that extends radially through the second pusher assembly 333, such as the collar 332, in accordance with the illustrated embodiment. The coupling assembly 350 can further include at least one third coupling member 360 illustrated as a second recess 362 that is carried by the casing 308. For instance, the insertion instrument 300 can include an inner housing 325 that is carried by the casing 308, for instance by the proximal wall 324 of the casing 308. The second recess 362 extends radially outward into the inner housing 325 in accordance with the illustrated embodiment. Alternatively, the second recess 362 could extend radially outward into the casing 308.

Furthermore, in accordance with the illustrated embodiment, the second recess 362 is disposed distal with respect to the channel 358 when the plunger 316 is in the first position illustrated in FIGS. 7C and 14B. The second recess 362 can further be radially offset with respect to the channel 358 when the plunger 316 is in the first position illustrated in FIGS. 7A and 13A. Alternatively, the second recess 362 can be radially aligned with respect to the second recess 362 (for instance if the track 342 does not include the intermediate track portion 342c, and can alternatively still be annular so as to circumscribe the radially inner surface of the casing 308 if desired.

The coupling assembly 350 can further include at least one fourth coupling member 368 illustrated as a latch 370 that is sized to partially fit in each of the first recess 354, the second recess 362. In accordance with the illustrated embodiment, the latch 370 is carried by the collar 332, and is configured as a leaf spring 371 that is disposed in the channel 358, which can be provided as a substantially U-shaped aperture or cut-out of the collar 332 so as to define the leaf spring 371. The leaf spring 371 carries a radially inward projection 373 that is sized to fit into the first recess of the plunger 316. The latch 370 can be further sized to be disposed in the channel 358, and is flexible radially inward and outward. Accordingly, the latch 370 can travel along the channel 358 between the first recess 354 (FIG. 14B) and the second recess 362 (FIG. 14D).

In accordance with the illustrated embodiment, the coupling assembly 350 is in the first mode of operation when the guide pin 344 is in the first track portion 342a, and remains in the first mode of operation when the guide pin 344 travels from the first track portion 342a to the intermediate track portion 342c, and further remains in the first mode of operation when the guide pin 344 travels along part of the second track portion 342b. In particular, the first recess 354 and the channel 358, and the projection 371 of the latch 370, can be positioned so as to be radially aligned when the guide pin 344 extends into the any of, and all of as illustrated, the first track portion 342a, the intermediate track portion 342c, and the portion of the second track portion 342b.

Accordingly, in the first mode of operation, the latch 370 is partially disposed in the first recess 354 of the plunger 316, and extends into the channel 358 of the collar 332. The latch projection 373 can be sized so as to be captured in the first recess 354, so as to couple the plunger 316 to the collar 332 with respect to translational movement. As a result, when the latch 370 is coupled to the plunger 316, the plunger 316 and the collar 332, and thus the first and second pusher assemblies 317 and 333, are coupled with respect to movement or translation along the longitudinal direction.

Figure 14C:
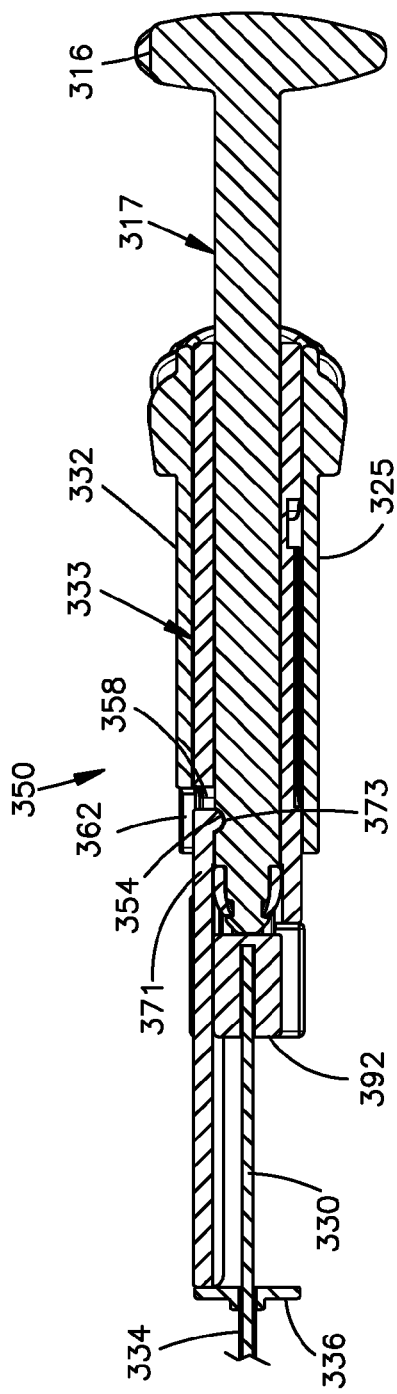
FIG. 14C is a sectional side elevation view of the coupling assembly illustrated in FIG. 14B, shown in a transition between the first mode of operation and a second mode of operation.
Figure 14D:
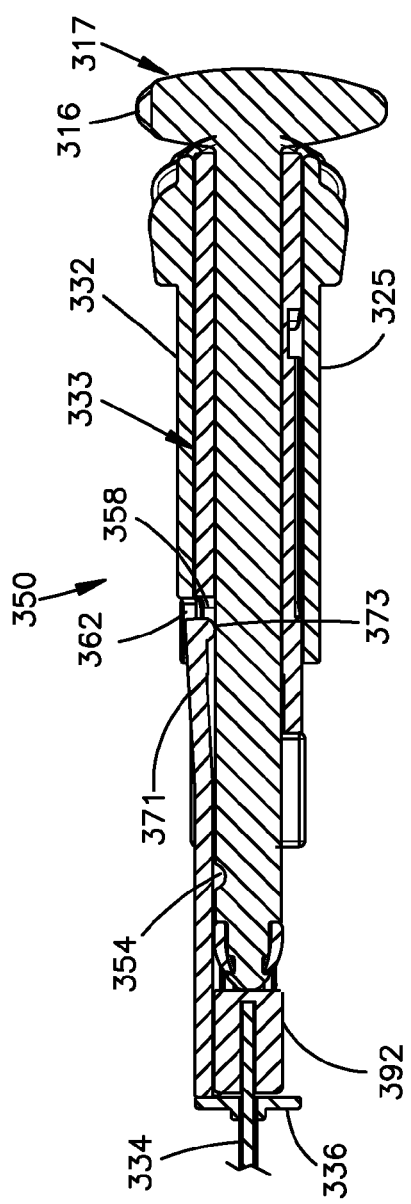
FIG. 14D is a sectional side elevation view of the coupling assembly illustrated in FIG. 14C, shown in the second mode of operation.
Figure 16E:
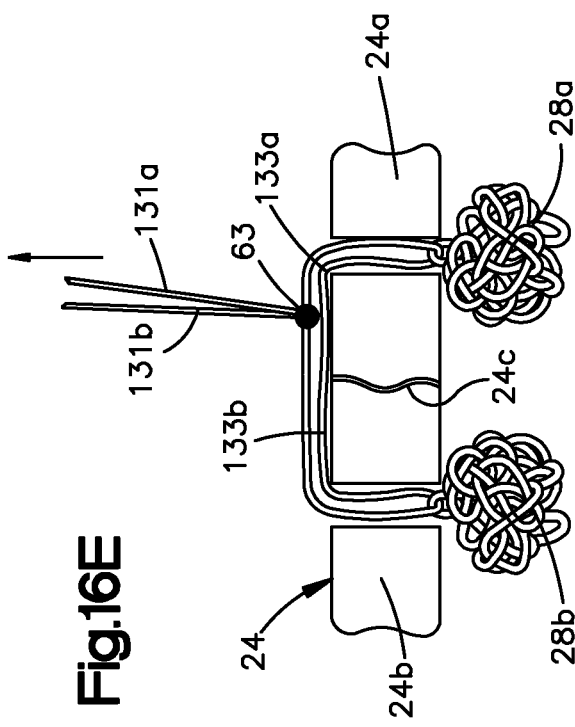
FIG. 16E is a schematic side elevation view of the anchor assembly as illustrated in FIG. 16D, showing locking of the locking member.
Figure 16F:
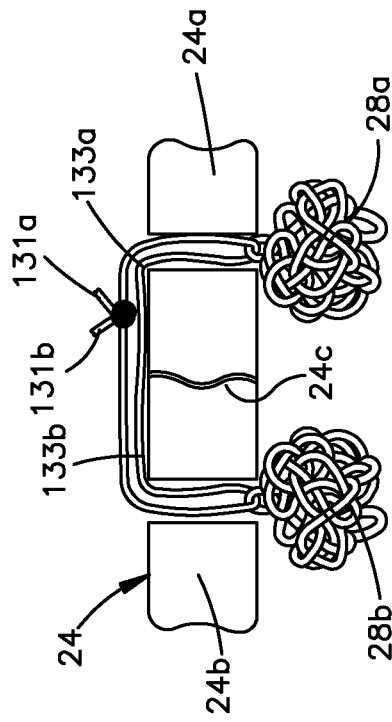
FIG. 16F is a schematic side elevation view of the anchor assembly as illustrated in FIG. 16E, show in a final assembled configuration.

Referring now to FIGS. 14C-D, because the second recess 362 is sized to receive the latch 370 in accordance with the illustrated embodiment, when the latch 370 moves from the first recess 354 into the second recess 362, the latch 370 decouples the first pusher assembly 317 from the second pusher assembly 333, and couples the second pusher assembly 333, and in particular the collar 332, to the casing 308 with respect to at least translation and can also couple the collar 332 to the casing 308 with respect to rotation. As described above, the casing 308 is fixed to the cannula 310 with respect to at least translation, and can further be fixed to the cannula 310 with respect to translation. In accordance with the illustrated embodiment, when the plunger 316 is rotated from the second position to the intermediate position such that the guide pin 344 travels along the intermediate track portion 342c (see FIGS. 13C-D), the first recess 354 and the channel 358 are brought into longitudinal alignment with the second recess 362.

During the first portion of the second stroke (see FIG. 13E), the plunger 316 and the collar 332 translate longitudinally until the first recess 354 and the channel 358 are aligned with the second recess 362 of the casing 308. During the transition between the first and second portions of the second stroke (see also FIG. 13F), the latch 370 is driven (for instance cams) out of the first recess 352 and thus moves from the first recess 352 into the second recess 362, as illustrated in FIGS. 14C-D. In accordance with an alternative embodiment, the plunger 316 can include a spring member that biases the latch 370 radially outward from the first recess 352 and into the second recess 362. Alternatively still, the insertion instrument 300 can be configured such that the latch 370 can cam out of the first recess 352 and move from the first recess into the second recess 362 the as the plunger 316 and the collar 332 rotate past the second recess 362 of the casing 308. Once the latch 370 has moved out of the first recess 354 and into the second recess 362 while remaining attached to the collar 332, the plunger 316 can continue to translate distally relative to the collar 332 during the second portion of the second stroke (see FIG. 13F), which causes the push rod 330 to translate distally relative to the push tube 334.

Operation of the insertion instrument 300 will now be described with initial reference to FIGS. 7A-D, 13A, and FIGS. 14A-D. In particular, the insertion instrument 300 can be constructed such that when the plunger 316, and thus the push rod 330, is in the first position, the first and second anchor bodies 28a and 28b are disposed in the cannula 310. In accordance with the illustrated embodiment, the first anchor body 28a is disposed longitudinally between the ejection port 442 and the plug 314 of the push tube 334. When the first pusher assembly 317, including the plunger 316 and the push rod 330, and the second pusher assembly 333, including the collar 332 and the push tube 334, are in the first position, the coupling assembly releasably couples the first pusher assembly 317 and the second pusher assembly 333 with respect to longitudinal movement and rotational movement. In particular, the latch 370 extends in both the first recess 354 and the channel 358, thereby releasably coupling the plunger 316 and the collar 332 with respect to longitudinal movement and rotational movement.

Referring now to FIGS. 8A-D, 13A-B, and 14B in particular, the tip 311 can be injected into the anatomical structure 24, for instance at the second target anatomical location 24b, until at least a portion (such as a distal portion) of the ejection port 442 extends distal of, or behind, the anatomical structure 24. In accordance with the illustrated embodiment, the insertion instrument can include a depth stop 383 that extends radially out from the cannula 310, and is configured to abut the anatomical structure 24 and provides resistance to further insertion of the cannula 310 into the anatomical structure 24 once the cannula 310 has been injected to a desired depth, for instance such that the ejection port 442 is disposed behind the anatomical structure 24. In this regard, the depth stop 383 can provide tactile feedback to the user that the cannula 310 has been injected into the target structure 24 at the desired depth. When a distal force is applied to the plunger 316 while the casing 308 remains stationary, for instance when a user grips the casing 308 relatively stationary while applying a distal force to the plunger 316, the first and second pusher assemblies 317 and 333 translate distally with respect to the casing 308 along the first stroke. As the first and second pusher assemblies 317 and 333 travel distally relative to the casing 308, the guide pin 344 travels proximally along the first track portion 342a of the collar 332 until the guide pin 344 reaches the proximal end 342a" of the first track portion 342a. As the second pusher assembly 333 travels distally, the plug 314 biases the second anchor body 28a to translate distally toward the tip 311. Furthermore, because the first pusher assembly 317 translates distally with the second pusher assembly 333 relative to the casing 308, and thus also the cannula 310, the pusher rod 330 biases the first anchor body 28b downstream toward the tip 311 during the first stroke.

Once the guide pin 344 has reached the proximal end 342a" of the first guide track portion 342a, the plug 314 has translated distal with respect to the proximal end of the ejection port 442, and thus has biased the second anchor body 28b out the ejection port 442 to a location behind the anatomical structure 24, for instance at the second target anatomical location 24b (see FIG. 1A) along the direction of Arrow B. Thus, the first track portion 342a has a longitudinal length sufficient such that movement of the guide pin 344 along the first track portion 342a causes the push tube 334 to eject the second anchor body 28b from the insertion instrument 300. Once the plunger 316 and the collar 332 have completed the first stroke, the plug 314 can be spaced proximally from the tip 311. It should be appreciated that the collar 332 defines a stop at the proximal end 342a" of the first track portion 342a that prevents further distal translation of the collar 332, and thus of the push tube 334 and the push rod 330, before the latch 370 is coupled to the casing 308, as described above with respect to FIG. 14C.

Next, referring to FIGS. 9A-D, once the second anchor body 28b has been ejected out the insertion instrument 300, the distal force can be removed from the plunger 316, which causes the spring member 365 to bias the second pusher assembly 333, for instance the collar 332, and thus also the first pusher assembly 317, proximally until the guide pin 344 is aligned with the offset position 342a''' of the first track portion 342a, as described above. Once the guide pin is in the offset position 342a', the guide pin 344 is aligned with the intermediate track portion 342c, and the plunger 316 can be rotated to the second track portion 342b.

Figure 9E:
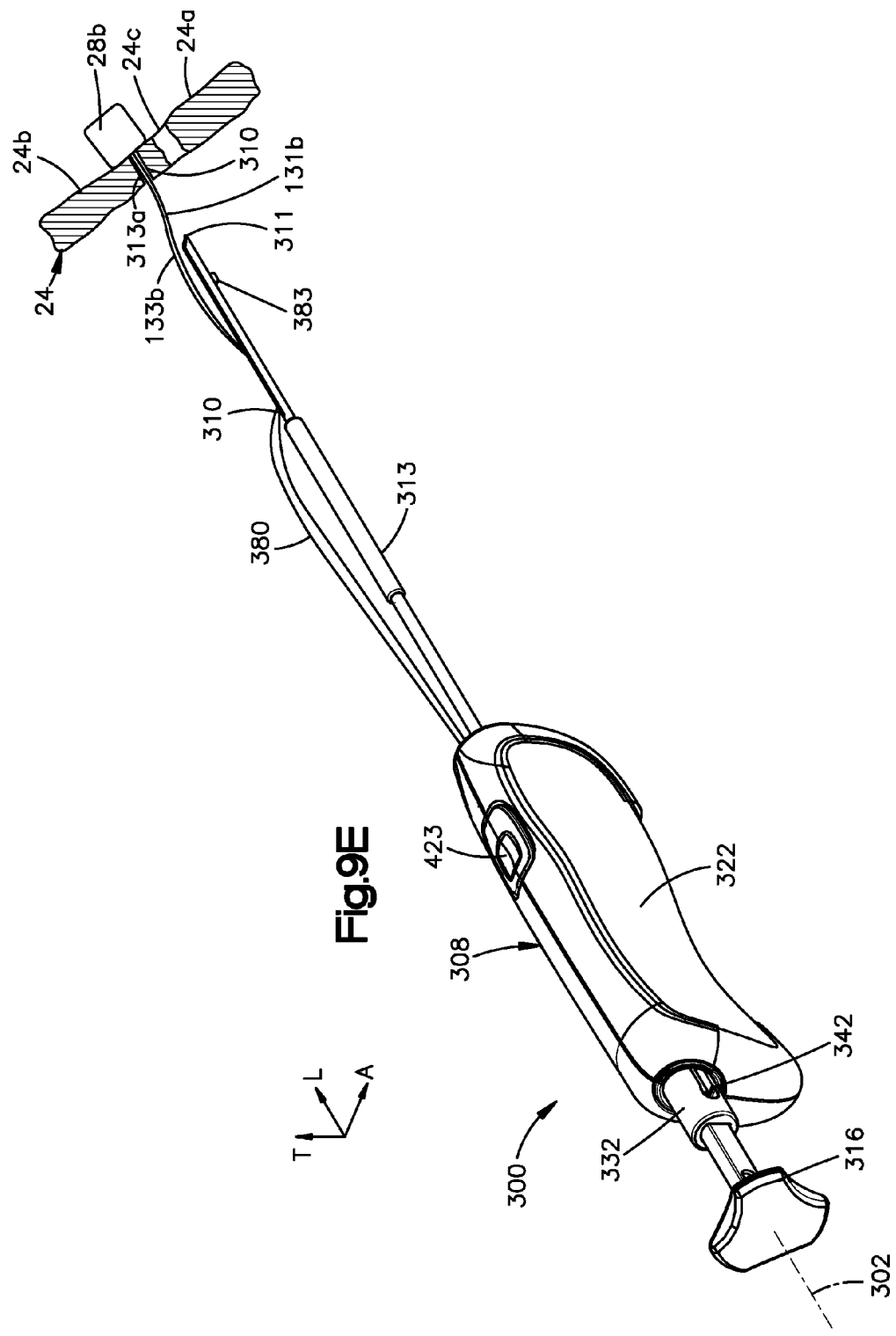
FIG. 9E is a perspective view of the fixation kit illustrated in FIG. 9A, showing the second anchor body in an expanded configuration.
Figure 10C:
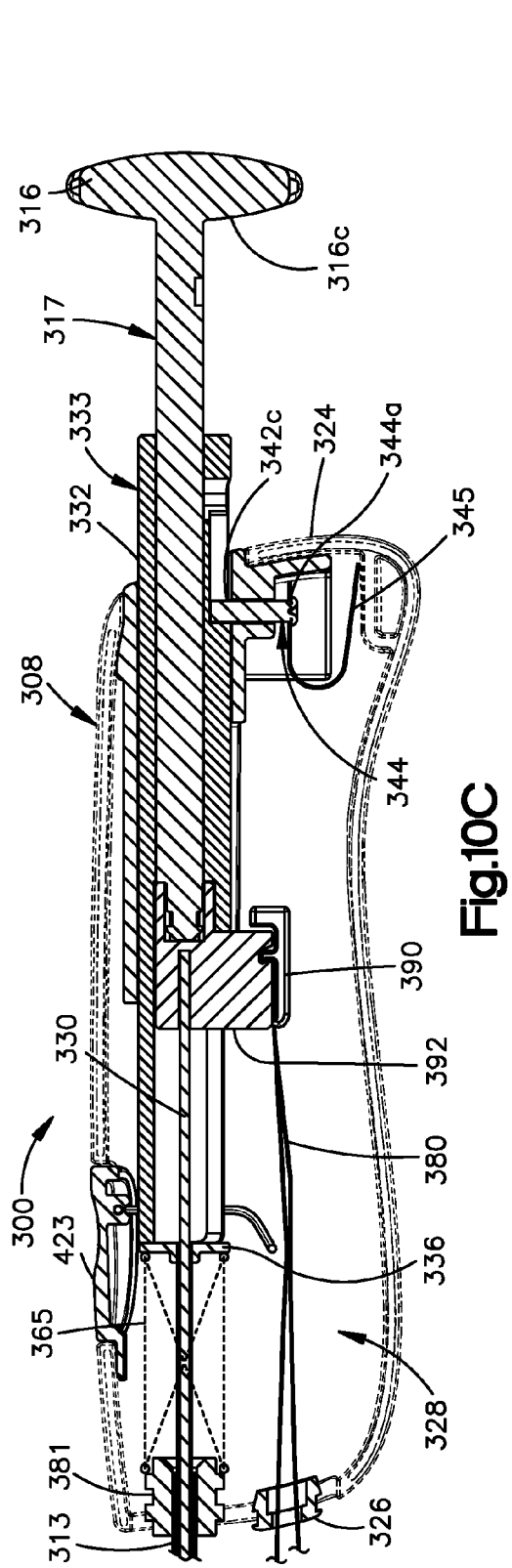
FIG. 10C is a sectional side elevation view of the casing of the insertion instrument illustrated in FIG. 10A.
Figure 10D:
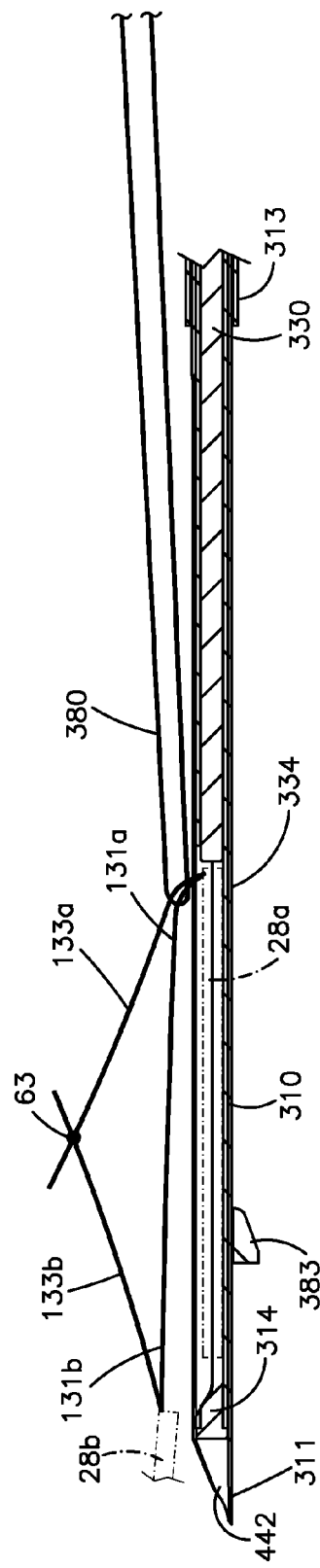
FIG. 10D is a sectional side elevation view of the cannula of the insertion instrument illustrated in FIG. 10A

At any time after completion of the first stroke and prior to ejection of the first anchor body 28a, the second anchor body 28b can be actuated to the expanded configuration illustrated in FIG. 1B. For instance, referring to FIG. 9E, the second anchor body 28b can be actuated by removing the insertion instrument from the target anatomy 24. As illustrated at FIG. 9B, and as described in more detail below with respect to, the insertion instrument 300 includes a strand retention assembly 390 that retains, for instance releaseably retains, at least one tensioning strand 380 that is operably coupled to the actuation portions 131a and 131b of the first and second anchor bodies 28a and 28b, extends proximally into the interior 328 of the casing 308 and is releasably connected to the retention assembly 390. The at least one tensioning strand 380 can be sized and positioned along the actuation strand 131 such that when tension is applied to the tensioning strand 380, for instance when removing the insertion instrument 300 proximally out of the anatomical structure 24, and in some embodiments translating the insertion instrument 310 further proximally after removal from the anatomical structure 24, the tensioning strand 380 communicates the tension to the actuation strand 131b, thereby actuating the second anchor body 28b to its expanded configuration. Alternatively still, a user can manually apply the actuation force to the respective actuation portion 131b as desired. The insertion instrument 300 can further define an elongate side slot 315 that extends through one radial side of the cannula 310 at a location proximal with respect to the ejection port 442. For instance, the slot 315 can extend from the ejection port 442 and proximally a sufficient distance and sized sufficiently such that the actuation portions 131a-b and attachment portions 133 can extends through the slot 315 and attach to the tensioning strand 380, which extends proximally into the casing 308. Alternatively, the at least one tensioning strand 380 can be attached to the actuation portions 131a-b inside the cannula 310, and can extend out the slot 315. Thus, the slot 315 can define a circumferential width that is greater than the thickness of the actuation strands 38a-b and the at least one tensioning strand 380, but less than the thickness of the anchor bodies 28a and 28b when the anchor bodies 28a and 28b are in their respective first configurations inside the cannula 310.

Referring now to FIGS. 10A-D, 13C-D, and FIGS. 14A-D, once the second anchor body 28b has been ejected and the guide pin 344 is at the offset position 342a''' of the first track portion 342a, and the insertion instrument 300 has been removed from the anatomical structure 24, the tip 311 of the insertion instrument 300 can be injected into the anatomical structure 24 at the first target anatomical location 24a in the manner described above with respect to the second target anatomical location 24b. The plunger 316 can be rotated along the direction of Arrow A before or after the tip 311 has been injected at the first target anatomical location 24a so as to travel along the intermediate stroke, which causes the guide pin 344 to translate along the intermediate track portion 342c toward the second track portion 342b. The plunger 316 can be rotated along the direction of Arrow A until the plunger 316 is in the intermediate position, whereby the guide pin 344 is longitudinally aligned with the second track portion 342b. Once the plunger 316 and collar 332 have rotated to the intermediate position, the plunger 316 and the collar 332 are again able to translate distally with respect to the casing 308, and the latch 370 is longitudinally aligned with the second recess 362.

Referring now to FIGS. 11A-D, 13D-E, and 14D, if the insertion instrument 300 was not injected into the first target anatomical location 24a prior to driving the plunger 316 to travel along the intermediate stroke, the insertion instrument 300 can be injected into the first target anatomical location 24a after driving the plunger 316 to travel along the intermediate stroke, but before driving the plunger 316 to translate along the second stroke. As the plunger 316 and the collar 332 are further driven distally with respect to the casing 308, the first and second pusher assemblies 317 and 333 translate distally with respect to the casing 308 along a first portion of the second stroke. Translation of the plunger 316 along the first portion of the second stroke causes the guide pin 344 to translate proximally from the intermediate portion to a location between the proximal and distal ends of the second track portion 342b.

As the plunger 316 translates distally with respect to the casing 308, the coupling assembly 350 causes the collar 332, and thus the push tube 334 including the plug 314, to correspondingly translate distally with respect to the casing 308 and cannula 310 until the first recess 354 becomes radially aligned with the second recess 362. Thus, it can be said that movement of the guide pin 344 along the second track portion 342b causes the latch 370 to move in alignment with the second recess 362. The second recess 362 can be positioned such that the latch 370 is radially aligned with the second recess 362 once the plug 314 has translated to a position distal with respect to the tip 311, and thus distal with respect to the ejection port 442, which can occur once the plunger 316 has translated along the first portion of the second stroke. Because the plug 314 has translated distal to the ejection port 442, the plug 314 is removed from interference with the first anchor body 28a as the first anchor body 28a is ejected out the cannula 310. Furthermore, because the push rod 330 and the push tube 334 translate together along the first portion of the second stroke, the push rod 330 continues to bias the first anchor body 28b downstream in the elongate opening 312 of the cannula 310 toward the tip 311. As the first and second recesses 354 and 362 become radially aligned at the transition between the first and second portions of the second stroke, the latch 370 is driven from the first recess 354 into the second recess 362.

Referring now to FIGS. 12A-D, 13E-F, and 14D, once the latch 370 is disposed in second recess 352, the second pusher assembly 333 becomes coupled to the casing 308 with respect to translation. Because the latch 370 is removed from the first recess 354, the first pusher assembly 317 is decoupled from the second pusher assembly 333 with respect to translation. Accordingly, the first pusher assembly 317 can translate with respect to the second pusher assembly 333 and the casing 308, and thus also with respect to the cannula 310. Thus, it can be said that the latch 370 moves into the second recess 362 so as to translatably decouple the push rod 330 and the push tube 334, such that the push rod 330 is translatable independently of the push tube 344 so as to eject the first anchor body 28a from the insertion instrument 330.

In accordance with the illustrated embodiment, as the first pusher assembly 317 is further biased distally with respect to the second pusher assembly 333 during the second portion of the second stroke, the plunger 316 and the push rod 330 translate distally with respect to the casing 308, and thus also the cannula 310. As a result, the push rod 330, for instance at its distal end, biases the second anchor body 28b to move distally relative to the plug 314. The plug 314 can define a ramp 376 at its proximal end. The ramp 376 can thus be disposed distal of the ejection port 442 and positioned along the longitudinal axis 302, and thus aligned with the first anchor body 28a as the pusher rod 330 translates along the longitudinal direction and ejects the first anchor body 28a out the cannula 310 along the longitudinal direction. The ramp 376 can define a tapered ejection surface 378 that is angled radially outward as it extends distally. Accordingly, as the pusher rod 330 biases the first anchor body 28a to translate distally from the ejection port 442 onto the ejection surface 378 as the pusher rod 330 translates relative to the plug 314, the first anchor body 28a rides along the ejection surface 378, which directs the first anchor body 28a away from the insertion instrument 300 at the first target anatomical location 24a. Thus, the second track portion 342b has a longitudinal length so as to allow the plug 314 to translate to a location distal of the tip 311, such that distal translation of the push rod 330 ejects the first anchor body 28a out the insertion instrument.

While the coupling assembly 350 is configured such that the collar 332 moves along the first stroke with the plunger 316, moves along the intermediate stroke with the plunger 316, and moves along a first portion of the second stroke with the plunger 316, it should be appreciated in accordance with alternative embodiments that the coupling assembly 350 can be configured such that the collar 332 translatably decouples from the plunger 316 after or during the first stroke, or after or during the intermediate stroke.

Referring now to FIG. 12E, once the first anchor body 28a has been injected to the first target location 24a at a location behind the anatomical structure 24, the first anchor body 28a can be actuated to its expanded configuration. For instance, the first anchor body 28a can be manually expanded by the user applying the actuation force F (FIG. 1A) to the respective actuation portion 131a. In accordance with the illustrated embodiment, the actuation strands 38a and 38b of the first and second anchor bodies 28a and 28b, respectively, can be a common strand. Accordingly, the actuation portion 131a is integral with the actuation portion 131b, and proximal translation of the insertion instrument 300, for instance upon removal of the insertion instrument 300 from the anatomical structure 24, can cause the insertion instrument 300 to apply a proximal tensile force onto the tensioning strand 380, which communicates the tensile force to the second anchor body 28b, thereby actuating the second anchor body 28 to its expanded configuration.

Referring now to FIGS. 15A-E, the coupling assembly 350 can be constructed in accordance with another embodiment, and can include at least one first coupling member 352 illustrated as a first recess 354 that extends radially into the first pusher assembly 317, such as the plunger 316, in accordance with the illustrated embodiment. The coupling assembly 350 can further include at least one second coupling member 356 illustrated as a channel 358, that extends radially through the second pusher assembly 333, such as the collar 332, in accordance with the illustrated embodiment. The coupling assembly 350 can further include at least one third coupling member 360 illustrated as a second recess 362 (FIG. 15C), that extends radially outward into the casing 308 in accordance with the illustrated embodiment. Furthermore, in accordance with the illustrated embodiment, the second recess 362 is disposed distal with respect to the channel 358 when the plunger 316 is in the first position illustrated in FIGS. 7A and 13A. The second recess 362 can further be radially offset with respect to the channel 358 when the plunger 316 is in the first position illustrated in FIGS. 7A and 13A. Alternatively, the second recess 362 can be radially aligned with respect to the second recess 362 (for instance if the track 342 does not include the intermediate track portion 342c, and can alternatively still be annular so as to circumscribe the radially inner surface of the casing 308 if desired.

The coupling assembly 350 can further include at least one fourth coupling member 368 illustrated as a latch 370 that is sized to partially fit in each of the first recess 354, the second recess 362. In accordance with the illustrated embodiment, the latch 370 is substantially spherical, and each of the first recess 354 and the second recess 362 can be substantially partially spherical, though it should be appreciated that the latch 370 and each of the first recess 354 and the second recess 362 can define any suitable shape as desired. The latch 370 can be further sized to be disposed in the channel 358, which can be in the form of a slot that is defined by a longitudinal dimension substantially equal to that of the latch 370, and is further defined by a radial dimension that is substantially equal to that of the latch 370. Accordingly, the latch 370 can travel along the channel 358 between the first recess 354 (FIGS. 15A-B) and the second recess 362 (FIGS. 15D-E).

In accordance with the illustrated embodiment, the coupling assembly 350 is in the first mode of operation when the guide pin 344 is in the first track portion 342a, and remains in the first mode of operation when the guide pin 344 travels from the first track portion 342a to the intermediate track portion 342c, and further remains in the first mode of operation when the guide pin 344 travels along part of the second track portion 342b. In particular, the first recess 354 and the channel 358 can be positioned so as to be radially aligned when the guide pin 344 extends into the any of, and all of as illustrated, the first track portion 342a, the intermediate track portion 342c, and the portion of the second track portion 342b. Further, the latch 370 defines a radial dimension substantially equal to that of the first recess 354 and the channel 358 combined, which is substantially equal to that of the channel 358 and the second recess 362, combined. Thus, the radial dimension of the latch 370 is also substantially equal to that of the channel 358 and the second recess 362 combined. It should also therefore be appreciated that the first recess 354 and the second recess 362 can define substantially the same radial dimension.

Accordingly, in the first mode of operation, the latch 370 is partially disposed in the first recess 354 of the plunger 316, and extends into the channel 358 of the collar 332. The latch 370 can be sized so as to be captured between the casing 308 and the plunger 316, and to extend through the collar 332 in the channel 358. Because the first recess 354 is shaped substantially equal to a portion of the latch 370 in the longitudinal and circumferential directions, longitudinal and rotational motion of the plunger 316 correspondingly causes the latch 370 to move longitudinally and rotationally, respectively, along with the plunger 316 when the latch 370 is disposed in the first recess 354. Furthermore, because the channel 358 is dimensioned substantially equal to that of the latch 370 in both the longitudinal and circumferential directions, longitudinal and rotational motion of the latch 370 correspondingly causes the collar 332 to move longitudinally and rotationally, respectively. As a result, when the latch 370 is disposed in the first recess 354 and the channel 358, the plunger 316 and the collar 332, and thus the first and second pusher assemblies 317 and 333, are coupled with respect to movement or translation along the longitudinal direction, and are further coupled with respect to rotation or movement in the radial direction.

Referring now to FIGS. 15C-E, because the second recess 362 is shaped substantially equal to a portion of the latch 370 in accordance with the illustrated embodiment, when the latch 370 moves from the first recess 354 into the second recess 362, the latch 370 decouples the first pusher assembly 317 from the second pusher assembly 333, and couples the second pusher assembly 333, and in particular the collar 332, to the casing 308 with respect to at least translation and can also couple the collar 332 to the casing 308 with respect to rotation. As described above, the casing 308 is fixed to the cannula 310 with respect to at least translation, and can further be fixed to the cannula 310 with respect to translation. In accordance with the illustrated embodiment, when the plunger 316 is rotated from the second position to the intermediate position such that the guide pin 344 travels along the intermediate track portion 342c (see FIGS. 13C-D), the first recess 354 and the channel 358 are brought into longitudinal alignment with the second recess 362.

During the first portion of the second stroke (see FIG. 13E), the plunger 316 and the collar 332 translate longitudinally until the first recess 354 and the channel 358 are aligned with the second recess 362 of the casing 308. During the transition between the first and second portions of the second stroke (see also FIG. 13F), the latch 370 is driven (for instance cams) out of the first recess 352 and thus moves from the first recess 352 into the second recess 362. In accordance with an alternative embodiment, the plunger 316 can include a spring member that biases the latch 370 radially outward from the first recess 352 and into the second recess 362. Alternatively still, the insertion instrument 300 can be configured such that the latch 370 can cam out of the first recess 352 and move from the first recess into the second recess 362 the as the plunger 316 and the collar 332 translate past the second recess 362 of the casing 308. Once the latch 370 has moved out of the first recess 354 and into the second recess 362 while remaining disposed in the channel 358 of the collar 332, the plunger 316 can continue to translate distally relative to the collar 332 during the second portion of the second stroke (see FIG. 13F), which causes the push rod 330 to translate distally relative to the push tube 334.

Referring now to FIGS. 16A-17D, the anchor assembly 20 can include at least one tensioning member, such as a tensioning strand 380 that can be stitched through the first and second actuation strands 38a and 38b, respectively, of the first and second anchor bodies 28a and 28b. The anchor assembly 20 can include as many tensioning strands as desired that extend through one or both of the first and second actuation strands 38a and 38b. The tensioning strand 380 defines a first end 380', a second end 380", and a middle portion 380''' that extends between the first and second ends 380' and 380".

The tensioning strand 380 can be stitched through the first actuation strand of at least one of the anchor bodies 28a and 28b. In accordance with the illustrated embodiment, the tensioning strand 380 is stitched through the first actuation strand, and in particular through the first actuation portion 131a and the first attachment portion 133a of the first anchor body 28a. For instance, the first tensioning stand 380a can be threaded onto a needle, which is driven through the first actuation strand 38a, so as to insert the tensioning strand 380 through the actuation strand 38a, such that the tensioning strand 380 is connected to the actuation strand 38a at a location closer to the first anchor body 28a than the second anchor body 28b.

Referring now to FIGS. 7C and 17A-D the insertion instrument 300 can include a retention assembly, such as a strand retention assembly 390, that is configured to retain the at least one tensioning strand 380, and in particular the first and second ends 380a' and 380" of the tensioning strand 380. In accordance with one embodiment, the retention assembly releasably retains the tensioning strands 380. As will now be described, the retention assembly 390 is translatably fixed to the first pusher assembly 317, and thus moves proximally and distally along the longitudinal direction L along with the plunger 316. Accordingly, the tensioning strand 308 provides sufficient slack for the implantation of the first and second anchor bodies 28a and 28b in the respective target anatomical locations 24a and 24b. After the second anchor body 28b has been ejected from the cannula 310, proximal movement of the insertion instrument 300, for instance when removing the instrument from the anatomical structure 24, causes the retention assembly 390 to move in the proximal direction, thereby applying the tensile actuation force to the second tensioning strand 380, which communicates the actuation force to the second actuation portion 131b of the second actuation strand 38b, and causes the second anchor body 28b to expand. Similarly, after the first anchor body 28a has been ejected from the cannula 310, proximal movement of the insertion instrument 300, for instance when removing the instrument from the anatomical structure 24, causes the retention assembly 390 to move in the proximal direction, thereby applying the tensile actuation force to the tensioning strand 380, which communicates the actuation force to the first actuation portion 131a of the first actuation strand 38a, and causes the first anchor body 28a to expand.

The retention assembly 390 includes a retention housing 392 having a housing body 394 that is supported, directly or indirectly, by the plunger 316 is coupled to the distal end 316a of the plunger 316 in accordance with the illustrated embodiment. The housing body 394 is further coupled to the push rod 330, which extends distally from the retention assembly 390. The retention housing 392 includes a first locking member 400 and a second locking member 402 that extend from opposite, for instance laterally opposite, ends of the housing body 394. The first and second locking members 400 and 402 are configured to retain the respective first and second opposed ends 380' and 380" of the tensioning strand 380. The first locking member 400 is configured to be disengaged so as to release the first end 380'. The second locking member 402 is configured to retain the second end 380" of the tensioning strand 380 when the first locking member 400 is released.

In accordance with the illustrated embodiment, the first locking member 400 includes a locking body 407, and a clip 409 that is configured to be removably secured to the locking body 407. For instance, the clip 409 can be hingeably attached to the locking body 407, or otherwise movably attached to the locking body 407 as desired. The retention housing 392 can define a retention channel 411 disposed between the locking body 407 and the clip 409. The retention channel 411 can have any suitable shape as desired, and defines a serpentine shape in accordance with the illustrated embodiment. When the clip 409 is secured to the locking body 407, the retention channel 411 has a thickness less than that of the first end 380' of the tensioning strand 380. The clip 409 includes an outwardly projecting release tab 413 that is configured to receive a release force so as to release the clip 409 from the locking body 407, thereby freeing the first end 380' of the retention strand 380 from the retention assembly 39, as is described in more detail below.

In accordance with the illustrated embodiment, the second locking member 402 includes a second locking body 415, and a second clip 417 that is configured to be secured to the second locking body 415. The retention housing 392 can define a second retention channel 419 disposed between the second locking body 415 and the second clip 417. The second retention channel 419 can have any suitable shape as desired, and defines a serpentine shape in accordance with the illustrated embodiment. When the second clip 417 is secured to the second locking body 415, the second retention channel 419 has a thickness less than that of the second end 380" of the tensioning strand 380.

Thus, during operation, the first end 380' of the tensioning strand 380 can extend through the first retention channel 411 and the clip 409 can be secured to the locking body 407, thereby releasably locking the first end 380' of the tensioning strand 380 in the first locking member 400. Similarly, the second end 380" of the tensioning strand 380 can extend through the second retention channel 419 and the second clip 417 can be secured to the second locking body 415, thereby releasably locking the second end 380" of the tensioning strand 380 in the second locking member 402. When the first and second ends 380' and 380" are secured to the retention assembly, the insertion instrument can translate proximally once the first and second anchors 28a and 28b have been implanted to thereby deliver the tensile actuation force to the tensioning strand 380, which communicates the tensile actuation force to the respective actuation portions of the anchor bodies, thereby causing the anchor bodies to expand in the manner described above.

The retention assembly 490 further includes an actuator assembly 421 that is configured to release the first locking member 400. In particular, the actuator assembly 421 can include an actuator or button 423 that is carried by the casing 308 (see FIG. 7C), and at least one biasing member, such as a pair of arms 425 that extend into the interior 328 of the casing 308 from the button 423. It is recognized that the first anchor body 28a is ejected from the instrument 300 once the plunger 316 has completed the second stroke. Accordingly, the actuator assembly 421 is positioned such that the arms contact the retention housing 492 once the plunger 316 has reached the end of the second stroke.

Figure 17A:
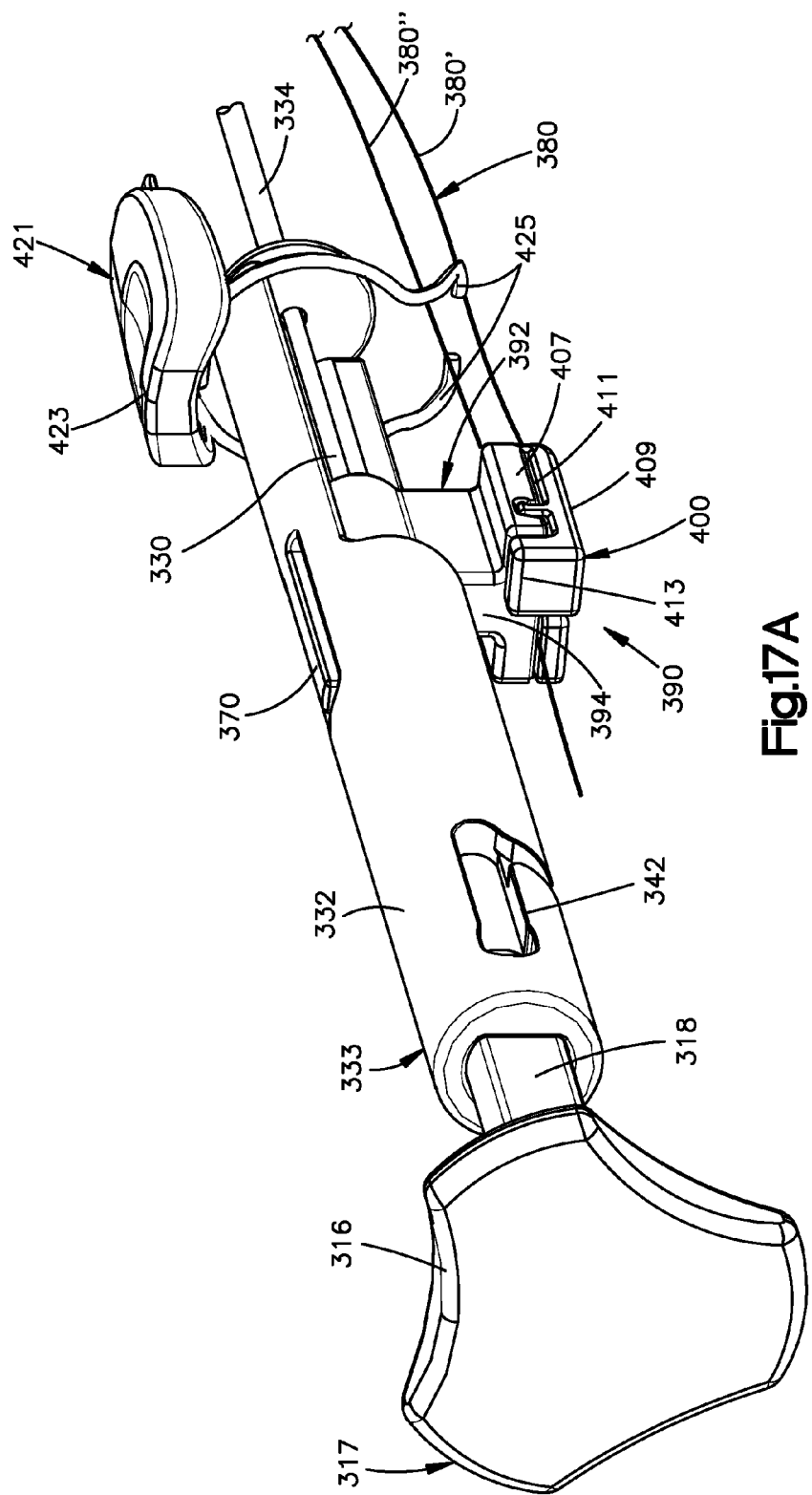
FIG. 17A is a perspective view of a strand retention assembly constructed in accordance with one embodiment, showing a releasable locking member.
Figure 17B:
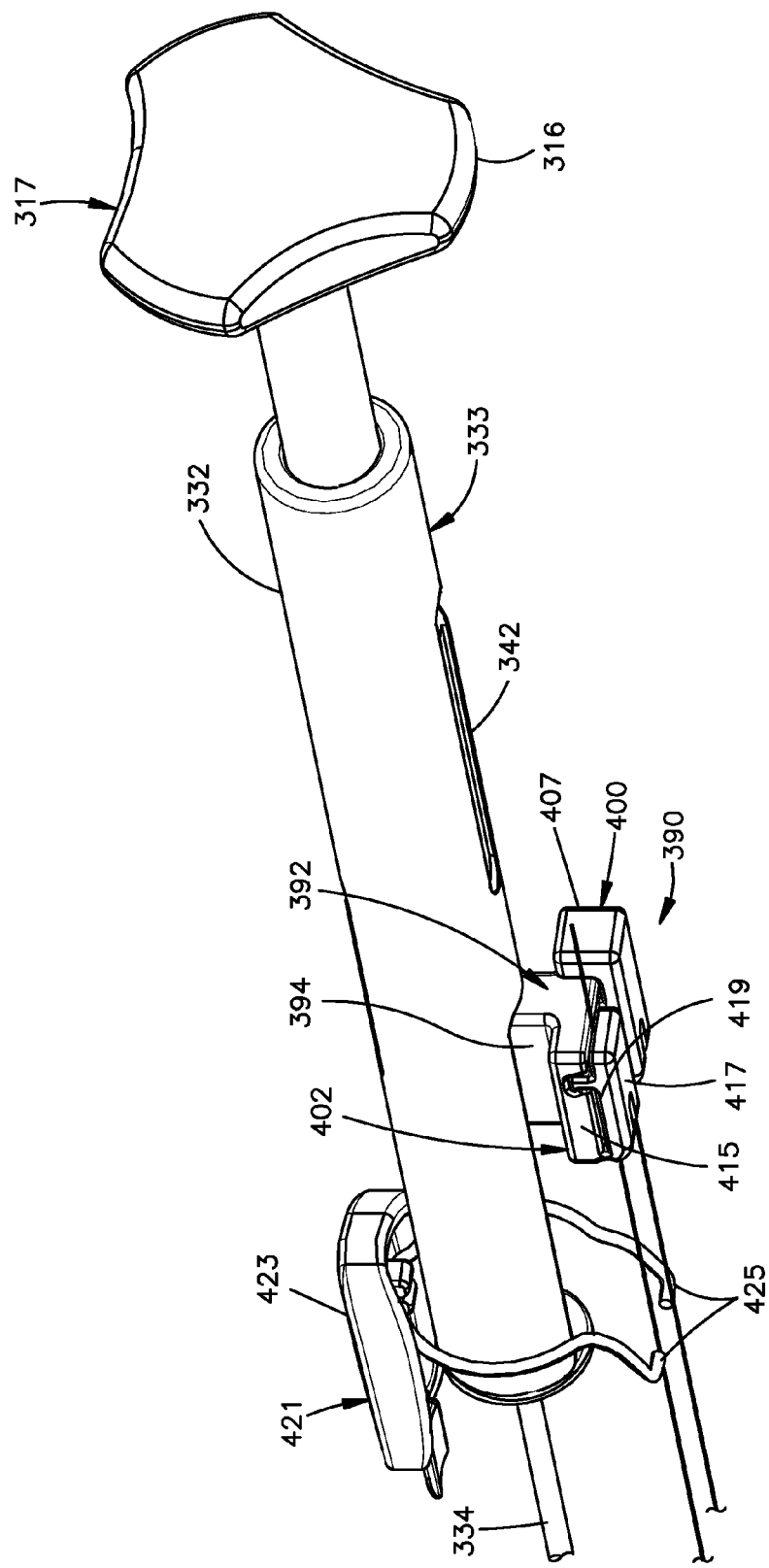
FIG. 17B is a perspective view of the strand retention assembly illustrated in FIG. 17A, showing a fixed locking member.
Figure 17C:
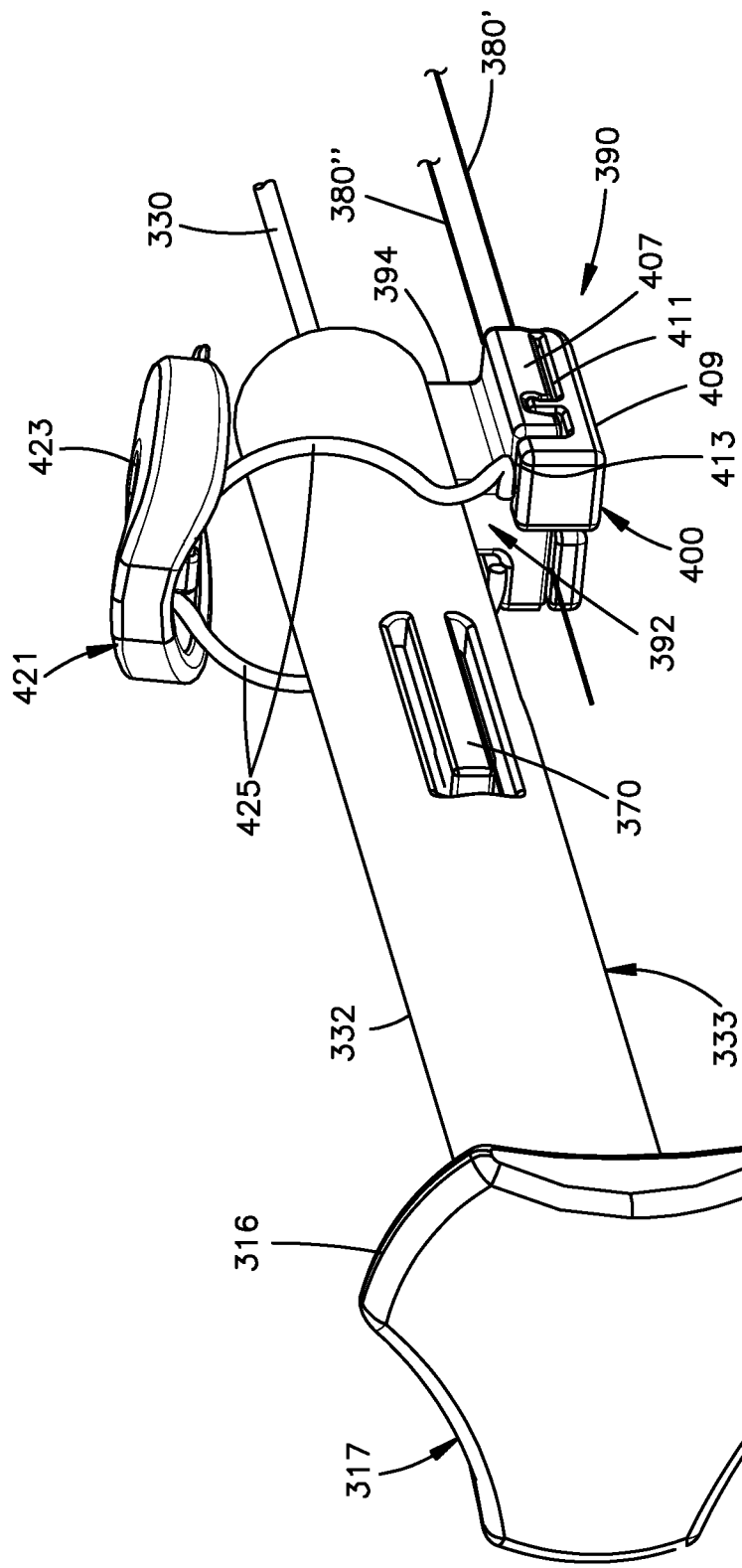
FIG. 17C is a perspective view of the strand retention assembly illustrated in FIG. 17A, operably coupled to an actuator.
Figure 17D:
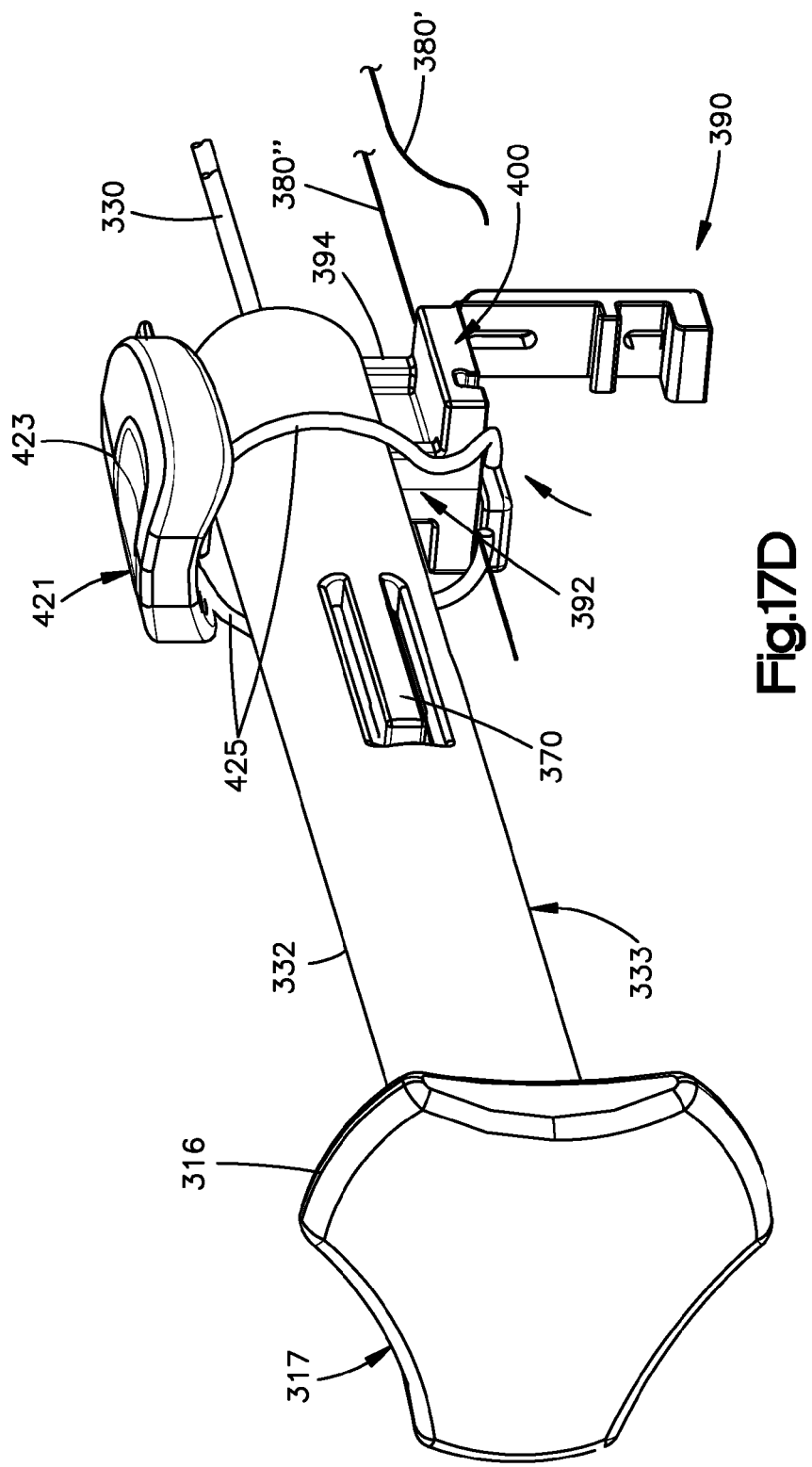
FIG. 17D is a perspective view of the strand retention assembly illustrated in FIG. 17C, shown in a released position.

Referring to FIGS. 12C and 17C, As the plunger 316 reaches the end of the second stroke, the arms 425 ride along outer surfaces of the first and second locking bodies 407 and 415, respectively, which causes the button 423 to raise radially outwardly from an unloaded position to a loaded position. Once the plunger 316 has reached the end of the second stroke, one of the arms is aligned with the release tab 413. Accordingly, the button 423 can be depressed, which causes one of the arms 425 to drive the release tab 413 away from the first locking body 407, which causes the clip 409 to move into an unlocked position whereby the clip 409 is removed from the locking body 407 a sufficient amount such that the retention channel 411 is thicker than the first end 380' of the tensioning strand 380. As a result, the first end 380' becomes unlocked from the retention assembly 390, and the instrument can be moved proximally so as to draw the tensioning strand 380 through the actuation strands of the anchor bodies.

Referring now to FIG. 18A, the anchor assembly 20 can alternatively include a pair of tensioning members, such as a first tensioning strand 380a and a second tensioning strand 380b that can be stitched through the first and second actuation strands 38a and 38b, respectively, of the first and second anchor bodies 28a and 28b. The anchor assembly 20 can include as many tensioning strands as desired that extend through one or both of the first and second actuation strands 38a and 38b. The first tensioning strand 380a defines a first end 380a', a second end 380a", and a middle portion 380a''' that extends between the first and second ends 380a' and 380a". Similarly, the second tensioning strand 380b defines a first end 380b', a second end 380b", and a middle portion 380b''' that extends between the first and second ends 380b' and 380b".

The first tensioning strand 380a can be stitched through the first actuation strand 38a, for instance through opposed ends of the first actuation strand 38a. For instance, the first tensioning stand 380a can be threaded onto a needle, which is driven through the first actuation strand 38a, so as to insert the first tensioning strand 380a through the first actuation strand 38a. The first tensioning strand 380a can extend through the first attachment portion 133a and the first actuation portion 131a of the first actuation strand 38a, and can loop back through the first actuation portion 131a and the first attachment portion 133a, at a location between the first and second anchor bodies 28a and 28b.

Similarly, the second tensioning strand 380b can be stitched through the second actuation strand 38b, for instance through opposed ends of the second actuation strand 380b. For instance, the second tensioning stand 380b can be threaded onto a needle, which is driven through the second actuation strand 38b so as to insert the second tensioning strand 380b through the second actuation strand 38b. The second tensioning strand 380b can extend through the first attachment portion 133b and the actuation portion 131b of the second actuation strand 38b, and can loop back through the second attachment portion 133b and the second actuation portion 131b at a location between the first and second anchor bodies 28a and 28b.

Referring now to FIGS. 19A-B, the strand retention assembly 390 can be constructed in accordance with an alternative embodiment to releasably retain the at least one tensioning strand 380. Thus, while the strand retention assembly 390 illustrated in FIGS. 19A-B are illustrated as retaining the pair of first and second tensioning strands 380a and 380b, the retention assembly 390 can alternatively releasably retain a single tensioning strand, for instance as described above with respect to FIGS. 16-17. In accordance with the embodiment illustrated in FIGS. 19A-B, the retention assembly 390 retains the first and second ends 380a' and 380" and 380b' and 380b" of the first and second tensioning strands 380a and 380b. In accordance with one embodiment, the retention assembly 390 releasably retains the first and second tensioning strands 380a and 380b. As will now be described, the retention assembly 390 is translatably fixed to the first pusher assembly 317, and thus moves proximally and distally along the longitudinal direction L along with the plunger 316. Accordingly, after the second anchor body 28b has been ejected from the cannula 310, movement of the plunger 316 and the push rod 330 in the proximal direction causes the retention assembly 390 to move in the proximal direction, thereby applying the tensile actuation force to the second tensioning strand 380b, which communicates the actuation force to the second actuation portion 131b of the second actuation strand 38b, and causes the second anchor body 28b to expand. Similarly, after the first anchor body 28a has been ejected from the cannula 310, movement of the plunger 316 and the push rod 330 in the proximal direction causes the retention assembly 390 to move in the proximal direction, thereby applying the tensile actuation force to the first tensioning strand 380a, which communicates the actuation force to the first actuation portion 131a of the first actuation strand 38a, and causes the first anchor body 28a to expand.

The retention assembly 390 includes a retention housing 392 having a housing body 394 that is supported, directly or indirectly, by the casing 308. In accordance with the illustrated embodiment, the retention housing 392 is disposed in the interior 328 of the casing 308, though the retention housing 392 can alternatively be carried external of the casing 308, and can be attached to the plunger 316 or any suitable alternative structure of the insertion instrument 300 as desired. The retention housing 392 defines a bore 396 that extends longitudinally into the housing body 394 along the proximal direction. In accordance with the illustrated embodiment, the bore 396 extends longitudinally through the housing body 394. The housing body 394 can define at least one interior surface 398 that defines a perimeter of the bore 396. The interior surface 398 can slope (for instance linearly, curvilinearly, or along any suitable alternative shape) radially outward as it travels proximally along a direction from a distal end of the housing body 394 to a proximal end of the housing body 394. Thus, the bore 396 can define a first cross-sectional dimension D3 along a direction substantially perpendicular to the longitudinal axis 302 at its first or proximal end, and a second cross-sectional dimension D4 along a direction substantially perpendicular to the longitudinal axis 302 at its second or distal end. Because the bore 396 can be tapered, the first cross-sectional dimension D3 can be less than the second cross-sectional dimension D4. The bore 396 can be tapered, for instance linearly, curvilinearly, or along any suitable alternatively shape as desired.

The retention assembly 390 can further include a first locking member 400 that is disposed inside the bore 396. The first locking member 400 has a cross-sectional dimension D5, for instance along a direction substantially perpendicular to the longitudinal axis 302, that is between the first cross-sectional dimension D3 and the second cross-sectional dimension D4. The first locking member 400 can be substantially spherical as illustrated, or can alternatively define any shape as desired. The retention assembly 390 is configured to retain at least one strand between the first locking member 400 and the interior surface 398 of the housing body 394. For instance, the first end of at least one or both of the tensioning strands 380a' and 380b' can extend between the first locking member 400 and the interior surface 398. The first locking member 400 is configured to bear against the interior surface 398 during operation of the instrument, thereby capturing the first ends 380a' and 380b' between the first locking member 400 and the interior surface 398 of the housing body 394, and preventing relative movement between each of the first ends 380a' and 380b' and the retention housing 392. Thus, the first locking member 400 can present a first locking surface, and the interior surface 398 can present a second locking surface that cooperates with the first locking surface so as to retain the first ends 380a' and 380b' of the first and second retention strands 380a and 380b in the retention assembly 390.

The retention assembly 390 can further include a second locking member 402 that is configured to be attached to the first locking member 400. In particular, the second locking member 402 can include a threaded plug 403 that is threadedly inserted into the proximal end of the housing body 394. Accordingly, the second locking member 402 can be disposed adjacent the tapered inner surface 398, and can close the proximal end of the tapered bore 396. Alternatively, the second locking member 402 can be integral with the housing body 394. The second locking member 402 defines at least one opening, such as a longitudinal opening 404, that is configured to receive the end of the one or more tensioning strands that are opposite the end of the tensioning strands that are captured between the first locking member 400 and the interior surface 398 of the housing body 394. Accordingly, the second locking member 402 is configured to receive each of the second ends 380a" and 380b" of the first and second tensioning strands 380a and 380b. The second locking member 402 can thus be aligned with the tapered bore 396, such that the second end 380a" and 380b" of each of the first and second strands 380a and 380b extends through the tapered bore 396 and is attached to the second locking member 402.

In accordance with the illustrated embodiment, the longitudinal opening 404 extends longitudinally between the bore 396 and the exterior of the plug 403, which can be the interior 328 of the casing 308. Each or both of the second ends 380a" and 380b" can be tied in a knot 406 at the proximal end of the longitudinal opening 404, such that the knot 406 abuts the proximal end of the second locking member 402. Thus, the retention assembly 390 is configured to fix the first and second ends 380a' and 380a" of the first tensioning strand 380a, and is further configured to fix the first and second ends 380b' and 380b" of the second tensioning strand 380b. The second ends 380a" and 380b" can alternatively or additionally extend between the first locking member 400 and the interior surface 398, and can be captured between the first locking member 400 and the interior surface 398 as desired so as to retain the second ends 380a" and 380b" in the retention assembly 390. The second locking member 402 can further include a second longitudinal opening 405 that is spaced from the longitudinal opening 404. The second longitudinal opening 405 is configured to receive the remainder of the first ends 380a' and 380b' that are captured between the first locking member 400 and the interior surface 398.

Figure 19C:
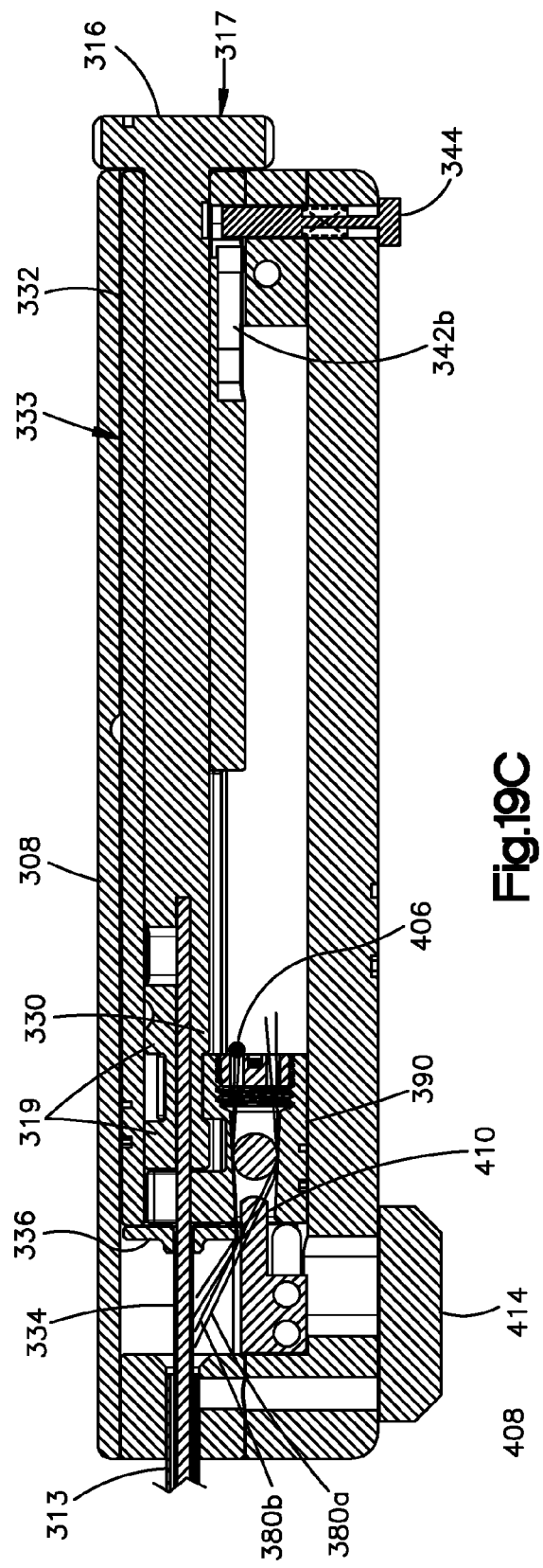
FIG. 19C is a sectional side elevation view of the casing of an insertion instrument similar to the insertion instrument as illustrated in FIG. 12C, but including a retention assembly constructed in accordance with an alternative embodiment.

Referring to FIG. 19C, the first pusher assembly 317 can include a pair of flanges 319 that project out from the plunger 316 so as to define a gap 321 that extends between the flanges 319. The gap 321 can be sized to receive the housing body 394, such that each of the flanges 319 abuts the proximal and distal ends of the housing body 394, respectively. Accordingly, proximal movement of the plunger 316 causes the distal one of the flanges 319 to bias the housing body 394 and thus the retention assembly 390, to move proximally along with the plunger 316, and therefore also along with the push rod 330. Similarly, distal movement of the plunger 316 causes the proximal one of the flanges 319 to bias the housing body 394 and thus the retention assembly 390, to move distally along with the plunger 316, and therefore also along with the push rod 330.

During operation, because the plunger 316 and the push rod 330 move distally in tandem along the first stroke and the second stroke, and because the first and second anchor bodies 28a and 28b move distally along with the push rod 330, the retention assembly 390 likewise moves distally along with the first and second anchor bodies 28a and 28b. Accordingly, the retention assembly 290 can operate so as to not induce tension in either of the first and second tensioning strands 380a and 380b, and thus in the respective first and second actuation strands 38a and 38b, before the first and second anchor bodies 28a and 28b have been ejected from the cannula 310. However, as will now be described, the insertion instrument 300, and in particular the plunger 316, can be actuated so as to apply the respective first and second actuation forces to the first and second anchor bodies 28a and 28b after the first and second anchor bodies have been ejected from the cannula 310.

For instance, referring now to FIGS. 8A-D and FIGS. 19A-B, once the plunger 316 has traveled along the first stroke, thereby ejecting the second bone anchor 28b from the cannula 310 at a location behind the anatomical structure 24 and the second anatomical location 24b, the plunger 316 can be translated proximally such that the guide pin 344 rides along the first track portion 342a along the distal direction until contacting the collar 332, which provides stop surface at the distal end of the first track portion 342a, thereby preventing further proximal translation of the plunger. Because contact between the anatomical structure 24 and the second anchor body 28b prevents the second anchor body 28b from translating proximally along with the retention assembly 390, the retention assembly applies a tensile force to the tensioning strand 380b, which is communicated to the second actuation strand 38b as the actuation force that causes the second anchor body 28b to move from the first configuration illustrated in FIG. 9A to the expanded configuration illustrated in FIG. 9E.

For instance, referring now to FIGS. 9A-E and FIGS. 19A-B, once the plunger 316 has traveled along the first stroke, thereby ejecting the second bone anchor 28b from the cannula 310 at a location behind the anatomical structure 24 at the second anatomical location 24b, the insertion instrument 300 can be translated proximally as it is removed from the anatomical tissue 24 as described above. Because contact between the anatomical structure 24 and the second anchor body 28b prevents the second anchor body 28b from translating proximally along with the insertion instrument 300, the retention assembly 390 applies a tensile force to the tensioning strand 380b, which is communicated to the second actuation strand 38b as the actuation force that causes the second anchor body 28b to move from the first configuration illustrated in FIG. 9A to the expanded configuration illustrated in FIG. 9E.

Similarly, referring now to FIGS. 18A-E and FIGS. 19A-B, once the plunger 316 has traveled along the second portion of the second stroke, thereby ejecting the first bone anchor 28a from the cannula 310 at a location behind the anatomical structure 24 at the first anatomical location 24a, the insertion instrument 300 can be translated proximally as it is removed from the anatomical tissue 24. Because contact between the anatomical structure 24 and the first anchor body 28a prevents the first anchor body 28a from translating proximally along with the retention assembly 390, the retention assembly 390 applies a tensile force to the first tensioning strand 380a, which is communicated to the first actuation strand 38a as the actuation force that causes the first anchor body 28a to move from the first configuration illustrated in FIG. 12A to the expanded configuration illustrated in FIG. 12E.

Once the first and second anchor bodies 28a and 28b have been actuated to their expanded configurations, the tensioning strands 380a and 380b can be released from the retention assembly 390. For instance, as will now be described, the retention assembly 390 can configured to release at one of the ends of the tensioning strands 380a and 380b. Alternatively, as described in more detail below, the insertion instrument 300 can include a cutting blade that is configured to sever the first and second tensioning strands 380a and 380b. Referring to FIG. 19C, the insertion instrument 300 can include a release member 408 that is coupled to the retention assembly 390 and is configured to iterate the retention assembly 390 to an unlocked configuration. The release member 480 can include any suitable linkage 410 that can be aligned with the first locking member 400. The release member 408 can include an actuator 414 that is carried by the casing 308 and coupled to the linkage 410, such that a user can manipulate the actuator 414, for instance slide the actuator proximally, so as to cause the linkage 410 to contact the first locking member 400 and bias the first locking member 400 proximally along the direction of Arrow 401 to an unlocked configuration, which creates a gap 412 between the first locking member 400 and the interior surface 398, as illustrated in FIG. 19B. The gap can be greater than a cross-sectional dimension of the tensioning strands 380a and 380b.

When the second ends 380a" and 380b" are tied at the second locking member 402, proximal translation of the insertion instrument 300 relative to the implanted anchor bodies 28a and 28b, causes the first ends 380a' and 380b' of the first and second tensioning strands 380a and 380b to travel out the retention assembly 390 through the gap, and further draws the respective first and second tensioning strands 380a and 380b through the respective actuation strands 38a and 38b, thereby removing the first and second tensioning strands 380a and 380b from the actuation strands 38a and 38b as illustrated in FIGS. 18C-18D. Alternatively, if the first and second ends 380a" and 380b" are retained by the first locking member 400 and not the second locking member 402, proximal translation of the insertion instrument 300 relative to the implanted anchor bodies 28a and 28b removes the tensioning strands 380a and 380b from the insertion instrument 300. The user can then manually draw the tensioning strands 380a and 380b through the respective actuation strands 38a and 38b so as to remove the first and second tensioning strands 380a and 380b from the actuation strands 38a and 38b.

Referring now to FIG. 18D, once the tensioning strands 380a and 380b have been removed from the actuation strands 38a and 38b, the user can draw the connector 63 toward the anatomical structure. It should be appreciated that the connector 63 can be attached to the actuation strands 38a and 38b when the first and second anchor bodies 28a and 28b are loaded in the insertion instrument 300. Alternatively, the user can connect the actuation strands 38a and 38b after the first and second anchor bodies 28a and 28b have been ejected. While the connector member 63 illustrated in FIGS. 18C-E is configured as a knot of the type described above, the connector member 63 can be alternatively configured as desired. In accordance with the embodiment illustrated in FIGS. 18C-E, a tensile force can be applied to the free end 70, which causes the connector member to translate toward the anatomical structure, thereby applying an approximation force to the actuation strands 38a and 38b, thereby approximating the tissue gap 24c. The portion of the actuation strands 38a and 38b that extend out from the connector member 63 can then be severed as desired.

Referring now to FIGS. 20A-B, and as described above, the insertion instrument 300 can include a cutting assembly 416 that includes a cutting blade 418, and is movable between a disengaged position whereby the cutting blade 418 is spaced from one of the ends, such as the first ends 380a' and 380b' of the tensioning strands 380a and 380b that are retained by the retention assembly 390, and an engaged position whereby the cutting blade severs the first ends 380a' and 380b' of the tensioning strands 380. It should be appreciated that the retention assembly 390 illustrated in FIGS. 20A-B can be configured as illustrated in FIG. 17, and that the retention assembly 390 can be attached to a single tensioning strand, such that the cutting blade 418 is configured to cut a first end of the single tensioning strand, such that removal of the insertion instrument 300 from the anchor bodies 28a and 28b draws the tensioning strand through and away from actuation strands 38a and 38b.

The cutting assembly 416 can include a longitudinally elongate shaft 420, and a switch 422 that is pivotally coupled between the elongate shaft 420 and the cutting blade 418, thereby coupling the elongate shaft 420 to the cutting blade 418. The cutting blade 418 can be carried by a blade housing 424, such that the elongate shaft 420 and the switch 422 are indirectly coupled to the cutting blade 418. The proximal end of the longitudinally elongate shaft 420 can extend proximally out of the casing 408, and the longitudinal shaft can extend in a side wall of the casing 408. The shaft 420 is movable longitudinally in the distal direction from a disengaged position to an engaged position. Distal movement of the shaft 420 causes the switch to pivot, thereby driving the cutting blade 418 to translate proximally and into the first ends 380a' and 380b' of the first and second tensioning strands 380a and 380b, thereby severing the first ends 380a' and 380b'. Once the tensioning strands 380a and 380b have been severed, the instrument can be translated proximally with respect to the ejected anchor bodies 28a and 28b so as to remove the tensioning strands 380a and 380b from the respective actuation strands 38a and 38b in the manner described above.

Figure 21A:
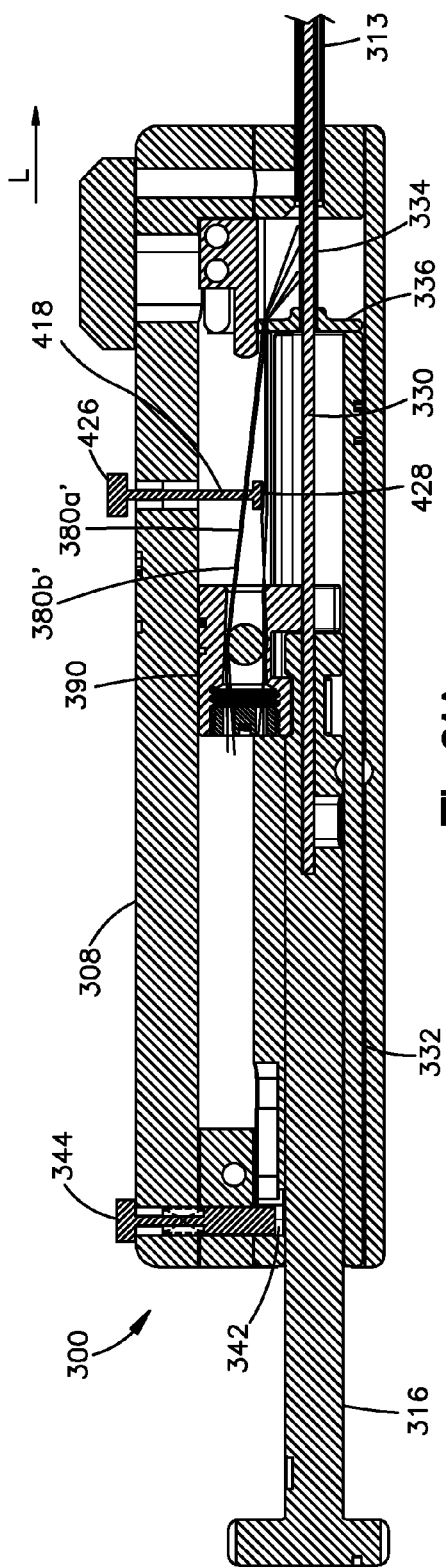
FIG. 21A is a sectional side elevation view of the insertion instrument as illustrated in FIG. 20A, but including a cutting assembly constructed in accordance with another embodiment, shown in a disengaged position.
Figure 21B:
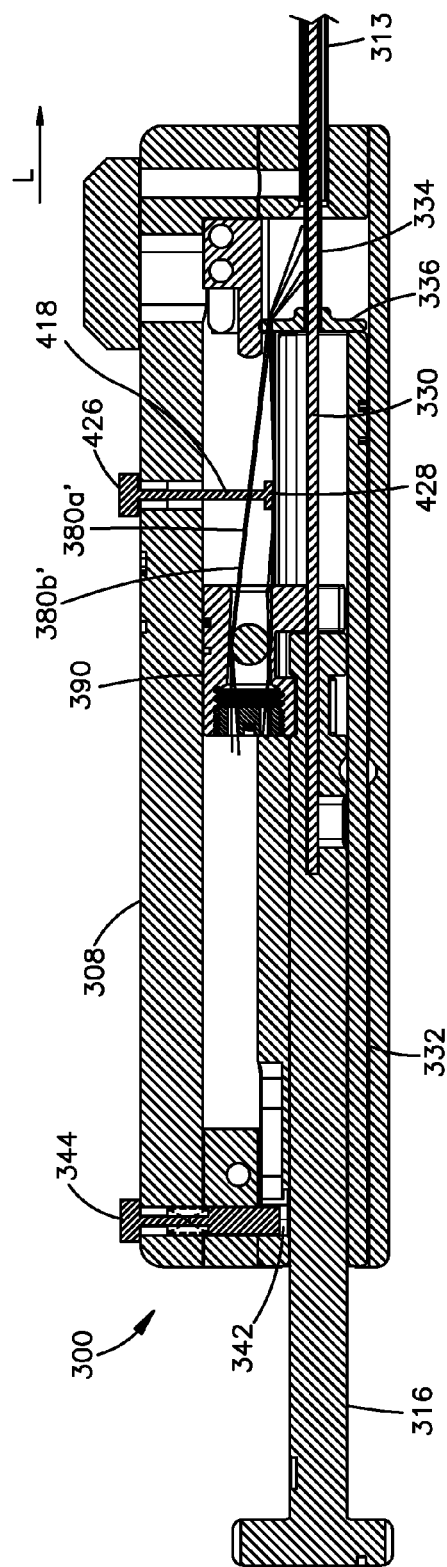
FIG. 21B is a sectional side elevation view of the insertion instrument as illustrated in FIG. 21A, but showing the cutting assembly in an engaged position.
Figure 22C:
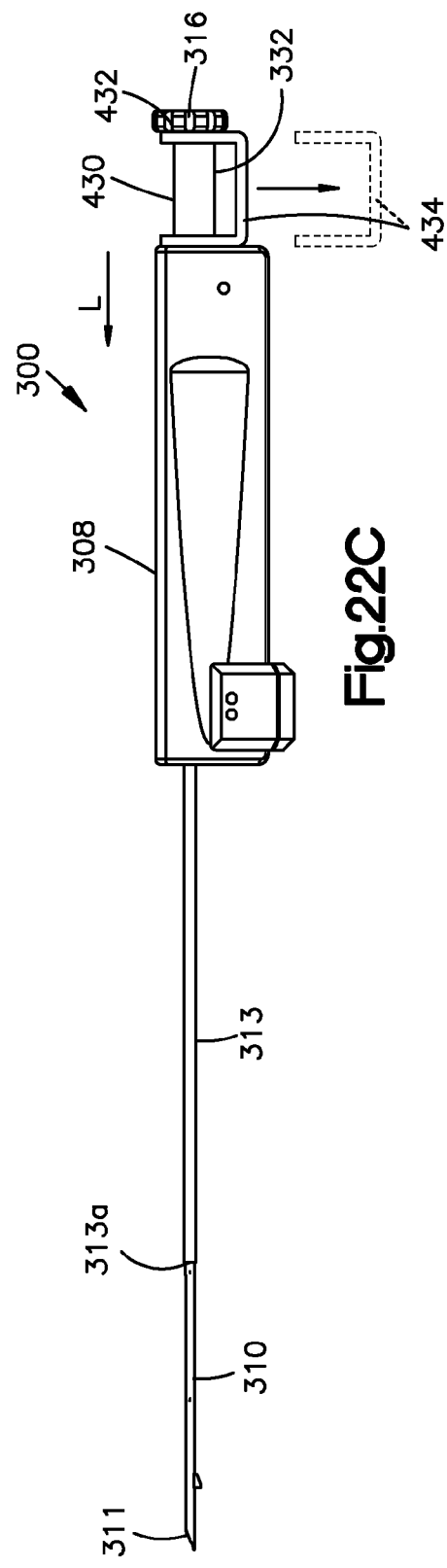
FIG. 22C is a side elevation view of the insertion instrument illustrated in FIG. 22B, but shown in a second position.
Figure 22D:
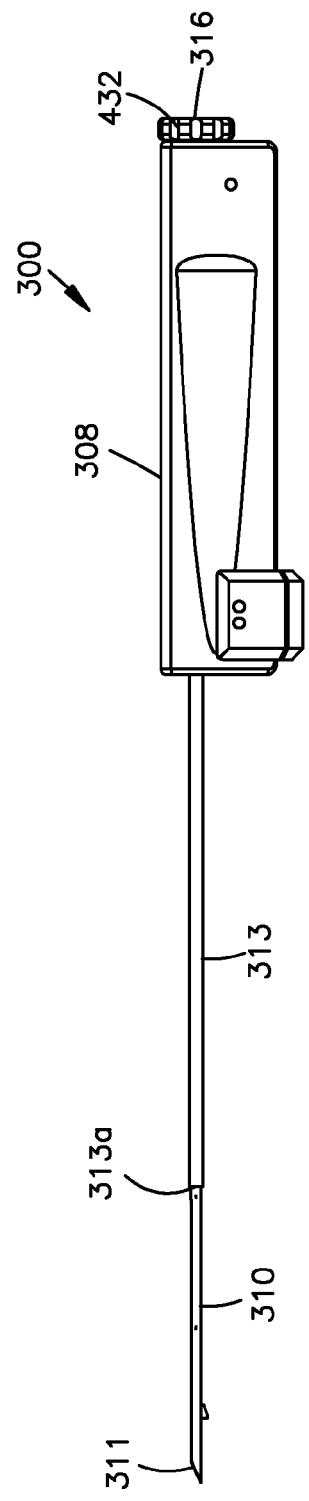
FIG. 22D is a side elevation view of the insertion instrument illustrated in FIG. 22C, but shown in a third position.

Referring now to FIGS. 21A and 21B, it should be appreciated that the cutting assembly 416 can be constructed in accordance with any alternative embodiment as desired. For instance, the cutting assembly 416 can include an actuator 426 that extends laterally out the side wall of the casing 408 along a direction angularly offset with respect to the longitudinal direction L, and is movable radially inward from the disengaged position to the engaged position. The actuator 426 can carry the cutting blade 418. Accordingly, as the actuator 426 moves radially inward, the cutting blade 418 severs the first and second ends 380a' and 380b' of the actuation strands 380a and 380b. The insertion instrument 300 can include a divider wall 428 that separates the first and second ends of the actuation strands 380a and 380b and is aligned with the cutting blade 418. Accordingly, the cutting blade 418 drives into the divider wall 428 and does not sever the second ends of the first and second actuation strands 380a and 380b. Of course, it should be appreciated that a single tensioning strand can be coupled to the actuation strand 38 of the anchor assembly 20 as described above, such that the cutting blade 418 can cut one of the first and second ends of the single tensioning strand.

Referring now to FIGS. 22A-D generally, the insertion instrument 300 can be constructed substantially as described above with respect to FIG. 7A-21B, but can include the guide system 329 that operably couples the casing 308 and the push rod 330 so as to guide relative movement between the casing 308 and the push rod 330 in accordance with another embodiment. For instance, the guide track 342 can be defined in the collar 332 as described above, but extends substantially linearly along the longitudinal direction L. Accordingly, as the plunger translates distally along the first and second strokes, the guide track 342 translates linearly with respect to the guide pin 344. It should be appreciated in the embodiment illustrated in FIGS. 22A-D, the second recess 362 illustrated in FIGS. 13C-E can be longitudinally aligned with the first recess 354, such that the latch 370 moves from the first recess 354 into the second recess 362 so as to decouple the plunger 316 from the collar 332 without rotating the plunger 316. The plunger 316 can include a shaft portion 430 that defines a portion of the key 318 as described above, and a distal end cap that can define a grip portion 432 that extends radially out from the proximal end of the shaft portion 430. The collar 332 can extend at least partially around the shaft portion 430, and can extend radially out from the shaft portion 430 in accordance with the illustrated embodiment.

The insertion instrument 300 can further include a clip 434 that has a longitudinal length substantially equal to the longitudinal distance between the grip portion 432 of the plunger 316 and the proximal end of the collar 332 when the plunger 316 is in the first position. The clip 434 can be removably secured to the shaft portion 430 of the plunger 316. Thus, as the plunger 316 translates distally, the grip portion 432 biases the clip 434 against the collar 332, which causes the collar 332 to translate along with the plunger 316. It should therefore be appreciated that the clip 434 couples the plunger 316 and the collar 332 with respect to distal translation along the longitudinal direction L. Accordingly, during operation, the plunger 316 and collar 332 can be translated distally from the first position to the second position in tandem along the first stroke in the manner described above. As the plunger 316 and collar 332 move along the first stroke, the guide pin 344 translates proximally within the entire guide track 342. The plunger 316 and collar 332 reach the second position when the clip 434 abuts the casing 308, at which point the latch member 370 moves from the first recess 354 into the second recess 358 as described above with respect to FIGS. 14C-D. Next, the clip 434 can be removed from the plunger 316, and the plunger 316 can translate distally with respect to the collar 332 along the second stroke. It should be appreciated that the plunger 316 can translate along the entire second stroke independent of the collar 332.

Accordingly, the push tube 334 ejects the second anchor body 38b as described above with respect to FIGS. 9A-E after the plunger and collar 332 have moved along the first stroke from the first position to the second position. Thus, the plunger 316 can be depressed a first distance that causes the second anchor body 28b to be ejected from the insertion instrument, and the clip 434 abuts the casing 308 once the plunger 316 has been depressed the first distance so as to prevent the plunger 316 from being depressed a second distance greater than the first distance until the collar 434 is removed from the plunger 316. The push rod 330 can then eject the first anchor body 28a after the plunger 136 has moved from the second position to the third position along the second stroke in the manner described above with respect to FIGS. 12A-E. The guide pin 344 can abut the proximal end of the guide track 342 when the second stroke has been completed. Furthermore, the grip portion 432 of the plunger 316 can abut the casing 308 once the plunger 316 has completed the second stroke and has moved to the third position. It should be appreciated in the embodiment illustrated in FIGS. 22A-D that because the plunger 316 is rotatably keyed to the collar 332 and thus rotatably fixed to the collar 332, and because the latch 370 (described above) rotatably couples the collar 332 to the casing 308, the plunger 316 is unable to rotate with respect to the casing 308 as the plunger 316 translates along the second stroke. Alternatively, the insertion instrument can be configured to allow the plunger 316 to rotate as desired so as to align the latch 370 with the second recess 362, as described above.

Figure 23A:
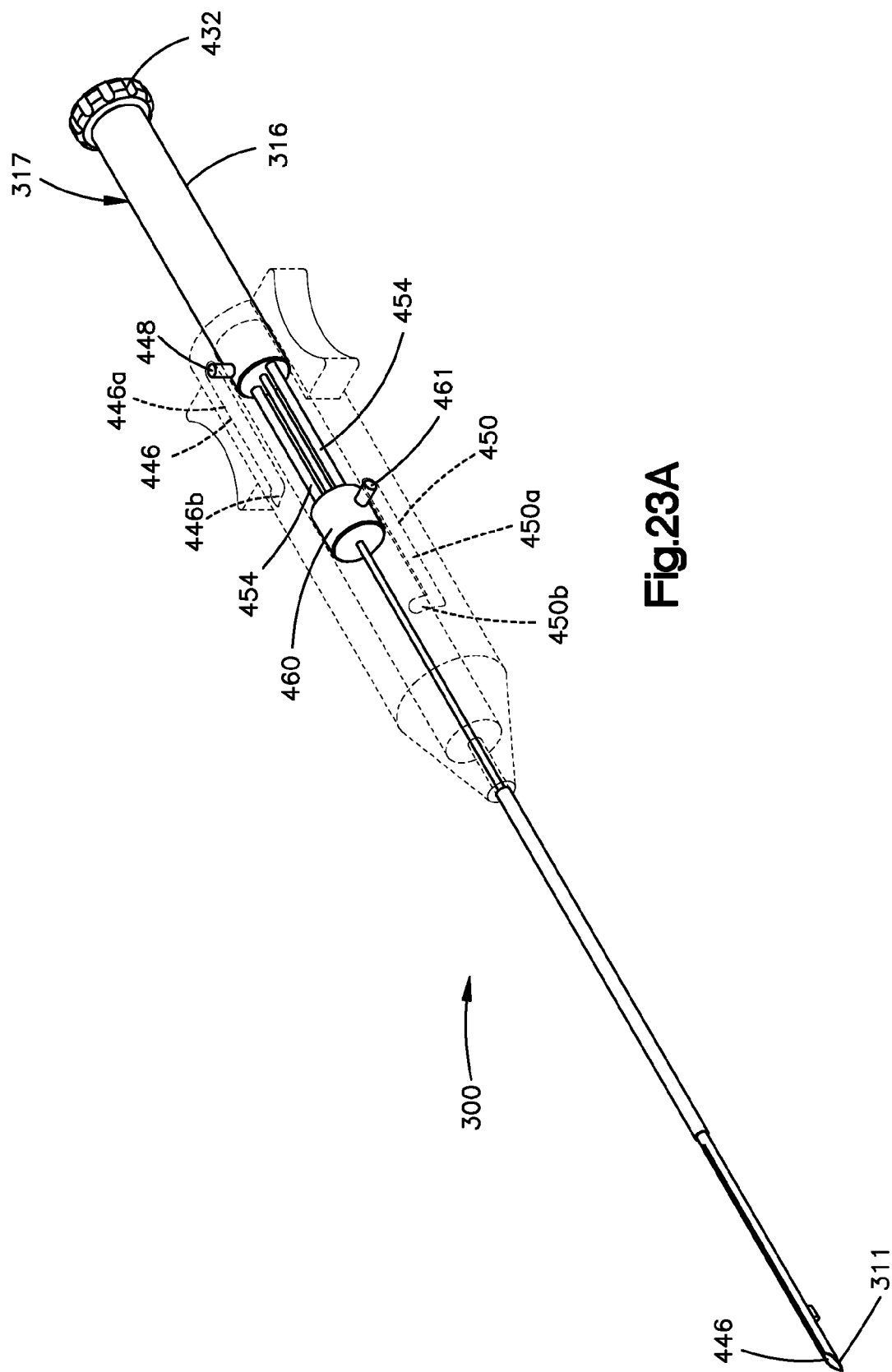
FIG. 23A is a perspective view of an insertion instrument constructed similar to the insertion instrument illustrated in FIG. 7A, but constructed in accordance with another embodiment, and shown in a first position.

As described above with respect to the insertion instrument illustrated in FIGS. 7A-13G, the guide track 342 can be carried by the casing 308, and the guide pin 344 can be carried by one of the pusher assemblies. Referring now to FIG. 23A, the insertion instrument 300 includes at least one guide track, such as a first guide track 446 that is carried by the casing 308, and at least a one guide member such as a first guide pin 448 carried by the pusher assembly 317, and in particular carried by the plunger 316, that rides in the first guide track 342.

As illustrated in FIG. 23B, the shaft portion 430 of the plunger 316 defines a distal surface 431, and further defines a first central aperture 440 that extends longitudinally into, or distally into, the distal surface 431. The shaft portion 430 of the plunger 316 further defines a radial aperture 435 that receives the guide pin 448. The first aperture 440 receives the push rod 330, such that the plunger 316 and the push rod 330 are coupled to each other with respect to both longitudinal translation and rotation. As illustrated in FIG. 23D, the push rod 330 extends from the plunger 316 and into the cannula 310, which is fixed to the casing 308 with respect to translation and rotation. Referring also to FIG. 23C, the tip 311 can be cannulated so as to define a distal ejection port 442 that is substantially aligned with the longitudinal axis 302, and thus also substantially aligned with the elongate opening 312 of the cannula 310. The push rod 330 is movable longitudinally inside the channel 312 in the manner described above. It should be appreciated that the insertion instrument 300 can alternatively define a side ejection port constructed substantially as described below. The cannula 310 can define a longitudinal slot 337, such that the attachment portions 133*a* and 133*b* of the actuation strands 38*a* and 38*b* (see FIG. 1A) that attach the first anchor body 28*a* to the second anchor body 28*b* can extend out the slot 337.

Referring now also to FIGS. 23D-E, the insertion instrument includes a guide system 444 that is configured to operably couple the casing 308 to the push rod 330 so as to guide relative movement between the casing 308 and the push rod 330. For instance, the guide system 444 includes the first guide member in the form of the first guide track 446 that is carried by the casing 308, and the second guide member illustrated as the first guide pin 448 that extends from the pusher assembly 317. The first guide track 446 can be configured as a slot that extends radially outward into the radially inner surface of the casing 308. Furthermore, in accordance with the illustrated embodiment, the first guide pin 448 extends radially out from the shaft portion 430 of the plunger 316, and rides within the first guide track 448. The first guide track 446 defines a first track portion 446*a* that extends substantially longitudinally, and an intermediate track portion 446*b* that extends circumferentially from the distal end of the first track portion 446*a*.

With continuing reference to FIG. 23E, the guide system 444 further includes a third guide member configured as a second guide track 450 that is carried by the casing 308, and is configured as a slot that extends radially outward into the inner surface of the casing 308. The second guide track 450 defines a first track portion 450*a* that extends substantially longitudinally, and an intermediate track portion 450*b* that extends circumferentially from the distal end of the second guide track 450*b*. The intermediate track portion 450*b* extends from the first track portion 450*a* the same direction that the intermediate track portion 446*b* extends from the first track portion 446*a*.

The first track portions 446*a* and 450*a* define a first stroke of movement for the plunger 316 that causes the push rod 330 to eject the second anchor out the ejection port 442. The intermediate track portions 446*ba* and 450*b* are configured such that the plunger is rotated so as to align a fifth guide member with a second track portion that is radially offset from the first track portions 446*a* and 450*a*. In particular, as illustrated in FIG. 23B, the insertion instrument 330 further includes a pair of apertures 452 that are disposed adjacent the central aperture 440 and extend longitudinally into the distal surface 431 of the shaft portion 430 of the plunger 416. The apertures 452 are each configured to receive respective fifth guide members configured as guide posts 454 (FIG. 23D) that extend distally from the plunger 416, and a sixth guide member illustrated as a guide housing 460 (FIG. 23E) that is disposed in the interior 328 of the casing 308 and fixed to the casing 308 with respect to translation. The guide housing 460 defines a seventh guide member configured as a radially outwardly extending second guide pin 461 that is configured to ride in the second guide track 450. The guide housing 460 further defines a guide member in the form of at least one aperture such as a pair of apertures that extend longitudinally through the guide housing 460 and define second track portions 462. The second track portions 462 are sized to receive the guide posts 454. The proximal end of the guide housing 460 can define a pair of recesses 464 that extend longitudinally into, but not through, the guide housing 460 at a location adjacent the second track portions 462. The recesses 464 can be arcuate shaped or alternatively shaped as desired.

Figure 23F:
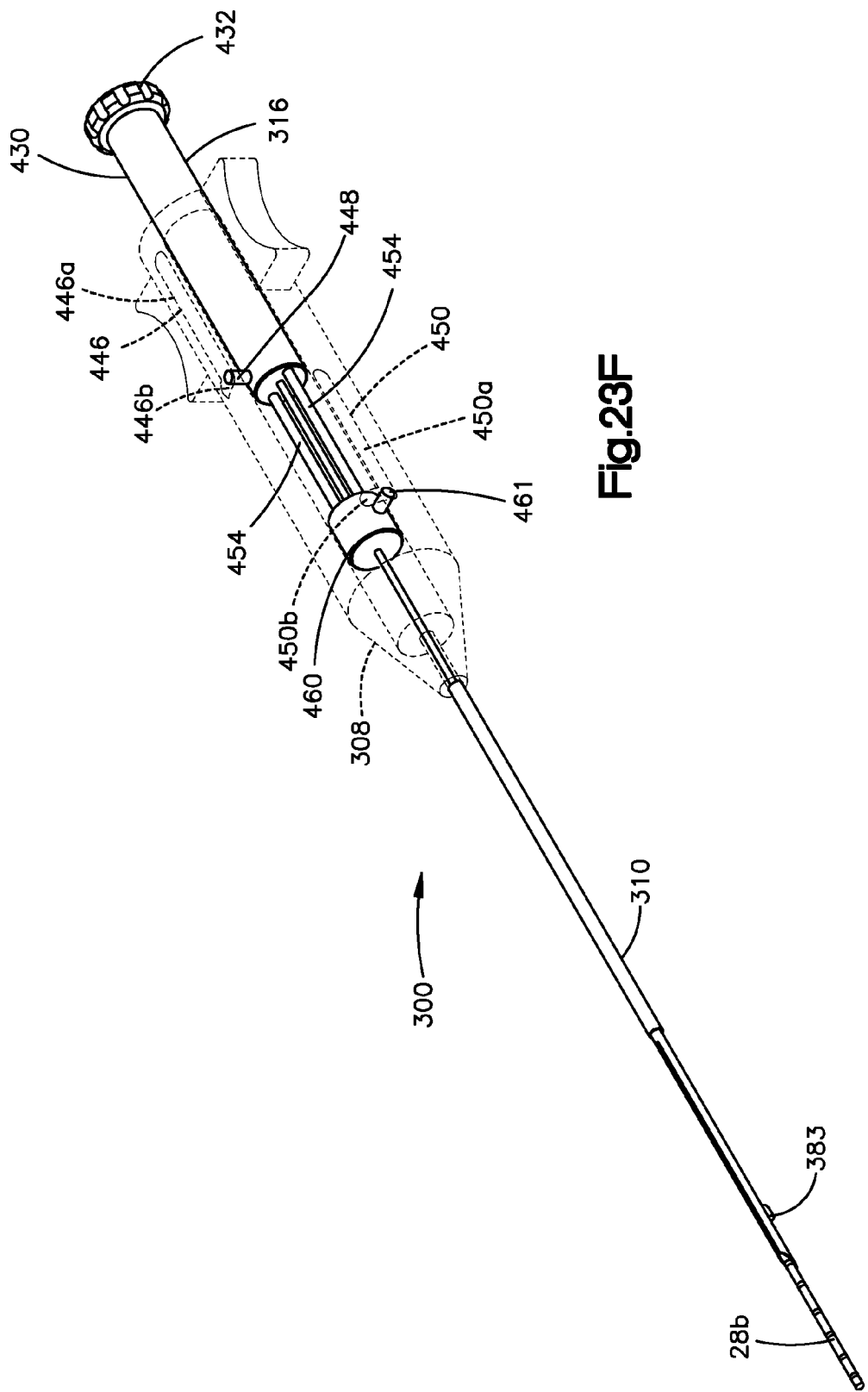
FIG. 23F is a perspective view of the insertion instrument illustrated in FIG. 23A, shown in a second position.

Referring now to FIGS. 23A and 23F, a distal biasing force can be applied to the plunger 316, which causes the plunger 316 and the push rod 330 to translate distally along the first stroke with respect to the casing 308 and thus the cannula 310 and the guide housing 460. The plunger 316 translates from the first position illustrated in FIG. 23A to the second position illustrated in FIG. 23F. As the plunger 316 translates distally from the first position to the second position, the first guide pin 448 translates distally along the first track portion 446*a* of the first guide track 446 until the first guide pin 448 is aligned with the intermediate track portion 446*b* of the first guide track 446. Likewise, as the plunger 316 translates distally from the first position to the second position, the second guide pin 461 translates distally in the first track portion 450*a* of the second guide track 450 until the second guide pin 461 is aligned with the intermediate track portion 450*b* of the second guide track 450. Once the plunger 316 has translated to the second position, the guide posts 454 are circumferentially offset from the respective second track portions 462, and abut the guide housing 460, for instance in the recesses 464.

Figure 23G:
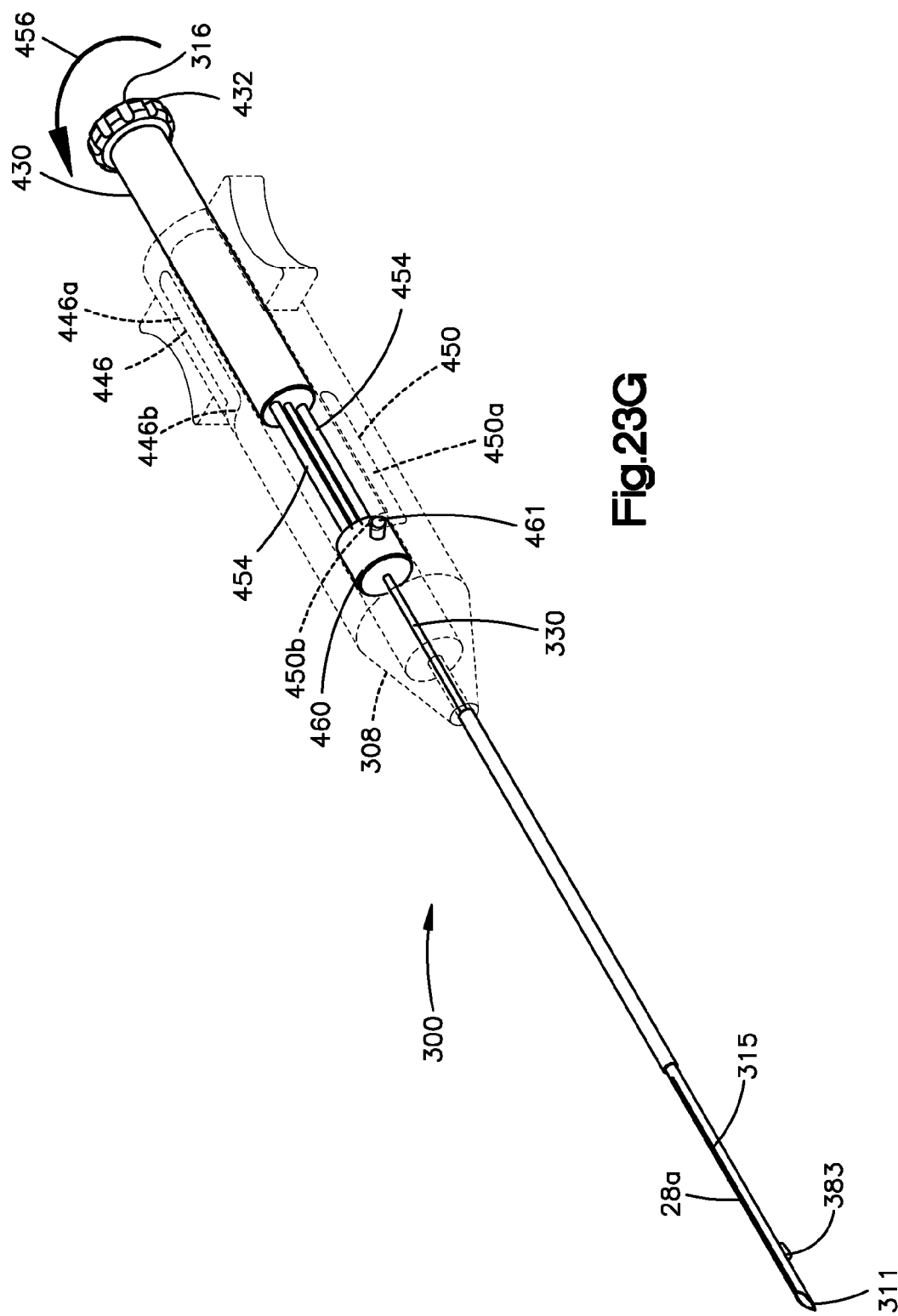
FIG. 23G is a perspective view of the insertion instrument illustrated in FIG. 23F, shown in an intermediate position.
Figure 23H:
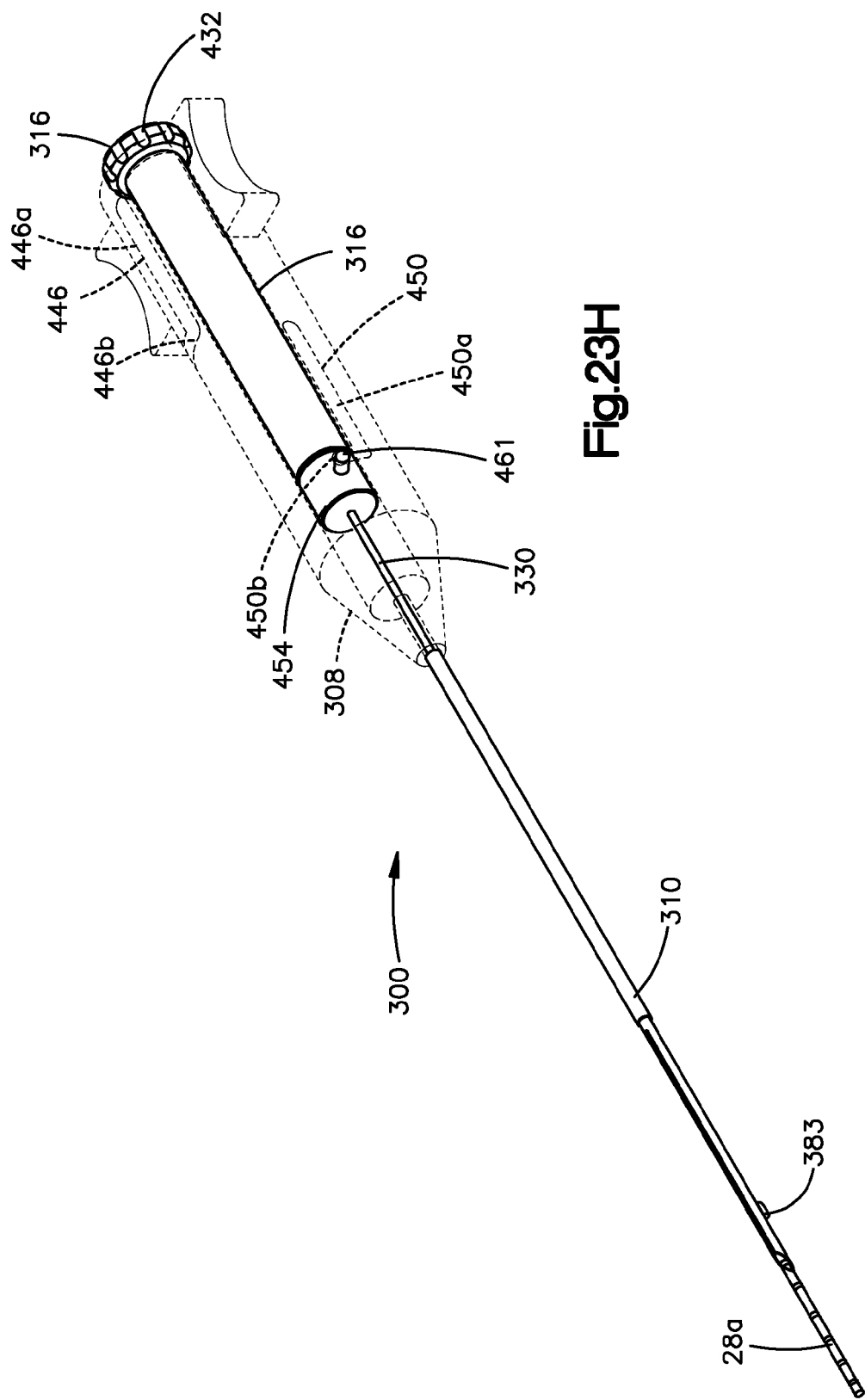
FIG. 23H is a perspective view of the insertion instrument illustrated in FIG. 23G, shown in a third position.

Referring now to FIG. 23G, the plunger 316 can be rotated along the direction of Arrow 456, which causes the first and second guide pins 448 and 461 to travel in the respective intermediate track portions 446*b* and 450*b*, until reaching the end of the intermediate track portions 446*b* and 450*b*, which define respective stops that prevent the plunger 316 from continuing to rotate relative to the casing 308, and further prevents the guide posts 454 from rotating relative to the guide housing 460. Once the plunger 316 has finished rotating, the guide posts 454 are aligned with the second track portions 462. Accordingly, as illustrated in FIG. 23H, the plunger 316 can be further translated distally along the second stroke from the second position to a third position, at which point the plunger 316 abuts the guide housing 460 and is prevented from traveling distally further. Thus, the guide housing 460 defines a stop that prevents the plunger 316 from translating distally beyond the third position.

As the plunger 316 translates along the second stroke, the push rod 330 translates distally within the channel 312 of the cannula 310, and ejects the first anchor body 28*a* out the ejection port 442. After each anchor body 28*a* and 28*b* has been ejected from the instrument to a location behind the anatomical structure 24 (see FIG. 1A), an actuation force can be applied to each anchor body 28*a* and 28*b*. For instance, the insertion instrument 330 can include a retention assembly of the type described above, such as the retention assembly 390 or any suitable alternatively constructed retention assembly. Alternatively, the user can manually apply the actuation force to the respective actuation strands 131*a* and 131*b*. A connector member can then attach the actuation strands 131*a* and 131*b* together in the manner described above.

Referring now to FIGS. 24A-25D generally, it should be appreciated that an insertion instrument can be configured having a first and second cannulas supported by the casing in a side-by-side orientation that retain first and second anchor bodies, and first and second pusher assemblies operatively associated with the first and second cannulas, respectively, so as to eject the first and second anchor bodies out the respective first and second cannulas. It can be desirable to ensure that a desired cannula from which the anchor body is to be ejected is distally disposed with respect to the other cannula, such that the desired cannula can be inserted into the underlying tissue without also inserting the other cannula.

As illustrated in FIG. 24A, an insertion instrument 300 includes a casing 308 that includes a body portion 308a and a handle portion 308b that extends out from the body portion 308a. The insertion instrument 300 further includes a first cannula 310a that extends distally from the casing 308, and in particular from the body portion 308a, and a second cannula 310b that extends distally from the casing 308, and in particular from the body portion 308a, at a location adjacent the first cannula 310a. The first and second cannulas 310a and 310b can extend substantially parallel to each other as illustrated. Accordingly, the first and second cannulas 310a and 310b can be described as being in a side-by-side relationship. The first and second cannulas 310a and 310b can define respective longitudinally elongate channels 312a and 312b that retain respective first and second anchor bodies 28a and 28b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports that extend longitudinally through the respective tips 311a and 311b.

Each of the first and second pusher assemblies 317a and 317b includes first and second plungers 316a and 316b, respectively, and first and second pusher rods 330a and 330b, respectively, that extend distally from the corresponding plungers 316a and 316b. Each of the plungers 316a and 316b define respective shaft portions 430a and 430b and respective end caps that can define first and second grip portion 432a and 432b that extends radially out from the proximal end of the corresponding shaft portions 430 and 430b. When the first and second plungers 316a and 316b are in their respective first positions, the first and second grip portions 432a and 432b are proximally spaced from the casing 308. The insertion instrument 300 can further include first and second lock-out tabs 468a and 468b that are removably attached to the first and second plungers 316a and 316b. For instance, in accordance with the illustrated embodiment, the first and second lock-out tabs 468a and 468b are attached to the respective first and second shaft portions 430a and 430b at a location longitudinally between the corresponding grip portions 432a and 432b and the casing 308. Accordingly, the first and second lock-out tabs 468a and 468b interfere with the respective grip portions 432a and 432b, and prevent the plungers 316 from translating distally relative to the casing 308 to a depth that would eject the respective first and second anchor bodies 28a and 28b.

The insertion instrument 330 can further include a swap actuator 470 in the form of a trigger that extends partially into the casing 308, and can extend out from the handle portion 308b. The swap actuator 470 is configured to be moved from a first position to an actuated position so as to reverse a relative position of the first and second tips 311a and 311b. The swap actuator 470 can be coupled to the first pusher assembly 317a, such that proximal translation of the actuator 470 causes the first pusher assembly 317a, including the first plunger 316a and the first cannula 310a, to translate proximally. As illustrated in FIG. 24A, the first tip 311a of the first cannula 310a is disposed distally with respect to the second tip 311b of the second cannula 310b. Furthermore, the distal end of the second push rod 330b can extend slightly out from the respective second tip 311b, such that the longitudinal distance between the distal end of the second push rod 330b and the distal end of the first tip 311a defines an insertion depth into underlying tissue. Otherwise stated, the second push rod 330b can define a depth stop for insertion of the first tip 311a into underlying tissue. It should thus be appreciated that the first tip 311a can be injected into underlying tissue, for instance at the first target anatomical location 24a (see FIG. 1A) without causing the second tip 311b to inject into the underlying tissue. As is described in more detail below, actuation of the swap actuator 470 from a first position to a second position causes the first tip 311a to move proximally with respect to the casing 308 and the second tip 311b, such that the second tip 311b can be injected into the underlying tissue, for instance at the second target anatomical location 24b (see FIG. 1B) without causing the first tip 311a to inject into the underlying tissue.

Figure 24B:
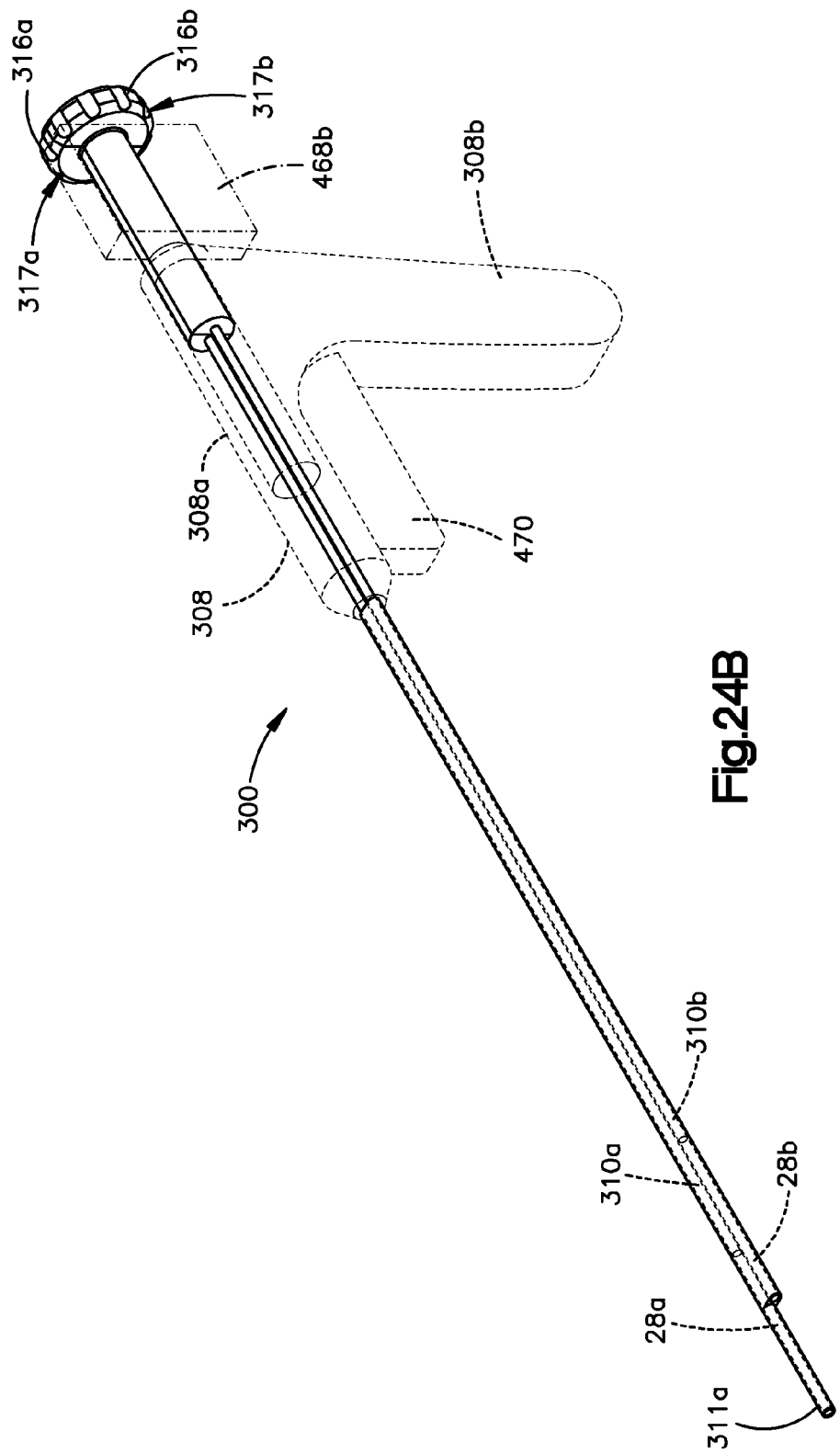
FIG. 24B is a perspective view of the insertion instrument illustrated in FIG. 24A, after removal of a first lockout tab from the first pusher assembly.

During operation, referring to FIG. 24B, the first lock-out tab 468a can be removed from the first plunger 316a, such that the first plunger 316a can travel distally with respect to the casing 308 from the first position illustrated in FIG. 24A to a second position as illustrated in FIG. 24C, whereby the first grip portion 432a abuts the casing 308. Because the first push rod 330a is translatably fixed to the first plunger 316a, distal translation of the first plunger 316a causes the first push rod 330a to likewise translate in the first cannula 310a. The first push rod 330a abuts the first anchor body 28a, such that distal translation of the first push rod 330a ejects the first anchor body 28a out the first ejection port, for instance into the first target anatomical location.

Figure 24D:
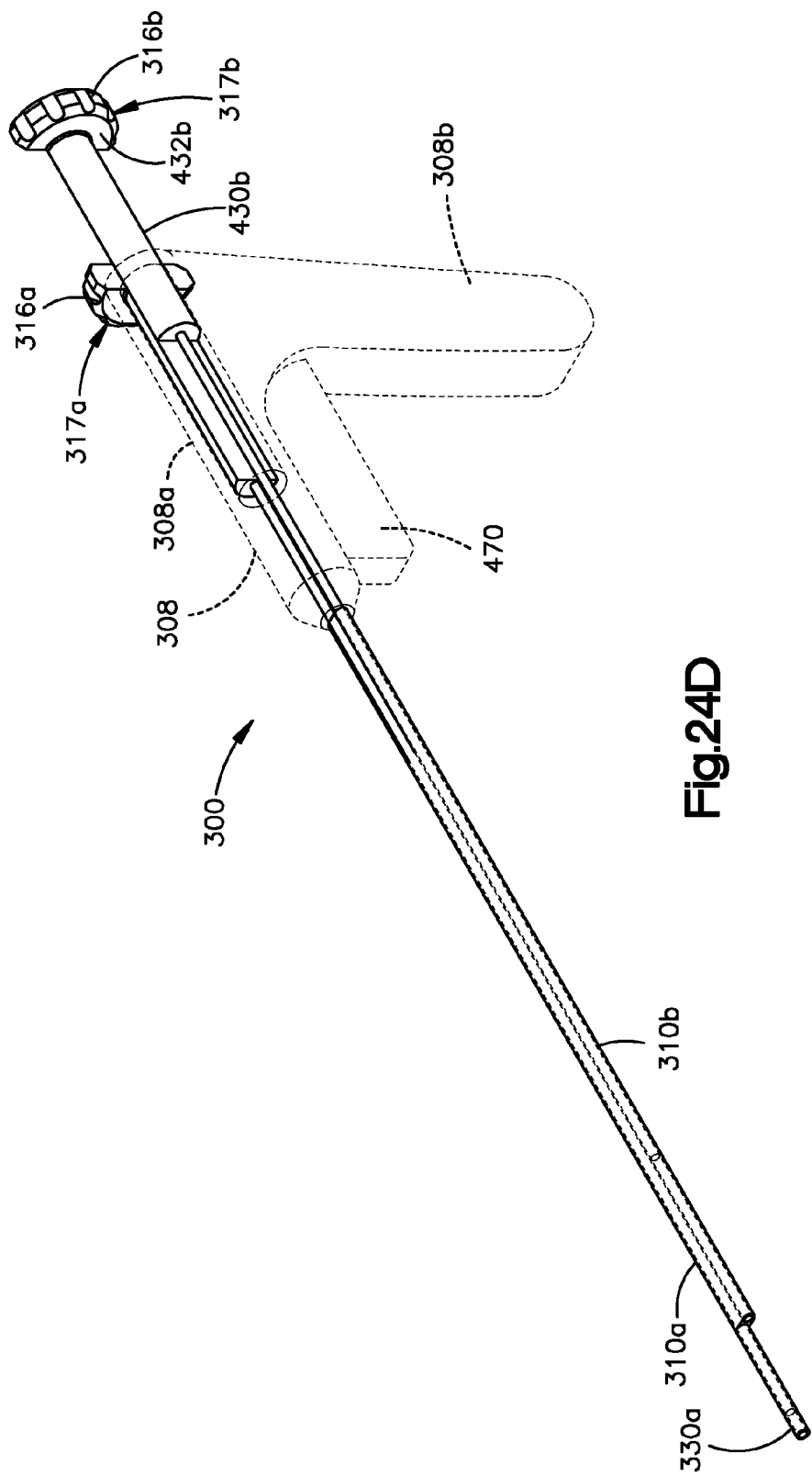
FIG. 24D is a perspective view of the insertion instrument illustrated in FIG. 24C, after removal of a second lockout tab from the second pusher assembly.
Figure 24E:
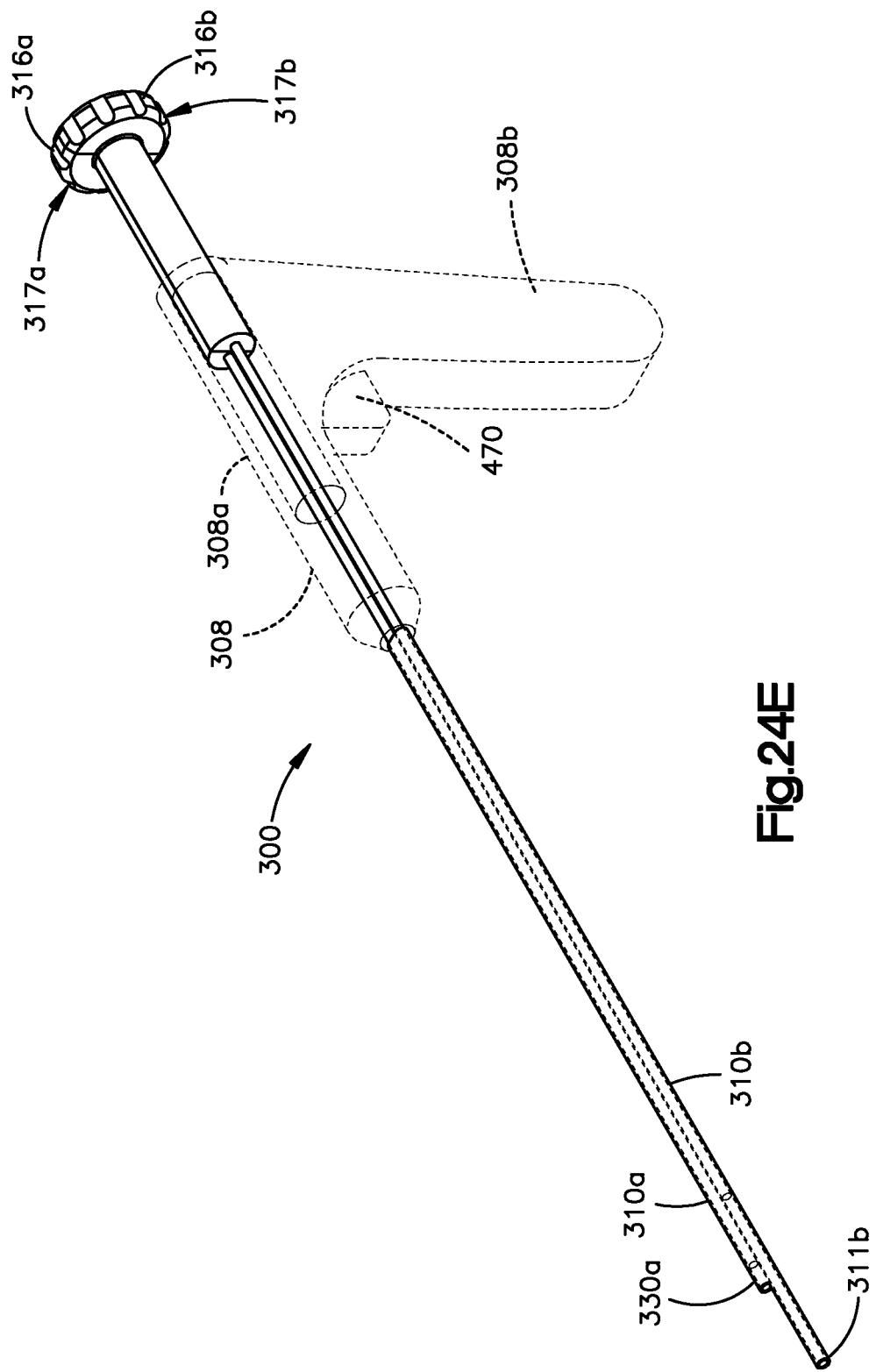
FIG. 24E is a perspective view of the insertion instrument illustrated in FIG. 24D, after actuation of a swap actuator.

Next, referring to FIG. 24D, the second lock-out tab 468b can be removed from the second plunger 316b, as illustrated in FIG. 24D. Referring to FIG. 24E, the swap actuator 470 can be actuated, for instance can be moved proximally, to retract the first tip 311a proximally with respect to the second cannula 310b until the first tip 311a is disposed proximally with respect to the second tip 311b. Furthermore, the distal end of the first push rod 330a can extend slightly out from the respective first tip 311a, such that the longitudinal distance between the distal end of the first push rod 330a and the distal end of the second tip 311b defines an insertion depth of the second tip 311b into the underlying anatomical structure. Otherwise stated, the first push rod 330a can define a depth stop for insertion of the second tip 311a into underlying tissue. It should thus be appreciated that the second tip 311b can be injected into underlying tissue, for instance at the second target anatomical location 24b (see FIG. 1A) without causing the first tip 311a to inject into the underlying tissue. In accordance with the illustrated embodiment, actuation of the swap actuator 470 further causes the first plunger 316a to translate proximally to the first position illustrated in FIG. 24A.

Figure 24F:
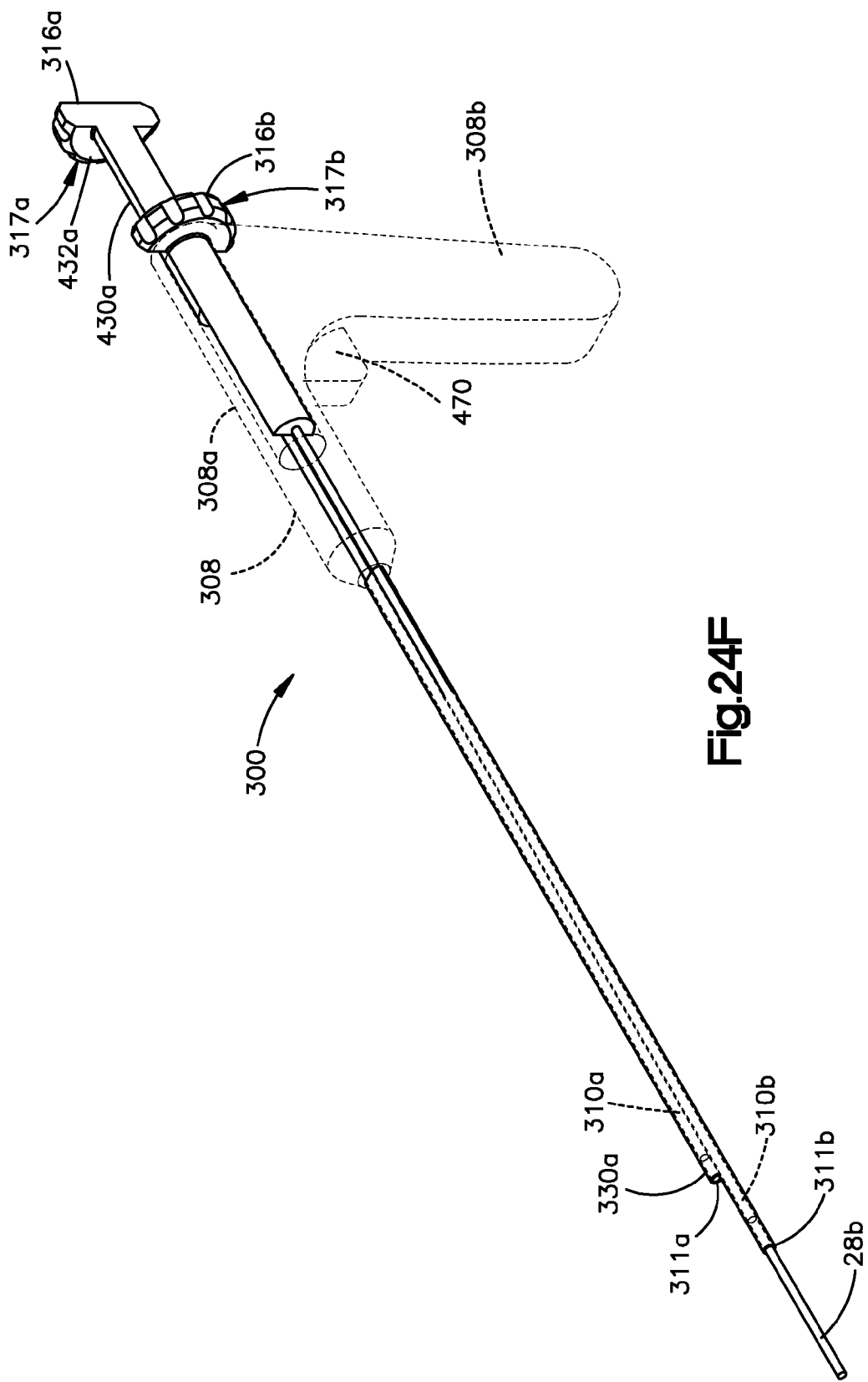
FIG. 24F is a perspective view of the insertion instrument illustrated in FIG. 24E, after actuation of the second pusher assembly to a second position.
Figure 25A:
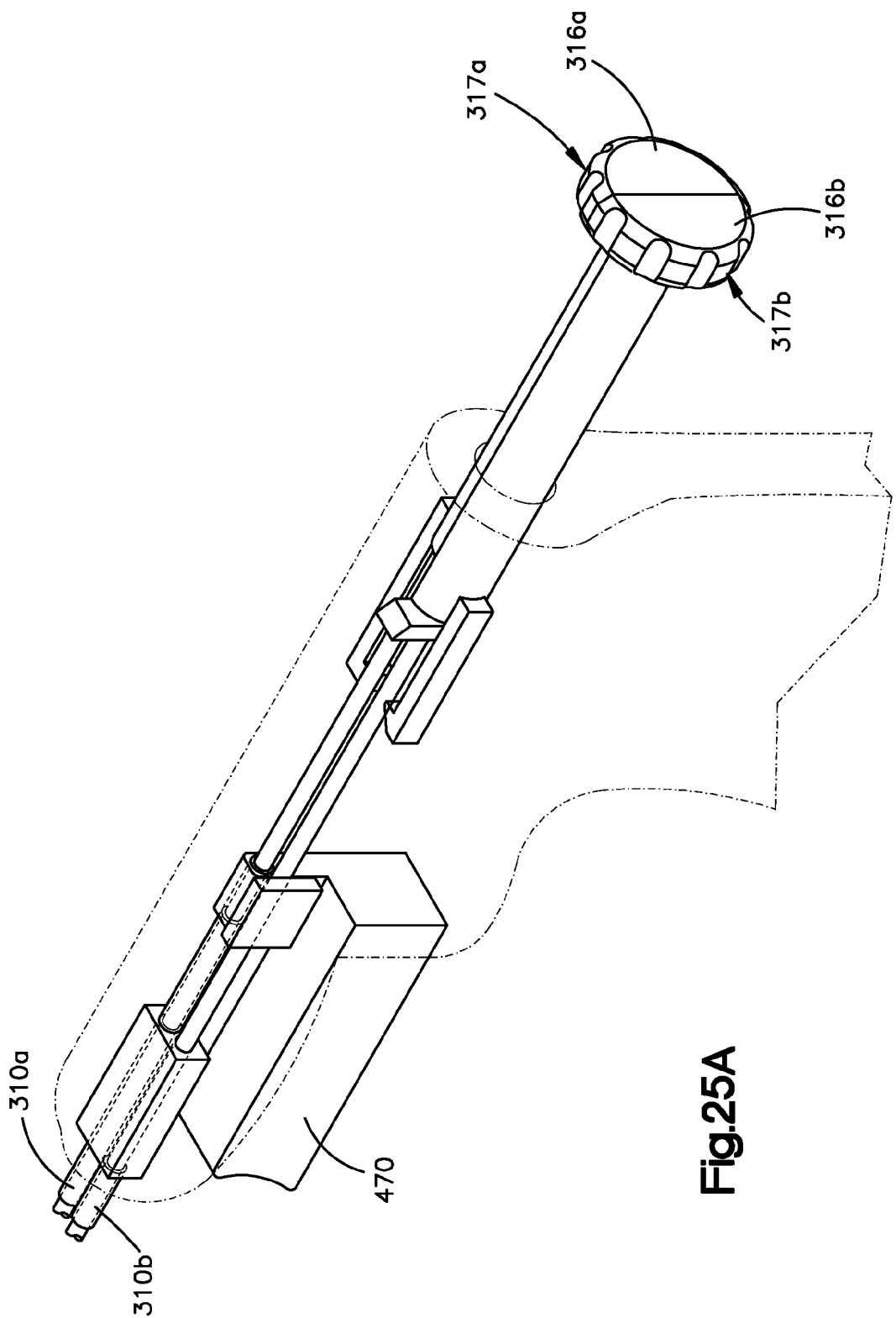
FIG. 25A is a perspective view of components of the insertion instrument illustrated in FIG. 24A, showing each of the first and second pusher assemblies in the first position.
Figure 25B:
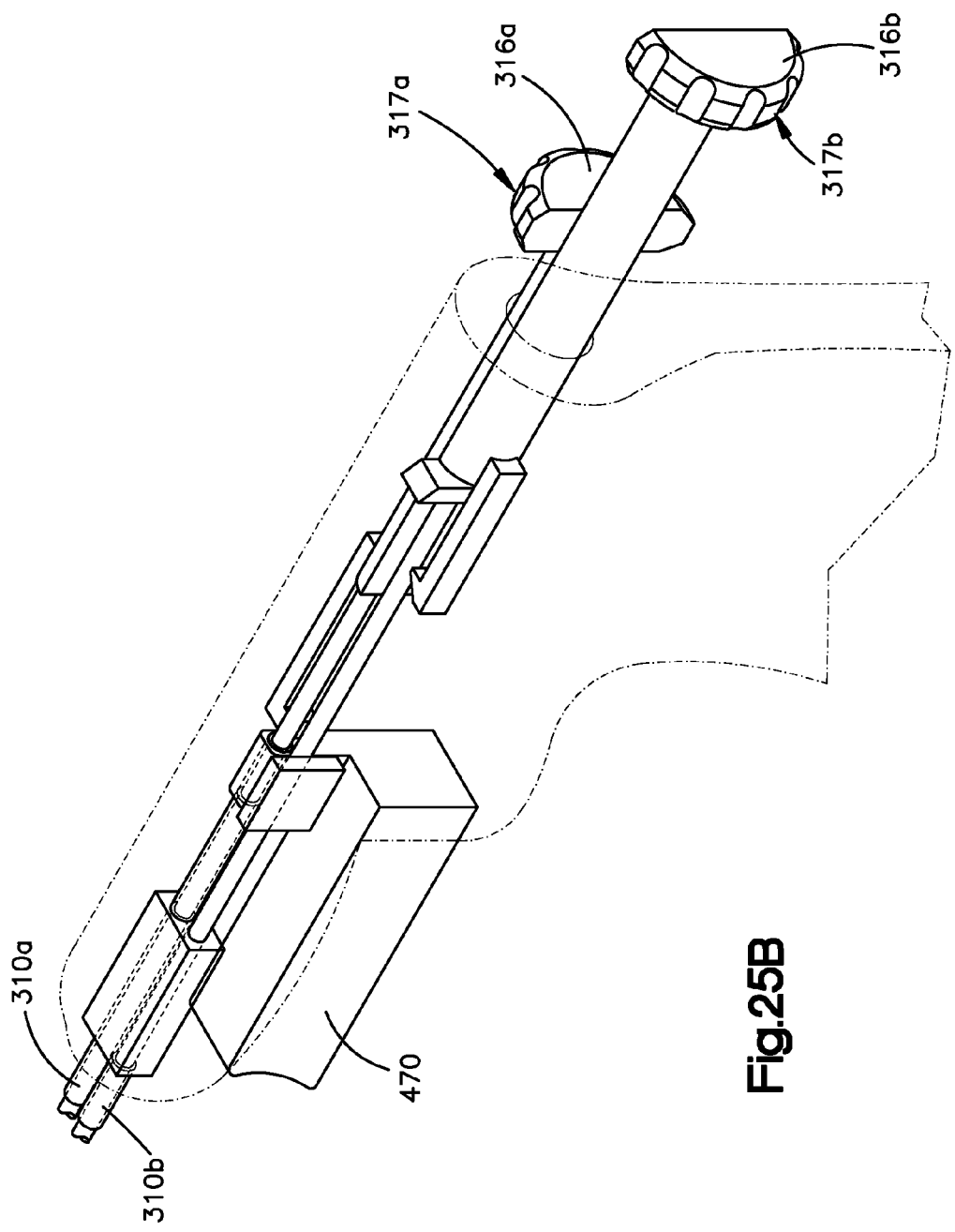
FIG. 25B is a perspective view of the components of the insertion instrument illustrated in FIG. 25A, after the first pusher assembly has been actuated to the second position.
Figure 25C:
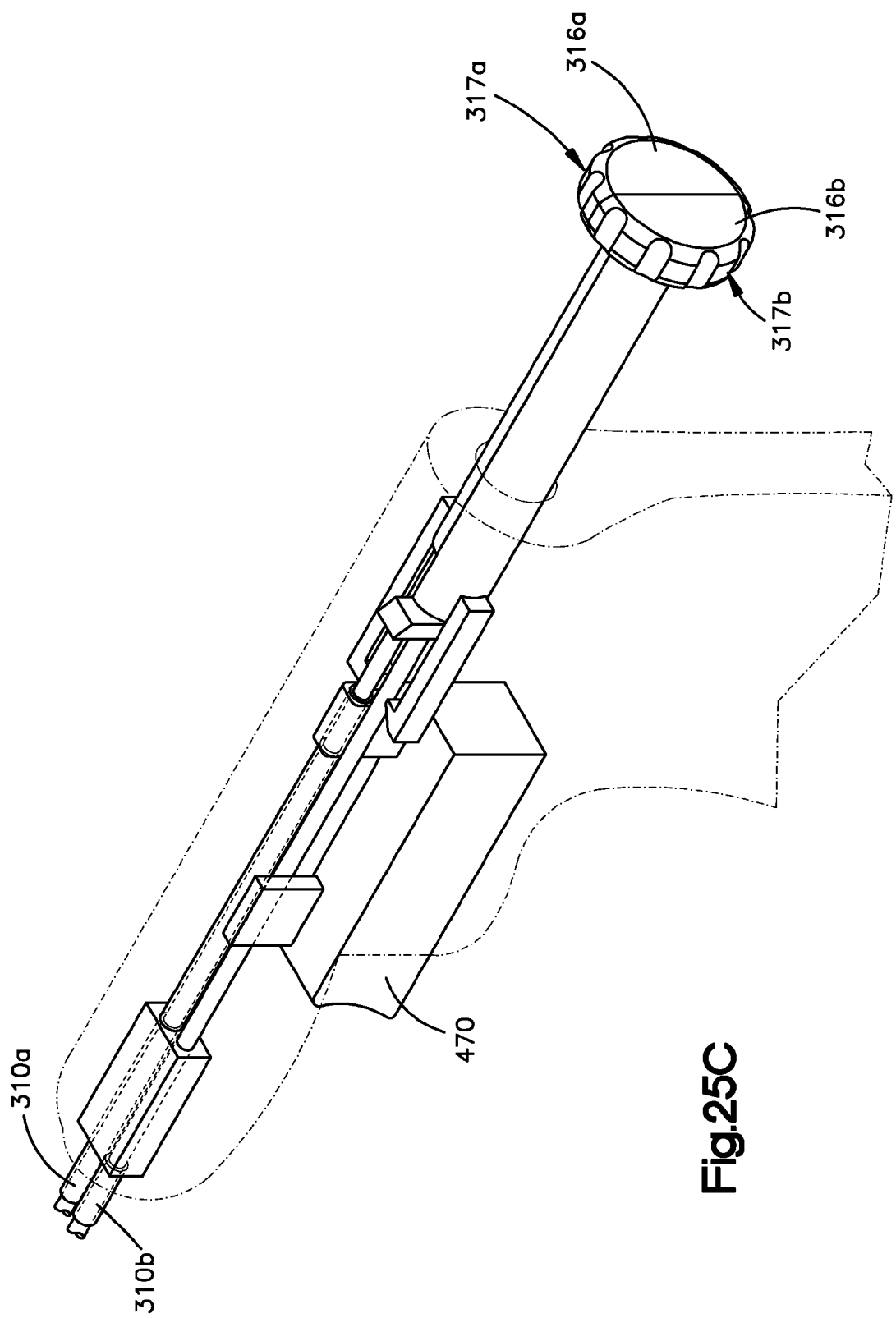
FIG. 25C is a perspective view of the components of the insertion instrument illustrated in FIG. 25B, after actuation of the swap actuator.
Figure 25D:
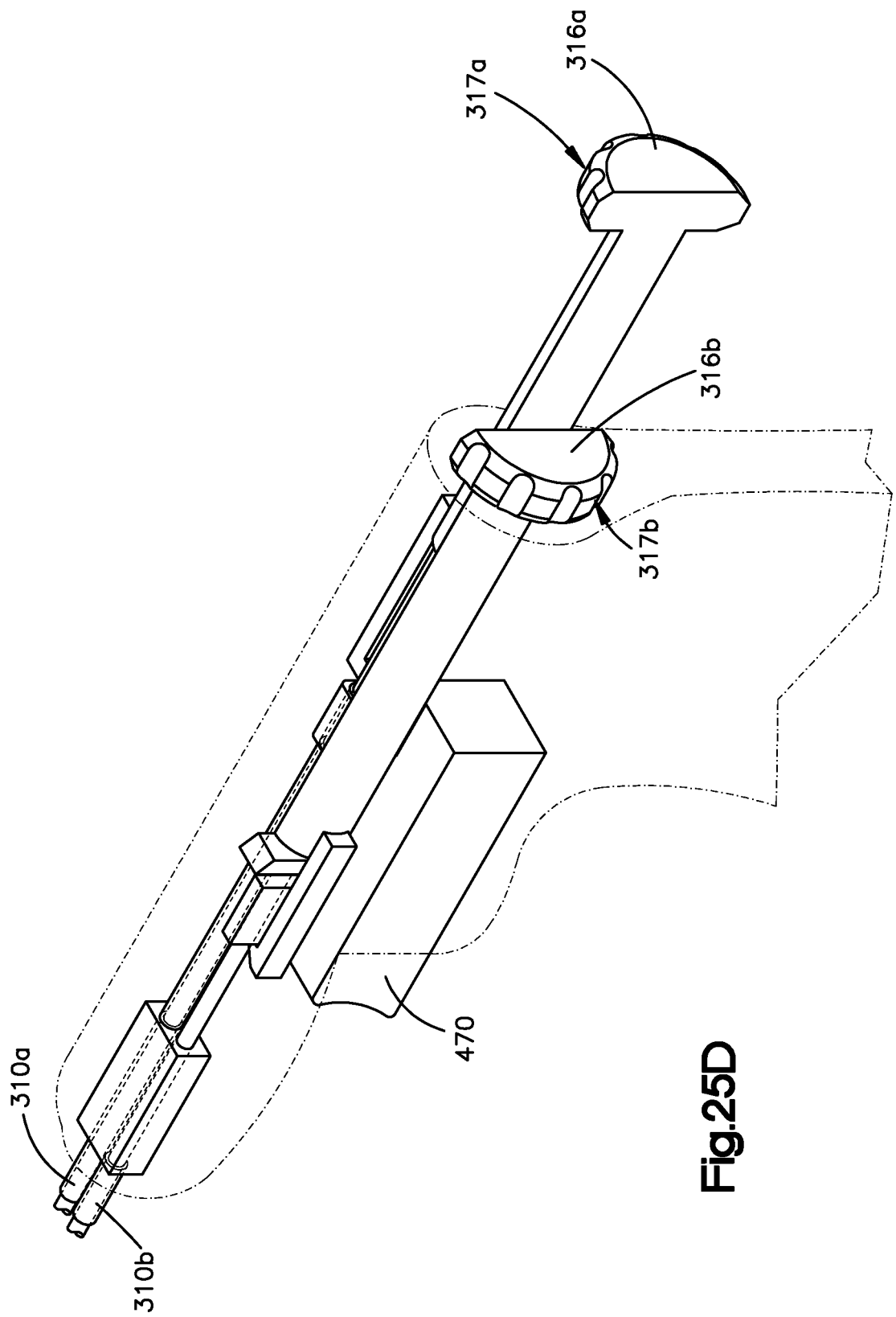
FIG. 25D is a perspective view of the components of the insertion instrument illustrated in FIG. 25C, after the second pusher assembly has been actuated to the second position.

Referring now to FIG. 24F, the second plunger 316b can travel distally with respect to the casing 308 from the first position illustrated in FIG. 24E to a second position as illustrated in FIG. 24F whereby the second grip portion 432b abuts the casing 308. Because the second push rod 330b is translatably fixed to the second plunger 316b, distal translation of the second plunger 316b causes the second push rod 330b to likewise translate in the second cannula 310b, thereby ejecting the second anchor body 28b out the second ejection port 442b and into the second target anatomical location.

Operation of the insertion instrument 300 illustrated in FIGS. 24A-25D will now be further described with particular reference to FIGS. 25A-D. In particular, the insertion instrument 300 includes at least one latch assembly such as a first latch assembly 305a, a second latch assembly 305b, and a third latch assembly 305c. The first latch assembly 305a is configured to lock the swap actuator 470 in its proximal position once it has been moved proximally from a first position illustrated in FIG. 24D to a second recessed position illustrated in FIG. 24E. For instance, the first latch assembly 305 can include a latch member 307 that is supported by the casing 308 extends proximally toward a proximal abutment surface 307a configured to abut the swap actuator 470 once the swap actuator 470 is in its second proximal position, thereby interfering with distal movement of the swap actuator 470 relative to the casing 308. As the swap actuator 470 moves proximally, the latch member 307 can deflect inwardly away from the swap actuator 470 so as to allow proximal translation of the swap member 470 relative to the latch member 307. Once the swap actuator 470 has been moved from its first initial position to its second proximal position relative to the casing 308, the latch member 307 moves outward under its spring force such that the proximal abutment surface 307a abuts the swap actuator 470 and prevents the swap actuator 407 from moving distally from its second position with respect to the casing 308.

The second latch assembly 305b includes a first latch member 347 carried by the swap actuator 470 and movable with the swap actuator 470, and a second latch member 349 that is carried by the first plunger 316a, and is movable with the first plunger 316a. The first latch member 347 is attached to the first cannula 310a, such that the first latch member 347 causes the first cannula 310a to translate with the swap actuator 470. The second latch member 349 includes a body 349a, a first attachment portion such as a hook at the distal end of the body 349a, and a second attachment portion such as an abutment surface at the proximal end of the body (the second latch member 349 can be constructed as the mirror image of the second latch member 353 of the third latch assembly 305c described below). Accordingly, as the first plunger 316a is translated from its first position illustrated in FIG. 24A to its second position illustrated in FIG. 24B, the hook deflects inwardly away from the first latch member and rides along and past the first latch member 347. Once the first plunger 316a is in its second position illustrated in FIG. 24B such that the first anchor body 28a has been ejected, the hook of the second latch member 349 moves outward under its spring force such that the hook is disposed distal of the first latch member 347, and the abutment surface of the second latch member is disposed proximal of the first latch member 347. Accordingly, the first latch member 347 is captured between the hook of the second latch member 349 and the abutment surface of the second latch member 349. Thus, the first and second latch members 349 are coupled with respect to translation.

Accordingly, once the first anchor body 28a has been ejected from the first cannula 310a, the second latch member 349 is attached to the first latch member 347, which translatably couples the first plunger 316a to the swap actuator 470 with respect to translation. Furthermore, because the first latch member 347 is carried by the swap actuator 470 and is further attached to the first cannula 310a, movement of the swap actuator 470 proximally causes both the first cannula 310a and the first plunger 316 to move proximally to a position whereby the first tip 311a and the first push rod 330a are disposed proximal with respect to the second tip 311b, while the first push rod 330a remains disposed distal of the first tip 311a. Furthermore, because the first plunger 316a is coupled to the swap actuator 470 with respect to relative translation both proximally and distally, and because the swap actuator 470 is coupled to the casing 308 with respect to at least proximal translation, the first plunger 316 is prevented from translating proximally with respect to the casing 308 once the first anchor body 28a has been ejected. The first push rod 330a can thus provide an insertion depth stop for the second tip 311b as described above.

The third latch assembly 305c includes a first latch member 351 carried by the casing 308, and a second latch member 353 carried by the second plunger 316b. The second latch member 353 includes a body 353a, a first attachment portion 353b such as a hook at the distal end of the body 353a, and a second attachment portion 353c such as an abutment surface disposed at the proximal end of the body 353a. When the second plunger 316b is translated distally from its first position illustrated in FIG. 24E to its second distal position illustrated in FIG. 24F, for instance when ejecting the second anchor body 28b, the hook can deflect inwardly, away from the first latch member 351 and ride along and move past the first latch member 351. Once the second plunger 316b is in its second position illustrated in FIG. 24F such that the second anchor body 28b has been ejected, the hook of the second latch member 353 moves outwardly under its spring force at a location distal of the first latch member 351, and the abutment surface of the second latch member 353 is disposed proximal of the first latch member 351. The first latch member 351 is thus captured between the hook of the second latch member 353 and the abutment surface of the second latch member 353. As a result, the second plunger 316b is prevented from moving proximally or distally with respect to the casing 308 once the second anchor body 28b has been ejected, and the blunt distal end of the second push rod 330b remains distal to the second tip 311b.

Once the anchor bodies 28a and 28b have been ejected, a tensile force can be applied to the actuation portions 131a and 131b (see FIG. 1A) so as to expand the anchor bodies 28a and 28b in the manner described above. For instance, first and second tensioning strands 380a and 380b (see FIGS. 18A-18B) can be attached between the respective actuation portions 131a and 131b, and the respective lock-out tabs 468a and 468b. Accordingly, after the lock-out tabs 468a and 468b have been removed from the respective plungers 316a and 316b and the respective first and second anchor bodies 28a and 28b have been ejected, proximal movement of the lock-out tabs 468a and 468b with respect to the anchor bodies 28a and 28b causes the tensile force to be applied to the corresponding tensioning strands 380a and 380b, which communicates the tensile force to the actuation portions 131a and 131b so as to expand the anchor bodies 28a and 28b. Alternatively, the tensioning strands 380a and 380b can be secured in the casing 308 in any manner described above.

Referring now to FIGS. 26A-B, the insertion instrument 300 can include a retention assembly 490 constructed in accordance with an alternative embodiment that is configured to apply an actuation force to the first and second actuation strands 38a and 38b (see FIG. 1A). For instance, the retention assembly 490 can retain the first and second actuation strands 38a and 38b directly. In accordance with the illustrated embodiment, the retention assembly 490 retains both the actuation portions 131a and 131b and the attachment portions 133a and 133b of the first and second anchor bodies 28a and 28b, respectively, for instance when the attachment portions 133a and 133b are not attached when loaded in the insertion instrument 300. Alternatively, if the attachment portions 133a and 133b are pre-attached to each other when loaded in the insertion instrument 300, the retention assembly can retain only the actuation portions 131a and 131b. Alternatively still, as described above, at least one tensioning strand can be stitched through the first and second actuation strands 38 and 38b, respectively, and can further be retained in the retention assembly 490. Regardless of the configuration, the retention assembly can be configured to apply an actuation force to the actuation strands 38a and 38b that causes the respective anchor bodies 28a and 28b to move to their expanded configurations.

In accordance with the illustrated embodiment, the retention assembly 490 can be mounted to either or both of the cannulas, such as the first cannula 310a as shown in FIG. 26A. The retention assembly 490 can include a first locking member such as a retention housing 492 that is mounted to the first cannula 310a and defines a lateral strand-receiving gap 493 extending therein. In particular, the retention housing includes a first or proximal housing portion 492a and a second or distal housing portion 492b, such that the gap 493 is disposed between the first and second housing portions 492a and 492b. The retention assembly 490 can further include a second locking member such as a pincher 494 that can be threadedly mounted to the retention housing 492, for instance to the first housing portion 492a at a location is aligned with the gap 493. Rotation of the pincher 494 relative to the retention housing 492 in a first direction causes the pincher 494 to translate into the gap 493 toward the second housing portion 492b. Rotation of the pincher 494 relative to the retention housing 492 in a second direction opposite the first direction causes the pincher 494 to translate out of the gap 493 and away from the second housing portion 492b.

Accordingly, during operation, one or more target strands 379, such as the actuation strand or strands 38a and 38b or at least one tensioning strand can be loaded into the gap 493, and the pincher 494 can be rotated in the first direction until the retention assembly 490 captures the target strands 379 between a distal end of the pincher 494 and the second housing portion 492b. Once the first and second anchor bodies 28a and 28b have been ejected into the respective first and second target anatomical locations (see FIG. 1A), the insertion instrument can be translated proximally away from the anatomical location, thereby applying the actuation force, either directly or indirectly, to the first and second actuation strands 38a and 38b, thereby actuating the anchor bodies 28a and 28b to their expanded configurations. The pincer 494 can then be rotated along the second direction so as to increase the gap 493 until the insertion instrument 300 can be pulled free from the target strands 379. Alternatively or additionally, for instance when the target strands 379 are provided as tensioning strands, the tensioning strands can be cut while captured in the retention assembly 490. Because the cannulas 310a and 310b can define longitudinal slots that extend through one side of the cannulas 310a and 310b, the actuation strands 38a and 38b can be freed from the respective cannula, for instance out the longitudinal slot, when the corresponding anchor bodies 28a and 28b are ejected from the cannula.

Referring now to FIGS. 27A-28B generally, the insertion instrument 300 can be configured having a first and second cannulas 310a and 310b supported by the casing 308 in a side-by-side orientation that retain first and second anchor bodies 28a and 28b, and first and second pusher assemblies 317a and 317b operatively associated with the first and second cannulas 310a and 310b, respectively, so as to eject the first and second anchor bodies 28a and 28b out the respective first and second cannulas 310a and 310b. Furthermore, as described above, it can be desirable to ensure that a desired cannula from which the anchor body is to be ejected is distally disposed with respect to the other cannula, such that the desired cannula can be inserted into the underlying tissue without also inserting the other cannula.

Figure 27A:
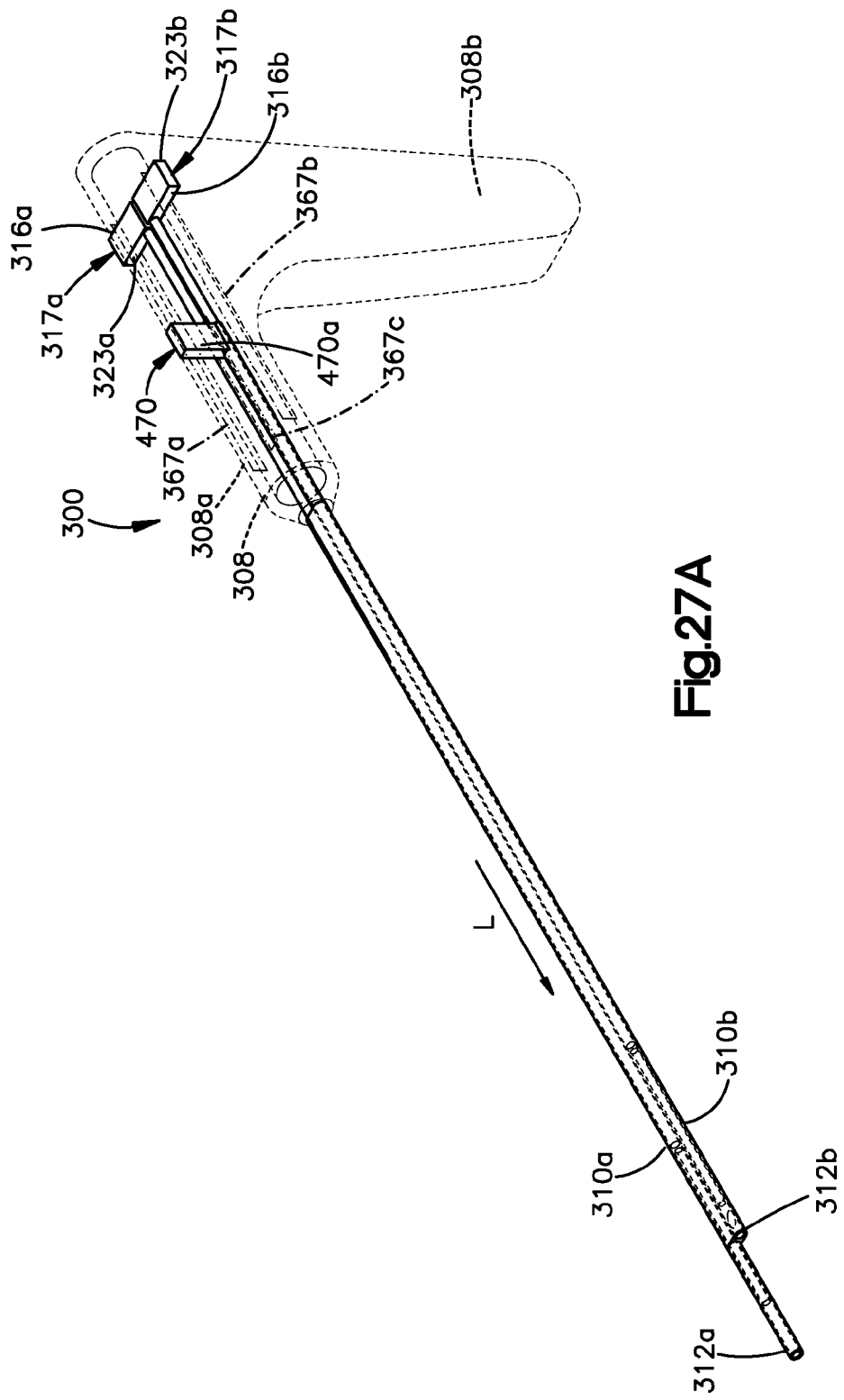
FIG. 27A is a perspective view of an insertion instrument constructed in accordance with another embodiment, the insertion instrument including first and second pusher assemblies disposed in a side-by-side relationship, showing each of the pusher assemblies in a first position.

As illustrated in FIG. 27A, the insertion instrument 300 includes a casing 308 that includes a body portion 308a and a handle portion 308b that extends out from the body portion 308a. The insertion instrument 300 further includes a first cannula 310a that extends distally from the casing 308, and in particular from the body portion 308a, and a second cannula 310b that extends distally from the casing 308, and in particular from the body portion 308a, at a location adjacent the first cannula 310a. The first and second cannulas 310a and 310b can extend substantially parallel to each other as illustrated. Accordingly, the first and second cannulas 310a and 310b can be described as being in a side-by-side relationship. The first and second cannulas 310a and 310b can define respective longitudinally elongate channels 312a and 312b that retain respective first and second anchor bodies 28a and 28b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports 442a and 442b that extend longitudinally through the respective tips 311a and 311b.

Each of the first and second pusher assemblies 317a and 317b includes first and second plungers 316a and 316b, respectively, that extends out the casing 308, such as the body portion 308a of the casing 308. The first and second plungers 316a and 316b can extend proximally out the casing 308 as described above with respect to FIGS. 24A-F, or can extend out the casing along a direction angularly offset with respect to the longitudinal direction L so as to present respective tabs 323a and 323b that project out the casing 308. Each of the first and second pusher assemblies 317a and 317b can further include first and second pusher rods 330a and 330b, respectively, that extend distally from the corresponding plungers 316a and 316b. When the first and second plungers 316a and 316b are in their respective first positions (FIG. 27A), the first and second anchor bodies 28a and 28b are disposed in the respective cannulas 310a and 310b. The plungers 316a and 316b can be moved to respective second positions (FIG. 27D) so as to eject the respective first and second anchor bodies 28a and 28b out the respective cannulas 310a and 310b.

The insertion instrument 330 can further include a swap actuator 470 that can include a swap tab 470a that extends out from the casing 308, and can extend out from the body portion 308a at a location between the first and second tabs 323a and 323b. The casing 308 can defines slots 367a-c that extend through the upper end of the body portion 308 and are longitudinally elongate, and positioned such that the first and second tabs 323a and 323b extend out the first and second slots 367a and 367b, and the swap tab 470a extends out the third slot 367c at a location between the first and second tabs 323a and 323b. The slots 367a-c can thus provide tracks that define the longitudinal movement of the first and second pusher assemblies 317a and 317b and the swap actuator 470 as the tabs 323a-b and 470a ride in the respective slots 367a-c. The swap actuator 470 is configured to be moved from a first position to an actuated position so as to reverse a relative position of the first and second tips 311a and 311b. For instance, as illustrated in FIG. 27A, the first tip 311a of the first cannula 310a is disposed distally with respect to the second tip 311b of the second cannula 310b. It should thus be appreciated that the first tip 311a can be injected into underlying tissue, for instance at the first target anatomical location 24a (see FIG. 1A) without causing the second tip 311b to inject into the underlying tissue. As is described in more detail below, actuation of the swap actuator 470 from a first position (FIG. 27A) to a second position along the direction of Arrow 355 (FIG. 27C) causes the second tip 311b to move distally with respect to the first tip 311a, such that the second tip 311b can be injected into the underlying tissue, for instance at the second target anatomical location 24b (see FIG. 1B) without causing the first tip 311a to inject into the underlying tissue.

Figure 27B:
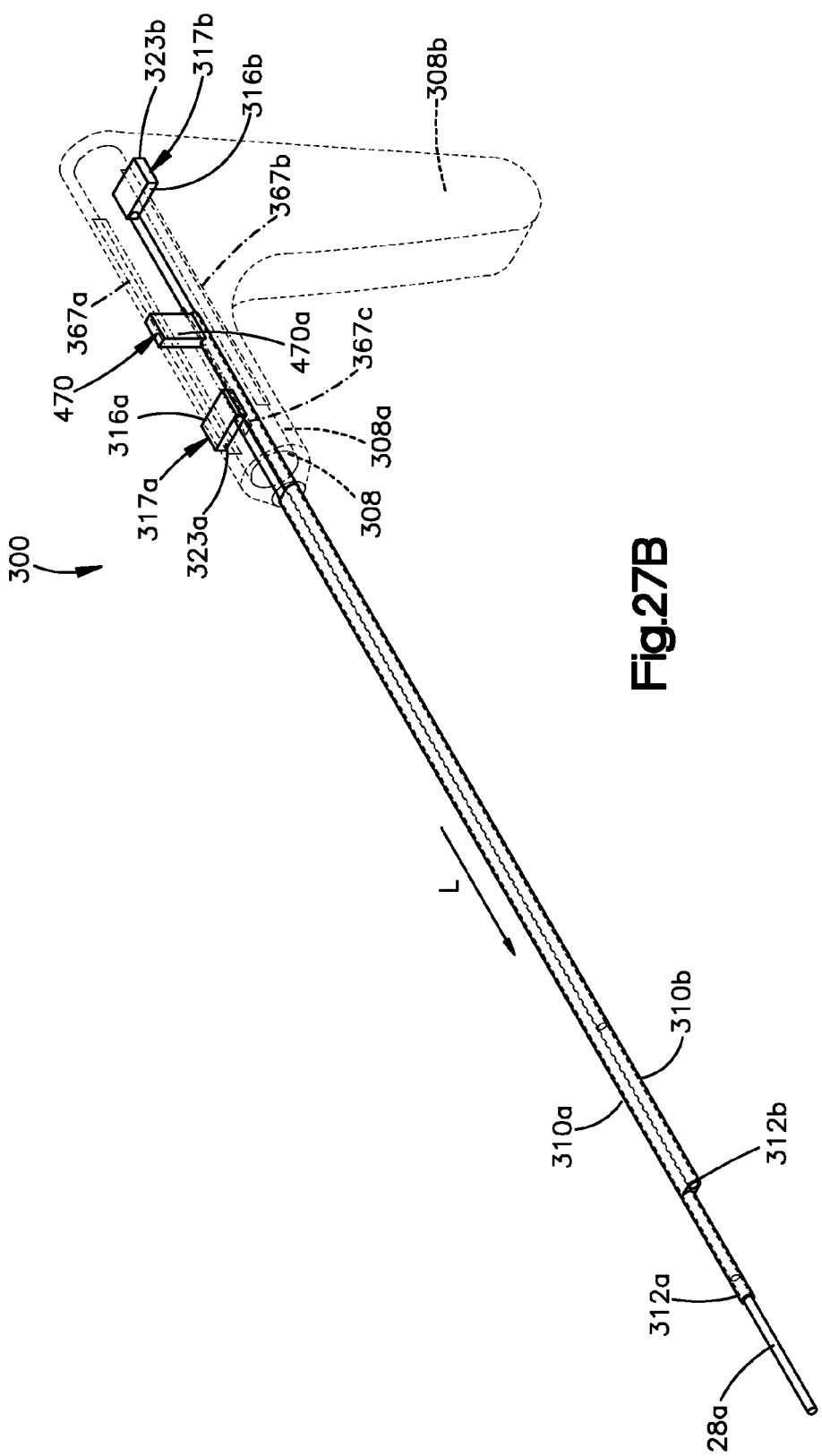
FIG. 27B is a perspective view of the insertion instrument illustrated in FIG. 27A, after actuation of the first pusher assembly to a position configuration.

During operation, referring to FIGS. 27A-B, the first plunger 316a can be translated distally along the direction of Arrow 357 from the first position to the second position, which causes the first push rod 330a to likewise translate distally in the first cannula 310a. The first push rod 330a abuts the first anchor body 28a, such that the first push rod 330a ejects the first anchor body 28a out the first cannula 310a, for instance into the first target anatomical location, as the first push rod 300a translates distally to the second position. The first plunger tab 323a abuts the casing 308 at the distal end of the first slot 367a when the first pusher assembly 317a is in the second position, whereby the first anchor body 28a has been ejected. Thus, when the first plunger tab 323a is in the second position, the plunger 316a is prevented from further distal translation. Thus, the user is provided with tactile feedback that the first anchor body 28a has been ejected.

Figure 27C:
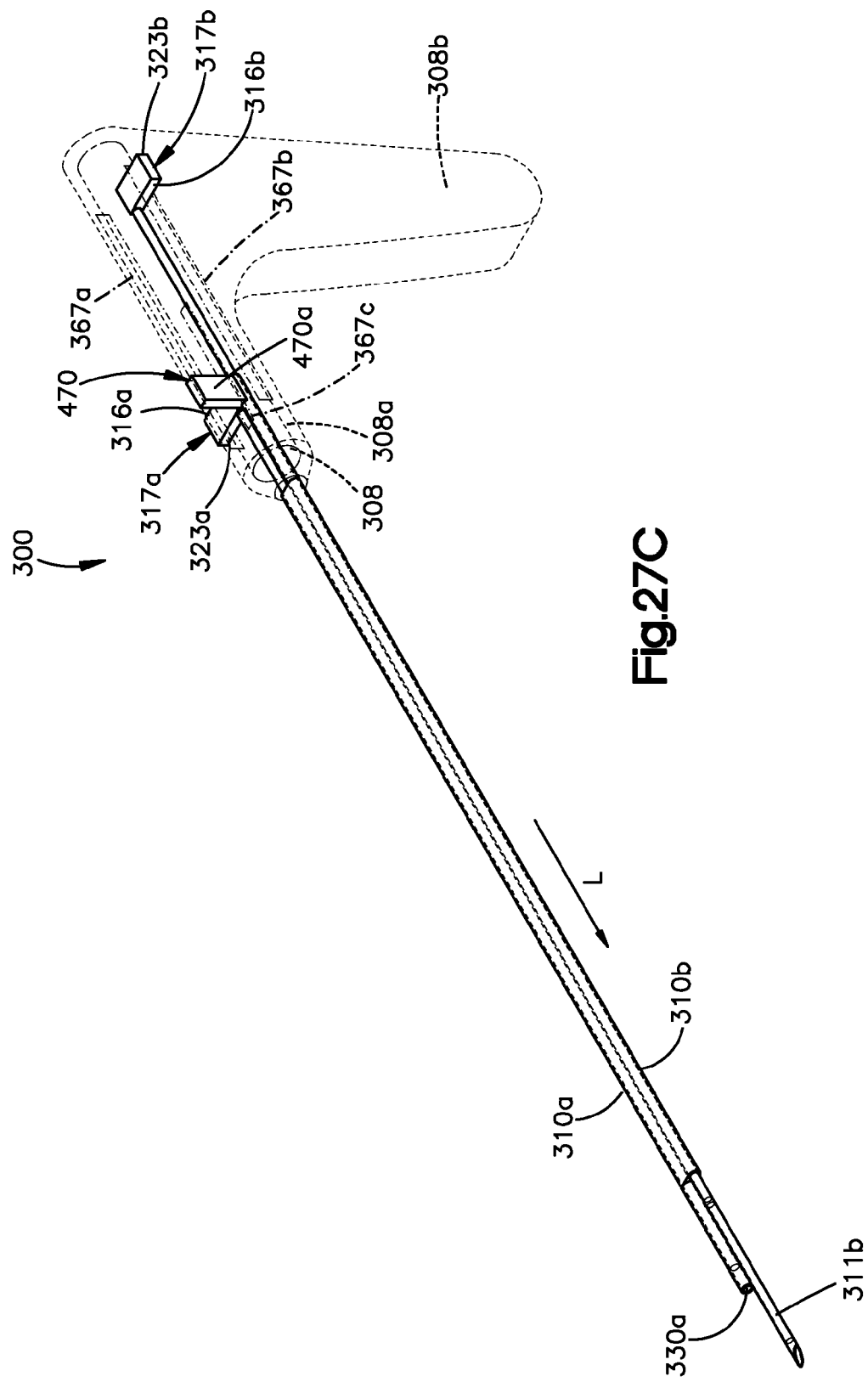
FIG. 27C is a perspective view of the components of the insertion instrument illustrated in FIG. 27B, after actuation of the swap actuator from a first position to an actuated position.

Next, referring to FIG. 27C, the swap actuator 470 can be actuated, for instance can be moved distally along the direction of Arrow 355, from the first position to the actuated position, which causes the second tip 311b to advance, or translate distally, with respect to the casing 308 and the first cannula 310a until the second tip 311b is disposed distally with respect to the first tip 311a. It should thus be appreciated that the second tip 311b can be injected into underlying tissue, for instance at the second target anatomical location 24b (see FIG. 1A) without causing the first tip 311a to inject into the underlying tissue. For instance, the distal end of the first push rod 330a, which is disposed distal with respect to the first tip 311a, can provide a depth stop for the insertion of the second tip 311b into the second target anatomical location. Thus, the second tip 311b can be injected until the first push rod 330a abuts the anatomical structure. In accordance with the illustrated embodiment, actuation of the swap actuator 470 further causes the second plunger 316b, and thus the second push rod 330b, to translate distally as illustrated in FIG. 27C. The swap tab 470a abuts the casing 308 at the distal end of the third slot 367c once the swap actuator 470 has been moved to the actuated position, such that the swap actuator 470 is prevented from further distal translation. Thus, the user is provided with tactile feedback that the swap actuator 470 has been actuated.

Figure 27D:
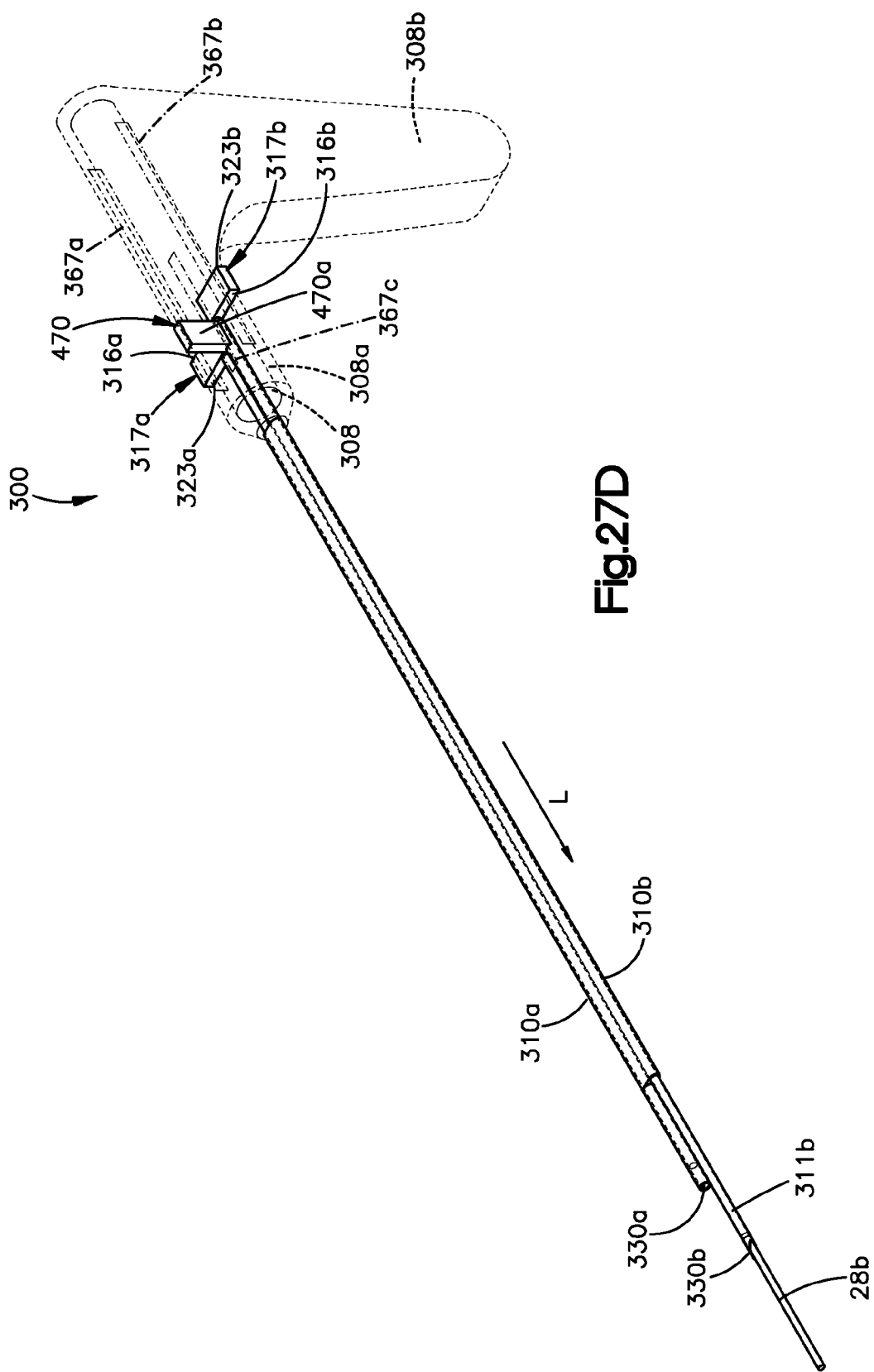
FIG. 27D is a perspective view of the insertion instrument illustrated in FIG. 27C, after actuation of the second pusher assembly to a second position.

Referring now to FIG. 27D, the second plunger 316b can be translated distally along the direction of Arrow 359 from the first position to the second position, which causes the second push rod 330b to likewise translate distally in the second cannula 310b. The second push rod 330b abuts the second anchor body 28b, such that the second push rod 330b ejects the second anchor body 28b out the second cannula 330b, for instance into the second target anatomical location, as the second push rod 300b translates distally to the second position. The second plunger tab 323b abuts the casing 308 at the distal end of the second slot 367b when the second pusher assembly 317b is in the second position, whereby the second anchor body 28b has been ejected. Thus, when the plunger tab 323b is in the second position, the plunger 316b is prevented from further distal translation. Thus, the user is provided with tactile feedback that the second anchor body 28b has been ejected.

Figure 28A:
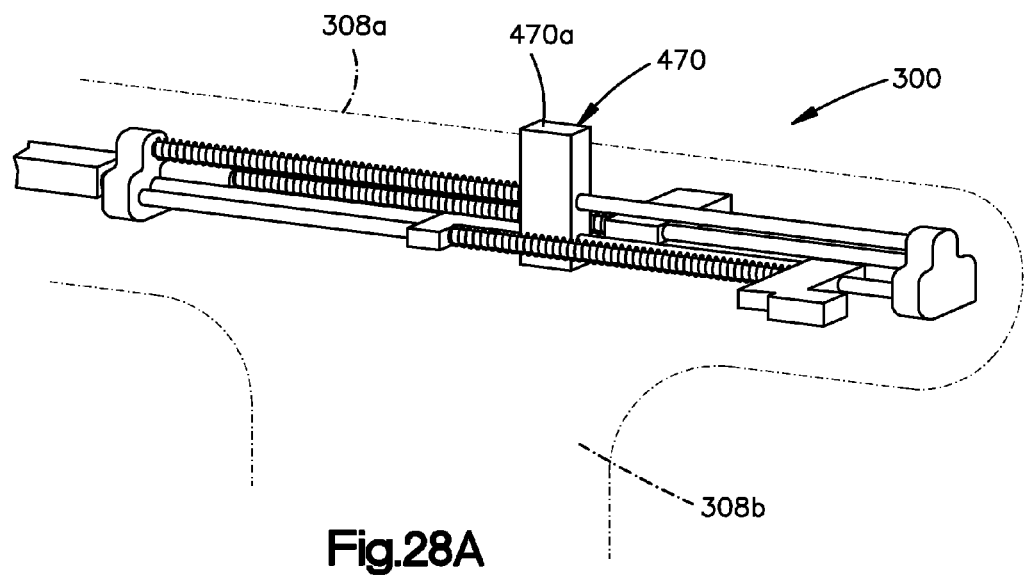
FIG. 28A is a perspective view of components of the insertion instrument illustrated in FIG. 27A, shown with the swap actuator in the first position.
Figure 28B:
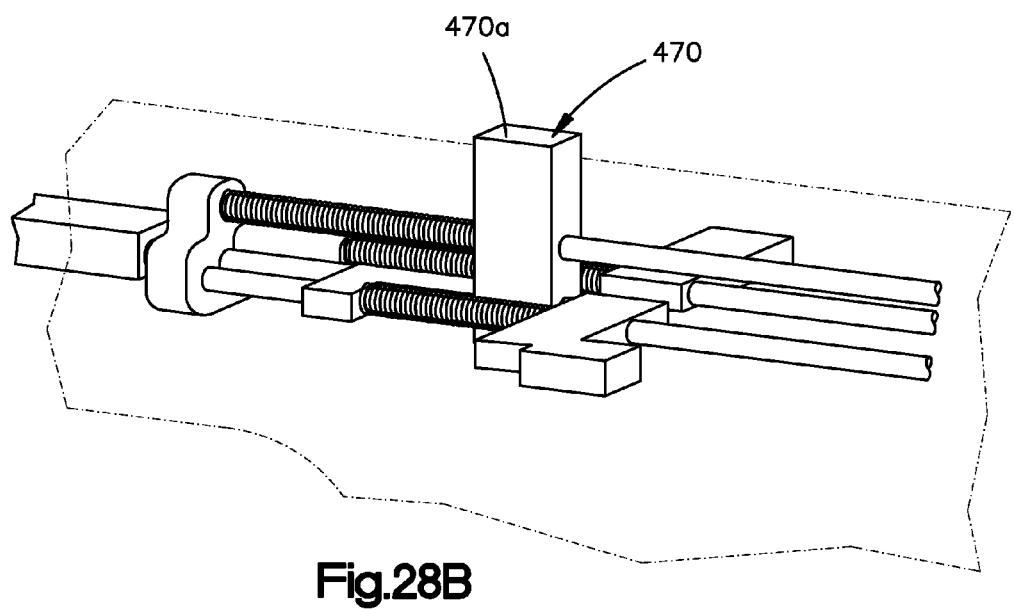
FIG. 28B is a perspective view of components of the insertion instrument illustrated in FIG. 28A, shown with the swap actuator in the second position.

Operation of the insertion instrument 300 illustrated in FIGS. 27A-28B will now be further described with particular reference to FIGS. 28A-B. In particular, the insertion instrument 300 includes at least one latch assembly such as a first latch assembly 482, a second latch assembly 484, and a third latch assembly 486. The first latch assembly 482 is configured to lock the swap actuator 470 in its distal position once it has been moved distally from a first position illustrated in FIG. 27B to a second recessed position illustrated in FIG. 27C. For instance, the first latch assembly 482 can include a latch member 488 that is supported by the casing 308 and configured to latch onto the swap actuator 470 so as to be coupled to the swap actuator 470 with respect to translation. The latch member 488 defines a body 488a, a first attachment portion 488b in the form of a hook carried by the body 488a, and a second attachment portion 488c in the form of an abutment surface carried by the body 488a disposed distal of the first attachment portion 488b. As the swap actuator 470 moves distally, the first attachment portion 488a can deflect inwardly away from the swap actuator 470 so as to allow distal translation of the swap member 470 relative to the latch member 488, such as an outwardly projecting tab 470a of the swap actuator 470. Once the swap actuator 470 has been moved from its first initial position to its second distal position relative to the casing 308, the swap actuator 470 contacts the abutment surface and the hook can deflect outward under the spring force of the body 488a, such that the swap actuator 470, for instance the tab 470a, becomes captured between the first and second attachment portions 488b and 488c. Accordingly, the latch member 488 prevents the swap actuator 470 from moving proximally and distally relative to the casing once the swap actuator 470 has been moved to its proximal position that advances the second pusher assembly 317b distally with respect to the first pusher assembly 316a.

The insertion instrument 300 can further include at least one first guide member 483a such as a guide wire that is translatably fixed to the casing 308. For instance, the insertion instrument 300 can include a mount 485 that is supported by the casing 308 and is attached to the first guide member 483a. The first guide member 483 can extend through the swap actuator 470 so as to guide the swap actuator to translate distally.

The second latch assembly 484 is configured to lock the first plunger 316a, and thus the first pusher assembly 317a, in its proximal position proximal position once it has been moved distally from a first position illustrated in FIG. 27A to a second distal position illustrated in FIG. 27B that causes the first push rod 330a to eject the first anchor body 28a. For instance, the second latch assembly 484 can include a latch member 489 that is supported by the casing 308 and configured to latch onto the first plunger 316a so as to be coupled to the first plunger 316a with respect to translation. The second latch member 489 can be constructed substantially identically with respect to the first latch member 488, and thus defines a body, a first attachment portion in the form of a hook carried by the body, and a second attachment portion in the form of an abutment surface carried by the body and disposed distal of the hook. As the first plunger 316a moves distally, the first attachment portion can deflect inwardly away from the first plunger 316a so as to allow distal translation of the first plunger 316a relative to the second latch member 489, such as an outwardly projecting tab 316c of the first plunger 316a. Once the first plunger 316a has been moved from its first initial position to its second distal position relative to the casing 308, the first plunger 316a contacts the abutment surface and the hook can deflect outward under the spring force of the body of the latch member 489, such that the first plunger 316a, for instance the tab 316c, becomes captured between the first and second attachment portions of the latch member 489. Accordingly, the latch member 489 prevents the first plunger 316a from moving proximally and distally relative to the casing 308 once the first plunger 316 has been moved to its distal position that ejects the first anchor body 28a from the first cannula 310a.

The insertion instrument 300 can further include at least one second guide member 483b such as a guide wire that is translatably fixed to the casing 308. For instance, the mount 485 can be attached to the second guide member 483b, which can extend distally through the first plunger 316a so as to guide the first plunger 316a to translate distally.

The third latch assembly 486 is configured to lock the second plunger 316b, and thus the second pusher assembly 317b, in its distal position proximal position once it has been moved distally from a first position illustrated in FIG. 27C to a second distal position illustrated in FIG. 27D that causes the second push rod 330b to eject the second anchor body 28b. For instance, the third latch assembly 486 can include a third latch member 495 that is supported by the casing 308 and configured to latch onto the second plunger 316b so as to be coupled to the second plunger 316b with respect to translation. The third latch member 495 can be constructed substantially identically with respect to the first and second latch members 488 and 489, and thus defines a body 495a, a first attachment portion 495b in the form of a hook carried by the body 495a, and a second attachment portion 495c in the form of an abutment surface carried by the body 495a at a location distal of the hook. As the second plunger 316b moves distally, the first attachment portion 495b can deflect inwardly away from the second plunger 316b so as to allow proximal translation of the second plunger 316b relative to the third latch member 495, such as an outwardly projecting tab 316d of the second plunger 316b. Once the second plunger 316b has been moved from its first initial position to its second proximal position relative to the casing 308, the second plunger 316b, for instance at the tab 316d, contacts the abutment surface 495c and the hook 495b can deflect outward under the spring force of the latch member body 495a, such that the second plunger 316b becomes captured between the first and second attachment portions of the latch member 495. Accordingly, the latch member 495 prevents the second plunger 316b from moving proximally and distally relative to the casing 308 once the second plunger 316b has been moved to its distal position that ejects the second anchor body 28b from the second cannula 310b.

The insertion instrument 300 can further include at least one third guide member 483c such as a guide wire that is translatably fixed to the casing 308. For instance, the mount 485 can be attached to the third guide member 483c, which can extend distally through the second plunger 316b so as to guide the second plunger 316b to translate distally. Furthermore, the insertion instrument 300 can include an attachment member 496 in the form of an attachment wire that attaches the second plunger 316b to the swap actuator 470 with respect to distal translation of the swap actuator 470. For instance, distal translation of the swap actuator 470 causes the second plunger 316b to translate distally along with the swap actuator 470. A distal force applied to the second plunger 316b can allow the second plunger 316b to translate distally relative to the swap actuator 470. In accordance with one embodiment, the attachment member 496 can be translatably fixed to the swap actuator 470, and can be attached to the second plunger 316b so that it interferes with the second plunger 316 with respect to proximal movement 316b of the second plunger 316b relative to the attachment member 493. The swap actuator 470 can include a second tab 470b that is attached to the second cannula 310b with respect to translation, such that distal translation of the swap actuator 470 causes the second cannula 310b to translate distally along with the swap actuator 470. Accordingly, distal translation of the swap actuator 470 causes the attachment member 496 to drag the second plunger 316b, the second cannula 310b, and the second push rod 330b distally until the second tip 311b is disposed distal of the first tip 311a. Because the first pusher rod 330a remains disposed distal of the first tip 311a after the first anchor body 28a has been ejected, the distal end of the first pusher rod 330a can define an insertion depth stop for the second tip 311b in the manner described above.

The attachment member 496 can extend at least partially through the second plunger 496b so as to allow the second plunger 496b to translate distally with respect to the attachment member 496 and therefore also with respect to the swap actuator 470. As a result, once the swap actuator 470 has been translated distally, thereby also translating the second cannula 310b and the second pusher assembly 317b distally, translation of the second plunger 316b causes the second push rod 330b to eject the second anchor body 28b from the second cannula 310b in the manner described above.

Referring now to FIGS. 29A-29G generally, the insertion instrument 300 can be configured having a first and second cannulas 310a and 310b supported by the casing 308 in a side-by-side orientation that retain first and second anchor bodies 28a and 28b, and first and second pusher assemblies 317a and 317b operatively associated with the first and second cannulas 310a and 310b, respectively, so as to eject the first and second anchor bodies 28a and 28b out the respective first and second cannulas 310a and 310b. Furthermore, as described above, it can be desirable to ensure that a desired cannula from which the anchor body is to be ejected is distally disposed with respect to the other cannula, such that the desired cannula can be inserted into the underlying tissue without also inserting the other cannula.

As illustrated in FIG. 29A, the insertion instrument 300 includes a casing 308 that includes a first casing portion 308*a* and a second casing portion 308*b* that is disposed adjacent the first casing portion 308*b*. The insertion instrument 300 further includes a first cannula 310*a* that extends distally from the first casing portion 308*a*, and a second cannula 310*b* that extends distally from the second casing portion 308*b*. The first and second casing portions 308*a* and 308*b* can extend substantially parallel to each other as illustrated. Accordingly, the first and second cannulas 310*a* and 310*b* can be described as being in a side-by-side relationship. The first and second cannulas 310*a* and 310*b* can define respective longitudinally elongate channels that retain respective first and second anchor bodies 28*a* and 28*b* in the manner described above. The first and second cannulas 310*a* and 310*b* can further include longitudinally elongate side slots 337*a* and 337*b*, respectively, that extend into one side of the cannulas and are in communication with the respective elongate channels. Accordingly, the attachment portions 133*a-b* of the actuation strands 38*a* and 38*b* can extend out the respective side slots 337*a* and 337*b* and attach to each other (see FIG. 1A) when the first and second anchor bodies 28*a* and 28*b* are loaded in the respective first and second cannulas 310*a* and 310*b*.

The insertion instrument 300 can further include first and second pusher assemblies 317*a* and 317*b* operatively associated with the first and second cannulas 310*a* and 310*b*, respectively. Thus, the first pusher assembly 317*a* is configured to eject the first anchor body 28*a* out the first cannula 310*a*, and the second pusher assembly 317*b* is configured to eject the second anchor body 28*b* out the second cannula 310*b*. The first and second cannulas 310*a* and 310*b* can define respective first and second tapered tips 311*a* and 311*b*, and first and second distal ejection ports that extend longitudinally through the respective tips 311*a* and 311*b*.

Each of the first and second pusher assemblies 317*a* and 317*b* includes first and second plungers 316*a* and 316*b*, respectively, that are disposed outside the respective first and second casing portions 308*a* and 308*b* at a location proximal with respect to the casing portions 308*a* and 308*b* as illustrated. Each of the first and second pusher assemblies 317*a* and 317*b* can further include first and second pusher rods 330*a* and 330*b*, respectively, that extend distally from the corresponding plungers 316*a* and 316*b*, through the respective first and second casing portions 308*a* and 308*b*, and into the respective first and second cannulas 310*a* and 310*b*. When the first and second plungers 316*a* and 316*b* are in their respective first positions (FIG. 29A), the first and second anchor bodies 28*a* and 28*b* are disposed in the respective cannulas 310*a* and 310*b*. The plungers 316*a* and 316*b* can be moved to respective second positions (FIG. 29F) so as to eject the respective first and second anchor bodies 28*a* and 28*b* out the respective cannulas 310*a* and 310*b*.

The insertion instrument 330 can further include a swap actuator 470 that can include a swap button 470*a* that extends laterally through the first casing portion 308*a* and into the second casing portion 308*b*. The swap actuator 470 is configured to selectively couple and decouple the first and second casing portions with respect to relative translation in the longitudinal direction L. For instance, as illustrated in FIGS. 29B and 29G, the first and second casing portions 308*a* and 308*b* can be slidably coupled along the longitudinal direction. For instance, one of the casing portions, such as the first casing portion 308*a*, can define a slot 375 extending along at least a portion of its longitudinal length. The other casing portion, such as the second casing portion 308*b*, can include a slider member such as a projection 377 that is configured to ride inside the slot so as to guide longitudinal movement of the first and second casing portions 308*a* and 308*b* relative to each other. The slot 375 and the projection 377 can flare angularly outward in a dovetail arrangement such that the first and second casing portions 308*a* and 308*b* are prevented from separating along a direction angularly offset from the longitudinal direction L. The swap actuator 470 is configured to move the first and second casing portions 308*a* and 308*b* relative to each other along the longitudinal direction such that the respective tips 311*a* and 311*b* move from a first relative position to a second relative position that is opposite the first relative position.

For instance, as illustrated in FIG. 29A, the first tip 311*a* of the first cannula 310*a* can be initially disposed distally with respect to the second tip 311*b* of the second cannula 310*b*. It should thus be appreciated that the first tip 311*a* can be injected into underlying tissue, for instance at the first target anatomical location 24*a* (see FIG. 1A) without causing the second tip 311*b* to inject into the underlying tissue. As is described in more detail below, actuation of the swap actuator 470 from a first position (FIG. 29D) to a second position causes the second tip 311*b* to move distally with respect to the first tip 311*a* such that the second tip 311*b* is positioned distal of the first tip 311*a*. Accordingly, the second tip 311*b* can be injected into the underlying tissue, for instance at the second target anatomical location 24*b* (see FIG. 1B) without causing the first tip 311*a* to inject into the underlying tissue.

During operation, referring to FIG. 29C, the first plunger 316*a* can be translated distally from the first position to the second position, which causes the first push rod 330*a* to likewise translate distally in the first cannula 310*a*. The first push rod 330*a* abuts the first anchor body 28*a*, such that the first push rod 330*a* ejects the first anchor body 28*a* out the first cannula 310*a*, for instance into the first target anatomical location, as the first push rod 300*a* translates distally to the second position. The first plunger 316*a* can abuts the first casing portion 308*a* when the first pusher assembly 317*a* is in the second position, whereby the first anchor body 28*a* has been ejected. Thus, when the first plunger 316*a* is in the second position, the first plunger 316*a* is prevented from further distal translation. Thus, the user is provided with tactile feedback that the first anchor body 28*a* has been ejected.

Next, referring to FIGS. 29C, 29D, and 29G, the swap actuator 470 can be actuated so as to reverse the relative position of the first and second tips 311*a* and 311*b* in the manner described above. For instance, the swap actuator 470 can include a button 472 that extends laterally through the first casing portion 308*a* and into the second casing portion 308*a*. The second casing portion 308*b* can include a spring member 474 that biases the button 472 outward toward its first position. The button 472 can include at least one flange 476 that abuts a wall of the second casing portion 308*b* so as to prevent the force of the spring member 474 from ejecting the button 472 out the first casing portion 308*a*.

The first casing portion 308*a* can include a pair of apertures 478*a-b* sized to receive the button 472 such that the button 472 extends out the first casing portion 308*a*. The first aperture 478*a* is disposed proximal with respect to the second aperture 478*b*. When the button 472 extends through the first aperture 478*a*, the first tip 311*a* is disposed distal with respect to the second tip 311*b*. Furthermore, interference between the button 472 and the first casing portion 308*a* prevents the first casing portion 308*a* from translating longitudinally relative to the second casing portion 308*b*. When the button 472 is depressed into the slot 375, and thus into the projection 377, interference between the button 472 and the first casing portion 308a is removed, such that the first and second casing portions 308a and 308b are configured to translate longitudinally relative to each other. For instance, the second casing portion 308b, and thus the second cannula 310b, can slide distally with respect to the first casing portion 308a, and thus the first cannula 310a, until the button 472 is driven through the second aperture 478b as illustrated in FIG. 29D. When the button 472 extends through the second aperture 478b, the second tip 311b is disposed distal with respect to the first tip 311a. It should thus be appreciated that the second tip 311b can be injected into underlying tissue, for instance at the second target anatomical location 24b (see FIG. 1A) without causing the first tip 311a to inject into the underlying tissue.

Referring now to FIGS. 29D-E, the insertion instrument 300 can further include a lock-out tab 468 that is removably attached to the second push rod 330b at a location longitudinally between the corresponding plunger 316b and the second casing portion 308b. Accordingly, the lock-out tab 468 interferes with the distal translation of the plunger 316b relative to the second casing portion 308b to a depth that would eject the respective second anchor body 28b. The lock-out tab 468 can remain attached to the second push rod 330b until the first anchor body 28a has been ejected and the swap actuator 470 has been actuated. The insertion instrument 300 can further include a lock-out tab operatively associated with the first pusher assembly 317 in the manner described with respect to the second pusher assembly 317b.

Referring now to FIGS. 29E-F, once the lock-out tab 468 has been removed from the second push rod 430, the second plunger 316b can be translated distally from the first position to the second position, which causes the second push rod 330b to likewise translate distally in the second cannula 310b. The second push rod 330b abuts the second anchor body 28b, such that the second push rod 330b ejects the second anchor body 28b out the second cannula 330b, for instance into the second target anatomical location, as the second push rod 300b translates distally to the second position. The grip portion 432b of the second plunger 416b abuts the casing 308 at the distal end after the second anchor body 28b has been ejected, thereby providing the user with tactile feedback that the second anchor body 28b has been ejected.

Referring now to FIGS. 30A-D generally, the insertion instrument 300 can be configured having a first and second cannulas 310a and 310b supported by the casing 308 in a side-by-side orientation that retain first and second anchor bodies, respectively. Each of the first and second cannulas 310a and 310b is supported by the casing 308 so as to be translatably movable with respect to the casing 308. The insertion instrument 300 further includes a reciprocal motion assembly 500 that is configured to drive the first and second cannulas 310a and 310b in opposite directions. For instance, when the first cannula 310a is driven distally with respect to the casing 308, the reciprocal motion assembly 500 drives the second cannula 310b proximally with respect to the casing 308. Similarly, when the first cannula 310a is driven proximally with respect to the casing 308, the reciprocal motion assembly 500 drives the second cannula 310b distally with respect to the casing 308. Similarly, when the second cannula 310b is driven distally with respect to the casing 308, the reciprocal motion assembly 500 drives the first cannula 310a proximally with respect to the casing 308. Similarly, when the second cannula 310b is driven proximally with respect to the casing 308, the reciprocal motion assembly 500 drives the first cannula 310a distally with respect to the casing 308.

The insertion instrument 300 can include a pusher assembly 317 having a plunger 316 and first and second pusher members 330a and 330b. The first pusher member 330a extends into the first cannula 330a and is configured to eject a first anchor body out the first cannula 330a in the manner described above. Similarly, the second pusher member 330b extends into the second cannula 330b and is configured to eject a second anchor body 28b out the second cannula 330b in the manner described above. The insertion instrument 300 further can include a selective plunger engagement assembly 502 that is operable so as to selectively engage the plunger between one of the first and second push rods 330a and 330b. Thus, the plunger 316 can be translatably coupled to the first push rod 330a, such that distal translation of the plunger 316 causes the push rod 330a to translate distally and eject the first anchor body 28a out of the respective first cannula 330a. The plunger 316 can be translatably coupled to the second push rod 330b, such that distal translation of the plunger 316 causes the push rod 330b to translate distally and eject the second anchor body 28b out of the respective first cannula 330b.

Figure 30C:
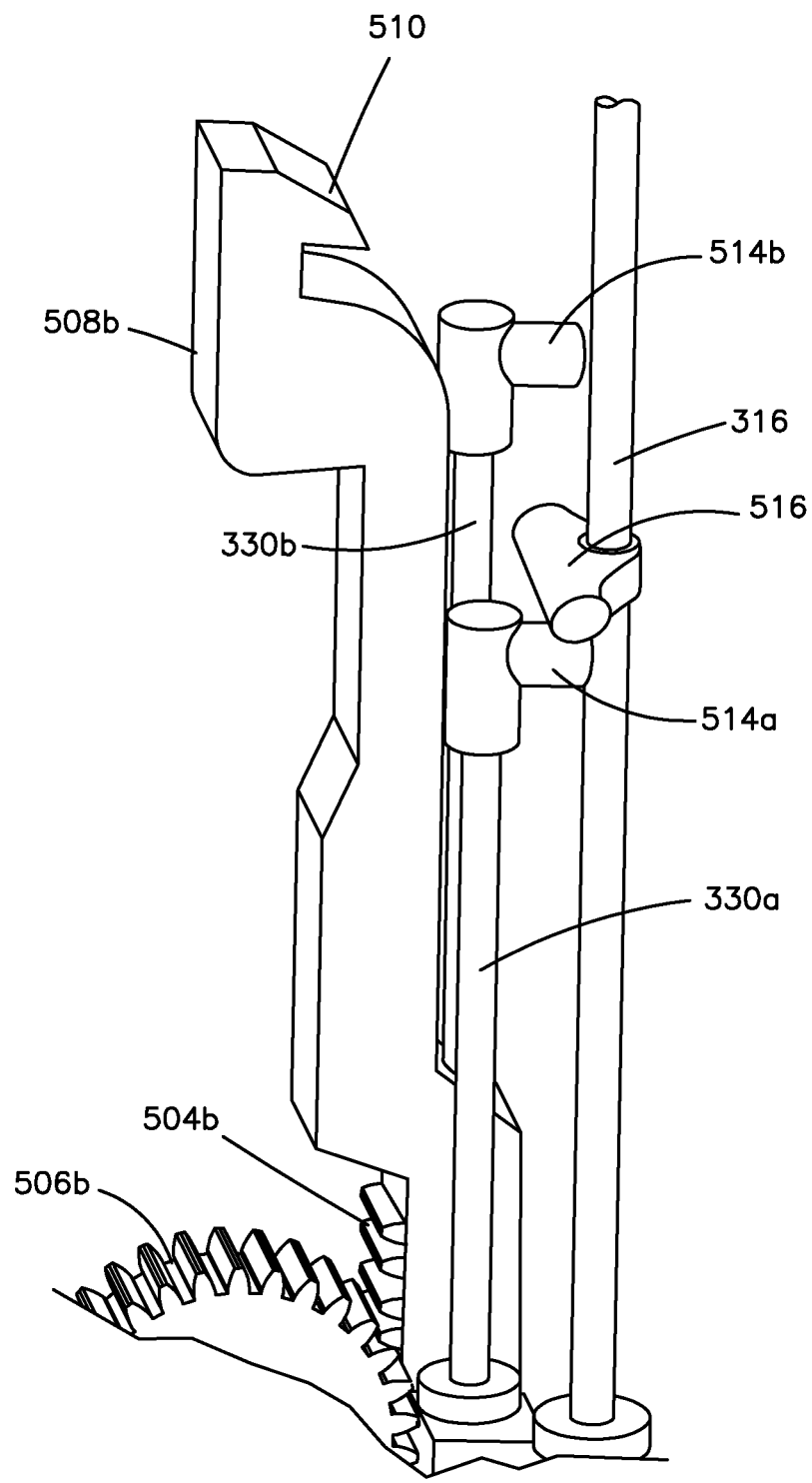

Referring now to FIGS. 30A-C, the reciprocal motion assembly 500 includes a first force transfer member, such as a toothed first rack 504a that is attached to the first cannula 310a and is translatably fixed to the first cannula 310a. The first rack 504a can be integral with the first cannula 310a or discretely attached to the first cannula 310a as desired. In accordance with the illustrated embodiment, the first rack 504a extends proximally from the first cannula 310a. The reciprocal motion assembly 500 can further include a second force transfer member such as a second toothed rack 504b that is attached to the second cannula 310b and is translatably fixed to the second cannula 310b. The second rack 504b can be integral with the second cannula 310b or discretely attached to the second cannula 310b as desired. In accordance with the illustrated embodiment, the second rack 504b extends proximally from the second cannula 310b.

The reciprocal motion assembly 500 can further include a third force transfer member such as a first gear 506a, which can be a spur gear, that mates with the first rack such that rotation of the first gear 506a drives the first rack 504a to translate substantially linearly, for instance proximally or distally. The first cannula 310a translates along with the first rack 504a. The reciprocal motion assembly 500 can further include a fourth force transfer member such as a second gear 506b, which can be a spur gear, that mates with the second rack 504b such that rotation of the second gear 506b drives the first rack 504a to translate substantially linearly, for instance proximally or distally. The second cannula 310b translates along with the second rack 504b. Furthermore, the first and second gears 506a and 506b are mated such that rotation of one of the first and second gears 506a and 506b in a first rotational direction along their respective axes of rotation 508a and 508b drives the other of the first and second gears 506a and 506b to rotate in a second rotational direction opposite the first rotational direction. The first and second gears 506a and 506b can be supported in the casing 308 such that the axes of rotation 508a and 508b remains stationary as the gears 506a and 506b rotate.

The second rack 504b can include a handle 508b that extends out the casing 308. During operation, for instance when the first cannula 310a extends distal with respect to the second cannula 310b, the handle 508b can be driven distally, which causes the second cannula 310b and the second rack 504b to translate distally, thereby rotating the second gear 506b along a direction of rotation. The second gear 506b drives the first gear 506a to rotate along an opposite direction of rotation, which causes the first cannula 310a to translate proximally toward the casing 308. Thus, as the second cannula 310b is driven distally, the reciprocal motion assembly drives the first cannula 310 in an opposite direction, such as proximally as illustrated.

When the second cannula 310b extends distal with respect to the first cannula 310a, the handle 508b can be driven proximally, which causes the second cannula 310b and the second rack 504b to translate proximally, thereby rotating the second gear 506b along a direction of rotation. The second gear 506b drives the first gear 506a to rotate along an opposite direction of rotation, which causes the first cannula 310a to translate distally away from the casing 308. Thus, as the second cannula 310b is driven proximally, the reciprocal motion assembly drives the first cannula 310a in an opposite direction, such as distally as illustrated.

The handle 508b can include a hook 510 that latches onto the casing 308 so as to provide a safety catch that prevents distal translation of the handle 508, and thus also distal translation of the second rack 504b. The hook 510 can be configured to latch onto the casing 308 when the second cannula 310b is retracted, and the first cannula 310a is extended and disposed distal with respect to the second cannula 310b.

Figure 30D:
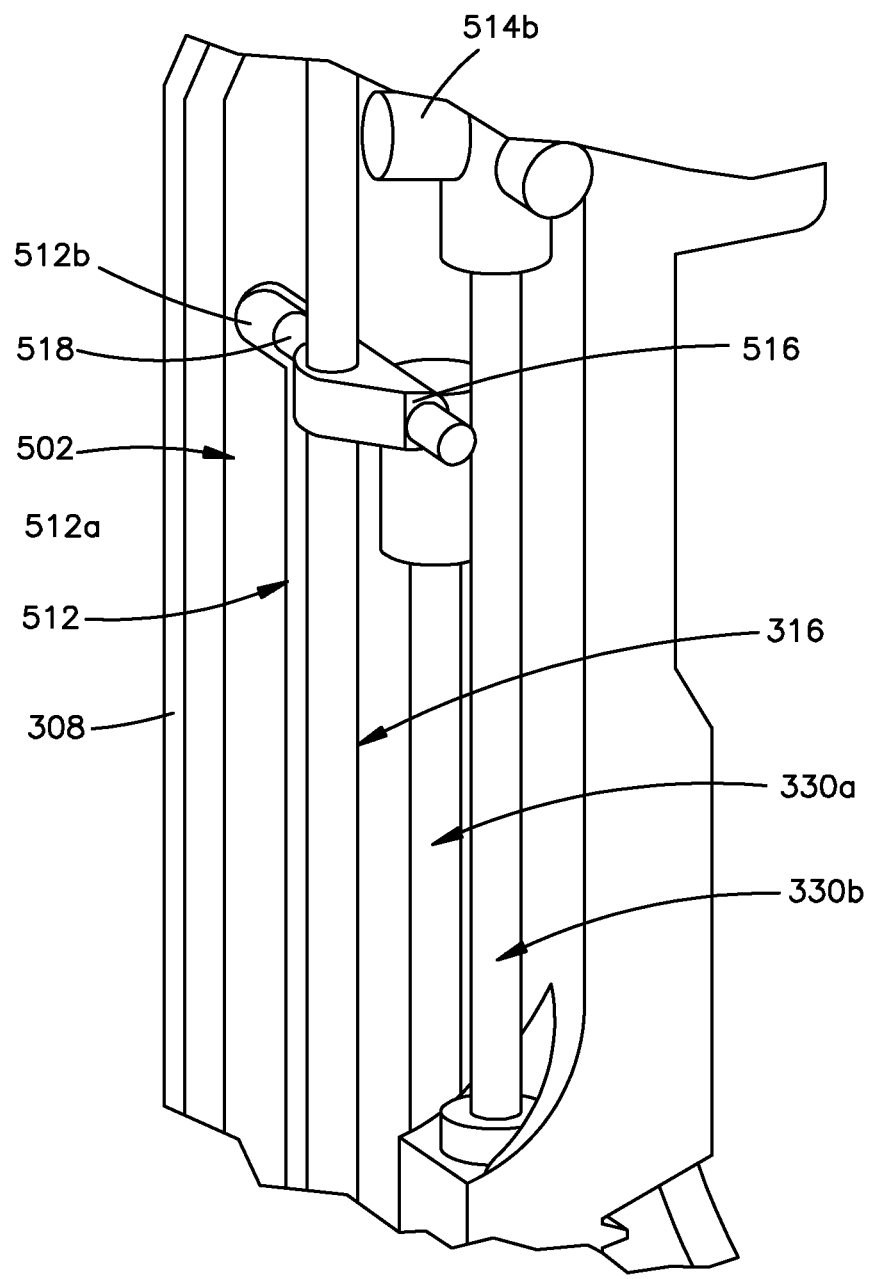

Referring now to FIGS. 30C-D, the selective plunger engagement assembly 502 includes a track 512 carried by the casing 308. The track 512 can extend radially outward into an inner wall of the casing 308. The track includes a first portion 512a that extends substantially longitudinally and parallel to the cannulas 310a and 310b and the push rods 330a and 330b. The track further includes a second portion 512b that extends from the first portion 512a, for instance from the proximal end of the first portion 512a, and extends proximally and outward, such as laterally outward, from the first portion 512b. Thus, it can be said that the second portion 512b is offset with respect to the first portion 512a. In accordance with the illustrated embodiment, the second portion 512b is angularly offset with respect to the first portion 512a.

The plunger 316 is configured to ride in the track 512, and is movable distally along the track 512 so as to drive a select one of the first and second push rods 330a and 330b distally within a respective one of the first and second cannulas 310a and 310b so as to eject the respective one of the first and second anchors out the insertion instrument. In accordance with the illustrated embodiment, the first and second push rods 330a and 330b carry first and second engagement members 514a and 514b. The engagement members 514a and 514b can be spaced from each other so as to provide clearance as the first and second cannulas 310a and 310b are driven reciprocally. It should be appreciated that because the first and second push rods 330a and 330b extend into the respective first and second cannulas 310a and 310b, the push rods 330a and 330b are likewise driven reciprocally during reciprocal movement of the cannulas 310a and 310b.

The plunger 316 carries a biasing member 516 that is longitudinally aligned with each of the engagement members 514a and 514b when the plunger 316 is disposed in the first track portion 512a. The plunger 316 further carries a follower 518 that is sized and shaped so as to ride in the track 512 and guide the travel path of the plunger 316 as the plunger is driven proximally and distally. The plunger 316 can include a proximal end that extends out, for instance proximally out, from the casing 308. Thus, the plunger 316 can be driven distally along the first track portion 512a and proximally along the first track portion 512a. The plunger can further be driven proximally along the second track portion 512b, which causes the biasing member 516 to move out of longitudinal alignment with the engagement members 514a and 514b. Thus, the cannulas 310a and 310b, and the respective push rods 330a and 330b, can move reciprocally without the engagement members 514a and 514b interfering with each other, and further without the engagement members 514a and 514b interfering with the biasing member 516 of the plunger 316.

When it is desired to eject one of the anchor bodies out of the respective cannula, for instance the first cannula 310a, the first push rod 330a can be placed into alignment with the plunger 316. For instance, the reciprocal motion assembly 500 can be actuated as desired so as to position the respective engagement member 514a distal of the proximal end of the first track portion 512a. Accordingly, the plunger 316 can be driven distally along the track 512. Once the plunger 512 travels distally along the first track portion 512a, the biasing member 516 engages the engagement member 514a, and drives the push rod 330a distally in the respective cannula 310a, thereby ejecting the anchor body out the cannula 310a as described above.

Once it is desired to eject the second anchor body from the second cannula 310b, the plunger 316 can be driven proximally onto the second track portion 512b until the biasing member 516 is out of longitudinal alignment with the engagement members 514a and 514b of the first and second push rods 330a and 330b. Next, the reciprocal motion assembly 500 can be actuated so as to drive the second cannula 310b and second push rod 330b distally, which causes the first cannula 310a and the first push rod 330a to translate proximally, until the first engagement member 514a is disposed proximal of the proximal end of the first track portion 512a, and the second engagement member 514b is disposed distal of the proximal end of the first track portion 512a. Thus, the second cannula 310b is disposed distal with respect to the first cannula 310a. Next, the plunger 316 can be driven distally, which causes the biasing member 516 to engage the second engagement member 514b, which drives the second push rod 330b distally in the second cannula 330b so as to eject the second anchor out the insertion instrument.

Figure 31:
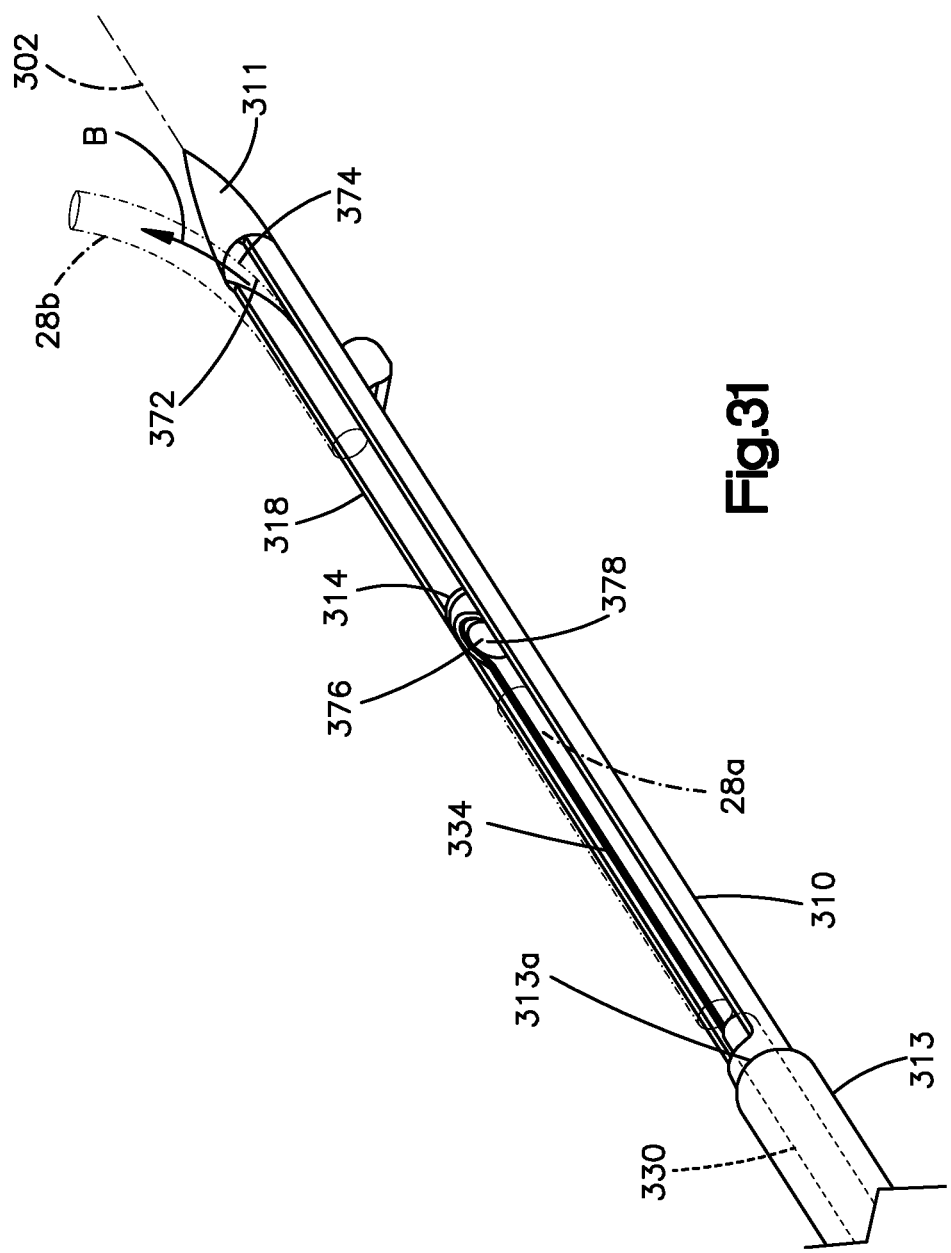

Referring now to FIG. 31, while various insertion instruments 300 have been described as including a distal ejection port 442, the insertion instruments 300 can define a side ejection port 318 as an alternative to the distal ejection port 442. For instance, the side ejection port 318 can be defined as a slot that extends radially through a distal portion of the cannula 310 at a location proximal with respect to the tip 311. The tip 311 can be closed so as to prevent the anchor bodies 28a and 28b from ejecting out the distal ejection port 442 that is defined by the tip 311. The side ejection port 318 can define a circumferential dimension at least substantially equal to or greater than the largest cross-sectional dimension of each of the first and second anchor bodies 28a and 28b, such that the anchor bodies 28a and 28b are sized to travel through the side ejection port 318. Furthermore, the side ejection port 318 can define a longitudinal length that is substantially equal to or greater than the longitudinal length of each of the first and second anchor bodies 28a and 28b. The longitudinal length of the side ejection port 318 can be slightly less than that of each of the first and second anchor bodies 28a and 28b, for instance, if the first and second anchor bodies 28a and 28b are angularly offset with respect to the longitudinal axis 302 as they are ejected out the side ejection port 318.

The tip 311 can define a ramp 372 at its proximal end. The ramp 372 can thus be disposed at the distal end of the side ejection port 318 and substantially aligned with the longitudinal axis 302. The ramp 372 can define a tapered ejection surface 374 that is angled radially outward toward the side ejection port 318 as it extends distally. Accordingly, as the plug 314 biases the second anchor body 28b distally from the elongate opening 312 of the cannula 310 onto the ejection surface 374 as the plunger 316 and push tube 334 collar 332 move from the first position to the second position, second anchor body 28b rides along the ejection surface 374, which directs the second anchor body 28b out the side ejection port 318 along the direction of Arrow B, thereby ejecting the second anchor body 28b out the insertion instrument 300 at the second target anatomical location 24b (see FIG. 1A). When the at least the distal portion of the side ejection port 318 is disposed behind the anatomical structure 24, the second anchor body 28b is ejected from the insertion instrument 300 at a location behind the anatomical structure 24, as further shown in FIG. 1A. The insertion instrument 300 can be configured such that the plug 314 is disposed proximal to and adjacent to the tip 311 when the push rod 330 and the push tube 334 become decoupled. Accordingly, translation of the push rod 330 relative to the push tube 334 causes the push rod to eject the first anchor 28a along the ramp surface 378 of the plug 314 in the manner described above, and out the side ejection port 318.

With reference to FIGS. 32A-32C, any of the anchor assemblies described herein can be used to repair an anatomical defect 803 by joining a soft tissue 801 to a bone 802. For example, the anchor assemblies 20 can be used for rotator cuff repair and for partial articular-side supraspinatus tendon avulsion (PASTA) repair. Any of the insertion instruments described above can be used to insert, such as inject or drive, the anchor assembly 20 into, such as completely through, the soft tissue 801 and bone 802. In this method, the soft tissue 801 can be a tendon of the rotator cuff, and the bone 802 can be a humerus. Rotator cuff tendons include supraspinatus, infraspinatus, teres minor, and subscapularis. The anatomical defect 803 can be a tear of the tendon of the rotator cuff. The method of repairing an anatomical defect 803 includes placing a portion of soft tissue 801 over the bone 802 at the desired anchor insertion site 805 by, for example, manually moving the soft tissue 801 in the direction indicated by arrow 804. The user can also hold the soft tissue 801 in place by using, for example, grasping forceps. An anchor assembly 20 can be inserted within an insertion instrument, such as insertion instrument 300. As used in this detailed description, the term "inserting" includes injecting and driving. Using any of the insertion instruments described above, the user pierces the soft tissue 801. For example, the user can use insertion instrument 300 (FIG. 23G) to insert the anchor assembly 20 into, such as entirely through, the soft tissue 801. The anchor assembly 20 is inserted, such as injected or driven, into an opening 806 in the bone 802. For example, an opening 806 can be created in the bone 802 before inserting the anchor assembly 20 into that bone 802 with any other suitable insertion instrument, such as a drill or an awl. Further, the opening 806 can extend into the cortical wall 807 and the spongiosa 808 of the bone 802. As used herein, the spongiosa includes the cancellous portion of a bone. As seen in FIG. 32B, the distal tip 311 (FIG. 23G) can pierce the soft tissue 801 while the anchor assembly 20 is inserted through the soft tissue 801. The insertion instrument 300 is advanced toward the bone 802 until the distal tip 311 abuts or contacts the bone 802 in order to fix the position of the soft tissue 802 with respect to the bone 802. The insertion instrument is then inserted, such as injected or driven, in the opening 806 in the bone 802 at the desired anchor insertion site 805.

After inserting a portion of the insertion instrument 300 into the bone 802, the insertion instrument 300 is actuated to deploy the anchor assembly 20 in the opening 806. The anchor body 28a of the anchor assembly 20 is then actuated to the expanded configuration as described in detail above. In the expanded configuration, the anchor body 28 is located in the spongiosa 808 of the bone 208 and abuts an inner portion 809 of the cortical wall 808 of the bone 802 as shown in FIG. 32C. The anchor body 28a can alternatively be expanded only into the spongiosa 808—i.e. so that it does not abut the cortical wall 808. In the depicted embodiment, the anchor assembly 20 includes one anchor body 28a; it is envisioned, however, that another anchor body 28b (FIG. 1A) of the anchor assembly 20 can be inserted into the soft tissue 801 and into the bone 802 using the same steps described above. As used in this detailed description, the term "through" means that something, such as the anchor body 28a, can be inserted at least partially into or completely through a body, such as soft tissue 801. In the depicted embodiment, after expanding the anchor body 28a, the actuation strand or strands 38a of the anchor 22a can be placed in tension and maintained in tension by using any suitable connector member. For example, if the anchor 22a includes more than one actuation strands 38a, the actuation strands 38a can be tied in knot 66 to maintain them in tension. If more than one anchor body is inserted into the soft tissue 801 and the bone 802, the actuation strands 38a and 38b (FIG. 1H) can be pre-connected together using any other suitable connector member 63 (FIG. 1H) as described in detail above. The connector member 63 (FIG. 1H) can be a pre-tied sliding knot, a single braided splice, or a double braided splice as described above. The connector member 63 can also be a woven splice or any anchor assembly disclosed in the co-pending U.S. Utility patent application entitled "Insertion Instrument for Anchor Assembly" filed on Oct. 27, 2011, the entire disclosure of which is incorporated by reference herein. This method provides osteoporotic fixation by buttressing against the cortex. Also, this method allows atraumatic trans-tendon delivery for PASTA repairs. There is no need to complete the tear. In any form of trans-tissue delivery of the anchor 22a, all suture strands 38a do not necessarily need to pass through (or extend into) the tissue as is required for standard (non-trans-tissue) suture anchor delivery. In trans-tissue delivery, the surgeon could elect to perform a simple stitch repair as shown in FIG. 32B and can then grasp suture strand 38a between the tissue and bone and retrieve it around tissue 801. In this trans-tissue delivery method, the suture strand 38a can have two limbs, and the surgeon can grab one limb of the suture strand 38a between the tissue and the bone and retrieve it around the tissue 801. Since this method does not uses metal anchors, the anchor assemblies 20 occupy less space. This method also decreases the risk of suture tearing through the soft tissue by allowing the use of more anchors and tissue fixation points. In other words, because the anchors are deployable in close proximity to one another, it is less likely that the sutures will tear through the soft tissue.

With respect to FIGS. 32D-32G, anchor assemblies 20 having two or more anchor bodies, such as anchor bodies 28a and 28b, can be used to fix the soft tissue 801 to the bone 802. The anchor bodies 28a and 28b can be inserted in the desired target site as described above with respect to FIGS. 32A-32C. For instance, as seen in FIG. 32D, only one anchor assembly 20 can be used to fix the soft tissue 801 to the bone 802. Alternatively, two or more anchor assemblies 20 can be arranged along a single row as shown in FIG. 32E. Further, two or more pairs of anchor assemblies 20 can be generally arranged side by side as shown in FIG. 32F For example, the user can fix the bone 802 to the soft tissue 801 by anchoring four anchor assemblies 20. In the embodiment depicted in FIG. 32F, each pair of anchor assemblies 20 can be arranged in X-shaped configuration as shown in FIG. 32H. In an X-shaped configuration, the actuation strands 38a and 38b of each actuation assembly 20 cross one another, forming an X-shaped pattern. The pairs of anchor assemblies 20 arranged in an X-shaped pattern (as shown in FIG. 32H) can also be arranged in an overlapping manner. All the actuation strands 38a and 38b of all the anchor assemblies 20 can be connected to each other using any of the connector members 63 described above. When more than one anchor assembly 20 is used, the anchor assemblies 20 establish more contact area between the bone 802 and the soft tissue 801, thereby establishing a larger biological footprint for tissue-to-bone healing. Aside from repairing rotator cuff injuries, the anchor assembly 20 can be used as a meniscal repair anchor for fixing a meniscus to a bone.

Figure 33:
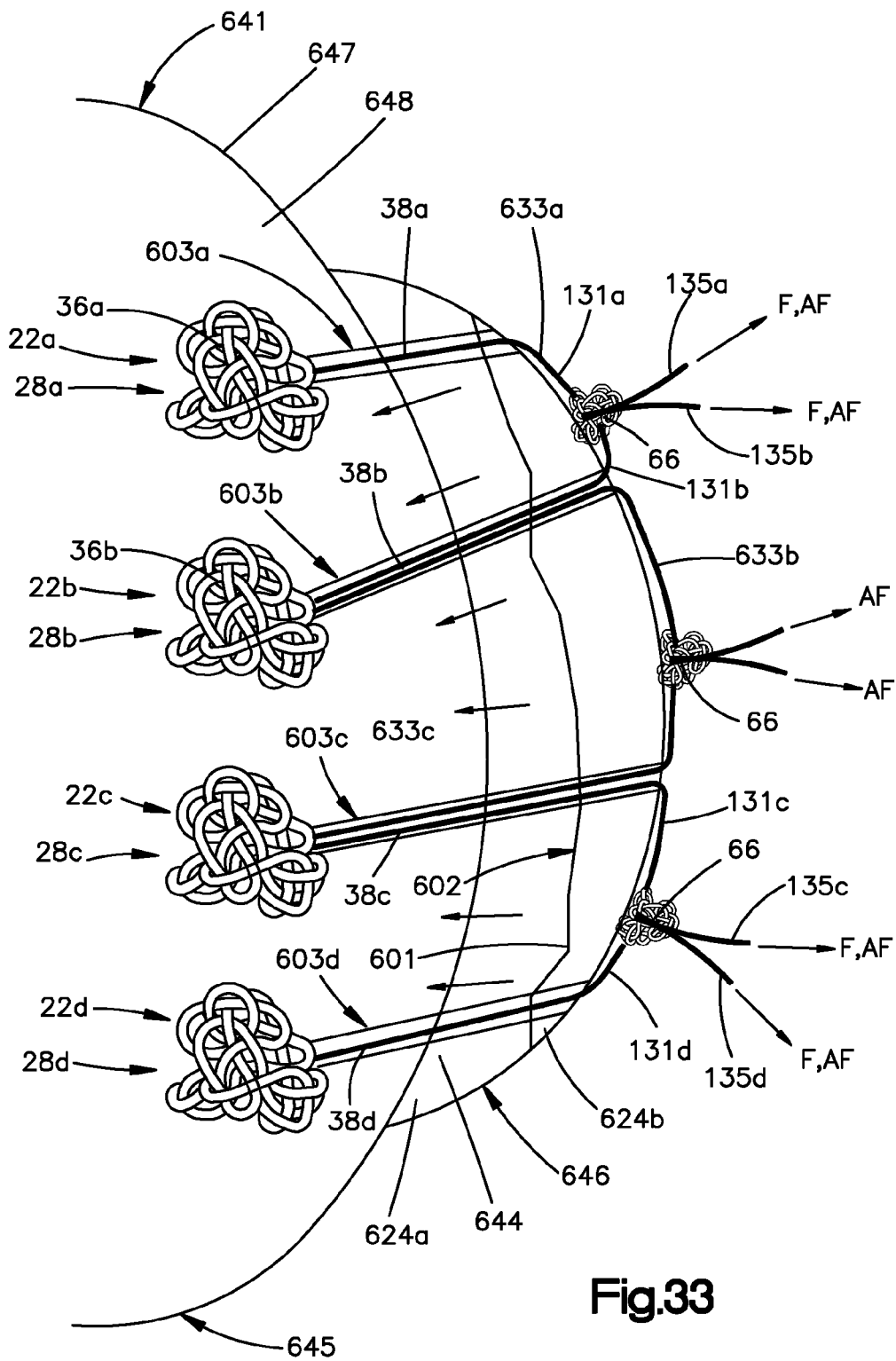

With reference to FIG. 33, any of the anchor assemblies described herein can be used to repair an anatomical defect by joining soft tissue to bone. For instance, an anatomical defect, such as a rotator cuff tear 601, can be repaired by joining soft tissue 646, such as tendon and/or muscle 644, to a portion of a bone 641, such as a humerus 645. Typically, rotator cuff injuries involve a tear 601 of the tendons or muscles 44. This tear 601 can create a gap 602 between two or more soft tissue portions, such as first and second soft tissue portions 624a and 624b of the tendon and/or muscle 644. In the interest of brevity, the method of repairing of an anatomical defect, such as the rotator cuff tear 601, is described and illustrated with respect to the anchor assembly 20 depicted in FIG. 1G. However, any one of the anchor assemblies described herein can be used to approximate the gap 602 created by the tear 601.

With continued reference to FIG. 33, the method includes creating at least two openings 603a, 603b through the bone 641, such as the humerus 645. The openings 603a and 603b can extend from the cortex 647 of the bone 641 up to the spongiosa 648 of the bone 641. Any suitable process, device, or tool can be used to make the openings 603a and 603b. For instance, the openings 603a and 603b can be created by drilling through the bone 641. In such case, a drill is used to create the openings 603a and 603b. In the depicted method, the openings 603a and 603b are created by drilling through the cortex 647 of the humerus 645 and up to the spongiosa 648 of the humerus 645. The openings 603a and 603b can be a hole, bore, or any void extending through the cortex 647 of the bone 641. Each of the openings 603a and 603b is configured and sized to receive the expandable portion 36a or 36b in the first configuration and a portion of the actuation strand 38a or 38b.

With continued reference to FIG. 33, the first anchor body 28a and a portion of the actuation strand 37a are inserted into, such as completely through, a portion of the soft tissue 646, such as tendon and/or muscle 644, and into, such as completely through, the opening 606a of the bone 641 (e.g., humerus 645) until the expandable portion 36a of the anchor body 28a reaches the spongiosa 648. During this insertion, the expandable portion 36b can be in the first configuration (i.e., non expanded configuration). Further, the anchor 22a can further include an attachment portion 633a, such as an attached strand, that is configured to attach the respective anchor to another anchor, such as an attachment portion of the other anchor. The first anchor body 28a and the portion of the actuation member 37a can be inserted through the soft tissue 644 and the bone 641 using any of the insertion instruments described herein. The process and method of using the different insertion instruments are described above. A portion of the actuation strand 38a, such as actuation portion 131a, extends out beyond the outer boundaries of the soft tissue 646 (e.g., tendon and/or muscle 644).

With continued reference to FIG. 33, the second anchor 22b can further include an attachment portion 633b, such as an attachment strand, that is configured to attach the respective anchor to another anchor, such as an attachment portion of the other anchor. The second anchor body 28b, a portion of the actuation strand 38b, and a portion of the attachment portion 633b are inserted through a portion of the soft tissue 646 and through the opening 603b of the bone 641 until the expandable portion 36b of the anchor body 28b reaches the spongiosa 648 of the bone 641. During this insertion, the expandable portion 36b can be in the first configuration (i.e., non-expanded configuration). A portion of the actuation strand 38b, such as actuation portion 131b, and a portion of the attachment portion 633b extend out beyond the outer boundaries of the soft tissue 646. An actuation force F can be applied to the actuation strands 38a and 38b, and in particular to the actuation portions 131a, 131b, so as to actuate the respective expandable portions 36a and 36b from the first configuration to the expanded configuration. Next, the first and second actuation strands 38a and 38b can be tied into the knot 66 before applying tension to the actuation strands 38a and 38b. Next, the approximation force AF can be applied to the terminal portions 135a of the first actuation strand 38a to draw the respective anchor, such as the first anchor 22a, toward to the other anchor 22b, as described in detail above. Then, the terminal portion 135b of the second actuation strand 38b can be placed in tension so as to lock the knot 66, thereby fixing the actuation strands 38a and 38b in tension as described in detail above. In doing so, the gap 602 created by the tear 601 is approximated, and the soft tissue 646, such as tendon and/or muscle 644, is fixed to the bone 641 (e.g., humerus 645.) The knot 66 can alternatively be configured as any other connector member suitable to connect the actuation strands 38a and 38b.

With continued reference to FIG. 33, more than two anchors can be used to repair an anatomical defect, such as rotator cuff tear 601. In addition to openings 603a and 603b, this method, openings 603c and 603d are made through the bone 641 (e.g. humerus 645). Each of the openings 603c and 603d can extend through the cortex 647 up to the spongiosa 648 of the bone 641. As discussed above with respect to openings 603a and 603b, each 603c and 603d can be created by drilling through the cortex 647 of the humerus 645 and up to the spongiosa 648 of the humerus 645. The openings 603c and 603d can be a hole, bore, or any void extending through the cortex 647 of the bone 641. Each of the openings 603c and 603d is configured and sized to receive the expandable portion of an anchor in the first configuration, a portion of the actuation strand, and a portion of an attachment portion of the anchor.

With continued reference to FIG. 33, a third anchor 22c is substantially similar or identical to the anchor 28b and can include an anchor body 28c, an actuation strand 37c, and an attachment portion 633c. The attachment portion 633c of the anchor 22c can be a strand and is configured to attach anchor 22c to another anchor. The anchor body 28c can include an expandable portion 36c. The third anchor body 28c, a portion of an actuation strand 37c, and a portion of the attachment portion are inserted through a portion of the soft tissue 646, such as tendon and/or muscle 644, and through the opening 603c. During this insertion, the expandable portion 36c can be in the first configuration (i.e., non-expanded configuration). After this insertion, a portion of the actuation strand 38c, such as actuation portion 131c, and a section of attachment portion 633c extend out beyond the outer boundaries of the soft tissue 646 (e.g., tendon and/or muscle 644).

A fourth anchor 22d is substantially similar or identical to the anchors 22a and can include an anchor body 28d and an actuation strand 37d. The anchor body 28d can include an expandable portion 36d. The third anchor body 28d and a portion of the actuation strand 37d are inserted through a portion of the soft tissue 646, such as tendon and/or muscles 644, and a through the opening 603d. During insertion, the expandable portion 36d of the anchor body 28d can be in the first configuration (i.e., non-expanded configuration). After insertion, a portion of the actuation strand 38d, such as actuation portion 131d, extends out beyond the outer boundaries of the soft tissue. 646. An actuation force F can be applied to the actuation strands 38a and 38b, and in particular to the actuation portions 131a, 131b, so as to actuate the respective expandable portions 36a and 36b from the first configuration to the expanded configuration. Next, the third and fourth actuation strands 38c and 38c can be tied into a knot 66 before applying tension to the actuation strands 38c and 38c. Next, the approximation force AF can be applied to the terminal portions 135c and/or 135d of the respective actuation strands 38c and 38d to draw the respective anchor, such as the third anchor 22c, toward the other anchor 22d as described in detail below. Then, the terminal portion 135d of the actuation strand 38d can be placed in tension so as to lock the knot 66, thereby fixing the actuation strands 38c and 38d in tension as described in detail above. In doing so, the gap 602 created by the tear 601 is approximated, and the soft tissue 646 is fixed to the bone 641. The knot 66 can alternatively be configured as any other connector member capable of connecting the actuation strands 38c and 38d. Next, the attachment portion 633b of the anchor 22b and the attachment portion 633c can be tied into a knot 66. Then, an approximation force F is applied to the attachment portion 633b and/or 633c to draw the respective anchor, such as anchor 22b toward the other anchor 22c.

Figure 34:
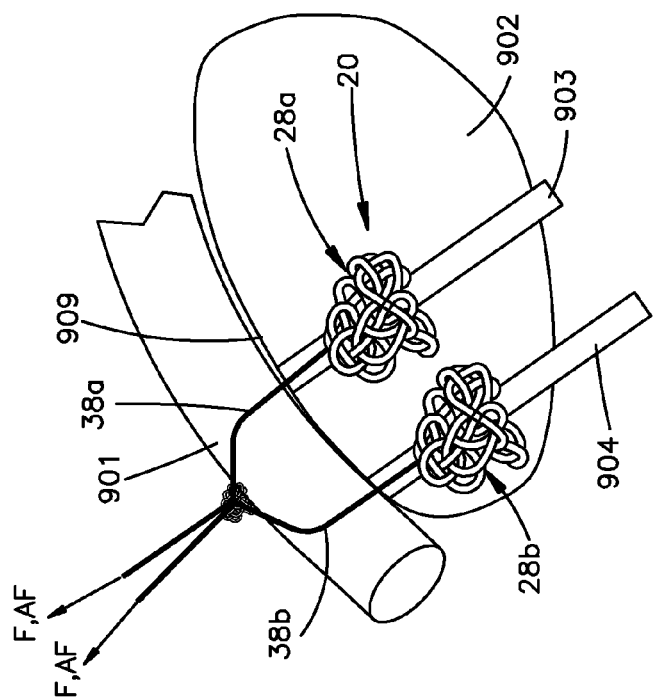

With reference to FIG. 34, any of the anchor assemblies 20 described herein can be used to repair a Bankart lesion. In a Bankart lesion, the anterior/inferior portion of the labrum 901 is torn away from the glenoid fossa 902. To repair a Bankart lesion, the torn labrum is reconnected to the glenoid fossa 902. In other words, to repair a Bankart lesion, a soft tissue, such as the labrum 901, is connected to a bone, such as the glenoid fossa 902. The method described herein can also be used to repair a hip labral tear. Thus, the labrum 901 also refers to the labrum of the hip, and the reference number 902 can also identify an acetabulum of the hip joint. The method of repairing a Bankart lesion includes implanting one or more anchor assemblies 20 in any of the arrangements shown in FIGS. 32C, 32D, 32E, and 32F. As discussed above, FIG. 32C shows an anchor assembly 20 having one anchor body 29a but can include more than one actuation strands 38a and 38b in order to increase the number of tissue fixation points per anchor. Each of the anchor assemblies 20 described in FIGS. 32D-32F have more than one anchor bodies 28a and 28b. In accordance with one embodiment, the method includes inserting, injecting, or otherwise driving anchor bodies 28a and 28b through the labrum 901 and the glenoid fossa 902. Any of the insertion instruments described herein can be used to insert the anchor bodies 28a and 28b through the labrum 901 and the glenoid fossa 902.

In order to insert the anchor bodies 28a and 28b through the glenoid fossa 902, the user can create openings 903 and 904 that extend into the glenoid fossa 902. The openings 903 and 904 can be created before inserting the anchor bodies 28a and 28b or while inserting the anchor bodies 28a and 28b. The openings 903 and 904 can be oriented at an oblique angle relative to each other. Thus, the openings 903 and 904 are not necessarily parallel to each other. Further, the openings 903 and 904 can be oriented diagonally relative to an outer rim 909 of the glenoid fossa 902. The user, for example, can use an insertion instrument capable of making an opening through the glenoid fossa 902 while inserting the anchor bodies 28a and 28b. Alternatively, a drill or any other suitable tool can be used drill a hole into the glenoid fossa 902 before inserting the anchor bodies 28a and 28b. Any of the insertion instruments described herein can be used to insert the anchor bodies 28a and 28b through the labrum 901. After inserting the anchor bodies 28a and 28b into the labrum 901 and in the respective openings 903 and 904, the anchor bodies 28a and 28b are actuated to the expanded configuration by, for example, applying an actuation force F on the respective actuation strands 38a and 38b. This method can also be used to repair a hip labral tear. To repair a hip labral tear, the labrum is reconnected to the acetabulum using the method described above.

With continued reference to FIG. 34, once the anchor bodies 28a and 28b have been actuated to the expanded configuration, the actuation strands 38a-b can be placed in tension by, for instance, applying an approximation Force AF to either or both of the actuation strands 38a and 38b, thereby inducing a tension in the actuation strands 38a-b of the first and second anchors 22a-b so as to apply a biasing force that draws the soft tissue, such as the labrum 901, toward the bone, such as the glenoid fossa 902 or acetabulum. At this point, the labrum 901 is fixed to the glenoid fossa 902. In this method of repairing a Bankart lesion, the openings 903 and 904 that extend into the glenoid fossa 902 are smaller than the openings or holes made in other procedures known in the art. These smaller openings 903 and 904 reduce the risk of post-operative glenoid rim fracture. Because this method does not employ metal anchors, it is easier to correct the position of the anchor bodies 28a and 28b after insertion, and the anchor bodies 28a and 28b occupy less space than conventional metal anchors. Since the anchor bodies 28a and 28b can be inserted with any of the insertion instruments described herein, the method allows atraumatic trans-tissue delivery of the anchor assembly.

Figure 35:
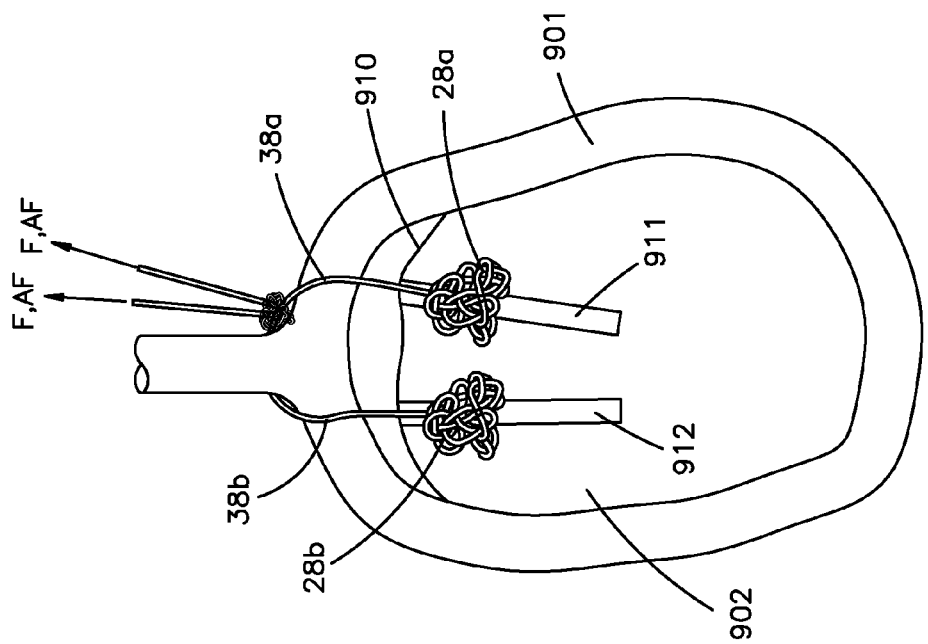

With reference to FIG. 35, any of the anchor assemblies described herein can be used to repair a superior labral tear from anterior to posterior (SLAP) lesion. In a SLAP lesion, a superior portion of the labrum 901 is detached from the glenoid rim 910. To repair this kind of injury, the superior portion of the labrum 901 is reconnected to the glenoid rim 910 of the glenoid fossa 902. In other words, to repair a SLAP lesion, a soft tissue, such as the labrum 901, is connected to a bone, such as the glenoid rim 910 of the glenoid fossa 902 The method of repairing a SLAP lesion includes implanting one or more anchor assemblies 20 in any of the arrangements shown in FIGS. 32C, 32D, 32E, and 32F. In accordance with one embodiment, the method includes inserting, injecting, or otherwise driving anchor bodies 28a and 28b through the labrum 901 and the glenoid fossa 902. Any of the insertion instruments described herein can be used to insert the anchor bodies 28a and 28b through the labrum 901 and the glenoid fossa 902. In order to insert the anchor bodies 28a and 28b through the glenoid fossa 902, the user can create openings 911 and 912 that extend into the glenoid fossa 902. The openings 911 and 912 can be created before inserting the anchor bodies 28a and 28b or while inserting the anchor bodies 28a and 28b. The openings 903 and 904 can be oriented at an oblique angle relative to each other. Thus, the openings 903 and 904 are not necessarily parallel to each other Further, the openings 911 and 912 can be oriented diagonally relative to the glenoid rim 910 of the glenoid fossa 902. The user, for example, can use an insertion instrument capable of making an opening through the glenoid fossa 902 while inserting the anchor bodies 28a and 28b. Alternatively, a drill or any other suitable tool can be used drill a hole into the glenoid fossa 902 before inserting the anchor bodies 28a and 28b. Any of the insertion instruments described herein can be used to insert the anchor bodies 28a and 28b through the labrum 901. After inserting the anchor bodies 28a and 28b into respective through the labrum 901 and in the respective openings 911 and 912, the anchor bodies 28a and 28b are actuated to the expanded configuration by, for example, applying an actuation force F on the respective actuation strands 38a and 38b.

With continued reference to FIG. 35, once the anchor bodies 28a and 28b have been actuated to the expanded configuration, the actuation strands 38a-b can be placed in tension by, for instance, applying an approximation Force AF to either or both of the actuation strands 38a and 38b, thereby inducing a tension in the actuation strands 38a-b of the first and second anchors 22a-b so as to apply a biasing force that draws the soft tissue, such as the labrum 901, toward the bone, such as the glenoid fossa 902 or acetabulum. At this point, the labrum 901 is fixed to the glenoid fossa 902. In this method of repairing a SLAP lesion, the openings 911 and 912 that extend into the glenoid fossa 902 are smaller than the openings or holes made in other procedures known in the art. These smaller openings 912 and 912 reduce the risk of post-operative glenoid rim fracture. Because this method does not employs metal anchors, it is easier to correct the position of the anchor bodies 28a and 28b after insertion, and the anchor bodies 28a and 28b occupy less space than conventional metal anchors. Since the anchor bodies 28a and 28b can be inserted with any of the insertion instruments described herein, the method allows atraumatic trans-tissue delivery of the anchor assembly. This method can also be used to repair a hip labral tear.

With reference to FIG. 36, any of the anchor assemblies described herein can be used to repair a biceps tendon injury. In biceps tendon injury, a biceps tendon, such as distal biceps tendon 950 is detached from the radius bone 951 of the forearm. To repair this kind of injury, the distal biceps tendon 950 (i.e., soft tissue) is fixed to the radius bone 951 (i.e., bone) using one or more of the anchor assemblies 20 described herein. The anchor bodies 28a and 28b are inserted through the tendon 950 and through respective openings 952 and 953 that extend through the radius bone 951. The openings 952 and 953 can be substantially parallel to each other and can extend through the cortical wall 954 of the radius bone 951 at two different locations. Further, the openings 952 and 953 can be created before insertion of the anchor bodies 28a and 28b as discussed above with respect to FIGS. 32A-32C. A drill can be used to create the openings 952 and 953 before inserting the anchor bodies 28a and 28b. Any of the insertion instruments described herein can be used to insert the anchor bodies 28a and 28b through the tendon 950 and in the respective openings 952 and 953. The anchor bodies 28 and 28b are inserted through the respective openings 952 and 953 through a first portion of the cortical wall 954, and they are advanced until they are positioned outside the radius 951 at a location adjacent to another portion of the cortical wall 954 of the radius bone 951. The anchor bodies 28a and 28b are then actuated into the expanded configuration as described in detail above. Then, the actuation strands 38a and 38b are placed in tension as described in detail above. Next, the actuation strands 38a and 38b are connected to each other via any suitable connector member. For instance, the actuation strands 38a and 38b can be tied into a knot 66. Alternatively, the actuation strands 38a and 38b can be pre-connected to each other. At this point, the distal biceps tendon 950 is anchored to the radius bone 951.

With reference to FIG. 37, any of the anchor assemblies described herein can be used to repair a defective or damaged annulus fibrosus 650. The defective or damaged annulus fibrosus 650 can have an anatomical defect, such as a tear 651. In FIG. 37, the anchor assembly is used to repair a radial tear, but any of the anchor assemblies described herein can be used to repair other kinds of injuries or anatomical defects in the annulus fibrosus 650, such as rim lesions or tears. A method of repairing a rim tear is described below with respect to FIG. 45. The tear 651 can define a gap 652 between a first soft tissue portion 653 and a second soft tissue portion 654. Any of the anchor assemblies described herein can be used to close or approximate the gap 652 defined between the first and second soft tissue portions 653 and 654. However, in the interest of brevity, the method of repairing the defective or damaged annulus fibrosus 650 is described and illustrated with respect to the anchor assembly 20 depicted in FIG. 1G.

With continued reference to FIG. 37, the first anchor body 28a of the first anchor 22a is inserted, such as injected or driven, at least into, such as completely through, the first tissue portion at a location adjacent the tear 651. Any of the insertion instruments described herein, such as insertion instrument 300, can be used to insert the anchor body 28 through the first tissue portion 654. The first anchor 22a can be inserted through the first tissue portion 653 until the anchor body 28a reaches a location behind the inner perimeter 654 of the annulus fibrosus 650. The first anchor body 28 can be actuated to its expanded configuration. For instance, the first anchor 28a can be manually expanded when the user applies an actuation force F (FIG. 1A) to the actuation portion 131a as described in detail above. The second anchor body 28b of the second anchor 22b is injected, driven or otherwise inserted through the second tissue portion 654 at location adjacent the tear 651. The second anchor body 28b can be actuated to the expanded configuration. For example, the second anchor 28b can be manually expanded when the user applies an actuation force F (FIG. 1G) to the actuation portion 131b. An approximation force AF (FIG. 1G) can be applied to at least one or both of the first and second actuation strands 38a and 38b to bias at least one or both of the anchor bodies 28a and 28b toward the other of the anchor bodies 28a and 28b to respective biased positions that to approximate the gap 652 as described in detail above. The first and second actuation portions 131a and 131b can then be tied together in a knot 66 at a location between the first and second anchor 22a and 22b. Alternatively, the first and second actuation portions 131a and 131b can be connected together using any other suitable connector member, such as any of the connector members 63 (FIG. 1G) described above.

With reference to FIG. 38, any of the anchor assemblies described herein can be used for joining or fixing a first bone to a second bone in order to treat an injury, such as a syndesmosis injury, or repair an anatomical defect. A syndesmostic injury is a disruption of the fibrous ligaments that hold the fibula 702 and tibia 701 together near the ankle joint 703. The anchor assembly 20 can be used to repair an anatomical defect, such as syndesmotic disruption, by fixing a first bone 704, such as the tibia 701, to a second bone 705, such as the fibula 702. For example, a method for fixating the first bone 704 to the second bone 705 includes creating a first opening 706 that extends through the first bone 704 and the second bone 705 and creating a second opening 707 that extends through the first bone 704 and the second bone 705. The first and second openings 706 and 707 can be created by, for example, drilling through the first bone and the second bone. The first and second openings 706 and 707 can be created in a substantially parallel orientation relative to each other. The first opening 706 can extend through a cortical wall 708 of the first bone 704 at two different locations and through a cortical wall 709 of the second bone 705 at one or two locations.

With continued reference to FIG. 38, an anchor assembly 20 is inserted through the first opening 706 such that the first anchor body 28*a* is positioned adjacent a cortical wall 708 of the first bone 704 and the second anchor body 28*b* is positioned adjacent the cortical wall 709 of the second bone 705. The first anchor body 28*a* can be inserted, such as injected or driven, at least into, or completely through, the first bone 704 without passing through soft tissue. Thus, the first anchor body 28*a* can be inserted directly into the bone 704. Alternatively, the first anchor body 28*a* can pass first through soft tissue and then be inserted into the first bone 704. The first anchor body 28*a* can be positioned outside the first opening 706 but adjacent the cortical wall 708. Similarly, the second anchor body 28*b* is positioned outside the second bone 705 but adjacent the cortical wall 709 of the second bone 705. Next, the first anchor body 28*a* can be actuated to the expanded configuration as described above. For instance, the anchor body 28*a* can be actuated to the expanded configuration by applying an actuation force F (FIG. 1A) on the actuation strand 38*a*. An approximation force AF (FIG. 1A) is then applied on the actuation strand 38*a* to apply tension to the anchor assembly 20 and draw the first bone 704 closer to the second bone 705. At this point, the expanded anchor body 28*a* is pressed against the cortical wall 708 of the first bone. A portion of the actuation strand 38*a* is then attached to the second anchor body 28*b* to maintain the actuation strand 38*a* in tension and thereby maintain the position of the first bone 704 relative to the second bone 705. In this embodiment, the second anchor body 28*b* is a substantially rigid non-expandable fixator configured and sized to be press-fit in the first opening 706. The non-expandable second anchor body 28*b* can be disc-shaped. Regardless of it shape, the second anchor body 28*b* is retained on the cortical wall 709 of the second bone 705, and the first anchor body 28*a* is retained on the cortical wall 708 of the first bone, thereby fixing the first bone 704, such as tibia 701, to the second bone 705, such as fibula 702. This method can include fixing the first bone 704 to the second bone 705 with one or more additional anchor assemblies 20. Each anchor assembly is inserted through its own opening extending through the first bone 704 and the second bone 705. For instance, an anchor assembly 20 can be inserted through the second opening 707 to aid in fixation of the first bone 704 to the second bone 705. The additional anchor assemblies 20 can be attached to the first and second bones 704 and 705 in a similar manner as described above with respect to the first anchor assembly 20 that is inserted through the first opening 706.

With reference to FIG. 39, an alternative method of fixing the first bone 704 to the second bone 705 is illustrated. In this method, the anchor assembly 20 can be used to repair an anatomical defect, such as syndesmotic disruption, by fixing the first bone 704, such as the tibia 701, to the second bone 705, such as the fibula 702. Alternatively, the method described herein can be used to approximate a first and second bone fragments separated by a fracture. Accordingly, the reference number 704 can identify a first bone fragment and the reference number 705 can identify a second bone fragment, wherein the first and second bone fragments are separated by, for example, a fracture or any other anatomical defect or injury. This method for fixating the first bone 704 to the second bone 705 creating a first opening 706 that extends through the first bone 704 and the second bone 705 and creating a second opening 707 that extends through the first bone 704 and the second bone 705. The first and second openings 706 and 707 can be created by, for example, drilling through the first bone and the second bone. The first and second openings 706 and 707 can be created in a substantially parallel orientation relative to each other. The first opening 706 can extend through a cortical wall 708 of the first bone 704 at two different locations and through a cortical wall 709 of the second bone 705 at two different locations.

With continued reference to FIG. 39, the first anchor body 28*a* and a portion of actuation strand 38*a* are inserted through the first opening 706. The first anchor body 28*a* is advanced through the first opening 706 until it is positioned outside first bone 704 but adjacent the cortical wall 708 of the first bone. Alternatively, the first anchor body 28*a* can be advanced through the first opening 706 until it reaches a location inside the spongiosa of the first bone 704. A second anchor body 28*b* and a portion of the actuation strand 38*b* are inserted through the second opening 707. The second anchor body 28*b* is advanced through the second opening 707 until it is positioned outside of the first bone 704 but adjacent the cortical wall 708 of the first bone. Alternatively, the second anchor body 28*a* can be advanced through the second opening 706 until it reaches a location inside the spongiosa of the second bone 704. The first anchor body 28*a* can be actuated to the expanded configuration as described in detail above. For instance, an actuation force F (FIG. 1A) can be applied on the actuation strand 38*a* to actuate the anchor body 28*a* to the expanded configuration as discussed in detail above. The second anchor body 28*b* is also actuated to the expanded configuration. For instance, the second anchor body 28*b* can be actuated to the expanded configuration by applying an actuating force F (FIG. 1A) on the actuation strand 38*b*. The first and second anchor bodies 28*a* and 28*b* can be expanded outside the spongiosa of the second bone 704 but adjacent the cortical wall so that these expanded anchor bodies 28*a* and 28*b* abut and contact the cortical wall 708. Alternatively, the first and second anchor 28*a* and 28*b* can be expanded inside the spongiosa of the second bone 704 such that the anchor bodies 28*a* and 28*b* do not necessarily contact the cortical wall 708. Also, the first and second anchor bodies 28*a* and 28*b* can be expanded inside the spongiosa of the second bone 704 at a location where the first and second anchor bodies 28*a* and 28*b* do contact at least a portion of the cortical wall 708. In accordance with one embodiment, an approximation force AF (FIG. 1A) can be applied to either or both actuation strands 38*a*, 38*b* to induce a tension in the actuation strands 38*a* and 38*b* so as to apply a biasing force that draws the first bone 704 and the second bone 705 together. The movement of the first and second anchors 22a and 22b toward each other causes the first bone 704 and second bone 705 to approximate toward each other. The actuation strand 38a and 38b can be maintained in tension after the first and second bone 704 and 705 have been approximated by, for example, attaching the first actuation strand 38a to the second actuation strand 38b using any suitable connection member, such as a knot 766. Thus, the first and second actuation strands 38a and 38b can be tied in a knot 766 to maintain the actuation strands 38a and 38b in tension and prevent, or at least inhibit, the first and second bones 704 and 705 from separating.

The anchor assembly 20 can also be used in other applications. For instance, one or more anchor assemblies 20 can be used to fix the acromio to the clavicle after joint dislocation. The anchor assembly 20 can also be used to fix the coracoid to the clavicle after dislocation. As discussed herein, the anchor assembly 20 can be used to fix syndesmotic disruptions from the fibula to the tibia. In pediatric cases, for example, the anchor assembly 20 can be used for repositioning bone fragments with an external cast. The anchor assembly 20 can also be used for anchoring in the pelvis area. The anchor assembly 20 can also be used for augmentation of a facet joint for non-fusion purposes. Additionally, the bone anchor 20 can be used for fixing a facet joint for fusion. The anchor assembly 20 can also serve as a rotational stabilizer for a pin fixator for femoral neck fractures. Moreover, the anchor assembly 20 can be used for fixing patella fractures. The anchor assemblies 20 can also be used to fix bones during distal interphalangeal joints (DIP) arthrodesis and during other hand and foot arthrodesis. The anchor assemblies 20 can also be used to fix bones during intramedullary rib fixation over tension for simple rib fractures. The anchor assemblies 20 can also be used for direct fixation of the humerus after fracture treatment with a plate or nail.

With reference to FIGS. 40A-40C, any of the anchor assemblies described herein can be used for reconstruction of an acromioclavicular (AC) joint. The AC joint is a joint at the top of the shoulder that connects the acromion to the clavicle. To reconstruct the AC joint, a clavicle 750, or first bone, can be connected to a coracoid process 751, or second bone. One or more anchor assemblies 20 can be used to connect the clavicle 750 to the coracoid process 751. One or more anchor assemblies 20 can be inserted or otherwise driven through the clavicle 750, the coracoclavicular ligament 752 or soft tissue, and the coracoid process 751. An opening or hole 753 can be created through the clavicle 750. The opening 753 can extend through a cortical wall 754 of the clavicle 750 at two different locations. Further, the opening 753 can also extend through a spongiosa 755 of the clavicle 750. The opening 753 can be created before inserting the anchor body 28a or 28b. Another opening or hole 756 can be created through the coracoid process 751. The opening 756 can extend into, such as completely through, a cortical wall 758 of the coracoid process 751 at two different locations. Further, the opening 756 can also extend through the spongiosa 757 of the coracoid process 751. The anchor body 28a is inserted, injected or otherwise driven through the opening 753, the coracoclavicular ligament 752, and through the opening 756 using any of the insertion instruments described herein or any other suitable instrument. The anchor body 28a is advanced through the opening 753, the coracoclavicular ligament 752, and through the opening 756 until is positioned outside the coracoid process 751 adjacent the cortical wall 758. The anchor body 28a is then actuated to the expanded configuration by, for instance, applying an actuation force on the actuation strand 38a as discussed in detail below. In the expanded configuration, the anchor body 28a abuts or contacts the cortical wall 758 of the coracoid process 751. Alternatively, the anchor body 28a can only be expanded in the spongiosa 757 of the coracoid process 751 and does not necessarily contact the cortical wall 758 of the coracoid process 751. The anchor assembly 20 can only include only one anchor body 28a as shown in FIGS. 40A and 40B or it can include two or more anchor bodies 28a and 28b as illustrated in FIG. 40C.

In the method depicted in FIGS. 40A and 40B, the actuation strand 38a is placed in tension as described above. Then, a connector member, such as knot 66, is formed to maintain the actuation strand in tension. When the connector member, such as knot 66, maintains the actuation strand 38a in tension, the anchor assembly 20 fixes the clavicle 750, or first bone, to the coracoid process 751.

In the method depicted in FIG. 40C, the anchor bodies 28a and 28b are actuated to their expanded configuration by, for example, applying an actuation force the respective actuation strands 38a and 38b. The actuation strands 38a and 38b are then placed in tension, and a connector member, such as a knot 66, is used to maintain the actuation strands 38a and 38b in tension, thereby fixing the clavicle 750, or first bone, to the coracoid process 751, or second bone.

With continued reference to FIGS. 40A-40C, the second bone can alternatively be the acromion. Thus, reference number 751 can also identify a clavicle. Therefore, the method described herein with respect to FIGS. 40A-40C can also be used to join the clavicle to an acromion. Further, the method described herein can also be used to join two bone fragments separated by an anatomical defect or injury. Reference number 750 can therefore identify a first bone fragment and reference number 751 can also identify a second bone fragment, wherein the first and second bone fragments are separated by an anatomical defect or injury, such as a fracture. The method described herein can also be used to join to facet joints together. Thus, reference number 750 can identify a first facet joint and reference number 751 can identify a second facet joint. In addition, reference number 750 can identify a first bone or first bone fragment, such as clavicle, acromion, fibula, tibia, facet joint, femur or any other suitable bone or bone fragments. The method described herein can also be used to join a tibia to a femur. Thus, reference number 750 can alternatively identify a tibia and reference number 751 can identify a femur. Reference number 751 can identify a second bone or second bone fragment, such as a clavicle, acromion, fibula, tiba, femor, facet joint, or any other suitable bone or bone fragment. Further still, reference number 751 can alternatively identify an auxiliary member such as a mesh or graft.

With reference to FIGS. 41A and 41B, a method of fixing an auxiliary or fixation member, such as a graft or a mesh, to soft tissue or bone is illustrated. Any of the anchor assemblies described herein can be used to fix the auxiliary member 850 to soft tissue or bone. In the depicted embodiment, the auxiliary member 850 can be a graft 851 and can be connected to a bone 852, such as a femur 853 and/or tibia 854. Although FIGS. 41A and 41B illustrate a method of performing anterior cruciate ligament (ACL) reconstruction, this method can be used to fix any auxiliary member or graft to a bone or soft tissue.

With continued reference to FIGS. 41A and 41B, the method includes creating a first opening 856 into, such as completely through, a bone 849, such as the tibia 854, or first bone or soft tissue. Another opening 855, such as a tunnel or hole, is created into the bone 852, such as the femur 853. The cross-sectional dimension of the opening 856 can be larger than the cross-sectional dimension of the opening 855. The opening 856 extends through a cortical wall 857 of the tibia 854 at two different locations. The opening 855 extends through a cortical wall 858 of the femur 853. Another opening 859 is created that extends from the opening 855 to the cortical wall 858 of the femur 853. Still another opening 860 is created that extends from the opening 855 to the cortical wall 858 of the femur 853. Each of the openings 859 and 860 is in communication with opening 855 and is smaller than the opening 855. The openings 859 and 860 can be oriented substantially parallel to each other, and each is configured and sized to receive a corresponding actuation strand 38a or 38b of the anchor assembly 20. The openings 855, 856, 859, and 860 can be created before or during insertion of the anchor assembly 20 as discussed in detail above.

With continued reference to FIGS. 41A and 41B, any of the insertion instruments described herein can be used to insert, such as inject or drive, the anchor bodies 28a and 28b into the openings 855 and 856 and the corresponding opening 859 and 860. The anchor bodies 28a and 28b can be advanced until they are positioned outside the femur 853 but adjacent the cortical wall 858 of the femur 853. Alternatively, the anchor bodies 28a and 28b can be advanced into the opening 855 until they are positioned at a location between the cortical wall 858 and the spongiosa 861 of the femur 853. Further still, the anchor bodies 28a and 28b can be advanced into the opening 855 until they are located into an intermedullary canal of the bone 852, such the femur 853. The anchor bodies 28a and 28b are actuated to their expanded configuration as discussed in detail above. For instance, an actuation force F can be applied to each actuation portion 131a and 131b of each actuation strand 38a and 38b to actuate the anchor bodies 28a and 28b to the expanded configuration. Depending on their position, when expanded, the anchor bodies 28a and 28b can contact only the cortical wall 858, the cortical wall 858 and the spongiosa 861, or only the spongiosa 861. Then, an auxiliary member 850, such as graft 851 is attached, coupled or connected to the actuation strands 38a and 38b. For example, the graft 851 can be folded around the actuation strands 38a and 38b. The actuation strands 38a and 38b can be looped around the graft 851. Then, an approximation force AF is applied to each actuation portion 131a and 131b in order to place the actuation strands 38a and 38b in tension and drive the graft 851, which is attached to the actuation strands 38a and 38b, toward the femur 853 or any other desired location. The approximation force AF can be applied until at least a portion of the graft 851 is positioned in the opening 855.

With continued reference to FIGS. 41A and 41B, after the actuation strands 38a and 38b are placed in tension, the expanded anchor bodies 28a and 28b abut the cortical wall 858, the spongiosa 861, or both and fix the position of the auxiliary member 850, such as graft 851, relative to the femur 853 and the tibia 854. This method includes the creating of opening or tunnels through bone that are shorter than the openings or tunnels used in the conventional methods. Since this method does not employ metal anchors, it is easier to reposition the anchor because no metal implants have to be removed, and no hard polymeric components have to be drill out. Any of the anchor assemblies 20 described herein can be used to fix any suitable auxiliary member to soft tissue or bone. For example, the anchor assembly 20 can be used to fix a plate to osteoporotic bones using any anchor assembly 20. The anchor assembly 20 can also fix a prosthetic implant to muscles or tendons. In addition to fixing a graft to a bone, the anchor assembly 20 can be used to fix cranio maxillofacial fixation (CMF) meshes to bone. The anchor assembly 20 can fix any kind of mesh to soft tissue and/or bone. The first and/or second anchor assemblies 28a and 28b can be attached to the mesh, and then the mesh can be attached to bone or soft tissue as described above. The mesh can also be attached to the first and/or second actuation portions 131a and 131b. Reference number 851 can alternatively identify a mesh. The anchor assembly 20 can also provide anchoring in a pedicle in order to apply tension to a posterior construct. The anchor assembly 20 can also be used as an augmentation device or to prevent joint penetration of screws, pins, and blades. Moreover, the anchor assembly 20 can be used as a distal compression member in a clavicle nail or as a distal compression member in an ulna nail or any other suitable nail. The anchor assembly 20 can also be used to fix a total disc replacement implant, such as a cage or an artificial disc, during spine surgery. The anchor assembly 20 can also be used for fixing an artificial ligament to the ACL or the posterior cruciate ligament.

With reference to FIG. 41C-41F, an insertion assembly 862 for inserting and attaching the auxiliary member 850, such as graft 851, into the opening 855, such as a hole or tunnel, created in the bone 852, such as femur 853. The insertion assembly 862 can include an inserter 866, such as a fork inserter, and an attachment member 864 that is configured to attach the auxiliary member 850, such as the graft 851, within the opening 855. The attachment member 864 can be detachably connected to the inserter 866. The inserter 866 can include an elongated body 875 that defines a proximal end 865 and a distal end 876. In addition, the inserter 866 can include a handle 884 attached to the proximal end 865 of the elongated body 875. The handle 884 can have a substantially cylindrical shape and can define one or more annular recesses 885 configure to receive a user's fingers to facilitate grabbing by the user. The elongated body 875 can have a substantially rectangular cross-section and is configured and sized to fit in the opening 856 of the bone 849, such as the tibia 854 and in the opening 855 of the bone 852, such as the femur 853. The elongated body 875 has a proximal section 887 that is closer to the proximal end 846 than the distal end 876. The proximal section 887 defines an outer surface 888 that defines a cross-sectional dimension. The cross sectional dimension defined by the outer surface 888 can be substantially uniform along the length of the proximal section 887. The elongated body 875 can also have a distal section 889 that is closer to the distal end 876 than the proximal end 865. The distal section 889 defines an outer surface 890. The outer surface 890 defines a variable cross-sectional dimension along the length of the distal section 889. At least one or more portions of the outer surface 890 can have a substantially concave configuration such that the outer surface 890 defines a section 891 with a reduced cross-sectional dimension relative to the remaining portions of the outer surface 890. Thus, at least the distal section 889 of the elongated body 875 is configured and sized to fit in the opening 856 of the bone 849, such as the tibia 854 and in the opening 855 of the bone 852, such as the femur 853.

With reference to FIG. 41C-41F, the inserter 866 can include one or more prongs 877 (FIG. 41D) that extend distally from the distal end 876 of the elongated body 875. In the depicted embodiment, the inserter 866 includes four prongs 877 that have a substantially flat configuration. The four prongs 877 are arranged in pairs along two rows. In particular, two prongs 877 are arranged side by side along a first row and another two prongs 877 are arranged side by side along a second row. The inserter 866, however, can have more or fewer prongs 877. Regardless of the number of prongs 877, the prongs 877 are configured to be coupled to the attachment member 864.

With reference to FIG. 41F-41H, the attachment member 864, which can also be referred to as a saddle, includes a body 863 that defines a proximal end 879 and a distal end 878. The body 863 is configured and sized to fit within the opening 856 and the opening 855, and defines one or more grooves 880, such as openings, holes, or apertures, that extend into the proximal end 879 of the body. Each groove 880 is configured and sized to receive one of the prongs 877 of the inserter 866. The attachment member 864 can be detachably coupled to the inserter 866 by, for example, inserting each prong 877 in a corresponding groove 880. The body 863 can further define a front wall 886, a rear wall 867, a first side wall 868, and a second side wall 869. Moreover, the body 863 can define a distal or top wall 881 at its distal end 878. The distal wall 881 of the body 863 can have a substantially concave configuration. Each of the front wall 886 and the rear wall 867 can have a substantially concave configuration or shape. The body 863 further defines a slit 874, such as a slot, that extends from the first side wall 868 to the second side wall 869. The slit 874 is configured and sized to receive a portion of the anchor assembly 20, such as actuation strands 38*a* and 38*b*. Further, the slit 874 can extend at least into the body 863 in a direction from the proximal end 879 of the body 863 toward it distal end 878. The slit 874 is disposed in communication with a transverse opening 882 defined in the body 863. The transverse opening 882 can extend in a direction from the first side wall 868 to the second side wall 869 of the body 863, and is in communication with apertures 870*a* and 870*b*, such as recesses 871*a* and 871*b*, disposed along the first side wall 868 and the second side wall 869, respectively. The apertures 870*a* and 870*b* are configured and sized to receive the actuation strands 38*a* and 38*b*. Each of the apertures 870*a* and 870*b* can extend in a direction from the distal wall 881 toward the proximal end 879 of the body 863. Moreover, the apertures 870*a* and 870*b* are disposed in communication with the slit 874 defined by the body 863. Each of the apertures 870 and 870*b* can have a substantially concave configuration or shape.

With continued reference to FIG. 41C, the body 863 can further define an axial opening 883 disposed in communication with the transverse opening 882. The axial opening 883 can extend from a central portion of the transverse opening 882. Moreover, the axial opening 883 can extend in a direction from the transverse opening 882 toward the proximal end 879 of the body 863, and is configured and sized to receive at least the actuation or approximation portions 131*a* and 131*b* of the anchor assembly 20. The attachment member 864 can further include one or more engagement members 872, such as teeth 873, protruding out from the first side wall 868 and the second side wall 869. The teeth 873 can be slated with respect to the corresponding first side wall 868 and second side wall 869, and are configured to contact inner portions of the bone 852, such as the femur 853, surrounding the opening 855 in order to fix the attachment member 864 to the bone 852 in the opening 855.

With reference to FIGS. 41A-41H, the insertion assembly 862 can be used to position and attach the auxiliary member 850, such the graft 851, in the opening 855 of the bone 852, such as the femur 853. To do so, the attachment member 864 should be detached from the inserter 866. Alternatively, the attachment member 864 can already be detached from the inserter 866. Next, at least portions of the actuation strands 38*a* and 38*b* are positioned in the transverse opening 882 by, for example, inserting portions of the actuation strands 38*a* and 38*b* into the slit 874 from the proximal end 879 of the body 863. Once portions of the actuations strands 38*a* and 38*b* are positioned in the slit 874, the body 863 of the attachment member 864 can be advanced downwardly with respect to the actuation strands 38*a* and 38*b* until the portions of the actuation strands 38*a* and 38*b* are positioned in the transverse opening 882 and other portions of the actuation strands 38*a* and 38*b* are disposed in the apertures 870*a* and 870*b*. At this juncture, portions of the actuation or approximation portions 131*a* and 131*b* can be disposed in the axial opening 883 defined by the body 863. The auxiliary member 850, such as the graft 851, can then be disposed on the top or distal wall 881 and over the front wall 886 and the rear wall 867, thereby attaching the auxiliary member 850, such as the graft 851, to the attachment member 864. The attachment member 864 can be coupled to the inserter 866 by, for example, inserting the prongs 877 in the corresponding grooves 880.

With continued reference to FIGS. 41A-41C, with the auxiliary member 850, such as the graft 851, disposed on the distal wall 881, the front wall 886, and the rear wall 867 of the body 863, inserter 866 can be advance into the openings 856 and 855 until the attachment member 864 is disposed within the opening 855. The cross-sectional dimension of the opening 856 can be larger than the cross-sectional dimension of the opening 855 in order to allow the attachment member 864 to pass through the opening 856 without fixing itself to the bone surrounding the opening 856. The inserter 866 can be advanced toward the opening 855 by applying a force to the inserter 866. For example, a user can hold the inserter 866 through the handle 884 and then push the inserter 866 to advance the inserter 866 toward the opening 855. Alternatively, the user can apply a force to the inserter 866 using a mallet or any other suitable apparatus. While the inserter 866 is being advanced toward the opening 855, an approximation force AF can be simultaneously applied to the actuation or approximation portions 131*a* and 131*b* to advance the connector member 63 toward the opening 855. When the attachment member 863 is positioned in the opening 855, the engagement members 872, such as the teeth 873, contact or engage the portion of the bone 852 surrounding the opening 855 to fix the position of the attachment member 864 relative to the bone 852. As a consequence, the position of the auxiliary member 850, such as the graft 851, disposed on the attachment member 864 is fixed with respect to the bone 852. Thus, the auxiliary member 850 can be fixed in the opening 855 defined by the bone 852, such as the femur 853. The inserter 866 is then withdrawn or retracted from the opening 855, leaving behind the attachment member 864 and the auxiliary member 850, such as the graft 851. Once the engagement members 872, such as the teeth 873, are contacting the portion of the bone 852 surrounding the opening 855, the application of a force to the inserter 866 in a direction away from the opening 855 causes the prongs 877 to exit the grooves 877. Consequently, the inserter 866 is detached from the attachment member 864. The user can then completely withdraw the inserter 866 from the patient. Alternatively, the auxiliary member 850 and the attachment member 863 can be disposed in the opening 855 of the bone 852, such as the femur 853, without using the inserter 866. After coupling the auxiliary member 850, such as the graft 851, to the attachment member 863 as described above, the user can only apply an approximation force AF to the actuation or approximation portions 131*a* and 131*b* to advance the connector member 63 toward the opening 855, thereby drawing the attachment member 850 along with the auxiliary member 850 toward the opening 855. The user can apply the approximation force AF to the actuation or approximation portions 131*a* or 131*b* until at least a portion of the attachment member 863 and the auxiliary member 850 are disposed in the opening 855 of the bone 852, such as the femur 853.

With reference to FIGS. 42A and 42B, a method of using the anchor assembly 20 for fixing a first tissue portion to a second tissue portion is illustrated. The method described below can also be used to fix a meniscal scaffold or mesh to any suitable surrounding tissue (e.g., peripheral rim, capsule, adjoining meniscus, tibal plateau, etc.). In the depicted embodiment, the anchor assembly 20 is used to repair a meniscal tear or any kind of soft tissue tear or anatomical defect. In the case of a tear, such as a meniscal tear, the soft tissue can include a tear 1004 that defines a gap 1007. The method can employ any of the anchor assemblies 20 described herein and includes inserting, such as injecting or driving, the anchor body 28*a* into a soft tissue portion 1001 located on one side of the gap 1007 defined by the anatomical defect 1003, such as soft tissue tear 1004. The anchor body 28*a* can be advanced toward to opposite side of the gap 1007 and can be inserted, such as injected or driven, into a soft tissue portion 1006 on an opposite side of the gap 1007. The anchor body 28*b* can be inserted, such as injected or driven, into another soft tissue portion 1005 on one side of the gap 1007 defined by the anatomical defect 1003, such as tear 1004. The anchor body 28*b* can then be advanced toward the opposite side of the gap 1007 and can be inserted, such as injected or driven, into a soft tissue portion 1009 on an opposite side of the gap 1007. Any of the insertion instruments described herein can be used to drive the anchor bodies 28*a* and 28*b* through the corresponding soft tissue portions 1001, 1006 and 1005, 1009. Then, the anchor bodies 28*a* and 28*b* are actuated to their expanded configurations by for example, applying a force to the actuation portions 131*a* and 131*b* of the actuation strands 38*a* and 38*b*. An approximation force AF is then applied to the actuation portions 131*a* and 131*b* to draw one anchor body, such as anchor body 28*a*, toward the other anchor body 28*b*, thereby approximation the gap 1007 defined by the tear 1004. The actuator strands 38*a* and 38*b* are then connected while in tension to maintain the position of the expanded anchor bodies 28*a* and 28*b*. For instance, the actuation strands 38*a* and 38*b* can be tied together as described in detail above. At this point, the gap 1007 is approximated. The anchor assembly 20 can also be used to fix distal bicepts tendons together. In addition, the anchor assembly 20 can be used to fix one meniscus to another meniscus using the method described above. As such, reference numbers 1001 and 1005 can also identify respective soft tissue portions of a first meniscus, and the reference numbers 1006 and 1009 can also identify soft tissue portions of a second meniscus. Reference number 1007 can identify a gap between the first meniscus and the second meniscus. Thus, the first and second menisci can be joined together by, for example, employing the method described above.

With reference to FIGS. 43A and 43B illustrates a method of using an anchor assembly 20 to guide a cannulated bone anchor 1052, such as cannulated pedicle screw 1053 to the desired site. Any of the bone anchor assemblies 20 described herein can be used to guide the bone anchor to the target site. In this method, a cavity or opening 1051 is created inside a vertebral body 1050 using any suitable device, tools, or means. For instance, drill can be used to create the opening 1051. The cavity 1051 extends form a cortical wall 1054 to the spongiosa 1055 of the vertebral body 1050. Next, a cannulated guide wire 1056 can be inserted through the opening 1051. One or more anchor body 28*a* of the anchor assembly 20 can be inserted through the cannulated guide wire 1056 until it reaches the end of the opening 1051. Alternatively, the anchor body 28*a* can be inserted through the opening 1051 using any of the insertion instruments described herein. The guide wire 1056 or insertion instrument is then withdrawn from the opening 1051. The anchor body 28*a* is actuated to the expanded configuration as described in detail above. At this point, the anchor body 28*a* is fixed within the vertebral body 1050. Then, a bone anchor 1052, such as pedicle screw 1053 can be placed and advanced over the actuation strand 38*a* of the anchor assembly 20. The actuation strand 38*a* serves as a guide. Then, the bone anchor 1052 is anchored to the vertebral body 1050.

With reference to FIGS. 44A and 44B, a method of using the anchor assembly 20 as a tissue augmentation device is illustrated. Any of the anchor assemblies 20 described herein can be used as a soft tissue or bone augmentation device. Augmentation devices are used, for example, to treat bone degeneration, fractures, injuries and disorders, such as osteoporosis. Osteoporosis, for instance, leads to loss in bone density, and can be treated by implanting an augmentation device. This method includes the use of any of the anchor assemblies 20 described herein and a cannulated bone anchor 1100, such as cannulated bone screw 1101. The cannulated bone screw 1101 defines a bore or hole 1102 extending along its length. In use, the cannulated bone anchor 1101 is driven into a bone 1105 or any other body portion such as soft tissue. Next, the anchor body 28*a* is inserted through the bore 1102. The anchor body 28*a* can be advanced through the bore 1102 until it is positioned outside of the bone anchor 1101 and inside a body portion such as a target bone. A portion of the actuation strand 38*a*, however, can remain inside the bore 1102. At this point, the anchor body 28*a* is positioned within a bone. Then, the anchor body 28*a* is actuate to the expanded configuration by, for example, applying an actuation force to the actuation strand 38*a* as described in detail above. The expanded anchor body 28*a*, which is now positioned inside a bone, functions as an augmentation device or filler. The anchor assembly 20 can also be used as a soft tissue augmentation device.

With respect to FIG. 45, any of the anchor assemblies described herein can be used to repair a defective or damaged annulus fibrosus 1250. The defective or damaged annulus fibrosus 1250 can have an anatomical defect or injury, such as a rim lesion or tear 1251. As discussed above, one or more of the anchor assemblies described herein can be used to repair other kinds of anatomical defects or injuries in the annulus fibrosus. The tear 1251 can define a gap 1252 between a soft tissue portion 1253 of the annulus fibrosus 1250 and a bone 1254, such as a vertebral body 1255. In the interest of brevity, the method of repairing the rim tear 1251 is illustrated and described with respect to the anchor assembly 20 depicted in FIG. 1G.

With continued reference to FIG. 45, an opening 1256, such as a hole or aperture, is created in the bone 1254, such as the vertebral body 1255. The opening 1256 can be created adjacent to the opening 1256. Any suitable instrument or apparatus, such as a drill or an awl, can be used to create the opening 1256 in the bone 1254 (e.g., vertebral body 1255. The first anchor body 28*a* is inserted, such as injected or driven, in the opening 1256. In this method, soft tissue does not have to be pierced while creating the opening 1256 in the bone 1254 or when inserting the first anchor 22*a* in the opening 1256 of the bone 1254. The first anchor 22*a* can be advanced through the opening 1256 until the first anchor body 28*a* reaches the desired target site. For example, this desired target site can be in the spongiosa of the vertebral body 1255 or at a location adjacent the cortical wall of the vertebral body 1255. The first anchor body 28*a* can then be actuated to its expanded configuration as described in detail above. For instance, the first anchor 28*a* can be manually expanded when the user applies an actuation force F (FIG. 1A) to the actuation portion 131*a* as described in detail above. The second anchor 22*b* can be inserted, such as injected or driven, into the soft tissue portion 1253 located adjacent to the rim tear 1252. The second anchor 22*a* can then be actuated to the expanded configuration. For instance, the second anchor body 28*b* can then be actuated to the expanded configuration as described in detail above. For instance, the second anchor body 28*a* can be expanded manually when the user applies an actuation force F (FIG. 1G) to the actuation portion 131*b*. An approximation force AF (FIG. 1G) can then be applied to at least one or both anchors 22*a* and 22*b* to bias at least one or both of the anchor bodies 28*a* and 28*b* toward the other of the anchor bodies 28*a* and 28*b* in order to approximate the gap 1252 as described in detail above. The first and second actuation portions 131*a* and 131*b* can then be tied together in a knot 66 at a location between the first and second anchors 22*a* and 22*b*. Alternatively, the first and second actuation portions 131*a* and 131*b* can be connected together using any other suitable connector member, such as any of the connector members 63 (FIG. 1G) described above.

The embodiments described in connection with the illustrated embodiments have been presented by way of illustration, and the present invention is therefore not intended to be limited to the disclosed embodiments. Furthermore, the various structures, features, and methodologies associated with any embodiment described herein can apply to any other embodiment as described herein, unless otherwise indicated. For instance, unless otherwise indicated, any insertion instrument described herein can include a retention assembly as described herein in accordance with any suitable alternative embodiment, a cutting assembly as described herein or in accordance with any suitable alternatively embodiment, a swap assembly of the type described herein or constructed in accordance with any suitable alternative embodiment, a reciprocal motion assembly of the type described herein or constructed in accordance with any suitable alternative embodiment, and a selective plunger engagement assembly of the type described herein or constructed in accordance with any suitable alternative embodiment. Accordingly, those skilled in the art will realize that the invention is intended to encompass all modifications and alternative arrangements included within the spirit and scope of the invention, for instance as set forth by the appended claims.

We claim:

1. A method of treating an anatomical defect, comprising:
   inserting at least a portion of an anchor body at least into an anatomical location, the anchor body including an anchor body strand defining an eyelet and at least two openings, the anchor body strand including an expandable portion, the anchor body including an actuation member that extends through the at least two openings; and
   applying an actuation force to the actuation member along a direction away from the expandable portion so as to 1) draw the actuation member through the at least two openings, 2) cause the eyelet to be pulled through the anchor body and out of the anchor body, and 3) actuate the expandable portion from an initial configuration in which the expandable portion has an initial maximum thickness, to an expanded configuration in which the expandable portion has an expanded thickness that is greater than the initial maximum thickness.

2. The method according to claim 1, wherein the inserting step comprises advancing the expandable portion through a soft tissue portion until the expandable portion reaches the anatomical location.

3. The method according to claim 2, wherein the soft tissue portion is a rotator cuff tendon, and the step of advancing the expandable portion through the soft tissue portion comprises advancing the expandable portion through the rotator cuff tendon.

4. The method according to claim 2, wherein the soft tissue portion is a biceps tendon, and the step of advancing the expandable portion through the soft tissue portion comprises advancing the expandable portion through the biceps tendon until the expandable portion reaches the anatomical location.

5. The method according to claim 4, wherein the anatomical location is defined by a radius bone, and method comprises creating an opening that extends into the radius bone.

6. The method according to claim 2, wherein the soft tissue portion is a labrum, and the step of advancing the expandable portion through the soft tissue portion comprises advancing the expandable portion through the labrum until the expandable portion reaches the anatomical location.

7. The method according to claim 6, wherein the labrum is a glenoid labrum, the anatomical location is a glenoid fossa, and the step of advancing the expandable portion through the soft tissue portion comprises advancing the expandable portion through the glenoid labrum until the expandable portion reaches the glenoid fossa.

8. The method according to 6, wherein the labrum is a hip labrum, the anatomical location is an acetabulum, and the step of advancing the expandable portion through the soft tissue portion comprises advancing the expandable portion through the hip labrum until the expandable portion reaches the acetabulum.

9. The method according to claim 1, wherein the anatomical location is defined by bone, the method further comprising creating an opening in the bone.

10. The method according to claim 9, further comprising creating the opening prior to the inserting step.

11. The method according to claim 9, wherein the step of creating the opening comprises creating the opening in a cortical wall of the bone.

12. The method according to claim 9, wherein the inserting step comprises inserting the expandable member into the opening in the bone.

13. The method according to claim 9, further comprising creating the opening in a cancellous portion of the bone, wherein the applying step comprises applying the actuation force to the actuation member when the expandable portion is in the cancellous portion.

14. The method according to claim 1, wherein the anchor body is a first anchor body, the anchor body strand is a first anchor body strand, the expandable portion is a first expandable portion, actuation member is a first actuation member, the initial configuration is a first initial configuration, the expanded configuration is a first expanded configuration, the initial maximum thickness is a first initial maximum thickness, the expanded thickness is a first expanded thickness, the actuation force is a first actuation force, and the anatomical location is a first anatomical location, and the method further comprises:

inserting at least a portion of a second anchor body at least into a second anatomical location, the second anchor body defining at least two openings and including a second expandable portion and a second actuation member that extends through the at least two openings of the second anchor body;

applying a second actuation force to the second actuation member along a direction away from the second expandable portion so as to draw the second actuation member through the at least two openings of the second anchor body and actuate the second expandable portion from a second initial configuration, in which the second expandable portion has a second initial maximum thickness, to a second expanded configuration, in which the second expandable portion has a second expanded thickness that is larger than the second initial maximum thickness; and fixing a position of the second actuation member with respect to the first actuation member.

15. The method according to claim 14, wherein the step of inserting the at least a portion of the second anchor body at least into the second anatomical location comprises inserting the second expandable portion entirely through the second anatomical location.

16. The method according to claim 14, wherein the step of fixing the position of the second actuation member with respect to the first actuation member comprises tying a knot with the first and second actuation members after the steps of inserting the at least a portion of each of the first and second anchor bodies at least into respective first and second anatomical locations.

17. The method according to claim 14, wherein the first and second actuation members are connected together by a connector member, and the step of fixing the position of the second actuation members with respect to the first actuation members comprises adjusting the connector member from an unapproximated configuration toward an approximated configuration to fix the position of the second actuation member with respect to the first actuation member.

18. The method according to claim 14, further comprising applying an approximation force to either or both of the first and second anchor bodies to draw the first and second expandable portions toward either or both the first and second anatomical locations.

19. The method according to claim 14, wherein the first anatomical location is defined by a first bone and the second anatomical location is defined by a second bone, the step of inserting the at least a portion of the first anchor body at least into the first anatomical location comprises inserting the first expandable portion at least into the first bone, and the step of inserting the at least a portion of the second anchor body at least into the second anatomical location comprises inserting the second expandable portion at least into the second bone.

20. The method according to claim 19, wherein the step of inserting the first expandable portion into at least the first bone comprises inserting the first expandable portion into at least the first and second bones.

21. The method according to claim 20, wherein the step of inserting the second expandable portion at least into the second bone comprises inserting the second expandable portion at least into the first and second bones.

22. The method according to claim 19, further comprising creating a first opening that extends at least into the first bone, the first opening configured to receive the first expandable portion when the first expandable portion is in the first initial configuration.

23. The method according to claim 22, further comprising creating a second opening that extends at least into the second bone, the second opening configured to receive the first expandable portion when the first expandable portion is in the first initial configuration.

24. The method according to claim 19, wherein the first bone is a tibia, and the second bone is a fibula, and the step of inserting the first expandable portion at least into the first bone comprises inserting the first expandable portion at least into the tibia, and the step of inserting the second expandable portion at least into the second bone comprises inserting the second expandable portion at least into the fibula.

25. The method according to claim 24, wherein the step of inserting the first expandable portion at least into the tibia comprises inserting the first expandable portion at least into the tibia and the fibula, and the step of inserting the second expandable portion at least into the fibula comprises inserting the second expandable portion at least into the tibia and the fibula.

26. The method according to claim 19, wherein the first bone is a clavicle, and the second bone is a coracoid process, and the step of inserting the first expandable portion at least into the first bone comprises inserting the first expandable portion at least into the clavicle, and step of inserting the second expandable portion at least into the second bone comprises inserting the second expandable portion at least into the coracoid process.

27. The method according to claim 26, wherein the step of inserting the first expandable portion at least into the clavicle comprises inserting the first expandable portion at least into the clavicle and the coracoid process, and the step of inserting the second expandable portion at least into the coracoid process comprises inserting the second expandable portion at least into the clavicle and the coracoid process.

28. The method according to claim 19, wherein the first bone is an acromion, and the second bone is a clavicle, and the step of inserting the first expandable portion at least into the first bone comprises inserting the first expandable portion at least into the acromion, and the step of inserting the second expandable portion at least into the second bone comprises inserting the second expandable portion at least into the clavicle.

29. The method according to claim 28, wherein the step of inserting the first expandable portion of the at least into the acromion comprises inserting the first expandable portion at least into the acromion and the clavicle, and the step of inserting the second expandable portion at least into the clavicle comprises inserting at least the second expandable portion at least into the acromion and the clavicle.

30. The method according to claim 19, wherein the first bone is a first bone fragment, the second bone is a second bone fragment, the first and second bone fragments separated by a fracture, and the step of inserting the first expandable portion at least into the first bone comprises inserting the first expandable portion at least into the first bone fragment, and the step of inserting the second expandable portion at least into the second bone comprises inserting the second expandable portion at least into the second bone fragment.

31. The method according to claim 30, wherein the step of inserting the first expandable portion at least into the first bone fragment comprises inserting the first expandable portion at least into the first and second bone fragments, and the step of inserting the second expandable portion at least into the second bone fragment comprises inserting the second expandable portion at least into the first and second bone fragments.

32. The method according to claim 19, wherein the first bone is a first facet joint, the second bone is a second facet joint, and the step of inserting the first expandable portion at least into the first bone comprises inserting the first expandable portion at least into the first facet joint, and step of inserting the second expandable portion at least into the second bone comprises inserting the second expandable portion at least into the second facet joint.

33. The method according to claim 32, wherein the step of inserting the first expandable portion at least into the first facet joint comprises inserting the first expandable portion at least into the first and second facet joints, and the step of inserting the second expandable portion at least into the second facet joint comprises inserting the second expandable portion at least into the first and second facet joints.

34. The method according to claim 14, further comprising attaching an auxiliary member to the first and second actuation members.

35. The method according to claim 34, further comprising applying an approximation force to either or both of the first and second anchor bodies to draw the auxiliary member toward at least one of the first and second expandable portions.

36. The method according to claim 35, wherein the first anatomical location is defined by a tibia and the second anatomical location is defined by a femur, and the step of inserting the at least a portion of the first anchor body at least into the first anatomical location comprises inserting the first expandable portion at least into the tibia, and the step of inserting the at least a portion of the second anchor body at least into the second anatomical location comprises inserting the second expandable portion at least into the femur.

37. The method according to claim 36, wherein the step of inserting the first expandable portion at least into the tibia comprises inserting the first expandable portion at least into the tibia and the femur, and the step of inserting the second expandable portion at least into the femur comprises inserting the second expandable portion at least into the tibia and the femur.

38. The method according to claim 35, wherein the auxiliary member is a graft, the first anatomical location is defined by a tibia, the second anatomical location is defined by a femur, and the step of applying the approximation force comprises applying the approximation force to either or both of the first and second bodies until the graft is disposed in the femur.

39. The method according to claim 38, further comprising coupling the first and second actuation members to an attachment member that is configured to be attached to the femur, and coupling the graft to the attachment member.

40. The method according to claim 39, further comprising coupling the attachment member to an inserter, and advancing the inserter toward the femur until the attachment member and the graft are positioned in the femur.

41. The method according to claim 40, wherein the steps of advancing the inserter toward the femur and applying the approximation force to either or both of the first and second anchor bodies are performed simultaneously.

42. The method according to claim 39, further comprising advancing the attachment member toward the femur until the attachment member is disposed in the femur, wherein the step of advancing the attachment member toward the femur comprises applying the approximation force to either or both of the first and second anchor bodies until the graft is disposed in the femur.

43. The method according to claim 38, further comprising coupling the graft to the first and second actuation members.

44. The method according to claim 43, further comprising placing the graft through a loop formed by the first and second actuation members.

45. The method according to claim 34, wherein the auxiliary member is a mesh, the step of attaching the auxiliary member to the first and second actuation members comprising attaching the mesh to the first and second actuation members.

46. The method of according to claim 45, further comprising inserting the first expandable portion at least into the mesh.

47. The method according to claim 46, wherein the second anatomical location is defined by a bone, the method further comprising inserting the second expandable portion at least into the bone.

48. The method according to claim 46, wherein the second anatomical location is defined by soft tissue, the method further comprising inserting the second expandable portion at least into the soft tissue.

49. The method according to claim 14, wherein the first anatomical location is defined by a first soft tissue portion, the second anatomical location is defined by a second soft tissue portion, the step of inserting the at least a portion of the first anchor body at least into the first anatomical location comprises inserting the first expandable portion at least into the first soft tissue portion, and the step of inserting the at least a portion of the second anchor body at least into the second anatomical location comprises inserting the second expandable portion at least into the second soft tissue portion.

50. The method according to claim 49, wherein the step of inserting the first expandable portion at least into the first soft tissue portion comprises inserting the first expandable portion at least into the first and second soft tissue portions, and the step of inserting the second expandable portion at least into the second soft tissue portion comprises inserting the second expandable portion at least into the first and second soft tissue portions.

51. The method according to claim 49, wherein the first soft tissue portion and the second soft tissue portion are part of an annulus fibrosus, such that a tear of the annulus fibrous is disposed between the first and second tissue portions.

52. The method according to claim 14, wherein the first anatomical location is defined by first and second soft tissue portions of a meniscus, the second anatomical location is defined by third and fourth soft tissue portions of the meniscus, the first and third soft tissue portions located on a first side of a tear of the meniscus, the second and fourth tissue portions located on a second side of the tear that is opposite to the first side, the step of inserting the at least a portion of the first anchor body at least into the first anatomical location comprises inserting the first expandable portion at least into the first and second soft tissue portions of the meniscus such that the first expandable portion cross the tear, and the step of inserting the at least a portion of the second anchor body at least into the second anatomical location comprises inserting the second expandable portion through the third and fourth soft tissue portions of the meniscus such that the second expandable portion crosses the tear.

53. The method according to claim 52, further comprises applying an approximation force to the first or second anchor body to draw the first and second tissue portions of the meniscus toward each other so as to approximate a gap defined by the tear.

54. The method according to claim 14, wherein the first anatomical location is defined by a first portion of a meniscus, the second anatomical location is defined by a second portion of the meniscus, the step of inserting the at least a portion of the first anchor body at least into the first anatomical location comprises inserting the first expandable portion at least into the first portion of the meniscus, and the step of inserting the at least a portion of the second anchor body at least into the second anatomical location comprises inserting the second expandable portion through the second portion of the meniscus.

55. The method according to claim 54, wherein the step of inserting the first expandable portion at least into the first portion of the meniscus comprises inserting the first expandable portion at least into the first meniscus and the second portion of the meniscus, and the step of inserting the second expandable portion at least into the second portion of the meniscus comprises inserting the second expandable portion at least into the first portion of the meniscus and the second portion of the meniscus.

56. The method according to claim 14, wherein the first anatomical location is defined by a bone and the second anatomical location is defined by soft tissue, the step of inserting the at least a portion of the first anchor body at least into the first anatomical location comprises inserting the first expandable portion at least into the bone, and the step of inserting the at least a portion of the second anchor body at least into the second anatomical location comprises inserting the second expandable portion at least into the soft tissue.

57. The method according to claim 56, wherein the step of inserting the first expandable portion at least into the bone comprises inserting the first expandable portion at least into the bone and the soft tissue, and the step of inserting the second expandable portion at least into the soft tissue comprises inserting the second expandable portion at least into the bone and the soft tissue.

58. The method according to claim 14, wherein the first anatomical location is defined by a humerus and the second anatomical location is defined by rotator cuff tendon, the step of inserting the at least a portion of the first anchor body at least into the first anatomical location comprises inserting the first expandable portion at least into the humerus, and the step of inserting the at least a portion of the second anchor body at least into the second anatomical location comprises inserting the second expandable portion at least into the rotator cuff tendon.

59. The method according to claim 58, wherein the step of inserting the first expandable portion at least into the humerus comprises inserting the expandable portion at least into the humerus and the rotator cuff tendon, and the step of inserting the second expandable portion at least into the rotator cuff tendon comprises inserting the second expandable portion at least into the humerus and the rotator cuff tendon.

60. The method according to claim 14, wherein the first anatomical location is defined by a radius bone and the second anatomical location is defined by a distal biceps tendon, the step of inserting the at least a portion of the first anchor body at least into the first anatomical location comprises inserting the first expandable portion at least into the radius bone, and the step of inserting the at least a portion of the second anchor body at least into the second anatomical location comprises inserting the second expandable portion at least into the distal biceps tendon.

61. The method according to claim 60, wherein the step of inserting the first expandable portion at least into the radius bone comprises inserting the first expandable portion at least into the radius bone and the distal biceps tendon, and the step of inserting the second expandable portion at least into the distal biceps tendon comprises inserting the second expandable portion at least into the distal biceps tendon and the radius bone.

62. The method according to claim 14, wherein the first anatomical location is defined by a glenoid fossa and the second anatomical location is defined by a glenoid labrum, the step of inserting the at least a portion of the first anchor body at least into the first anatomical location comprises inserting the first expandable portion at least into glenoid fossa, and the step of inserting the at least a portion of the second anchor body at least into the second anatomical location comprises inserting the second expandable portion at least into the glenoid labrum.

63. The method according to claim 62, wherein the step of inserting the first expandable portion at least into the glenoid fossa comprises inserting the first expandable portion at least into the glenoid fossa and the glenoid labrum, and the step of inserting the second expandable portion at least into the glenoid labrum comprises inserting the second expandable portion at least into the glenoid fossa and the glenoid labrum.

64. The method according to claim 14, wherein the first anatomical location is defined by a acetabulum and the second anatomical location is defined by a labrum, and the step of inserting the at least a portion of the first anchor body at least into the first anatomical location comprises inserting the first expandable portion at least into the acetabulum, and the step of inserting the at least a portion of the second anchor body at least into the second anatomical location comprises inserting the second expandable portion at least into the labrum.

65. The method according to claim 64, wherein the step of inserting the first expandable portion at least into the acetabulum comprises inserting the first expandable portion at least into the acetabulum and the labrum, and the step of inserting the second expandable portion into at least the labrum comprises inserting the second expandable at least into the acetabulum and the labrum.

66. The method according to claim 14, wherein the first anatomical location is defined by a vertebral body and the second anatomical location is defined by an annulus fibrosus, the step of inserting the at least a portion of the first anchor body at least into the first anatomical location comprises inserting the first expandable portion at least into the vertebral body, and the step of inserting the at least a portion of the second anchor body at least into the second anatomical location comprises inserting the second expandable portion at least into the annulus fibrosus.

67. The method according to claim 14, further comprising:
inserting at least a portion of a third anchor body into a third anatomical location, the third anchor body defining at least two openings and including a third expandable portion and a third actuation member that extends through the at least two openings of the third anchor body; and;
applying a third actuation force to a third actuation member along a direction away from the third expandable portion so as to draw the third actuation member at through the at least two openings of the third anchor body and actuate the third expandable portion from a third initial configuration, in which the third expandable portion has a third initial maximum thickness, to a third expanded configuration, in which the third expandable portion has a third expanded maximum thickness that is larger than the third initial maximum thickness;

inserting at least a portion of a fourth anchor body into a fourth anatomical location, the fourth anchor body defining at least two openings and including a fourth expandable portion and a fourth actuation member;

applying a fourth actuation force to a fourth actuation member along a direction away from the fourth expandable portion so as to draw the fourth actuation member through the at least two openings of the fourth anchor body and actuate the fourth expandable portion from a fourth initial configuration, in which the fourth expandable portion has a fourth initial maximum thickness, to a third expanded configuration, in which the third expandable portion has a third expanded maximum thickness that is larger than the third initial thickness;

applying an approximation force to either or both of the third and fourth anchor bodies to apply tension to the third and fourth expandable portions; and fixing a position of the third and fourth actuation members with respect to each other to maintain the third and fourth actuation members in tension.

68. The method according to claim 67, wherein the step of fixing the position of the third and fourth actuation members with respect to each other comprises tying a knot between the third and fourth actuation members.

69. The method of claim 1, further comprising advancing a cannulated bone anchor along the actuation member until the cannulated bone anchor reaches the anatomical location.

70. A method of treating an anatomical defect, comprising:

inserting at least a portion of a first anchor body of a first anchor at least into a first anatomical location, the first anchor body including a first anchor body strand defining 1) an eyelet, 2) at least two openings, and 3) a first expandable portion, a first actuation member coupled to the first anchor body, the first actuation member extending through the at least two openings;

inserting at least a portion of a second anchor body of a second anchor at least into a second anatomical location, the second anchor body including a second expandable portion and a second actuation member coupled to the second anchor body;

applying a first actuation force to the first actuation member along a direction away from the first expandable portion so as to 1) draw the first actuation member through the at least two openings, 2) cause the eyelet to be pulled through the first anchor body and out of the first anchor body, and 3) actuate the first expandable portion from a first initial configuration in which the first expandable portion has a first initial maximum thickness, to a first expanded configuration in which the first expandable portion has a first expanded maximum thickness that is greater than the first initial maximum thickness; and applying a second actuation force to the second actuation member along a direction away from the second expandable portion so as to actuate the second expandable portion from a second initial configuration in which the second expandable portion has a second initial maximum thickness, to a second expanded configuration in which the expandable portion has a second expanded maximum thickness that is greater than the second initial maximum thickness.

71. The method according to claim 70, wherein the first expandable portion includes a woven substrate defining a plurality of openings, and the step of inserting the at least a portion of the first anchor body at least into the first anatomical location comprises inserting the woven substrate at least into the first anatomical location.

72. The method according to claim 71, wherein at least part of the first actuation member extends through the openings, and the step of applying the first actuation force to the first actuation member along the direction away from the first expandable portion comprises applying the first actuation force to the first actuation member such that the at least part of the first actuation member moves through the openings.

73. The method of claim 70, further comprising advancing a cannulated bone anchor along at least one of the first and second actuation members until the cannulated bone anchor reaches the respective anatomical location.

* * * * *